United States Patent
Scobie et al.

(10) Patent No.: US 9,944,640 B2
(45) Date of Patent: *Apr. 17, 2018

(54) PYRIMIDINE-2,4-DIAMINE DERIVATIVES FOR TREATMENT OF CANCER

(71) Applicant: THOMAS HELLEDAYS STIFTELSE FOR MEDICINSK FORSKNING, Stocksund (SE)

(72) Inventors: Martin Scobie, Uppsala (SE); Thomas Helleday, Stocksund (SE); Tobias Koolmeister, Stockholm (SE); Sylvain Jacques, Lyons (FR); Matthieu Desroses, Knivsta (SE); Marie-Caroline Jacques-Cordonnier, Lyons (FR)

(73) Assignee: THOMAS HELLEDAYS STIFTELSE FOR MEDICINSK FORSKNING, Stocksund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/447,818

(22) Filed: Mar. 2, 2017

(65) Prior Publication Data
US 2017/0217961 A1    Aug. 3, 2017

Related U.S. Application Data

(63) Continuation of application No. 14/647,400, filed as application No. PCT/SE2013/051387 on Nov. 26, 2013, now Pat. No. 9,604,937.
(Continued)

(30) Foreign Application Priority Data

Nov. 27, 2012 (SE) ...................................... 1251332

(51) Int. Cl.
C07D 471/04 (2006.01)
C07D 417/12 (2006.01)
(Continued)

(52) U.S. Cl.
CPC .......... *C07D 471/04* (2013.01); *A61K 31/505* (2013.01); *A61K 31/506* (2013.01);
(Continued)

(58) Field of Classification Search
None
See application file for complete search history.

(56) References Cited

U.S. PATENT DOCUMENTS 6,169,086 B1    1/2001  Ejima et al.
8,268,846 B2    9/2012  Wakefield et al.
(Continued)

FOREIGN PATENT DOCUMENTS

GB    0 681 712    10/1952
WO    WO-86/04583    8/1986
(Continued)

OTHER PUBLICATIONS

Vishwakarma et al., Database CAPLUS, Acc. No. 1986:406471, Indian Journal of Chemistry, Section B: Organic Chemistry Including Medicinal Chemistry (1985), 24B(5), pp. 466-471 (2 page abstract).*

(Continued)

*Primary Examiner* — Brian J Davis
(74) *Attorney, Agent, or Firm* — Foley & Lardner LLP

(57) ABSTRACT

A compound of formula I,

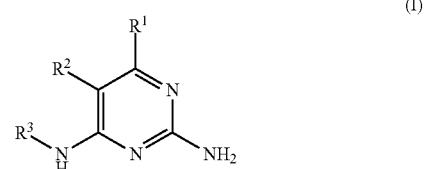

or a pharmaceutically-acceptable salt thereof. The compound is useful in the treatment of cancer or other diseases that may benefit from inhibition of MTH1.

25 Claims, 2 Drawing Sheets

Related U.S. Application Data

(60) Provisional application No. 61/797,022, filed on Nov. 27, 2012.

(51) Int. Cl.
| | |
|---|---|
| *C07D 401/04* | (2006.01) |
| *C07D 239/48* | (2006.01) |
| *C07D 405/12* | (2006.01) |
| *C07D 405/14* | (2006.01) |
| *C07D 405/04* | (2006.01) |
| *C07B 59/00* | (2006.01) |
| *A61K 31/505* | (2006.01) |
| *C07D 403/12* | (2006.01) |
| *A61K 31/506* | (2006.01) |
| *C07D 403/14* | (2006.01) |
| *C07D 409/04* | (2006.01) |
| *C07D 403/04* | (2006.01) |
| *C07D 453/02* | (2006.01) |
| *A61K 45/06* | (2006.01) |
| *A61K 31/5377* | (2006.01) |
| *C07D 401/14* | (2006.01) |

(52) U.S. Cl.
CPC .......... *A61K 31/5377* (2013.01); *A61K 45/06* (2013.01); *C07B 59/002* (2013.01); *C07D 239/48* (2013.01); *C07D 401/04* (2013.01); *C07D 401/14* (2013.01); *C07D 403/04* (2013.01); *C07D 403/12* (2013.01); *C07D 403/14* (2013.01); *C07D 405/04* (2013.01); *C07D 405/12* (2013.01); *C07D 405/14* (2013.01); *C07D 409/04* (2013.01); *C07D 417/12* (2013.01); *C07D 453/02* (2013.01); *C07B 2200/05* (2013.01)

(56) References Cited

U.S. PATENT DOCUMENTS

| | | | |
|---|---|---|---|
| 9,604,937 B2* | 3/2017 | Scobie | ............... A61K 31/505 |
| 2004/0204386 A1 | 10/2004 | Bhatt et al. | |
| 2008/0194577 A1 | 8/2008 | Cai et al. | |
| 2010/0016344 A1 | 1/2010 | Wakefield et al. | |
| 2011/0275611 A1 | 11/2011 | Axten et al. | |

FOREIGN PATENT DOCUMENTS

| | | |
|---|---|---|
| WO | WO-02/096867 | 12/2002 |
| WO | WO-03/015776 | 2/2003 |
| WO | WO-2004/080979 | 9/2004 |
| WO | WO-2005/026129 A1 | 3/2005 |
| WO | WO-2005/092899 | 10/2005 |
| WO | WO-2006/078886 | 7/2006 |
| WO | WO-2009/105220 | 8/2009 |
| WO | WO-2011/056916 | 5/2011 |
| WO | WO-2011/100285 | 8/2011 |
| WO | WO-2012/080729 | 6/2012 |
| WO | WO-2014/033480 A1 | 3/2014 |

OTHER PUBLICATIONS

Database CAPLUS in STN, Acc. No. 1955:60839, Hitchings et al., U.S. Pat. No. 2,691,655 (Oct. 12, 1954) (abstract).
Database CAPLUS in STN, Acc. No. 2010:84378, Wakefield et al., U.S. Pat. No. 8,268,846 B2 (Sep. 18, 2012) (abstract).
Engelhardt et al. "Bispyrimidines as Potent Histamine H4 Receptor Ligands: Delineation of Structure—Activity Relationships and Detailed H4 Receptor Binding Mode," Journal of Medicinal Chemistry, vol. 56, May 13, 2013, pp. 4264-4276.
Extract from STN Registry—database, STN International, File Registry—RN: 634582-11-9 Entered STN: Jan. 6, 2004; RN: 634195-10-1 Entered STN: Jan. 5, 2004; RN: 634195-07-6 Entered STN: Jan. 5, 2004, 1 page.
International Search Report and Written Opinion for PCT/SE2013/051387, dated Mar. 10, 2014.
Katiyar et al., "Syntheses of 2,4,6-trisubstituted pyrimidine derivatives as a new class of antifilarial topoisomerase II inhibitors," Bioorganic & Medicinal Chemistry Letters 15 (2005) pp. 47-50.
Kumar et al., "A Novel and Convenient Synthesis of 2-Amino-4-(N-alkyl-N-arylamino)-pyrimidine s using Polarized Ketene S,S- and S,N-acetals", Georg Thieme Verlag, vol. 9, Jan. 1, 1980, pp. 748-741.
Lee et al., "Discovery of a novel class of 2-aminopyrimidines as CDK1 and CDK2 inhibitors," Bioorganic & Medicinal Chemistry Letters vol. 21, 2001, pp. 4203-4205.
Medina et al., "Structure-Based Design of Potent and Selective 3-Phosphoinositide-Depdendent Kinase-1 (PDK1) Inhibitors," Journal of Medicinal Chemistry, vol. 54, No. 6, Mar. 24, 2011, pp. 1871-1895.
Mizar et al., "Three-component synthesis of 5:6 and 6:6 fused pyrimidines using KF-alumina as a catalyst," Tetrahedron letters 49 (2008), pp. 5283-5285.
Non-Final Office Action in U.S. Appl. No. 14/647,400 dated Apr. 27, 2016 (10 pages).
Notice of Allowance in U.S. Appl. No. 14/647,400 dated Nov. 28, 2016 (10 pages).
Rabbani et al., "Prevention of prostate-cancer metastasis in vivo by a novel synthetic inhibitor of urokinase-type plasminogen activator (uPA)," Int. J. Cancer (1995), 63, pp. 840-845.
Rai et al., "A roadblock for the tumor-suppressive effects of oncogenic RAS-induced ROS," Small TGPASES 2012, vol. 3, No. 2, Apr. 1, 2012, pp. 120-125.
Shi et al., "Modulation of Peripheral Serotonin Levels by Novel Tryptophan Hydroxylase Inhibitors for the Potential Treatment of Functional Gastrointestinal Disorders," Journal of Medicinal Chemistry, vol. 51, No. 13, Jul. 10, 2008, pp. 3684-3687.
Sunduru et al., "Discovery of new 1,3,5-triazine scaffolds with potent activity against *Mycobacterium tuberculosis* H37Rv," European Journal of Medicinal Chemistry, vol. 45, 2010, pp. 3335-3345.
Supplementary European Search Report issued on EP Application EP13859400, dated Jul. 11, 2016.
Svennson et al., "Crystall structure of human MTH1 and the 8-oxo-dGMP product complex," FEBS Letters, vol. 585, 2011, pp. 2617-2621.
Tani, Database CAPLUS 1975:140168, JP 4921147B, abstract, 1974.
Tani, Database CAPLUS 1975:140173, JP 4921147B, abstract, 1974.
Gong, et al., "Synthesis, SAR, and Antitumor Properties of Diamino-C, N-Diarylpyrimidine Positional Isomers: Inhibitors of Lysophosphatidic Acid Acyltransferase-beta," Bioorganic & Medicinal Chemistry Letters, 2004, 14, pp. 2303-2308.
Sander, et al., "2, 4-Diaminopyrimidines as Histamine $H_4$ Receptor Ligands-Scaffold Optimization and Pharmacological Characterization," Bioorganic & Medicinal Chemistry, 2009, 17, pp. 7186-7196.
Schreeb, et al., "Piperazine Modification in 2, 4, 6-Triaminopyrimidine Derivatives as Histamine $H_4$, Receptor Ligands," Pharmazine, 2013, 68, pp. 521-525.
Database Registry Extract, American Chemical Society [database online], Jul. 22, 2016 [retrieved on Aug. 1, 2016].

* cited by examiner

PYRIMIDINE-2,4-DIAMINE DERIVATIVES FOR TREATMENT OF CANCER

CROSS-REFERENCE TO RELATED APPLICATIONS

This application is a continuation of U.S. application Ser. No. 14/647,400, filed on May 26, 2015, which is a U.S. National Stage Application under 35 U.S.C. §371 of International Application No. PCT/SE2013/051387, filed on Nov. 26, 2013, which claims the benefit of U.S. Provisional Application No. 61/797,022, filed on Nov. 27, 2012, and Swedish Application No. 1251332-1, filed on Nov. 27, 2012, the entire disclosures of which are hereby incorporated by reference for any and all purposes.

FIELD OF THE INVENTION

The invention relates to novel compounds, compositions and methods for treatment of cancer. In particular, the invention relates to novel compounds, compositions and methods for the treatment of cancers through inhibition of MTH1.

BACKGROUND OF THE INVENTION

The listing or discussion of an apparently prior-published document in this specification should not necessarily be taken as an acknowledgement that the document is part of the state of the art or is common general knowledge.

Background

Dysfunctional redox regulation of cellular signalling and an increased ROS (Reactive oxygen species) tension have been demonstrated to play a crucial role in cancer etiology, progression and metastasis (Zhang et al., Antioxid Redox Signal 15(11)2011:2876-2908). ROS mediates tumor-promoting characteristics, such as e.g. unrestrained proliferation, survival signaling, increased migration, angiogenesis. ROS are generated during cell metabolism and are highly reactive with macromolecules such as DNA, proteins and lipids. Exposure of nucleic acids to ROS can create more than 20 oxidatively modified nucleotides, of which 8-oxo-7,8-dihydroxyguanine (8-oxo-dG) is most abundant. 8-oxo-dG plays a pivotal role in mutagenesis (Sekiguchi and Tsuzuki, Oncogene 21(58)2002:8895-906). To protect themselves from carcinogenic effects, mammalian cells are armed with a set of repair enzymes to remove the oxidized nucleotides to maintain genome integrity. One of these protective enzymes is MTH1 (MutT homologue 1, 8-oxo-dGTPase, NUDT1). Interestingly, MTH1 is upregulated in various cancer forms, suggesting that the cancer cell rely on MTH1 function to survive the increased DNA lesion (Human Proteinatlas, Koketsu et al., Hepatogastroenterology, 51(57)2004:638-41). Suppression of MTH1 level and activity by using RNAi technology, leads to reduced cancer cell survival, premature senescence and DNA strand breaks (Rai et al, PNAS, 106(1)2009:169-174), Helleday et al unpublished data). Interestingly, lung cancers which spontaneously form in OGG−/− mice are prevented from forming in crosses with the MTH1−/− mice, suggesting that MTH1 is required for lung cancer cells to survive (Sakumi et al., Cancer Res 63, 2003: 902). We have observed that downregulation of MTH1 protein levels in human colon cancer tumors in xenograft mice model reduced tumor growth and significantly shrinked the tumour (Helleday et al, unpublished data).

In tumour cells, reducing the capacity to eliminate oxidised dNTPs by inhibiting MTH1 activity, will reduce cancer cell survival and hence be a promising novel anticancer therapy, either as monotherapy or in cancer forms with high oxidative stress levels and/or in combination with radiotherapy and chemotherapy drugs.

Shortcomings and Complications with Current Treatment

Today's treatment of cancer is not effective for all patients with diagnosed disease also including a large proportion of patients that experience adverse effects from treatments with existing therapies or where resistance to on-going therapy is developed over time.

Prior Art

Engelhardt, H. et al. *Journal of Medicinal Chemistry* (2013), 56(11), 4264-4276 and US patent application US 2010/0016344 disclose certain 6-aryl-2,4-diaminopyrimidines having an additional pyrimidine appendage as histamine H4 receptor modulators. The compounds are claimed to be useful for a various diseases including cancer pain, but their use in the treatment of cancer as such is neither disclosed or suggested.

International patent application WO 2013/066839 discloses 6-(3-pyridyl)-(2,4-diaminopyrimidines as HDAC inhibitors. However, the substituent on the 4-amino group contains a prerequisite 5-trifluoromethyl-1,2,4-oxadiazol-3-yl group. 2,4-Diaminopyrimidines substituted in the 6-position with 3-aminoindazoles have been described in international patent application WO 2010/059658. Although also indazoles without the amino groups are mentioned, it is evident from the examples that the 3-amino substituent on the indazole is required for activity. The same document also describes 2,4-diaminopyrimidines substituted in the 6-position by a 3-cyano-2-fluorophenyl group. However, these compounds are merely precursors to the 3-aminoindazoles mentioned above and there is no disclosure or suggestions in the document that they possess any anti-cancer activity.

International patent application WO 2006/078886 describes 2,4-diaminopyrimidines substituted in the 6-position by an aryl group as wnt modulators. The 4-aryl group is lacking any substituents or must be substituted in the 3-position by methoxy. The document does not disclose or suggest compounds with any other substituent-pattern, nor does it mention or suggest the use of such compounds in the treatment of cancer. Moreover, in all examples the 4-amino group of the pyrimidine is substituted by either 1,3-benzodioxol-5-ylmethyl or by 4-hydroxy-phenethyl. Several scientific publications describe the use of one of the compounds (N4-(1,3-benzodioxol-5-ylmethyl)-6-(3-methoxyphenyl)-2,4-pyrimidinediamine) as a tool to investigate the wnt-pathway.

International patent application WO 86/04583 describes aziridinyl substituted anti-neoplastic compounds. There is only one compound that has both a 6-aryl substituent and a 4-N-alkyl group attached to 2-aminopyrimidine core. The compound has besides the aziridinyl group a fluorine in the 5-position of the pyrimidine ring. Both the aziridinyl and the fluorine are implied to be important for the activity and there is nothing that suggests that anti-neoplastic activity can be obtained without at least one of these substituents.

British patent application GB 681712 describes 2,4-diaminopyrimidines substituted in the 6-position by an aryl group for use in the treatment of cancer, but in only one example the aryl is phenyl and the 4-amino group is substituted by an alkyl. In this compound the phenyl is unsubstituted and the alkyl is methyl.

There is no disclosure in this documents of compounds in which the 6-phenyl may be substituted by other groups than chloro or nitro in the para-position, that the 6-phenyl may contain more than one substituent or that the 4-alkylamino-group is larger than methyl or may carry substituents.

Two publications from the group of H. Junjappa (*Indian Journal Chemistry* (1985), 24B 466; *Synthesis* (1980), 748) describe the synthesis of certain 2-amino-4-(N-alkylamino)-6-arylpyrimidines. The publications do not mention or suggest the use of the synthesized compounds in the treatment of cancer.

There are numerous 2-amino-4-(N-alkylamino)-6-arylpyrimidines that are, or that at some point have been stated to be, commercially available but that do not have any ascribed pharmaceutical use, nor any other use, ascribed to them.

MTH1 inhibitors have been described in Streib, M. et al. *Angewandte Chemie, Int., Ed.* (2013), Vol. 52. The compounds are organometallic and are not 2-amino-4-(N-alkylamino)-6-aryl pyrimidines.

SUMMARY OF THE INVENTION

Although the finding of oncogenes and development of new anticancer treatments and diagnosis have improved the life length of cancer patients, there is still a high medical need to find more effective and less toxic treatments for e.g. breast cancer, leukemia, colon or lung cancer. Our preliminary data suggests that MTH1 inhibitors have the potential to be very effective against cancer forms with dysfunctional redox status, with minimal general toxic effects. MTH1 inhibition may also be a suitable adjuvant therapy to be used in conjunction with radiotherapies or other chemotherapeutic approaches.

The present invention aims at providing new treatments for cancer that can be achieved by inhibition of MTH1

DETAILED DESCRIPTION OF THE INVENTION

Figure 1:
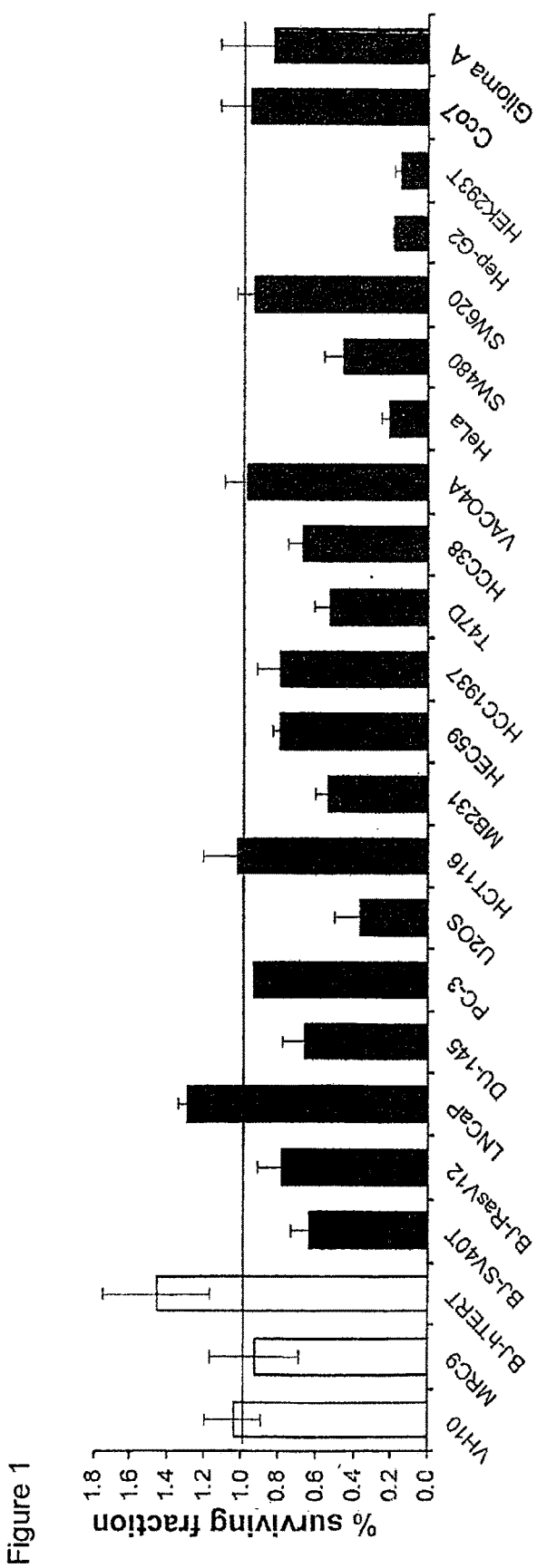
FIG. 1. Effect on cell survival following MTH1 siRNA depletion in various human cancer and normal cell lines.

There is provided a compound of formula I,

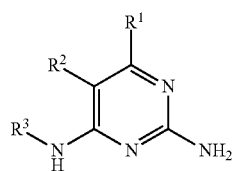

(I)

for use in the treatment of cancer
wherein:
$R^1$ represents heteroaryl connected to the pyrimidine of formula I via a carbon atom of the heteroaryl ring, which heteroaryl ring is optionally substituted by one or more substituents selected from $Y^1$, —$C_{1-6}$alkyl optionally substituted by one or more $Y^2$ and heterocycloalkyl optionally substituted by one or more $Y^3$; or aryl represented by

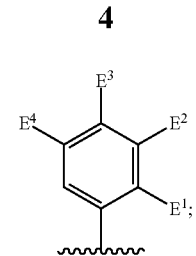

$E^1$ represents hydrogen, $Y^{1a}$, —$C_{1-6}$alkyl optionally substituted by one or more $Y^2$ or heterocycloalkyl optionally substituted by one or more $Y^3$;
$E^2$ represents hydrogen, $Y^{1b}$, —$C_{1-6}$alkyl optionally substituted by one or more $Y^2$ or heterocycloalkyl optionally substituted by one or more $Y^3$;
$E^3$ and $E^4$ each independently represents hydrogen, $Y^1$, —$C_{1-6}$alkyl optionally substituted by one or more $Y^2$ or heterocycloalkyl optionally substituted by one or more $Y^3$;
$R^2$ represents hydrogen, halogen, —CN, —$C_{1-12}$alkyl optionally substituted by one or more $Z^1$, or heterocycloalkyl optionally substituted by one or more $Z^2$;
$R^3$ represents —$C_{1-12}$alkyl optionally substituted by one or more $Z^1$ or heterocycloalkyl optionally substituted by one or more $Z^2$; or
$R^2$ and $R^3$ are linked together to form, along with the atoms to which they are attached, a 5- to 8-membered non-aromatic ring, wherein the link formed by $R^2$ and $R^3$ is optionally substituted by one or more substituents selected from $Z^3$ and —$C_{1-9}$alkyl optionally substituted by one or more $Z^4$;
each $Y^1$ independently represents halogen, —CN, —C(O)$R^a$, —C(O)N($R^b$)$R^c$, —C(O)O$R^d$, —N($R^e$)$R^f$, —N($R^g$)C(O)$R^h$, —N($R^i$)C(O)O$R^j$, —N($R^k$)C(O)N($R^l$)$R^m$, —NO$_2$, —N($R^n$)S(O)$_2$$R^o$, —O$R^p$, —OC(O)$R^q$, —OS(O)$_2$$R^r$, —S(O)$_m$$R^s$, —S(O)$_2$N($R^t$)$R^u$, heterocycloalkyl optionally substituted by one or more substituents selected from $W^2$, aryl optionally substituted by one or more substituents selected from $W^3$ or heteroaryl optionally substituted by one or more substituents selected from $W^3$;
$Y^{1a}$ represents halogen, —CN, —C(O)$R^a$, —C(O)N($R^b$)$R^c$, —C(O)O$R^d$, —N($R^e$)$R^f$, —N($R^g$)C(O)$R^h$, —N($R^i$)C(O)O$R^j$, —N($R^k$)C(O)N($R^l$)$R^m$, —NO$_2$, —N($R^n$)S(O)$_2$$R^o$, —O$R^{px}$, —OC(O)$R^q$, —OS(O)$_2$$R^r$, —S(O)$_m$$R^s$, —S(O)$_2$N($R^t$)$R^u$, heterocycloalkyl optionally substituted by one or more substituents selected from $W^2$, aryl optionally substituted by one or more substituents selected from $W^3$ or heteroaryl optionally substituted by one or more substituents selected from $W^3$;
$Y^{1b}$ represents halogen, —CN, —C(O)$R^a$, —C(O)N($R^b$)$R^c$, —C(O)O$R^d$, —N($R^e$)$R^f$, —N($R^g$)C(O)$R^h$, —N($R^i$)C(O)O$R^j$, —N($R^k$)C(O)N($R^l$)$R^m$, —NO$_2$, —N($R^n$)S(O)$_2$$R^o$, —O$R^{py}$, —OC(O)$R^q$, —OS(O)$_2$$R^r$, —S(O)$_m$$R^s$, —S(O)$_2$N($R^t$)$R^u$, heterocycloalkyl optionally substituted by one or more substituents selected from $W^2$, aryl optionally substituted by one or more substituents selected from $W^3$ or heteroaryl optionally substituted by one or more substituents selected from $W^3$;
each $R^a$, $R^b$, $R^c$, $R^d$, $R^e$, $R^g$, $R^h$, $R^i$, $R^k$, $R^l$, $R^m$, $R^n$, $R^p$, $R^q$, $R^s$, $R^t$ and $R^u$ independently represents hydrogen, —$C_{1-6}$alkyl optionally substituted by one or more substituents selected from $W^1$, heterocycloalkyl optionally substituted by one or more substituents selected from $W^2$, aryl optionally substituted by one or more substituents selected from $W^3$, or heteroaryl optionally substituted by one or more substituents selected from $W^3$; or any two $R^b$ and $R^c$, $R^e$ and $R^f$, $R^i$ and $R^m$ and/or $R^t$ and $R^u$ are linked together to form, along with the nitrogen atom to which they are attached, a 3- to 8-membered monocyclic or bicyclic ring, which ring optionally contains one or two further heteroatoms and which ring optionally is substituted by one or more substituents selected from $W^2$, $C_{1-3}$alkyl optionally substituted by one or more substituents selected from $W^1$, and =O;

each $R^f$, $R^j$, $R^o$, $R^r$ and $R^{px}$ independently represents $C_{1-6}$ alkyl optionally substituted by one or more substituents selected from $W^1$, heterocycloalkyl optionally substituted by one or more substituents selected from $W^2$, aryl optionally substituted by one or more substituents selected from $W^3$ or heteroaryl optionally substituted by one or more substituents selected from $W^3$;

$R^{py}$ represents hydrogen, —$C_{2-6}$ alkyl optionally substituted by one or more substituents selected from $W^1$, heterocycloalkyl optionally substituted by one or more substituents selected from $W^2$, aryl optionally substituted by one or more substituents selected from $W^3$, or heteroaryl optionally substituted by one or more substituents selected from $W^3$;

each $Y^2$ independently represents halogen, —CN, —C(O)$R^{b1}$, —C(O)N($R^{c1}$)$R^{d1}$, —C(O)O$R^{e1}$, —N($R^{f1}$)$R^{g1}$, —N($R^{h1}$)C(O)$R^{i1}$, —N($R^{j1}$)C(O)O$R^{k1}$, —N($R^{l1}$)C(O)N($R^{m1}$)$R^{n1}$, —N($R^{o1}$)S(O)$_2R^{p1}$, —O$R^{q1}$, —OC(O)$R^{r1}$, —OS(O)$_2R^{s1}$, —S(O)$_mR^{t1}$, —S(O)$_2$N($R^{u1}$)$R^{v1}$, heterocycloalkyl optionally substituted by one or more substituents selected from $W^1$, aryl optionally substituted by one or more substituents selected from $W^2$, heteroaryl optionally substituted by one or more substituents selected from $W^2$, or =O;

each $Y^3$ independently represents halogen, —$R^{a1}$, —CN, —C(O)$R^{b1}$, —C(O)N($R^{c1}$)$R^{d1}$, —C(O)O$R^{e1}$, —N($R^{f1}$)$R^{g1}$, —N($R^{h1}$)C(O)$R^{i1}$, —N($R^{j1}$)C(O)O$R^{k1}$, —N($R^{l1}$)C(O)N($R^{m1}$)$R^{n1}$, —N($R^{o1}$)S(O)$_2R^{p1}$, —O$R^{q1}$, —OC(O)$R^{r1}$, —OS(O)$_2R^{s1}$, —S(O)$_mR^{t1}$, —S(O)$_2$N($R^{u1}$)$R^{v1}$, heterocycloalkyl optionally substituted by one or more substituents selected from $W^1$, aryl optionally substituted by one or more substituents selected from $W^2$, heteroaryl optionally substituted by one or more substituents selected from $W^2$, or =O;

each $R^{a1}$, $R^{b1}$, $R^{c1}$, $R^{d1}$, $R^{e1}$, $R^{f1}$, $R^{h1}$, $R^{i1}$, $R^{j1}$, $R^{l1}$, $R^{m1}$, $R^{n1}$, $R^{o1}$, $R^{q1}$, $R^{r1}$, $R^{t1}$, $R^{u1}$ and $R^{v1}$ independently represents hydrogen, $C_{1-6}$ alkyl optionally substituted by one or more substituents selected from $W^1$, heterocycloalkyl optionally substituted by one or more substituents selected from $W^2$, aryl optionally substituted by one or more substituents selected from $W^3$, or heteroaryl optionally substituted by one or more substituents selected from $W^3$; or any two $R^{c1}$ and $R^{d1}$, $R^{f1}$ and $R^{g1}$, $R^{m1}$ and $R^{n1}$ and/or $R^{u1}$ and $R^{v1}$ are linked together to form, along with the nitrogen atom to which they are attached, a 3- to 8-membered monocyclic or bicyclic ring, which ring optionally contains one or two heteroatoms and which ring optionally is substituted by one or more substituents selected from $W^2$, $C_{1-3}$alkyl optionally substituted by one or more substituents selected from $W^1$, and =O;

each $R^{g1}$, $R^{k1}$, $R^{p1}$ and $R^{s1}$ independently represents —$C_{1-6}$ alkyl optionally substituted by one or more substituents selected from $W^1$, heterocycloalkyl optionally substituted by one or more substituents selected from $W^2$, aryl optionally substituted by one or more substituents selected from $W^3$, or heteroaryl optionally substituted by one or more substituents selected from $W^3$;

each $Z^1$ independently represents halogen, —CN, —C(O)$R^{b2}$, —C(O)N($R^{c2}$)$R^{d2}$, —C(O)O$R^{e2}$, —N($R^{f2}$)$R^{g2}$, —N($R^{h2}$)C(O)$R^{i2}$, —N($R^{j2}$)C(O)O$R^{k2}$, —N($R^{l2}$)C(O)N($R^{m2}$)$R^{n2}$, —N($R^{o2}$)S(O)$_2R^{p2}$, —O$R^{q2}$, —OC(O)$R^{r2}$, —OS(O)$_2R^{s2}$, —S(O)$_mR^{t2}$, —S(O)$_2$N($R^{u2}$)$R^{v2}$, heterocycloalkyl optionally substituted by one or more substituents selected from $W^5$, aryl represented by

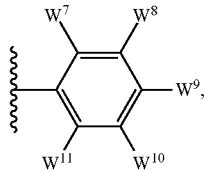

heteroaryl having 1 to 3 nitrogen atoms, one oxygen atom and/or one sulfur atom and optionally substituted by one or more substituents selected from $W^6$, or =O;

each $Z^2$ and $Z^3$ independently represents halogen, —$R^{a2}$, —CN, —C(O)$R^{b2}$, —C(O)N($R^{c2}$)$R^{d2}$, —C(O)O$R^{e2}$, —N($R^{f2}$)$R^{g2}$, —N($R^{h2}$)C(O)$R^{i2}$, —N($R^{j2}$)C(O)O$R^{k2}$, —N($R^{l2}$)C(O)N($R^{m2}$)$R^{n2}$, —N($R^{o2}$)S(O)$_2R^{p2}$, —O$R^{q2}$, —OC(O)$R^{r2}$, —OS(O)$_2R^{s2}$, —S(O)$_mR^{t2}$, —S(O)$_2$N($R^{u2}$)$R^{v2}$, heterocycloalkyl optionally substituted by one or more substituents selected from $W^5$, aryl optionally substituted by one or more substituents selected from $W^6$, or heteroaryl optionally substituted by one or more substituents selected from $W^6$;

each $Z^4$ independently represents halogen, —CN, —C(O)$R^{b2}$, —C(O)N($R^{c2}$)$R^{d2}$, —C(O)O$R^{e2}$, —N($R^{f2}$)$R^{g2}$, —N($R^{h2}$)C(O)$R^{i2}$, N($R^{j2}$)C(O)O$R^{k2}$, —N($R^{l2}$)C(O)N($R^{m2}$)$R^{n2}$, —N($R^{o2}$)S(O)$_2R^{p2}$, —O$R^{q2}$, —OC(O)$R^{r2}$, —OS(O)$_2R^{s2}$, —S(O)$_mR^{t2}$, S(O)$_2$N($R^{u2}$)$R^{v2}$, heterocycloalkyl optionally substituted by one or more substituents selected from $W^5$, aryl optionally substituted by one or more substituents selected from $W^6$, heteroaryl optionally substituted by one or more substituents selected from $W^6$, or =O;

each $R^{a2}$, $R^{b2}$, $R^{c2}$, $R^{d2}$, $R^{e2}$, $R^{f2}$, $R^{h2}$, $R^{i2}$, $R^{j2}$, $R^{l2}$, $R^{m2}$, $R^{n2}$, $R^{o2}$, $R^{r2}$, $R^{t2}$, $R^{u2}$ and $R^{v2}$ independently represents hydrogen, $C_{1-6}$ alkyl optionally substituted by one or more substituents selected from $W^4$, heterocycloalkyl optionally substituted by one or more substituents selected from $W^5$, aryl optionally substituted by one or more substituents selected from $W^6$, or heteroaryl optionally substituted by one or more substituents selected from $W^6$; or any two $R^{c2}$ and $R^{d2}$, $R^{f2}$ and $R^{g2}$, $R^{m2}$ and $R^{n2}$ and/or $R^{u2}$ and $R^{v2}$ are linked together to form, along with the nitrogen atom to which they are attached, a 3- to 8-membered monocyclic or bicyclic ring, which ring optionally contains one or two heteroatoms and which ring optionally is substituted by one or more substituents selected from $W^5$, $C_{1-3}$alkyl optionally substituted by one or more substituents selected from $W^4$), and =O;

each $R^{g2}$, $R^{k2}$, $R^{p2}$, $R^{q2}$ and $R^{s2}$ independently represents $C_{1-6}$ alkyl optionally substituted by one or more substituents selected from $W^4$, heterocycloalkyl optionally substituted by one or more substituents selected from $W^5$, aryl optionally substituted by one or more substituents selected from $W^6$, or heteroaryl optionally substituted by one or more substituents selected from $W^6$;

each $W^1$ and $W^4$ independently represents halogen, —CN, —N($R^{f3}$)$R^{g3}$, —N($R^{h3}$)C(O)$R^{i3}$, —N($R^{j3}$)C(O)O$R^{k3}$, —N($R^{l3}$)C(O)N($R^{m3}$)$R^{n3}$, —N($R^{o3}$)S(O)$_2R^{p3}$, —O$R^{q3}$, —OC(O)$R^{r3}$, —OS(O)$_2R^{s3}$, —S(O)$_mR^{t3}$, —S(O)$_2$N($R^{u3}$)$R^{v3}$, heterocycloalkyl optionally substituted by one or more substituents selected from $G^1$, aryl optionally substituted by one or more substituents selected from $G^2$, heteroaryl optionally substituted by one or more substituents selected from $G^2$, or =O;

each $W^2$, $W^3$, $W^5$ and $W^6$ independently represents halogen, —$R^{a3}$, —CN, —C(O)$R^{b3}$, —C(O)N($R^{c3}$)$R^{d3}$, —C(O)O$R^{e3}$, —N($R^{f3}$)$R^{g3}$, —N($R^{h3}$)C(O)$R^{i3}$, —N($R^{j3}$)C(O)O$R^{k3}$, —N($R^{l3}$)C(O)N($R^{m3}$)$R^{n3}$, —N($R^{o3}$)S(O)$_2R^{p3}$, —O$R^{q3}$, —OC(O)$R^{r3}$, —OS(O)$_2R^{s3}$, —S(O)$_mR^{t3}$, —S(O)$_2$N($R^{u3}$)$R^{v3}$, heterocycloalkyl optionally substituted by one or more substituents selected from $G^1$, aryl optionally substituted by one or more substituents selected from $G^2$, heteroaryl (optionally substituted by one or more substituents selected from $G^2$, or =O;

each $W^7$, $W^8$, $W^{10}$ and $W^{11}$ independently represents hydrogen, halogen, —$R^{a3}$, —CN, —C(O)$R^{b3}$, —C(O)N($R^{c3}$)$R^{d3}$, —C(O)O$R^{e3}$, —N($R^{f3}$)$R^{g3}$, —N($R^{h3}$)C(O)$R^{i3}$, —N($R^{j3}$)C(O)O$R^{k3}$, —N($R^{l3}$)C(O)N($R^{m3}$)$R^{n3}$, —N($R^{o3}$)S(O)$_2R^{p3}$, —O$R^{q3}$, —OC(O)$R^{r3}$, —OS(O)$_2R^{s3}$, —S(O)$_mR^{t3}$, —S(O)$_2$N($R^{u3}$)$R^{v3}$, heterocycloalkyl optionally substituted by one or more substituents selected from $G^1$, aryl optionally substituted by one or more substituents selected from $G^2$, or heteroaryl optionally substituted by one or more substituents selected from $G^2$;

$W^9$ represents hydrogen, halogen, —$R^{a3}$, —CN, —C(O)$R^{b3}$, —C(O)N($R^{c3}$)$R^{d3}$, —C(O)O$R^{e3}$, —N($R^{f3}$)$R^{g3}$, —N($R^{h3}$)C(O)$R^{i3}$, —N($R^{j3}$)C(O)O$R^{k3}$, —N($R^{l3}$)C(O)N($R^{m3}$)$R^{n3}$, —N($R^{o3}$)S(O)$_2R^{p3}$, —O$R^{q3x}$, —OC(O)$R^{r3}$, —OS(O)$_2R^{s3}$, —S(O)$_mR^{t3}$, —S(O)$_2$N($R^{u3}$)$R^{v3}$, heterocycloalkyl optionally substituted by one or more substituents selected from $G^1$, aryl optionally substituted by one or more substituents selected from $G^2$, or heteroaryl optionally substituted by one or more substituents selected from $G^2$;

each $R^{a3}$, $R^{b3}$, $R^{c3}$, $R^{d3}$, $R^{e3}$, $R^{f3}$, $R^{h3}$, $R^{i3}$, $R^{j3}$, $R^{l3}$, $R^{m3}$, $R^{n3}$, $R^{o3}$, $R^{q3}$, $R^{r3}$, $R^{t3}$, $R^{u3}$ and $R^{v3}$ independently represents hydrogen or $C_{1-6}$ alkyl optionally substituted by one or more $G^3$; or any two $R^{c3}$ and $R^{d3}$, $R^{f3}$ and $R^{g3}$, $R^{m3}$ and $R^{n3}$ and/or $R^{u3}$ and $R^{v3}$ are linked together to form, along with the nitrogen atom to which they are attached, a 4- to 6-membered ring, which ring optionally contains one heteroatom and which ring optionally is substituted by one or more $G^2$;

each $R^{g3}$, $R^{k3}$, $R^{p3}$, $R^{q3}$ and $R^{s3}$ independently represents $C_{1-6}$ alkyl optionally substituted by one or more $G^3$;

$R^{q3x}$ represents $C_{2-6}$ alkyl optionally substituted by one or more $G^3$;

each $G^1$ and $G^2$ independently represents halogen, —$R^{a4}$, —CN, —C(O)$R^{b4}$, —C(O)N($R^{c4}$)$R^{d4}$, —C(O)O$R^{e4}$, —N($R^{f4}$)$R^{g4}$, —N($R^{i4}$)C(O)$R^{i4}$, —N($R^{j4}$)C(O)O$R^{k4}$, —N($R^{l4}$)C(O)N($R^{m4}$)$R^{n4}$, —N($R^{o4}$)S(O)$_2R^{p4}$, —O$R^{q4}$, —OC(O)$R^{r4}$, —OS(O)$_2R^{s4}$, —S(O)$_mR^{t4}$, —S(O)$_2$N($R^{u4}$)$R^{v4}$, or =O;

$G^3$ represents halogen, —CN, —C(O)$R^{b4}$, —C(O)N($R^{c4}$)$R^{d4}$, —C(O)O$R^{e4}$, —N($R^{f4}$)$R^{g4}$, —N($R^{h4}$)C(O)$R^{i4}$, —N($R^{j4}$)C(O)O$R^{k4}$, —N($R^{l4}$)C(O)N($R^{m4}$)$R^{n4}$, —N($R^{o4}$)S(O)$_2R^{p4}$, —O$R^{q4}$, —OC(O)$R^{r4}$, —OS(O)$_2R^{s4}$, —S(O)$_mR^{t4}$, —S(O)$_2$N($R^{u4}$)$R^{v4}$, or =O;

each $R^{a4}$, $R^{b4}$, $R^{c4}$, $R^{d4}$, $R^{e4}$, $R^{f4}$, $R^{h4}$, $R^{i4}$, $R^{j4}$, $R^{l4}$, $R^{m4}$, $R^{n4}$, $R^{o4}$, $R^{q4}$, $R^{r4}$, $R^{t4}$, $R^{u4}$ and $R^{v4}$ independently represents hydrogen or $C_{1-6}$ alkyl optionally substituted by one or more —F; or any two $R^{c4}$ and $R^{d4}$, $R^{f4}$ and $R^{g4}$, $R^{m4}$ and $R^{n4}$ and/or $R^{u4}$ and $R^{v4}$ are linked together to form, along with the nitrogen atom to which they are attached, a 3- to 6-membered ring, which ring optionally substituted by one or more —F, —CH$_3$, —CH$_2$CH$_3$, —CHF$_2$, —CF$_3$, —CH$_2$CF$_3$, or =O;

each $R^{g4}$, $R^{k4}$, $R^{p4}$ and $R^{s4}$ independently represent $C_{1-6}$ alkyl optionally substituted by one or more —F;

each m independently represents 0, 1 or 2;

provided that formula I does not represent
6-(3-pyridinyl)-$N^4$-[[4-[5-(trifluoromethyl)-1,2,4-oxadiazol-3-yl]phenyl]methyl]-2,4-pyrimidinediamine,
6-(3-pyridinyl)-$N^4$-[[5-[5-(trifluoromethyl)-1,2,4-oxadiazol-3-yl]-2-pyridinyl]methyl]-2,4-pyrimidinediamine,
6-(3-pyridinyl)-$N^4$-[[5-[5-(trifluoromethyl)-1,2,4-oxadiazol-3-yl]-2-pyridinyl]-methyl]-2,4-pyrimidinediamine or
$N^4$-[2-(1-aziridinyl)ethyl]-5-fluoro-6-phenyl-2,4-pyrimidinediamine, or a pharmaceutically acceptable salt thereof;

which compounds may be referred to herein as "the compounds of the invention".

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin. For the avoidance of doubt, solvates are also included within the scope of the invention.

Compounds of the invention may contain double bonds and may thus exist as E (entgegen) and Z (zusammen) geometric isomers about each individual double bond. All such isomers and mixtures thereof are included within the scope of the invention.

Compounds of the invention may also exhibit tautomerism. All tautomeric forms and mixtures thereof are included within the scope of the invention.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

Unless otherwise specified, $C_{1-q}$ alkyl groups (where q is the upper limit of the range) defined herein may be straight-chain or, when there is a sufficient number (i.e. a minimum of two or three, as appropriate) of carbon atoms, be branched-chain, and/or cyclic (so forming a $C_{3-q}$-cycloalkyl group). When there is a sufficient number (i.e. a minimum of four) of carbon atoms, such groups may also be part cyclic. Such alkyl groups may also be saturated or, when there is a sufficient number (i.e. a minimum of two) of carbon atoms, be unsaturated (forming, for example, a $C_{2-q}$ alkenyl or a $C_{2-q}$ alkynyl group).

Unless otherwise specified, $C_{1-q}$ alkylene groups (where q is the upper limit of the range) defined herein may (in a similar manner to the definition of $C_{1-q}$ alkyl) be straight-chain or, when there is a sufficient number (i.e. a minimum of two or three, as appropriate) of carbon atoms, be branched-chain, and/or cyclic (so forming a $C_{3-q}$-cycloalkylene group). When there is a sufficient number (i.e. a minimum of four) of carbon atoms, such groups may also be part cyclic. Such alkylene groups may also be saturated or, when there is a sufficient number (i.e. a minimum of two) of carbon atoms, be unsaturated (forming, for example, a $C_{2-q}$alkenylene or a $C_{2-q}$alkynylene group). Particular alkylene groups that may be mentioned include those that are straight-chained and saturated.

The term "halo", when used herein, includes fluoro, chloro, bromo and iodo (for example, fluoro and chloro).

Heterocycloalkyl groups that may be mentioned include non-aromatic monocyclic and bicyclic heterocycloalkyl groups (which groups may further be bridged) in which at least one (e.g. one to four) of the atoms in the ring system is other than carbon (i.e. a heteroatom), and in which the total number of atoms in the ring system is between three and twelve (e.g. between five and ten and, most preferably, between three and eight, e.g. a 5- or 6-membered heterocycloalkyl group). Further, such heterocycloalkyl groups may be saturated or unsaturated containing one or more double and/or triple bonds, forming for example a $C_{2-q}$ (e.g. $C_{4-q}$) heterocycloalkenyl (where q is the upper limit of the range) or a $C_{7-q}$ heterocycloalkynyl group. $C_{2-q}$ heterocycloalkyl groups that may be mentioned include 7-azabicyclo-[2.2.1]heptanyl, 6-azabicyclo[3.1.1]heptanyl, 6-azabicyclo[3.2.1]-octanyl, 8-azabicyclo[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo-[2.2.1]heptanyl, 6-oxabicyclo[3.2.1]-octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuryl, tetrahydropyridyl (such as 1,2,3,4-tetrahydropyridyl and 1,2,3,6-tetrahydropyridyl), thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom. Further, in the case where the substituent is another cyclic compound, then the cyclic compound may be attached through a single atom on the heterocycloalkyl group, forming a so-called "spiro"-compound. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form. At each occurrence when mentioned herein, a heterocycloalkyl group is preferably a 3- to 8-membered heterocycloalkyl group (e.g. a 5- or 6-membered heterocycloalkyl group).

The term "aryl", when used herein, includes $C_{6-14}$ (e.g. $C_{6-10}$ aromatic groups. Such groups may be monocyclic or bicyclic and, when bicyclic, be either wholly or partly aromatic. $C_{6-10}$ aryl groups that may be mentioned include phenyl, naphthyl, 1,2,3,4-tetrahydronaphthyl, indanyl, and the like (e.g. phenyl, naphthyl and the like). For the avoidance of doubt, the point of attachment of substituents on aryl groups may be via any carbon atom of the ring system.

The term "heteroaryl" (or heteroaromatic), when used herein, includes 5- to 10-membered heteroaromatic groups containing one or more heteroatoms selected from oxygen, nitrogen and/or sulfur. Such heteroaryl group may comprise one, or two rings, of which at least one is aromatic. Substituents on heteroaryl/heteroaromatic groups may, where appropriate, be located on any atom in the ring system including a heteroatom. The point of attachment of heteroaryl/heteroaromatic groups may be via any atom in the ring system including (where appropriate) a heteroatom. Bicyclic heteroaryl/heteroaromatic groups may comprise a benzene ring fused to one or more further aromatic or non-aromatic heterocyclic rings, in which instances, the point of attachment of the polycyclic heteroaryl/heteroaromatic group may be via any ring including the benzene ring or the heteroaryl/heteroaromatic or heterocycloalkyl ring. Examples of heteroaryl/heteroaromatic groups that may be mentioned include pyridinyl, pyrrolyl, furanyl, thiophenyl, oxadiazolyl, thiadiazolyl, thiazolyl, oxazolyl, pyrazolyl, triazolyl, tetrazolyl, isoxazolyl, isothiazolyl, imidazolyl, imidazopyrimidinyl, pyrimidinyl, indolyl, azaindolyl, pyrazinyl, indazolyl, pyrimidinyl, quinolinyl, isoquinolinyl, benzofuranyl, benzothiophenyl, benzoimidazolyl, benzoxazolyl, benzothiazolyl and benzotriazolyl. The oxides of heteroaryl/heteroaromatic groups are also embraced within the scope of the invention (e.g. the N-oxide). As stated above, heteroaryl includes polycyclic (e.g. bicyclic) groups in which one ring is aromatic (and the other may or may not be aromatic). Hence, other heteroaryl groups that may be mentioned include e.g. benzo[1,3]dioxolyl, benzo[1,4]dioxinyl, indolinyl, 5H,6H,7H-pyrrolo[1,2-b]pyrimidinyl, 1,2,3,4-tetra-hydroquinolinyl and the like.

Heteroatoms that may be mentioned include phosphorus, silicon, boron and, preferably, oxygen, nitrogen and sulfur.

For the avoidance of doubt, in cases in which the identity of two or more substituents in a compound of the invention may be the same, the actual identities of the respective substituents are not in any way interdependent.

For the avoidance of doubt, when $R^1$ is defined as

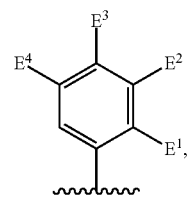

it is connected to the rest of formula I by the bond interrupted by the wiggly line, and formula I can thus be represented by

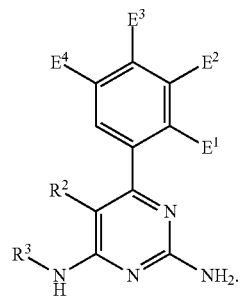

Likewise, when $R^3$ is —$C_{1-12}$ alkyl substituted by $Z^1$, and $Z^1$ is represented by

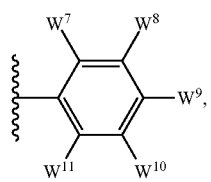

then, if e.g. $R^3$ is $C_2$alkyl, then formula I can be represented by

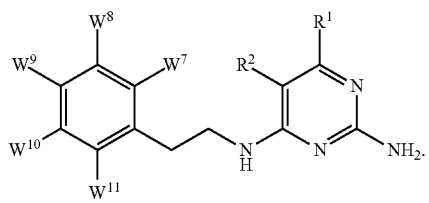

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Hence, the compounds of the invention also include deuterated compounds, i.e. in which one or more hydrogen atoms are replaced by the hydrogen isotope deuterium.

All individual features (e.g. preferred features) mentioned herein may be taken in isolation or in combination with any other feature (including preferred features) mentioned herein (hence, preferred features may be taken in conjunction with other preferred features, or independently of them).

The skilled person will appreciate that compounds of the invention that are the subject of this invention include those that are stable. That is, compounds of the invention include those that are sufficiently robust to survive isolation from e.g. a reaction mixture to a useful degree of purity.

Particular compounds of formula I that may be mentioned include those in which:

$R^2$ represents hydrogen or —$C_{1-12}$alkyl optionally substituted by one or more $Z^1$; and $R^3$ represents —$C_{1-12}$alkyl optionally substituted by one or more $Z^1$ or heterocycloalkyl optionally substituted by one or more $Z^2$.

For example, compounds of formula I that may be mentioned include those in which $R^2$ represents methyl, or preferably, hydrogen and $R^3$ represents:

(a) —$C_{1-12}$alkyl (for example —$C_{1-6}$alkyl) optionally substituted by two, or preferably, one $Z^1$ or (b) —$C_{2-6}$alkyl optionally substituted by two, or preferably, one $Z^1$ or heterocycloalkyl optionally substituted by two, or preferably, one $Z^2$; or (c) —$C_{1-2}$alkyl optionally substituted with one or more —F; or (d)

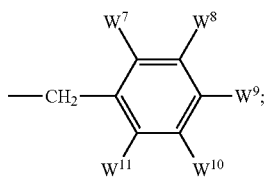

(e) —$C_{1-12}$alkyl (for example —$C_{1-6}$alkyl) substituted by heteroaryl having 1 to 3 nitrogen atoms, one oxygen atom and/or one sulfur atom and which heteroaryl is optionally substituted by one or more substituents selected from $W^3$; or (f) a —$C_{3-6}$alkyl or a heterocycloalkyl selected from cyclopropyl, cyclobutyl, cyclopentyl, cyclohexyl, cyclopropylmethyl, cyclobutylmethyl, cyclopentylmethyl, cyclopropylethyl, cyclobutylethyl, cyclopropylpropyl, oxetanyl, tetrahydrofuryl, tetrahydropyranyl, azetidinyl, pyrrolidinyl, piperidinyl, piperazinyl or morpholinyl wherein the $C_{3-6}$alkyl is optionally substituted by two, or preferably, one $Z^1$ and the heterocycloalkyl is optionally substituted by two, or preferably, one $Z^2$.

Particular compounds of formula I that may be mentioned include those in which:

$R^2$ and $R^3$ are linked together to form, along with the atoms to which they are attached, a 5- to 8-membered non-aromatic ring, wherein the link formed by $R^2$ and $R^3$ is optionally substituted by one or more substituents selected from $Z^3$ or —$C_{1-9}$alkyl optionally substituted by one or more $Z^4$.

For example, compounds of formula I that may be mentioned include those in which $R^2$ and $R^3$ are linked together to form, along with the atoms to which they are attached, a 5- to 6-membered non-aromatic ring, wherein the non-aromatic ring is:

(a) unsubstituted; or (b) substituted by one or more substituents selected from $Z^3$; or (c) substituted by —$C_{1-9}$alkyl optionally substituted by one or more $Z^4$; or (d) substituted by one or more substituents selected from $Z^3$ and substituted by —$C_{1-9}$alkyl optionally substituted by one or more $Z^4$.

Particular compounds of formula I that may be mentioned include those in which:

$E^1$ is $Y^{1a}$ or —$C_{1-6}$alkyl optionally substituted by one or more $Y^2$ and at least one of $E^2$, $E^3$ and $E^4$ represents $Y^{1b}$ or —$C_{1-6}$alkyl optionally substituted by one or more $Y^2$.

Preferred compounds of formula I that may be mentioned include those in which:

$E^1$ is $Y^{1a}$ or —$C_{1-3}$alkyl optionally substituted by one or more $Y^2$ and at least one of $E^2$ and $E^4$ represents $Y^{1b}$, —$C_{1-3}$alkyl optionally substituted by one or more $Y^2$.

Particular compounds of formula I that may be mentioned include those in which $R^1$ represents heteroaryl.

Preferred compounds of formula I where $R^1$ represents heteroaryl that may be mentioned are those where $R^1$ represents benzofuranyl, benzothiophenyl, dihydrobenzofuranyl, indazolyl, indolyl, isoquinolinyl, isoxazolyl, pyridinyl, pyrrolyl and quinolinyl.

Particularly preferred compounds of formula I where $R^1$ represents heteroaryl that may be mentioned are those where $R^1$ represents benzofuran-3-yl, benzothiophen-3-yl, dihydrobenzofuran-7-yl, indol-3-yl, indol-4-yl, indol-5-yl, isoquinolin-4-yl, isoxazol-4-yl, pyridin-3-yl, pyridin-4-yl, pyrrol-2-yl and quinolin-5-yl.

For example, compounds of formula I that may be mentioned include those in which $R^1$ represents indolyl, e.g. indol-3-yl, indol-4-yl or indol-5-yl, where the indolyl is optionally substituted on the nitrogen with —S(O)$_2$Ar$^x$, where Ar$^x$ is aryl or heteroaryl, preferably optionally substituted phenyl, e.g. unsubstituted phenyl or phenyl substituted in the 4-position by —F, —Cl, —CH$_3$ or —CF$_3$.

Particular compounds of formula I that may be mentioned include those in which $R^1$ is represented by

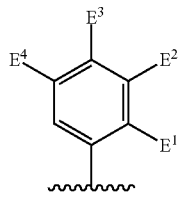

where:
$E^2$, $E^3$ and $E^4$ represent hydrogen and
$E^1$ represents hydrogen, or more preferably —F, —Cl, —CH$_3$, —CF$_3$, CN or —OCH$_3$; or
$E^1$, $E^3$ and $E^4$ represent hydrogen and
$E^2$ represents —F, —Cl, —CH$_3$, —CF$_3$, —CH=CHC(O)OCH$_3$, —CH$_2$NH$_2$, —CN, —CH$_2$N(H)C(O)CH=CH$_2$, —CH$_2$OH, —C(O)N(H)(4-methylphenyl), —N(H)C(O)CH$_3$, —N(H)C(O)CH=CH$_2$, —N(H)C(O)CH=CHCH$_2$NMe$_2$, —N(H)C(O)CH=CHPh, —N(H)C(O)C≡CH, —N(H)C(O)(2-hydroxyphenyl), —N(H)C(O)(6-hydroxypyrid-2-yl), —N(H)C(O)(5-chloro-2-hydroxyphenyl), —N(H)C(O)CH$_2$CH$_2$C(O)(1-pyrrolidinyl), —N(H)C(O)CH$_2$(OH), —N(H)C(O)CH(OH)Ph, —N(H)C(O)C(O)CH$_3$, —N(H)C(O)C(O)Ph, —N(H)S(O)$_2$CH=CH$_2$, or —OCH$_3$; or
$E^1$, $E^2$ and $E^4$ represent hydrogen and
$E^3$ represent —F, —Cl, —CH$_3$, —CF$_3$, —C(CH$_3$)$_3$, —CH=CH$_2$, —CH=CHC(O)OH, —CH=CHC(O)OCH$_3$, —CH$_2$NH$_2$, —CN, —CH$_2$N(H)C(O)CH=CH$_2$, —CH$_2$OH, —C(O)H, C(O)CH$_3$, —C(O)CF$_3$, —C(O)N(H)CH$_3$, —C(O)N(H)CH$_2$(2-furanyl), —C(O)(4-morpholinyl), —C(O)OH, —C(O)OCH$_3$, —N(H)C(O)CH$_3$, —N(H)C(O)CH=CH$_2$, —N(H)S(O)$_2$CH$_3$, —OCH(CH$_3$)$_2$, —OCH$_3$, —OCF$_3$, —S(O)$_2$CH$_3$, or —S(O)$_2$(4-morpholinyl).

Other particular compounds of formula I that may be mentioned include those in which $R^1$ is represented by

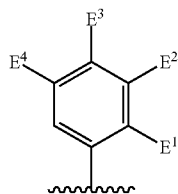

where:
$E^3$ and $E^4$ represent hydrogen; and
$E^1$ represents —F and $E^2$ represent —F, —Cl, —CH$_3$ or —CF$_3$; or
$E^1$ represents —Cl and $E^2$ represents —F, —Cl, —CH$_3$ or —CF$_3$; or
$E^1$ represents —CH$_3$ and $E^2$ represents —F, —Cl, —CH$_3$, —CF$_3$, —CN or —N(H)C(O)CH=CH$_2$; or $E^2$ and $E^4$ represent hydrogen; and
$E^1$ represents —F and $E^3$ represents —F or phenyl; or
$E^1$ represents —Cl and $E^3$ represents —F or —Cl; or
$E^1$ represents —CH$_3$ and $E^3$ represents —Cl or —OCH$_2$phenyl; or
$E^1$ represents —OCH$_3$ and $E^3$ represents —F; or
$E^2$ and $E^3$ represent hydrogen; and
$E^1$ represents —F and $E^4$ represents —Cl, —CH$_3$ or —CN; or
$E^1$ represents —Cl and $E^4$ represent —F, —Cl, —CH$_3$, —CF$_3$ or —OCH$_3$; or
$E^1$ represents —CH$_3$ and $E^4$ represent —F, —Cl, —CH$_3$, —CF$_3$, —CN, —N(H)C(O)CH=CH$_2$ or —S(O)$_2$(4-morpholinyl); or
$E^1$ represents —CF$_3$ and $E^4$ represents —F or —CF$_3$; or
$E^1$ represents —CN and $E^4$ represents —Cl; or
$E^1$ represents —OCH$_3$ and $E^4$ represents —F, —Cl, Br, —CH$_3$, —CH(CH$_3$)$_2$, —C(CH$_3$)$_3$, —CN or —OCH$_3$; or
$E^1$ and $E^4$ represent hydrogen; and
$E^2$ represents —F and $E^3$ represents —F, —Cl, —OH or —OCH$_3$; or
$E^2$ represents —Cl and $E^3$ represents —F or —C(O)(4-morpholinyl); or
$E^2$ represents —CH$_3$ and $E^3$ represents —F or —OCH$_3$; or
$E^1$ represents —OCH$_3$ and $E^3$ represents —OH; or
$E^1$ represents-CH$_2$OCH$_3$ and $E^3$ represents (piperidin-4-yl)methoxy or ((1-tertbutoxycarbonyl)piperidin-4-yl)methoxy; or
$E^1$ and $E^3$ represent hydrogen; and
$E^2$ and $E^4$ represent —F; or
$E^2$ and $E^4$ represent —CF$_3$; or
$E^4$ represents hydrogen; and
$E^1$, $E^2$ and $E^3$ represent —F; or
$E^1$ and $E^2$ represent —Cl and $E^3$ represents —Cl, —OH or —OCH$_3$; or
$E^1$ and $E^2$ represent —CH$_3$ and $E^3$ represents —F or —OCH$_3$; or
$E^2$ and $E^3$ represent —Cl and $E^1$ represents —CH$_3$; or
$E^2$ represents hydrogen; and
$E^1$, $E^3$ and $E^4$ represent —F; or
$E^3$ and $E^4$ represent —Cl and $E^1$ represents —CH$_3$; or
$E^1$ and $E^4$ represent —Cl and $E^1$ represents —OCH$_3$; or
$E^1$ and $E^4$ represent —CH$_3$ and $E^3$ represents —F, —CH$_3$ or —OCH$_3$; or
$E^1$ represents —F, $E^3$ represents —CH$_3$ and $E^4$ represents —Cl; or
$E^1$ represents —Cl, $E^3$ represents —F and $E^4$ represents —CH$_3$; or
$E^1$ represents —Cl, $E^3$ represents —CH$_3$ and $E^4$ represents —F; or
$E^1$ and $E^4$ represent —CH$_3$ and $E^3$ represents —F; or
$E^1$ represents —CH$_3$, $E^4$ represents —Cl and $E^3$ represents —CF$_3$ or —OCH$_3$; or
$E^1$ represents hydrogen; and
$E^2$ and $E^4$ represent —CH$_3$ and $E^3$ represents —OH; or
$E^3$ represents hydrogen; and
$E^1$ and $E^2$ represent —Cl and $E^4$ represents —CH$_3$.

Preferred particular compounds of formula I that may be mentioned include those in which $R^1$ is represented by

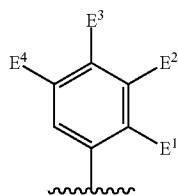

where:
E¹, E³ and E⁴ represent hydrogen and
E² represents —CH=CHC(O)OCH₃, —CH₂NH₂, —CH₂N(H)C(O)CH=CH₂, —CH₂OH, —N(H)C(O)CH=CH₂, —N(H)C(O)CH=CHCH₂NMe₂, —N(H)C(O)CH=CHPh, —N(H)C(O)C≡CH, —N(H)C(O)CH₂(OH), —N(H)C(O)CH(OH)Ph, —N(H)C(O)C(O)CH₃, —N(H)C(O)C(O)Ph or —N(H)S(O)₂CH=CH₂; or
E¹, E² and E⁴ represent hydrogen and
E³ represents —CH=CH₂, —CH=CHC(O)OH, —CH=CHC(O)OCH₃, —CH₂NH₂, —CH₂N(H)C(O)CH=CH₂, —CH₂OH, —C(O)H, —C(O)CH₃, —C(O)CF₃, —N(H)C(O)CH=CH₂; or
E³ and E⁴ represent hydrogen; and
E¹ represents —F and E² represents —F, —Cl, or —CF₃; or
E¹ represents —Cl and E² represents —Cl, —CH₃ or —CF₃; or
E¹ represents —CH₃ and E² represents —Cl, —CH₃, —CN or —N(H)C(O)CH=CH₂; or
E² and E⁴ represent hydrogen; and
E¹ and E³ represent —F; or
E¹ represents —Cl and E³ represents —F or —Cl; or
E¹ represents —CH₃ and E³ represents —Cl; or
E² and E³ represent hydrogen; and
E¹ represents —F and E⁴ represents —Cl, —CH₃ or —CN; or
E¹ represents —Cl and E⁴ represents —F, —Cl, —CH₃ or —CF₃; or
E¹ represents —CH₃ and E⁴ represent, —Cl, —CH₃, —CF₃, —CN or —N(H)C(O)CH=CH; or
E¹ represents —CF₃ and E⁴ represents —F or —CF₃; or
E¹ represents —CN and E⁴ represents —Cl; or
E⁴ represents hydrogen; and
E¹, E² and E³ represent —F; or
E¹ and E² represent —CH₃ and E³ represents —F₃; or
E² and E³ represent —Cl and E¹ represents —CH₃; or
E² represents hydrogen; and
E¹, E³ and E⁴ represent —F; or
E³ and E⁴ represent —Cl and E¹ represents —CH₃; or
E¹ and E⁴ represent —CH₃ and E³ represents —F or —CH₃; or
E¹ represents —F, E³ represents —CH₃ and E⁴ represents —Cl; or
E¹ represents —Cl, E³ represents —F and E⁴ represents —CH₃; or
E¹ represents —Cl, E³ represents —CH₃ and E⁴ represents —F; or
E¹ and E⁴ represent —CH₃ and E³ represents —F; or
E¹ represents —CH₃, E³ represents —CF₃ and E⁴ represents —Cl; or
E¹ represents hydrogen; and
E² and E⁴ represent —CH₃ and E³ represents —OH; or
E³ represents hydrogen; and
E¹ and E² represent —Cl and E⁴ represents —CH₃.

Preferred compounds of formula I that may be mentioned include those in which:

(a) $Z^1$ is not present or is selected from —F, —CN, —C(O)$R^{b2}$, —C(O)N($R^{c2}$)$R^{d2}$, —C(O)O$R^{e2}$, —N($R^{f2}$)$R^{g2}$, —N($R^{h2}$)C(O)$R^{i2}$, —N($R^{j2}$)C(O)O$R^{k2}$, —N($R^{l2}$)C(O)N($R^{m2}$)$R^{n2}$, —N($R^{o2}$)S(O)$_2R^{p2}$, —O$R^{q2}$, —S(O)$_mR^{r2}$, —S(O)$_2$N($R^{u2}$)$R^{v2}$, heterocycloalkyl optionally substituted by one or more substituents selected from $W^5$, aryl represented by

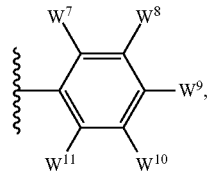

or heteroaryl having 1 to 3 nitrogen atoms, one oxygen atom and/or one sulfur atom and optionally substituted by one or more substituents selected from $W^6$; or (b) $Z^2$ is not present or is selected from —F, —$R^{a2}$, —C(O)N($R^{c2}$)$R^{d2}$, —N($R^{f2}$)$R^{g2}$, —N($R^{h2}$)C(O)$R^{i2}$, —N($R^{j2}$)C(O)O$R^{k2}$, —N($R^{l2}$)C(O)N($R^{m2}$)$R^{n2}$, —N($R^{o2}$)S(O)$_2R^{p2}$, —O$R^{q2}$, —S(O)$_mR^{r2}$, —S(O)$_2$N($R^{u2}$)$R^{v2}$, heterocycloalkyl optionally substituted by one or more substituents selected from $W^5$, aryl optionally substituted by one or more substituents selected from $W^6$, or heteroaryl optionally substituted by one or more substituents selected from $W^6$.

Other preferred compounds of formula I that may be mentioned include those in which:

(a) $Z^3$ is not present or is selected from —F, —$R^{a2}$, —C(O)N($R^{c2}$)$R^{d2}$, —N($R^{f2}$)$R^{g2}$, —N($R^{h2}$)C(O)$R^{i2}$, —N($R^{j2}$)C(O)O$R^{k2}$, —N($R^{l2}$)C(O)N($R^{m2}$)$R^{n2}$, —N($R^{o2}$)S(O)$_2R^{p2}$, —O$R^{q2}$, —S(O)$_mR^{r2}$, —S(O)$_2$N($R^{u2}$)$R^{v2}$, heterocycloalkyl optionally substituted by one or more substituents selected from $W^5$, aryl optionally substituted by one or more substituents selected from $W^6$, or heteroaryl optionally substituted by one or more substituents selected from $W^6$; and/or (b) $Z^4$ is not present or is selected from —F, —C(O)N($R^{c2}$)$R^{d2}$, —N($R^{f2}$)$R^{g2}$, —N($R^{h2}$)C(O)$R^{i2}$, —N($R^{j2}$)C(O)O$R^{k2}$, —N($R^{l2}$)C(O)N($R^{m2}$)$R^{n2}$, —N($R^{o2}$)S(O)$_2R^{p2}$, —O$R^{q2}$, —S(O)$_mR^{r2}$, —S(O)$_2$N($R^{u2}$)$R^{v2}$, heterocycloalkyl optionally substituted by one or more substituents selected from $W^5$, aryl optionally substituted by one or more substituents selected from $W^6$, or heteroaryl optionally substituted by one or more substituents selected from $W^6$.

Particularly preferred compounds of formula I that may be mentioned include those in which $Z^1$ represents —F, —CN, —C(O)NH₂, —C(O)N($R^{c2}$)$R^{d2}$, —C(O)-(4-morpholinyl), —C(O)OEt, —N(H)C(O)Me, —N(H)C(O)$R^{i2}$, —N(H)C(O)CH₂NMe₂, —N(H)C(O)OCMe₃, —N(H)C(O)OCH₂Ph, —N(Me)C(O)OCMe₃, —N(H)C(O)N(H)Me, —N(H)C(O)N(H)CHMe₂, —N(H)S(O)₂Me, —OMe, —OCF₃ and —OEt.

Preferred compounds of formula I where $Z^1$ represents heterocycloalkyl that may be mentioned are those where $Z^1$ represents dihydropyridinyl, imidazolinyl, morpholinyl, oxanyl, piperazinyl, piperidinyl, pyrrolidinyl and quinuclidinyl, wherein the heterocycloalkyl is optionally substituted by one or more substituents selected from $W^5$.

Preferred compounds of formula I where $Z^1$ represents

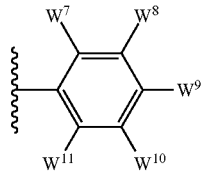

that may be mentioned are those where each $W^7$, $W^{10}$ and $W^{11}$ independently represents hydrogen, halogen, —$R^{a3}$ or —CN; and one of $W^8$ and $W^9$ represents hydrogen, halogen, —$R^{a3}$ or —CN and the other represents halogen, —$R^{a3}$, —CN, —C(O)$R^{b3}$, —C(O)N($R^{c3}$)$R^{d3}$, —C(O)O$R^{e3}$, —N($R^{f3}$)$R^{g3}$, —N($R^{h3}$)C(O)$R^{i3}$, —N($R^{j3}$)C(O)O$R^{k3}$, —N($R^{l3}$)C(O)N($R^{m3}$)$R^{n3}$, —N($R^{o3}$)S(O)$_2$$R^{p3}$, —O$R^{q3x}$, —OC(O)$R^{r3}$, —OS(O)$_2$$R^{s3}$, —S(O)$_m$$R^{t3}$, —S(O)$_2$N($R^{u3}$)$R^{v3}$, heterocycloalkyl optionally substituted by one or more substituents selected from $G^1$, aryl optionally substituted by one or more substituents selected from $G^2$, or heteroaryl optionally substituted by one or more substituents selected from $G^2$.

Particularly preferred compounds of formula I where $Z^1$ represents

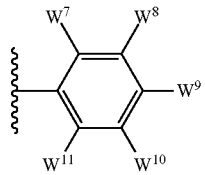

that may be mentioned are those where each $W^7$, $W^{10}$ and $W^{11}$ independently represents —F, —Cl, —CH$_3$, —CF$_3$, or more preferably, hydrogen; and one of $W^8$ and $W^9$ (preferably $W^8$) represents —F, —Cl, —CH$_3$, —CF$_3$, or more preferably, hydrogen, and the other (preferably $W^9$) represents halogen, —$R^{a3}$, —CN, —C(O)$R^{b3}$, —C(O)N($R^{c3}$)$R^{d3}$, —C(O)O$R^{e3}$, —N($R^{f3}$)$R^{g3}$, —N($R^{h3}$)C(O)$R^{i3}$, —N($R^{j3}$)C(O)O$R^{k3}$, —N($R^{l3}$)C(O)N($R^{m3}$)$R^{n3}$, —N($R^{o3}$)S(O)$_2$$R^{p3}$, —O$R^{q3x}$, —OC(O)$R^{r3}$, —OS(O)$_2$$R^{s3}$, —S(O)$_m$$R^{t3}$, —S(O)$_2$N($R^{u3}$)$R^{v3}$, heterocycloalkyl optionally substituted by one or more substituents selected from $G^1$, aryl optionally substituted by one or more substituents selected from $G^2$, or heteroaryl optionally substituted by one or more substituents selected from $G^2$.

For example, particular compounds of formula I that may be mentioned include those wherein:

(a) $W^8$, $W^9$, $W^{10}$ and $W^{11}$ represents hydrogen and $W^7$ represents —Cl or —S(O)$_2$CH$_3$; or (b) $W^7$, $W^9$, $W^{10}$ and $W^{11}$ represents hydrogen and $W^8$ represents —F, —Br, —CN, —N(H)C(O)CH$_3$, —OCH$_3$ or —S(O)$_2$CH$_3$; or (c) $W^7$, $W^{10}$ and $W^{11}$ represents hydrogen and:

(i) $W^8$ and $W^9$ represents —F or —Cl; or (ii) $W^8$ represents —F and $W^9$ represents —CH$_3$.

More particularly preferred compounds of formula I where $Z^1$ represents

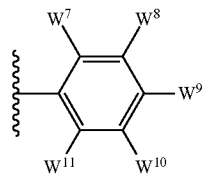

that may be mentioned are those where $W^7$, $W^8$, $W^{10}$ and $W^{11}$ are hydrogen and $W^9$ represents halogen, —$R^{a3}$, —CN, —C(O)$R^{b3}$, —C(O)N($R^{c3}$)$R^{d3}$, —C(O)O$R^{e3}$, —N($R^{f3}$)$R^{g3}$, —N($R^{h3}$)C(O)$R^{i3}$, —N($R^{j3}$)C(O)O$R^{k3}$, —N($R^{l3}$)C(O)N($R^{m3}$)$R^{n3}$, —N($R^{o3}$)S(O)$_2$$R^{p3}$, —O$R^{q3x}$, —S(O)$_m$$R^{t3}$, —S(O)$_2$N($R^{u3}$)$R^{v3}$, heterocycloalkyl optionally substituted by one or more substituents selected from $G^1$, aryl optionally substituted by one or more substituents selected from $G^2$, or heteroaryl optionally substituted by one or more substituents selected from $G^2$.

For example, more particularly preferred compounds of formula I that may be mentioned are those where $W^7$, $W^8$, $W^{10}$ and $W^{11}$ are hydrogen and $W^9$ represents —F, —Cl, —CH$_3$, cyclopropyl, —CF$_3$, —CN, —NH$_2$, —N(CH$_3$)$_2$, —N(H)C(O)CH$_3$, —N(H)C(O)OC(CH$_3$)$_3$, —SO$_2$CH$_3$, —SO$_2$NH$_2$, —S(O)$_2$N(CH$_3$)$_2$, —S(O)$_2$-4-morpholinyl, 4-methylpiperazin-1-yl, 4-methylpiperidin-1-ylmethyl and 1,2,3-thiadiazol-4-yl.

Preferred compounds of formula I where $Z^1$ represents heteroaryl that may be mentioned are those where $Z^1$ represents benzimidazolyl, benzodioxinyl, benzoxazolyl, furanyl, imidazolyl, imidazopyridinyl, indolyl, isoquinolinyl, oxadiazolyl, oxazolyl, pyrazinyl, pyrazolyl, pyridyl, pyrrolopyridinyl, quinolinyl, thiazolyl, thiophenyl and triazolyl, wherein the heteroaryl is optionally substituted by one or more substituents selected from $W^6$.

Particularly preferred compounds of formula I where $Z^1$ represents heteroaryl that may be mentioned are those where $Z^1$ represents benzimidazol-2-yl, 1,4-benzodioxin-2-yl, benzoxazol-2-yl, furan-2-yl, imidazol-1-yl, imidazol-4-yl, imidazo-[1,2-a]pyridin-2-yl, indol-3-yl, indol-5-yl, isoquinolin-4-yl, 1,3,4-oxadiazol-2-yl, 1,2-oxazol-4-yl, pyrazin-3-yl, pyrazol-1-yl, pyrazol-4-yl, pyridin-2-yl, pyridin-3-yl, pyridin-4-yl, 5H,6H,7H-pyrrolo[3,4-b]pyridin-5-yl, thiazol-5-yl, thiophen-2-yl, 1,2,3-triazol-4-yl and 1,2,4-triazol-3-yl, wherein the heteroaryl is optionally substituted by one or more substituents selected from WP.

More particularly preferred compounds of formula I that may be mentioned are those where $W^6$ represents —F, —Cl, —Br, —CH$_3$, cyclopropyl, —CF$_3$, —CN, —NH$_2$, —N(CH$_3$)$_2$, —SO$_2$CH$_3$, —SO$_2$NH$_2$ and —SO)$_2$N(CH$_3$)$_2$.

In another embodiment of the invention there is provided a compound of formula

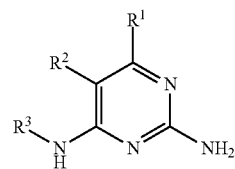

(I)

wherein:
$R^1$ represents:
indanyl, naphthyl, tetrahydronaphthyl or heteroaryl, the latter connected to the pyrimidine of formula I via a carbon atom of the heteroaryl ring, which indanyl, naphthyl, tetrahydronaphthyl and heteroaryl rings are optionally substituted by one or more substituents selected from $Y^1$, —$C_{1-6}$alkyl optionally substituted by one or more $Y^2$ and heterocycloalkyl optionally substituted by one or more $Y^3$; or aryl represented by

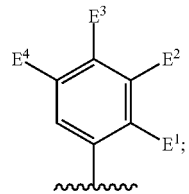

$E^1$, $E^2$, $E^3$ and $E^4$ represents hydrogen, $Y^1$, —$C_{1-6}$alkyl optionally substituted by one or more $Y^2$ or heterocycloalkyl optionally substituted by one or more $Y^3$, but where at least one of $E^1$, $E^2$, $E^3$ and $E^4$ is other than hydrogen;

$R^2$ represents hydrogen, halogen or —$C_{1-12}$alkyl optionally substituted by one or more $Z^1$;

$R^3$ represents —$C_{1-12}$alkyl substituted by one or more $Z^1$ or heterocycloalkyl optionally substituted by one or more $Z^2$; or $R^2$ and $R^3$ are linked together to form, along with the atoms to which they are attached, a 5- to 8-membered non-aromatic ring, wherein the link formed by $R^2$ and $R^3$ is optionally substituted by one or more substituents selected from $Z^3$ or —$C_{1-9}$alkyl optionally substituted by one or more $Z^4$;

each $Y^1$ independently represents halogen, —CN, —C(O)$R^a$, —C(O)N($R^b$)$R^c$, —C(O)O$R^d$, —N($R^e$)$R^f$, —N($R^g$)C(O)$R^h$, —N($R^i$)C(O)O$R^j$, —N($R^k$)C(O)N($R^l$)$R^m$, —NO$_2$, —N($R^n$)S(O)$_2$$R^o$, —O$R^p$, —OC(O)$R^q$, —OS(O)$_2$$R^r$, —S(O)$_m$$R^s$, —S(O)$_2$N($R^t$)$R^u$, heterocycloalkyl optionally substituted by one or more substituents selected from $W^2$, aryl optionally substituted by one or more substituents selected from $W^3$, or heteroaryl optionally substituted by one or more substituents selected from $W^3$;

each $R^a$, $R^b$, $R^c$, $R^d$, $R^e$, $R^g$, $R^h$, $R^i$, $R^k$, $R^l$, $R^m$, $R^n$, $R^p$, $R^q$, $R^s$, $R^t$ and $R^u$ independently represents hydrogen, —$C_{1-6}$ alkyl optionally substituted by one or more substituents selected from $W^1$, heterocycloalkyl optionally substituted by one or more substituents selected from $W^2$, aryl optionally substituted by one or more substituents selected from $W^3$, or heteroaryl optionally substituted by one or more substituents selected from $W^3$; or any two $R^b$ and $R^c$, $R^e$ and $R^f$, $R^i$ and $R^m$ and/or $R^t$ and $R^u$ are linked together to form, along with the nitrogen atom to which they are attached, a 3- to 8-membered monocyclic or bicyclic ring, which ring optionally contains one or two heteroatoms and which ring optionally is substituted by one or more substituents selected from $W^2$, $C_{1-3}$alkyl optionally substituted by one or more substituents selected from $W^1$, and =O;

each $R^f$, $R^j$, $R^o$ and $R^r$ independently represent —$C_{1-6}$ alkyl optionally substituted by one or more substituents selected from $W^1$, heterocycloalkyl optionally substituted by one or more substituents selected from $W^2$, aryl optionally substituted by one or more substituents selected from $W^3$ or heteroaryl optionally substituted by one or more substituents selected from $W^3$;

each $Y^2$ independently represents halogen, —CN, —C(O)$R^{b1}$, —C(O)N($R^{c1}$)$R^{d1}$, —C(O)O$R^{e1}$, —N($R^{f1}$)$R^{g1}$, —N($R^{h1}$)C(O)$R^{i1}$, —N($R^{j1}$)C(O)O$R^{k1}$, —N($R^{l1}$)C(O)N($R^{m1}$)$R^{n1}$, —N($R^{o1}$)S(O)$_2$$R^{p1}$, —O$R^{q1}$, —OC(O)$R^{r1}$, —OS(O)$_2$$R^{s1}$, —S(O)$_m$$R^{t1}$, —S(O)$_2$N($R^{u1}$)$R^{v1}$, heterocycloalkyl optionally substituted by one or more substituents selected from $W^1$, aryl optionally substituted by one or more substituents selected from $W^2$, heteroaryl optionally substituted by one or more substituents selected from $W^2$;

each $Y^3$ independently represents halogen, —$R^{a1}$, —CN, —C(O)$R^{b1}$, —C(O)N($R^{c1}$)$R^{d1}$, —C(O)O$R^{e1}$, —N($R^{f1}$)$R^{g1}$, —N($R^{h1}$)C(O)$R^{i1}$, —N($R^{j1}$)C(O)O$R^{k1}$, —N($R^{l1}$)C(O)N($R^{m1}$)$R^{n1}$, —N($R^{o1}$)S(O)$_2$$R^{p1}$, —O$R^{q1}$, —OC(O)$R^{r1}$, —OS(O)$_2$$R^{s1}$, —S(O)$_m$$R^{t1}$, —S(O)$_2$N($R^{u1}$)$R^{v1}$, heterocycloalkyl optionally substituted by one or more substituents selected from $W^1$, aryl optionally substituted by one or more substituents selected from $W^2$, heteroaryl optionally substituted by one or more substituents selected from $W^2$, or =O;

each $R^{a1}$, $R^{b1}$, $R^{c1}$, $R^{d1}$, $R^{e1}$, $R^{f1}$, $R^{h1}$, $R^{i1}$, $R^{j1}$, $R^{l1}$, $R^{m1}$, $R^{n1}$, $R^{o1}$, $R^{q1}$, $R^{r1}$, $R^{t1}$, $R^{u1}$ and $R^{v1}$ independently represents hydrogen, $C_{1-6}$ alkyl optionally substituted by one or more substituents selected from $W^1$, heterocycloalkyl optionally substituted by one or more substituents selected from $W^2$, aryl optionally substituted by one or more substituents selected from $W^3$, or heteroaryl optionally substituted by one or more substituents selected from $W^3$; or any two $R^{c1}$, $R^{d1}$, $R^{f1}$ and $R^{g1}$, $R^{m1}$ and $R^{n1}$, and/or $R^{u1}$ and $R^{v1}$ are linked together to form, along with the nitrogen atom to which they are attached, a 3- to 8-membered monocyclic or bicyclic ring, which ring optionally contains one or two heteroatoms and which ring optionally is substituted by one or more substituents selected from $W^2$, $C_{1-3}$alkyl optionally substituted by one or more substituents selected from $W^1$, and =O;

each $R^{g1}$, $R^{k1}$, $R^{p1}$ and $R^{s1}$ independently represent —$C_{1-6}$ alkyl optionally substituted by one or more substituents selected from $W^1$, heterocycloalkyl optionally substituted by one or more substituents selected from $W^2$, aryl optionally substituted by one or more substituents selected from $W^3$, or heteroaryl optionally substituted by one or more substituents selected from $W^3$;

each $Z^1$ independently represents halogen, —CN, —C(O)$R^{b2}$, —C(O)N($R^{c2}$)$R^{d2}$, —C(O)O$R^{e2}$, —N($R^{f2}$)$R^{g2}$, —N($R^{h2}$)C(O)$R^{i2}$, —N($R^{j2}$)C(O)O$R^{k2}$, —N($R^{l2}$)C(O)N($R^{m2}$)$R^{n2}$, —N($R^{o2}$)S(O)$_2$$R^{p2}$, —O$R^{q2}$, —OC(O)$R^{r2}$, —OS(O)$_2$$R^{s2}$, —S(O)$_m$$R^{t2}$, —S(O)$_2$N($R^{u2}$)$R^{v2}$, heterocycloalkyl optionally substituted by one or more substituents selected from $W^5$, aryl represented by

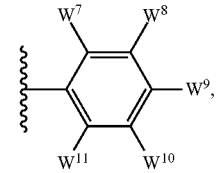

heteroaryl having 1 to 3 nitrogen atoms, one oxygen atom and/or one sulfur atom and optionally substituted by one or more substituents selected from $W^6$;

each $Z^2$ and $Z^3$ independently represents halogen, —$R^{a2}$, —CN, —C(O)$R^{b2}$, —C(O)N($R^{c2}$)$R^{d2}$, —C(O)O$R^{e2}$, —N($R^{f2}$)$R^{g2}$, —N($R^{h2}$)C(O)$R^{i2}$, —N($R^{j2}$)C(O)O$R^{k2}$, —N($R^{j2}$)C(O)N($R^{m2}$)$R^{n2}$, —N($R^{o2}$)S(O)$_2$$R^{p2}$, —O$R^{q2}$, —OC(O)R$^{r2}$, —OS(O)$_2$R$^{s2}$, —S(O)$_m$R$^{t2}$, —S(O)$_2$N(R$^{u2}$)R$^{v2}$, heterocycloalkyl optionally substituted by one or more substituents selected from W$^5$, aryl optionally substituted by one or more substituents selected from W$^6$, or heteroaryl optionally substituted by one or more substituents selected from W$^6$;

each Z$^4$ independently represents halogen, —CN, —C(O)R$^{b2}$, —C(O)N(R$^{c2}$)R$^{d2}$, —C(O)OR$^{e2}$, —N(R$^{f2}$)R$^{g2}$, —N(R$^{h2}$)C(O)R$^{i2}$, —N(R$^{j2}$)C(O)OR$^{k2}$, —N(R$^{l2}$)C(O)N(R$^{m2}$)R$^{n2}$, —N(R$^{o2}$)S(O)$_2$R$^{p2}$, —OR$^{q2}$, —OC(O)R$^{r2}$, —OS(O)$_2$R$^{s2}$, —S(O)$_m$R$^{t2}$, —S(O)$_2$N(R$^{u2}$)R$^{v2}$, heterocycloalkyl optionally substituted by one or more substituents selected from W$^5$, aryl optionally substituted by one or more substituents selected from W$^6$, heteroaryl optionally substituted by one or more substituents selected from W$^6$, or =O;

each R$^{a2}$, R$^{b2}$, R$^{c2}$, R$^{d2}$, R$^{e2}$, R$^{f2}$, R$^{h2}$, R$^{i2}$, R$^{j2}$, R$^{l2}$, R$^{m2}$, R$^{n2}$, R$^{o2}$, R$^{r2}$, R$^{t2}$, R$^{u2}$ and R$^{v2}$ independently represents hydrogen or C$_{1-6}$ alkyl optionally substituted by one or more substituents selected from W$^4$, heterocycloalkyl optionally substituted by one or more substituents selected from W$^5$, aryl optionally substituted by one or more substituents selected from W$^6$, or heteroaryl optionally substituted by one or more substituents selected from W$^6$; or any two R$^{c2}$ and R$^{d2}$, R$^{f2}$ and R$^{g3}$, R$^{m2}$ and R$^{n2}$ and/or R$^{u2}$ and R$^{v2}$ are linked together to form, along with the nitrogen atom to which they are attached, a 3- to 8-membered monocyclic or bicyclic ring, which ring optionally contains one or two heteroatoms and which ring optionally is substituted by one or more substituents selected from W$^5$, C$_{1-3}$alkyl optionally substituted by one or more substituents selected from W$^4$, and =O;

each R$^{g2}$, R$^{k2}$, R$^{p2}$, R$^{q2}$ and R$^{s2}$ independently represent —C$_{1-6}$ alkyl optionally substituted by one or more substituents selected from W$^4$, heterocycloalkyl optionally substituted by one or more substituents selected from W$^5$, aryl optionally substituted by one or more substituents selected from W$^6$, or heteroaryl optionally substituted by one or more substituents selected from W$^6$; each W$^1$ and W$^4$ independently represents halogen, —CN, —N(V)R$^{g3}$, —N(R$^{h3}$)C(O)R$^{i3}$, —N(R$^{j3}$)C(O)OR$^{k3}$, —N(R$^{l3}$)C(O)N(R$^{m3}$)R$^{n3}$, —N(R$^{o3}$)S(O)$_2$R$^{p3}$, —OR$^{q3}$, —OC(O)R$^{r3}$, —OS(O)$_2$R$^{s3}$, —S(O)$_m$R$^{t3}$, —S(O)$_2$N(R$^{u3}$)R$^{v3}$, heterocycloalkyl optionally substituted by one or more substituents selected from G$^1$, aryl optionally substituted by one or more substituents selected from G$^2$, heteroaryl optionally substituted by one or more substituents selected from G$^2$, or =O;

each W$^2$, W$^3$, W$^5$ and W$^6$ independently represents halogen, —R$^{a3}$, —CN, —C(O)R$^{b3}$, —C(O)N(R$^{c3}$)R$^{d3}$, —C(O)OR$^{e3}$, —N(R$^{f3}$)R$^{g3}$, —N(R$^{h3}$)C(O)R$^{i3}$, —N(R$^{j3}$)C(O)OR$^{k3}$, —N(R$^{l3}$)C(O)N(R$^{m3}$)R$^{n3}$, —N(R$^{o3}$)S(O)$_2$R$^{p3}$, —OR$^{q3}$, —OC(O)R$^{r3}$, —OS(O)$_2$R$^{s3}$, —S(O)$_m$R$^{t3}$, —S(O)$_2$N(R$^{u3}$)R$^{v3}$, heterocycloalkyl optionally substituted by one or more substituents selected from G$^1$, aryl optionally substituted by one or more substituents selected from G$^2$, heteroaryl (optionally substituted by one or more substituents selected from G$^2$, or =O;

W$^7$ and W$^{11}$ represents hydrogen;

each W$^8$ and W$^{10}$ independently represents hydrogen, halogen, —R$^{a3}$, —CN, —C(O)R$^{b3}$, —C(O)N(R$^{c3}$)R$^{d3}$, —C(O)OR$^{e3}$, —N(R$^{f3}$)R$^{g3}$, —N(R$^{h3}$)C(O)R$^{i3}$, —N(R$^{j3}$)C(O)OR$^{k3}$, —N(R$^{l3}$)C(O)N(R$^{m3}$)R$^{n3}$, —N(R$^{o3}$)S(O)$_2$R$^{p3}$, —OR$^{q3}$, —OC(O)R$^{r3}$, —OS(O)$_2$R$^{s3}$, —S(O)$_m$R$^{t3}$, —S(O)$_2$N(R$^{u3}$)R$^{v3}$, heterocycloalkyl optionally substituted by one or more substituents selected from G$^1$, aryl optionally substituted by one or more substituents selected from G$^2$, or heteroaryl optionally substituted by one or more substituents selected from G$^2$;

W$^9$ represents halogen, —R$^{a3}$, —CN, —C(O)R$^{b3}$, —C(O)N(R$^{c3}$)R$^{d3}$, —C(O)OR$^{e3}$, —N(R$^{f3}$)R$^{g3}$, —N(R$^{h3}$)C(O)R$^{i3}$, —N(R$^{j3}$)C(O)OR$^{k3}$, —N(R$^{l3}$)C(O)N(R$^{m3}$)R$^{n3}$, —N(R$^{o3}$)S(O)$_2$R$^{p3}$, —OR$^{q3x}$, —OC(O)R$^{r3}$, —OS(O)$_2$R$^{s3}$, —S(O)$_m$R$^{t3}$, —S(O)$_2$N(R$^{u3}$)R$^{v3}$, heterocycloalkyl optionally substituted by one or more substituents selected from G$^1$, aryl optionally substituted by one or more substituents selected from G$^2$, or heteroaryl optionally substituted by one or more substituents selected from G$^2$;

each R$^{a3}$, R$^{b3}$, R$^{c3}$, R$^{d3}$, R$^{e3}$, R$^{f3}$, R$^{h3}$, R$^{i3}$, R$^{j3}$, R$^{l3}$, R$^{m3}$, R$^{n3}$, R$^{o3}$, R$^{q3}$, R$^{r3}$, R$^{t3}$, R$^{u3}$ and R$^{v3}$ independently represents hydrogen or —C$_{1-6}$ alkyl optionally substituted by one or more G$^3$; or any two R$^{c3}$ and R$^{d3}$, R$^{f3}$ and R$^{g3}$, R$^{m3}$ and R$^{n3}$ and/or R$^{u3}$ and R$^{v3}$ are linked together to form, along with the nitrogen atom to which they are attached, a 4- to 6-membered ring, which ring optionally contains one heteroatom and which ring optionally is substituted by one or more G$^2$;

each R$^{g3}$, R$^{k3}$, R$^{p3}$, R$^{q3}$ and R$^{s3}$ independently represent C$_{1-6}$ alkyl optionally substituted by one or more G$^3$;

R$^{q3x}$ represents C$_{2-6}$ alkyl optionally substituted by one or more G$^3$;

each G$^1$ and G$^2$ independently represents halogen, —R$^{a4}$, —CN, —C(O)R$^{b4}$, —C(O)N(R$^{c4}$)R$^{d4}$, —C(O)OR$^{e4}$, —N(R$^{f4}$)R$^{g4}$, —N(R$^{h4}$)C(O)R$^{i4}$, —N(R$^{j4}$)C(O)OR$^{k4}$, —N(R$^{l4}$)C(O)N(R$^{m4}$)R$^{n4}$, —N(R$^{o4}$)S(O)$_2$R$^{p4}$, —OR$^{q4}$, —OC(O)R$^{r4}$, —OS(O)$_2$R$^{s4}$, —S(O)$_m$R$^{t4}$, —S(O)$_2$N(R$^{u4}$)R$^{v4}$, or =O;

G$^3$ represents halogen, —CN, —C(O)R$^{b4}$, —C(O)N(R$^{c4}$)R$^{d4}$, —C(O)OR$^{e4}$, —N(R$^{f4}$)R$^{g4}$, —N(R$^{h4}$)C(O)R$^{i4}$, —N(R$^{j4}$)C(O)OR$^{k4}$, —N(R$^{l4}$)C(O)N(R$^{m4}$)R$^{n4}$, —N(R$^{o4}$)S(O)$_2$R$^{p4}$, —OR$^{q4}$, —OC(O)R$^{r4}$, —OS(O)$_2$R$^{s4}$, —S(O)$_m$R$^{t4}$, —S(O)$_2$N(R$^{u4}$)R$^{v4}$, or =O;

each R$^{a4}$, R$^{b4}$, R$^{c4}$, R$^{d4}$, R$^{e4}$, R$^{f4}$, R$^{h4}$, R$^{i4}$, R$^{j4}$, R$^{l4}$, R$^{m4}$, R$^{n4}$, R$^{o4}$, R$^{q4}$, R$^{r4}$, R$^{t4}$, R$^{u4}$ and R$^{v4}$ independently represents hydrogen or —C$_{1-6}$ alkyl optionally substituted by one or more —F; or any two R$^{c4}$ and R$^{d4}$, R$^{f4}$ and R$^{g4}$, R$^{m4}$ and R$^{n4}$ and/or R$^{u4}$ and R$^{v4}$ are linked together to form, along with the nitrogen atom to which they are attached, a 3- to 6-membered ring, which ring optionally substituted by one or more —F, —CH$_3$, —CH$_2$CH$_3$, —CHF$_2$, —CF$_3$, —CH$_2$CF$_3$, or =O;

each R$^{g4}$, R$^{k4}$, R$^{p4}$ and R$^{s4}$ independently represent C$_{1-6}$ alkyl optionally substituted by one or more —F;

each m independently represents 0, 1 or 2;

provided that formula I does not represent 6-(3-pyridinyl)-N$^4$-[[4-[5-(trifluoromethyl)-1,2,4-oxadiazol-3-yl]phenyl]methyl]-2,4-pyrimidinediamine, 6-(3-pyridinyl)-N$^4$-[[5-[5-(trifluoromethyl)-1,2,4-oxadiazol-3-yl]-2-pyridinyl]methyl]-2,4-pyrimidinediamine, 6-(3-pyridinyl)-N$^4$-[[5-[5-(trifluoromethyl)-1,2,4-oxadiazol-3-yl]-2-pyridinyl]-methyl]-2,4-pyrimidinediamine, N$^4$-[2-(diethylamino)ethyl]-6-(3,4,5-trimethoxyphenyl)-2,4-pyrimidinediamine, N$^4$-[3-(4-morpholinyl)propyl]-6-(3,4,5-trimethoxyphenyl)-2,4-pyrimidinediamine, or N$^4$-[2-(4-morpholinyl)ethyl]-6-(3,4,5-trimethoxyphenyl)-2,4-pyrimidinediamine;

or a pharmaceutically acceptable salt thereof;

which compounds may be referred to herein as "the compounds of the invention".

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin. For the avoidance of doubt, solvates are also included within the scope of the invention.

Compounds of the invention may contain double bonds and may thus exist as E (entgegen) and Z (zusammen) geometric isomers about each individual double bond. All such isomers and mixtures thereof are included within the scope of the invention.

Compounds of the invention may also exhibit tautomerism. All tautomeric forms and mixtures thereof are included within the scope of the invention.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

Unless otherwise specified, $C_{1-q}$ alkyl groups (where q is the upper limit of the range) defined herein may be straight-chain or, when there is a sufficient number (i.e. a minimum of two or three, as appropriate) of carbon atoms, be branched-chain, and/or cyclic (so forming a $C_{3-q}$-cycloalkyl group). When there is a sufficient number (i.e. a minimum of four) of carbon atoms, such groups may also be part cyclic. Such alkyl groups may also be saturated or, when there is a sufficient number (i.e. a minimum of two) of carbon atoms, be unsaturated (forming, for example, a $C_{2-q}$ alkenyl or a $C_{2-q}$ alkynyl group).

Unless otherwise specified, $C_{1-q}$ alkylene groups (where q is the upper limit of the range) defined herein may (in a similar manner to the definition of $C_{1-q}$ alkyl) be straight-chain or, when there is a sufficient number (i.e. a minimum of two or three, as appropriate) of carbon atoms, be branched-chain, and/or cyclic (so forming a $C_{3-q}$-cycloalkylene group). When there is a sufficient number (i.e. a minimum of four) of carbon atoms, such groups may also be part cyclic. Such alkylene groups may also be saturated or, when there is a sufficient number (i.e. a minimum of two) of carbon atoms, be unsaturated (forming, for example, a $C_{2-q}$alkenylene or a $C_{2-q}$alkynylene group). Particular alkylene groups that may be mentioned include those that are straight-chained and saturated.

The term "halo", when used herein, includes fluoro, chloro, bromo and iodo (for example, fluoro and chloro).

Heterocycloalkyl groups that may be mentioned include non-aromatic monocyclic and bicyclic heterocycloalkyl groups (which groups may further be bridged) in which at least one (e.g. one to four) of the atoms in the ring system is other than carbon (i.e. a heteroatom), and in which the total number of atoms in the ring system is between three and twelve (e.g. between five and ten and, most preferably, between three and eight, e.g. a 5- or 6-membered heterocycloalkyl group). Further, such heterocycloalkyl groups may be saturated or unsaturated containing one or more double and/or triple bonds, forming for example a $C_{2-q}$ (e.g. $C_{4-q}$) heterocycloalkenyl (where q is the upper limit of the range) or a $C_{7-q}$ heterocycloalkynyl group. $C_{2-q}$ heterocycloalkyl groups that may be mentioned include 7-azabicyclo-[2.2.1]heptanyl, 6-azabicyclo[3.1.1]heptanyl, 6-azabicyclo[3.2.1]-octanyl, 8-azabicyclo[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, 7-oxabicyclo[2.2.1]heptanyl, 6-oxabicyclo[3.2.1]-octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuryl, tetrahydropyridyl (such as 1,2,3,4-tetrahydropyridyl and 1,2,3,6-tetrahydropyridyl), thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom. Further, in the case where the substituent is another cyclic compound, then the cyclic compound may be attached through a single atom on the heterocycloalkyl group, forming a so-called "spiro"-compound. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form. At each occurrence when mentioned herein, a heterocycloalkyl group is preferably a 3- to 8-membered heterocycloalkyl group (e.g. a 5- or 6-membered heterocycloalkyl group).

The term "aryl", when used herein, includes $C_{6-14}$ (e.g. $C_{6-10}$) aromatic groups. Such groups may be monocyclic or bicyclic and, when bicyclic, be either wholly or partly aromatic. $C_{6-10}$ aryl groups that may be mentioned include phenyl, naphthyl, 1,2,3,4-tetrahydronaphthyl, indanyl, and the like (e.g. phenyl, naphthyl and the like). For the avoidance of doubt, the point of attachment of substituents on aryl groups may be via any carbon atom of the ring system.

The term "heteroaryl" (or heteroaromatic), when used herein, includes 5- to 10-membered heteroaromatic groups containing one or more heteroatoms selected from oxygen, nitrogen and/or sulfur. Such heteroaryl group may comprise one, or two rings, of which at least one is aromatic. Substituents on heteroaryl/heteroaromatic groups may, where appropriate, be located on any atom in the ring system including a heteroatom. The point of attachment of heteroaryl/heteroaromatic groups may be via any atom in the ring system including (where appropriate) a heteroatom. Bicyclic heteroaryl/heteroaromatic groups may comprise a benzene ring fused to one or more further aromatic or non-aromatic heterocyclic rings, in which instances, the point of attachment of the polycyclic heteroaryl/heteroaromatic group may be via any ring including the benzene ring or the heteroaryl/heteroaromatic or heterocycloalkyl ring. Examples of heteroaryl/heteroaromatic groups that may be mentioned include pyridinyl, pyrrolyl, furanyl, thiophenyl, oxadiazolyl, thiadiazolyl, thiazolyl, oxazolyl, pyrazolyl, triazolyl, tetrazolyl, isoxazolyl, isothiazolyl, imidazolyl, imidazopyrimidinyl, pyrimidinyl, indolyl, azaindolyl, pyrazinyl, indazolyl, pyrimidinyl, quinolinyl, isoquinolinyl, benzofuranyl, benzothiophenyl, benzoimidazolyl, benzoxazolyl, benzothiazolyl and benzotriazolyl. The oxides of heteroaryl/heteroaromatic groups are also embraced within the scope of the invention (e.g. the N-oxide). As stated above, heteroaryl includes polycyclic (e.g. bicyclic) groups in which one ring is aromatic (and the other may or may not be aromatic). Hence, other heteroaryl groups that may be mentioned include e.g. benzo[1,3]dioxolyl, benzo[1,4]dioxinyl, indolinyl, 5H,6H,7H-pyrrolo[1,2-b]pyrimidinyl, 1,2,3,4-tetra-hydroquinolinyl and the like.

Heteroatoms that may be mentioned include phosphorus, silicon, boron and, preferably, oxygen, nitrogen and sulfur.

For the avoidance of doubt, in cases in which the identity of two or more substituents in a compound of the invention may be the same, the actual identities of the respective substituents are not in any way interdependent.

For the avoidance of doubt, when $R^1$ is defined as

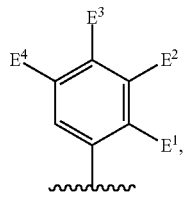

it is connected to the rest of formula I by the bond interrupted by the wiggly line, and formula I can thus be represented by

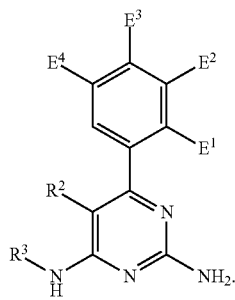

Likewise, when $R^3$ is —$C_{1-12}$ alkyl substituted by $Z^1$, and $Z^1$ is represented by

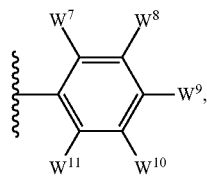

then, if e.g. $R^3$ is $C_2$alkyl, then formula I can be represented by

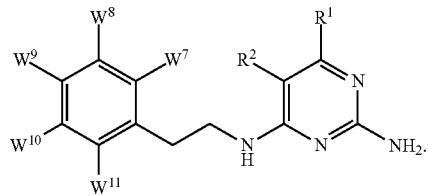

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Hence, the compounds of the invention also include deuterated compounds, i.e. in which one or more hydrogen atoms are replaced by the hydrogen isotope deuterium.

All individual features (e.g. preferred features) mentioned herein may be taken in isolation or in combination with any other feature (including preferred features) mentioned herein (hence, preferred features may be taken in conjunction with other preferred features, or independently of them).

The skilled person will appreciate that compounds of the invention that are the subject of this invention include those that are stable. That is, compounds of the invention include those that are sufficiently robust to survive isolation from e.g. a reaction mixture to a useful degree of purity.

Particular compounds of formula I that may be mentioned include those in which:

$R^2$ represents hydrogen or —$C_{1-12}$alkyl optionally substituted by one or more $Z^1$; and $R^3$ represents —$C_{1-12}$alkyl substituted by one or more $Z^1$ or heterocycloalkyl optionally substituted by one or more $Z^2$.

For example, compounds of formula I that may be mentioned include those in which $R^2$ represents methyl, or preferably, hydrogen and $R^3$ represents:

(a) —$C_{1-12}$alkyl (for example —$C_{1-6}$alkyl) substituted by two, or preferably, one $Z^1$ or;

(b) —$C_{2-6}$alkyl substituted by two, or preferably, one $Z^1$ or heterocycloalkyl optionally substituted by two, or preferably, one $Z^2$; or (c)

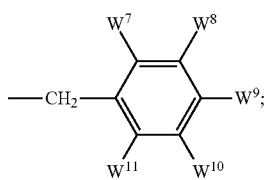

(d) —$C_{1-12}$alkyl (for example —$C_{1-6}$alkyl) substituted by heteroaryl having 1 to 3 nitrogen atoms, one oxygen atom and/or one sulfur atom and which heteroaryl is optionally substituted by one or more substituents selected from $W^3$; or (e) —$C_{3-6}$alkyl or a heterocycloalkyl selected from cyclopropyl, cyclobutyl, cyclopentyl, cyclohexyl, cyclopropylmethyl, cyclobutylmethyl, cyclopentylmethyl, cyclopropylethyl, cyclobutylethyl, cyclopropylpropyl, oxetanyl, tetrahydrofuryl, tetrahydropyranyl, azetidinyl, pyrrolidinyl, piperidinyl, piperazinyl or morpholinyl wherein the $C_{3-6}$alkyl is substituted by two, or preferably, one $Z^1$ and the heterocycloalkyl is optionally substituted by two, or preferably, one $Z^2$.

Particular compounds of formula I that may be mentioned include those in which: $R^2$ and $R^3$ are linked together to form, along with the atoms to which they are attached, a 5- to 8-membered non-aromatic ring, wherein the link formed by $R^2$ and $R^3$ is optionally substituted by one or more substituents selected from $Z^3$ or —$C_{1-9}$alkyl optionally substituted by one or more $Z^4$.

For example, compounds of formula I that may be mentioned include those in which $R^2$ and $R^3$ are linked together to form, along with the atoms to which they are attached, a 5- to 6-membered non-aromatic ring, wherein the non-aromatic ring is:
(a) unsubstituted; or
(b) substituted by one or more substituents selected from $Z^3$; or
(c) substituted by —$C_{1-9}$alkyl optionally substituted by one or more $Z^4$; or
(d) substituted by one or more substituents selected from $Z^3$ and substituted by —$C_{1-9}$alkyl optionally substituted by one or more $Z^4$.

Particular compounds of formula I that may be mentioned include those in which $R^1$ represents heteroaryl.

Preferred compounds of formula I where $R^1$ represents heteroaryl that may be mentioned are those where $R^1$ represents benzofuranyl, benzothiophenyl, dihydrobenzofuranyl, indazolyl, indolyl, isoquinolinyl, pyridinyl, pyrrolyl and quinolinyl.

Particularly preferred compounds of formula I where $R^1$ represents heteroaryl that may be mentioned are those where $R^1$ represents benzofuran-3-yl, benzothiophen-3-yl, dihydrobenzofuran-7-yl, indol-3-yl, indol-4-yl, indol-5-yl, isoquinolin-4-yl, pyridin-3-yl, pyridin-4-yl, pyrrol-2-yl and quinolin-5-yl.

For example, compounds of formula I that may be mentioned include those in which $R^1$ represents indolyl, e.g. indol-3-yl, indol-4-yl or indol-5-yl, where the indolyl is optionally substituted on the nitrogen with —$S(O)_2Ar^x$, where $Ar^x$ is aryl or heteroaryl, preferably optionally substituted phenyl, e.g. unsubstituted phenyl or phenyl substituted in the 4-position by —F, —Cl, —$CH_3$ or —$CF_3$.

Preferred compounds of formula I that may be mentioned include those in which $R^1$ is represented by

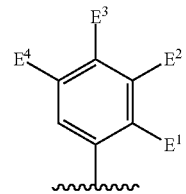

where:
$E^2$, $E^3$ and $E^4$ represent hydrogen and
$E^1$ represents —F, —Cl, —$CH_3$, —$CF_3$, CN or —$OCH_3$; or
$E^1$, $E^3$ and $E^4$ represent hydrogen and $E^2$ represents —F, —Cl, —$CH_3$, —$CF_3$, —CN; or
$E^1$, $E^2$ and $E^4$ represent hydrogen and $E^3$ represent —F, —Cl, —$CH_3$, —$CF_3$, —$C(CH_3)_3$, —$CH=CH_2$, —$OCF_3$, —$S(O)_2CH_3$, or —$S(O)_2$(4-morpholinyl).

Other preferred compounds of formula I that may be mentioned include those in which $R^1$ is represented by

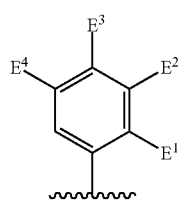

where:
$E^3$ and $E^4$ represent hydrogen; and
$E^1$ represents —F and $E^2$ represent —F, —Cl, —$CH_3$ or —$CF_3$; or
$E^1$ represents —Cl and $E^2$ represents —F, —Cl, —$CH_3$ or —$CF_3$; or
$E^1$ represents —$CH_3$ and $E^2$ represents —F, —Cl, —$CH_3$, —$CF_3$ or —CN; or
$E^2$ and $E^4$ represent hydrogen; and
$E^1$ represents —Cl and $E^3$ represents —F or —Cl; or
$E^1$ represents —$CH_3$ and $E^3$ represents —Cl; or
$E^1$ represents —$OCH_3$ and $E^3$ represents —F; or
$E^2$ and $E^3$ represent hydrogen; and
$E^1$ represents —F and $E^4$ represents —Cl, —$CH_3$ or —CN; or
$E^1$ represents —Cl and $E^4$ represent —F, —Cl, —$CH_3$, —$CF_3$ or —$OCH_3$; or
$E^1$ represents —$CH_3$ and $E^4$ represent —F, —Cl, —$CH_3$, —$CF_3$ or —CN; or
$E^1$ represents —$CF_3$ and $E^4$ represents —F or —$CF_3$; or
$E^1$ represents —CN and $E^4$ represents —Cl; or
$E^1$ represents —$OCH_3$ and $E^4$ represents —F, —Cl, Br, —$CH_3$, —$CH(CH_3)_2$, —$C(CH_3)_3$, —CN or —$OCH_3$; or
$E^1$ and $E^4$ represent hydrogen; and
$E^2$ represents —F and $E^3$ represents —F, —Cl, —OH or —$OCH_3$; or
$E^2$ represents —Cl and $E^3$ represents —F; or
$E^2$ represents —$CH_3$ and $E^3$ represents —F or —$OCH_3$; or
$E^1$ represents —$OCH_3$ and $E^3$ represents —OH; or
$E^1$ and $E^3$ represent hydrogen; and
$E^2$ and $E^4$ represent —F; or
$E^2$ and $E^4$ represent —$CF_3$; or
$E^4$ represents hydrogen; and
$E^1$, $E^2$ and $E^3$ represent —F; or
$E^1$ and $E^2$ represent —Cl and $E^3$ represents —Cl, —OH or —$OCH_3$; or
$E^1$ and $E^2$ represent —$CH_3$ and $E^3$ represents —F or —$OCH_3$; or
$E^2$ and $E^3$ represent —Cl and $E^1$ represents —$CH_3$; or
$E^2$ represents hydrogen; and
$E^1$, $E^3$ and $E^4$ represent —F; or
$E^3$ and $E^4$ represent —Cl and $E^1$ represents —$CH_3$; or
$E^1$ and $E^4$ represent —Cl and $E^1$ represents —$OCH_3$; or
$E^1$ and $E^4$ represent —$CH_3$ and $E^3$ represents —F, —$CH_3$ or —$OCH_3$; or
$E^1$ represents —F, $E^3$ represents —$CH_3$ and $E^4$ represents —Cl; or
$E^1$ represents —Cl, $E^3$ represents —F and $E^4$ represents —$CH_3$; or
$E^1$ represents —Cl, $E^3$ represents —$CH_3$ and $E^4$ represents —F; or
$E^1$ and $E^4$ represent —$CH_3$ and $E^3$ represents —F; or
$E^1$ represents —$CH_3$, $E^4$ represents —Cl and $E^3$ represents —$CF_3$ or —$OCH_3$; or $E^1$ represents hydrogen; and $E^2$ and $E^4$ represent —$CH_3$ and $E^3$ represents —OH; or $E^3$ represents hydrogen; and $E^1$ and $E^2$ represent —Cl and $E^4$ represents —$CH_3$.

Preferred compounds of formula I that may be mentioned include those in which:

(a) $Z^1$ represents halogen, —CN, —C(O)$R^{b2}$, —C(O)N($R^{c2}$)$R^{d2}$, —C(O)O$R^{e2}$, —N($R^{f2}$)$R^{g2}$, —N($R^{h2}$)C(O)$R^{i2}$, —N($R^{j2}$)C(O)N($R^{m2}$)$R^{n2}$, —N($R^{o2}$)S(O)$_2R^{p2}$, —O$R^{q2}$, —S(O)$_mR^{t2}$, —S(O)$_2$N($R^{u2}$)$R^{v2}$, heterocycloalkyl optionally substituted by one or more substituents selected from $W^5$, aryl represented by

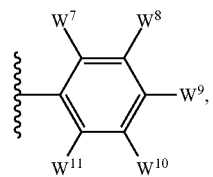

or heteroaryl having 1 to 3 nitrogen atoms, one oxygen atom and/or one sulfur atom and optionally substituted by one or more substituents selected from $W^6$; or (b) $Z^2$ is not present or is selected from —F, —$R^{a2}$, —C(O)N($R^{c2}$)$R^{d2}$, —N($R^{f2}$)$R^{g2}$, —N($R^{h2}$)C(O)$R^{i2}$, —N($R^{j2}$)C(O)O$R^{k2}$, —N($R^{j2}$)C(o)N($R^{m2}$)$R^{n2}$, —N($R^{o2}$)S(O)$_2R^{p2}$, —O$R^{q2}$, —S(O)$_mR^{t2}$, —S(O)$_2$N($R^{u2}$)$R^{v2}$, heterocycloalkyl optionally substituted by one or more substituents selected from $W^5$, aryl optionally substituted by one or more substituents selected from $W^6$, or heteroaryl optionally substituted by one or more substituents selected from $W^6$.

Other preferred compounds of formula I that may be mentioned include those in which:

(a) $Z^3$ is not present or is selected from —F, —$R^{a2}$, —C(O)N($R^{c2}$)$R^{d2}$, —N($R^{f2}$)$R^{g2}$, —N($R^{h2}$)C(O)$R^{i2}$, —N($R^{j2}$)C(O)O$R^{k2}$, —N($R^{j2}$)C(O)N($R^{m2}$)$R^{n2}$, —N($R^{o2}$)S(O)$_2R^{p2}$, —O$R^{q2}$, —S(O)$_mR^{t2}$, —S(O)$_2$N($R^{u2}$)$R^{v2}$, heterocycloalkyl optionally substituted by one or more substituents selected from $W^5$, aryl optionally substituted by one or more substituents selected from $W^6$, or heteroaryl optionally substituted by one or more substituents selected from $W^6$; and/or (b) $Z^4$ is not present or is selected from —F, —C(O)N($R^{c2}$)$R^{d2}$, —N($R^{f2}$)$R^{g2}$, —N($R^{h2}$)C(O)$R^{i2}$, —N($R^{j2}$)C(O)O$R^{k2}$, —N($R^{j2}$)C(O)N($R^{m2}$)$R^{n2}$, —N($R^{o2}$)S(O)$_2R^{p2}$, —O$R^{q2}$, —S(O)$_mR^{t2}$, —S(O)$_2$N($R^{u2}$)$R^{v2}$, heterocycloalkyl optionally substituted by one or more substituents selected from $W^5$, aryl optionally substituted by one or more substituents selected from $W^6$, or heteroaryl optionally substituted by one or more substituents selected from $W^6$.

More particularly preferred compounds of formula I that may be mentioned include those in which $Z^1$ represents —F, —CN, —C(O)N($R^{c2}$)$R^{d2}$, —N($R^{f2}$)$R^{g2}$, —N($R^{h2}$)C(O)$R^{i2}$, —N($R^{j2}$)C(O)N($R^{m2}$)$R^{n2}$, —N($R^{o2}$)S(O)$_2R^{p2}$, —O$R^{q2}$, —S(O)$_mR^{t2}$, —S(O)$_2$N($R^{u2}$)$R^{v2}$, heterocycloalkyl optionally substituted by one or more substituents selected from $W^5$, aryl represented by

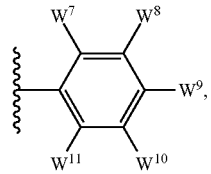

or heteroaryl having 1 to 3 nitrogen atoms, one oxygen atom and/or one sulfur atom and optionally substituted by one or more substituents selected from $W^6$.

Other more particularly preferred compounds of formula I that may be mentioned include those in which $Z^1$ represents —C(O)N($R^{c2}$)$R^{d2}$, —N($R^{f2}$)$R^{g2}$, —N($R^{h2}$)C(O)$R^{i2}$, —N($R^{j2}$)C(O)N($R^{m2}$)$R^{n2}$, —N($R^{o2}$)S(O)$_2R^{p2}$, —O$R^{q2}$, —S(O)$_mR^{t2}$, —S(O)$_2$N($R^{u2}$)$R^{v2}$ or aryl represented by

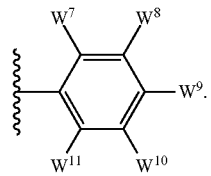

Further compounds of formula I that may be mentioned include those in which $R^{c2}$, $R^{f2}$, $R^{h2}$, $R^{j2}$, $R^{m2}$, $R^{o2}$, and $R^{u2}$ represents hydrogen; and $R^{d2}$, $R^{g2}$, $R^{i2}$, $R^{n2}$, $R^{p2}$, $R^{q2}$, $R^{t2}$ and $R^{v2}$ represents aryl optionally substituted by one or more substituents selected from $W^6$, or heteroaryl optionally substituted by one or more substituents selected from $W^6$.

Preferred compounds of formula I that may be mentioned are those where $Z^1$ represents —O$R^{q2}$ and $R^{q2}$ represents aryl optionally substituted by one or more substituents selected from $W^6$, or heteroaryl optionally substituted by one or more substituents selected from $W^6$.

More preferred compounds of formula I that may be mentioned are those where $Z^1$ represents —N($R^{f2}$)$R^{g2}$, $R^{f2}$ represents hydrogen and $R^{g2}$ represents aryl optionally substituted by one or more substituents selected from $W^6$, or heteroaryl optionally substituted by one or more substituents selected from $W^6$.

Further preferred compounds of formula I that may be mentioned are those where $Z^1$ represents —N($R^{o2}$)S(O)$_2R^{p2}$, $R^{o2}$ represents hydrogen and $R^{p2}$ represents aryl optionally substituted by one or more substituents selected from $W^6$, or heteroaryl optionally substituted by one or more substituents selected from $W^6$.

Preferred compounds of formula I where $Z^1$ represents heterocycloalkyl that may be mentioned are those where $Z^1$ represents dihydropyridinyl, imidazolinyl, oxanyl, piperazinyl, piperidinyl, pyrrolidinyl and quinuclidinyl, wherein the heterocycloalkyl is optionally substituted by one or more substituents selected from $W^5$.

Preferred compounds of formula I where $Z^1$ represents

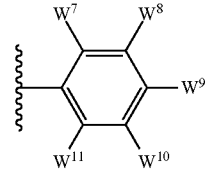

that may be mentioned are those where:
(a) each $W^8$ and $W^{10}$ are independently selected from —F, —$CH_3$, —CN, —$CF_3$, or more preferably hydrogen and $W^9$ is selected from —$R^{a3}$, —CN, —C(O)$R^{b3}$, —C(O)N($R^{c3}$)$R^{d3}$, —C(O)O$R^{e3}$, —N($R^{f3}$)$R^{g3}$, —N($R^{h3}$)C(O)$R^{i3}$, —N($R^{j3}$)C(O)O$R^{k3}$, —N($R^{l3}$)C(O)N($R^{m3}$)$R^{n3}$, —N($R^{o3}$)S(O)$_2R^{p3}$, —O$R^{q3x}$, —OC(O)$R^{r3}$, —OS(O)$_2R^{s3}$, —S(O)$_mR^{t3}$, —S(O)$_2N$($R^{u3}$)$R^{v3}$, heterocycloalkyl optionally substituted by one or more substituents selected from $G^1$, aryl optionally substituted by one or more substituents selected from $G^2$, or heteroaryl optionally substituted by one or more substituents selected from $G^2$; and
(b) each $W^9$ and $W^{10}$ are independently selected from —F, —$CH_3$, —CN, —$CF_3$, or more preferably hydrogen and $W^8$ is selected from —$R^{a3}$, —CN, —C(O)$R^{b3}$, —C(O)N($R^{c3}$)$R^{d3}$, —C(O)O$R^{e3}$, —N($R^{f3}$)$R^{g3}$, —N($R^{h3}$)C(O)$R^{i3}$, —N($R^{j3}$)C(O)O$R^{k3}$, —N($R^{l3}$)C(O)N($R^{m3}$)$R^{n3}$, —N($R^{o3}$)S(O)$_2R^{p3}$, —O$R^{q3x}$, —OC(O)$R^{r3}$, —OS(O)$_2R^{s3}$, —S(O)$_mR^{t3}$, —S(O)$_2N$($R^{u3}$)$R^{v3}$, heterocycloalkyl optionally substituted by one or more substituents selected from $G^1$, aryl optionally substituted by one or more substituents selected from $G^2$, or heteroaryl optionally substituted by one or more substituents selected from $G^2$.

For example, particular compounds of formula I that may be mentioned include those wherein $W^8$ and $W^{10}$ represents hydrogen and $W^9$ represents —F, —$CH_3$, cyclopropyl, —$CF_3$, —CN, —$NH_2$, —N($CH_3$)$_2$, —N(H)C(O)$CH_3$, —N(H)C(O)OC($CH_3$)$_3$, —$SO_2CH_3$, —$SO_2NH_2$, —S(O)$_2N$($CH_3$)$_2$, —S(O)$_2$-4-morpholinyl, 4-methylpiperazin-1-yl, 4-methylpiperidin-1-ylmethyl and 1,2,3-thiadiazol-4-yl; or $W^9$ and $W^{10}$ represents hydrogen and $W^e$ represents —F, —Cl, —CN, —$CH_3$, —$NMe_2$, —S(O)$_2NH_2$ or —S(O)$_2NMe_2$.

Preferred compounds of formula I where $Z^1$ represents heteroaryl that may be mentioned are those where $Z^1$ represents benzimidazolyl, benzodioxinyl, benzoxazolyl, imidazolyl, imidazopyridinyl, indolyl, isoquinolinyl, oxadiazolyl, oxazolyl, pyrazinyl, pyrazolyl, pyridyl, pyrrolopyridinyl, quinolinyl, thiazolyl, thiophenyl and triazolyl, wherein the heteroaryl is optionally substituted by one or more substituents selected from $W^6$.

Particularly preferred compounds of formula I where $Z^1$ represents heteroaryl that may be mentioned are those where $Z^1$ represents benzimidazol-2-yl, 1,4-benzodioxin-2-yl, benzoxazol-2-yl, imidazol-1-yl, imidazol-4-yl, imidazo[1,2-a]pyridin-2-yl, indol-3-yl, indol-5-yl, isoquinolin-4-yl, 1,3,4-oxadiazol-2-yl, 1,2-oxazol-4-yl, pyrazin-3-yl, pyrazol-1-yl, pyrazol-4-yl, pyridin-2-yl, pyridin-3-yl, pyridin-4-yl, 5H,6H,7H-pyrrolo[3,4-b]pyridin-5-yl, thiazol-5-yl, thiophen-2-yl, 1,2,3-triazol-4-yl and 1,2,4-triazol-3-yl, wherein the heteroaryl is optionally substituted by one or more substituents selected from $W^6$.

More particularly preferred compounds of formula I that may be mentioned are those where $W^6$ represents —F, —Cl, —Br, —$CH_3$, cyclopropyl, —$CF_3$, —CN, —$NH_2$, —N($CH_3$)$_2$, —$SO_2CH_3$, —$SO_2NH_2$ and —SO)$_2N$($CH_3$)$_2$.

In yet another embodiment of the invention there is provided a compound of formula I,

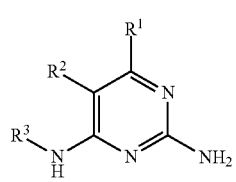

(I)

wherein:
$R^1$ represents heteroaryl connected to the pyrimidine of formula I via a carbon atom of the heteroaryl ring, which heteroaryl ring is substituted by one or more substituents selected from $Y^1$, —$C_{1-6}$alkyl optionally substituted by one or more $Y^2$ and heterocycloalkyl optionally substituted by one or more $Y^3$; or aryl represented by

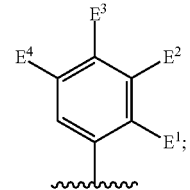

$E^1$ represents $Y^{1a}$ or —$C_{1-6}$alkyl optionally substituted by one or more $Y^2$; and at least one of $E^2$, $E^3$ and $E^4$ represents $Y^{1b}$ or —$C_{1-6}$alkyl optionally substituted by one or more $Y^2$;
$R^2$ represents hydrogen, halogen, —CN, —$C_{1-12}$alkyl optionally substituted by one or more $Z^1$, or heterocycloalkyl optionally substituted by one or more $Z^2$;
$R^3$ represents —$C_{1-12}$alkyl optionally substituted by one or more $Z^1$ or heterocycloalkyl optionally substituted by one or more $Z^2$; or
$R^2$ and $R^3$ are linked together to form, along with the atoms to which they are attached, a 5- to 8-membered non-aromatic ring, wherein the link formed by $R^2$ and $R^3$ is optionally substituted by one or more substituents selected from $Z^3$ and —$C_{1-9}$alkyl optionally substituted by one or more $Z^4$;
each $Y^1$ independently represents halogen, —CN, —C(O)$R^a$, —C(O)N($R^b$)$R^c$, —C(O)O$R^d$, —N($R^e$)$R^f$, —N($R^g$)C(O)$R^h$, —N($R^i$)C(O)O$R^j$, —N($R^k$)C(O)N($R^l$)$R^m$, —$NO_2$, —N($R^n$)S(O)$_2R^o$, —O$R^p$, —OC(O)$R^q$, —OS(O)$_2R^r$, —S(O)$_mR^s$, —S(O)$_2N$($R^t$)$R^u$, heterocycloalkyl optionally substituted by one or more substituents selected from $W^2$, aryl optionally substituted by one or more substituents selected from $W^3$ or heteroaryl optionally substituted by one or more substituents selected from $W^3$;
$Y^{1a}$ represents halogen, —CN, —C(O)$R^a$, —C(O)N($R^b$)$R^c$, —C(O)O$R^d$, —N($R^e$)$R^f$, —N($R^g$)C(O)$R^h$, —N($R^i$)C(O)O$R^j$, —N($R^k$)C(O)N($R^l$)$R^m$, —$NO_2$, —N($R^n$)S(O)$_2R^o$, —O$R^{px}$, —OC(O)$R^q$, —OS(O)$_2R^r$, —S(O)$_mR^s$, —S(O)$_2N$($R^t$)$R^u$, heterocycloalkyl optionally substituted by one or more substituents selected from $W^2$, aryl optionally substituted by one or more substituents selected from $W^3$ or heteroaryl optionally substituted by one or more substituents selected from $W^3$;
$Y^{1b}$ represents halogen, —CN, —C(O)$R^a$, —C(O)N($R^b$)$R^c$, —C(O)O$R^d$, —N($R^e$)$R^f$, —N($R^g$)C(O)$R^h$, —N($R^i$)C(O)O$R^j$, —N($R^k$)C(O)N($R^l$)$R^m$, —$NO_2$, —N($R^n$)S(O)$_2R^o$, —O$R^p$, —OC(O)$R^q$, —OS(O)$_2R^r$, —S(O)$_mR^s$, —S(O)$_2N$($R^t$)$R^u$, heterocycloalkyl optionally substituted by one or more substituents selected from $W^2$, aryl optionally substituted by one or more substituents selected from $W^3$ or heteroaryl optionally substituted by one or more substituents selected from $W^3$;
each $R^a$, $R^b$, $R^c$, $R^d$, $R^e$, $R^g$, $R^h$, $R^i$, $R^k$, $R^l$, $R^m$, $R^n$, $R^p$, $R^q$, $R^s$, $R^t$ and $R^u$ independently represents hydrogen, —$C_{1-6}$alkyl optionally substituted by one or more substituents selected from $W^1$, heterocycloalkyl optionally substituted by one or more substituents selected from $W^2$, aryl optionally substituted by one or more substituents selected from W³, or heteroaryl optionally substituted by one or more substituents selected from W³; or any two $R^b$ and $R^c$, $R^e$ and $R^f$, $R^l$ and $R^m$ and/or $R^t$ and $R^u$ are linked together to form, along with the nitrogen atom to which they are attached, a 3- to 8-membered monocyclic or bicyclic ring, which ring optionally contains one or two further heteroatoms and which ring optionally is substituted by one or more substituents selected from W², $C_{1-3}$alkyl optionally substituted by one or more substituents selected from W¹, and =O;

each $R^f$, $R^j$, $R^o$, $R^r$ and $R^{px}$ independently represents $C_{1-6}$ alkyl optionally substituted by one or more substituents selected from W¹, heterocycloalkyl optionally substituted by one or more substituents selected from W², aryl optionally substituted by one or more substituents selected from W³ or heteroaryl optionally substituted by one or more substituents selected from W³;

each Y² independently represents halogen, —CN, —C(O)$R^{b1}$, —C(O)N($R^{c1}$)$R^{d1}$, —C(O)O$R^{e1}$, —N($R^{f1}$)$R^{g1}$, —N($R^{h1}$)C(O)$R^{i1}$, —N($R^{j1}$)C(O)O$R^{k1}$, —N($R^{l1}$)C(O)N($R^{m1}$)$R^{n1}$, —N($R^{o1}$)S(O)$_2$$R^{p1}$, —O$R^{q1}$, —OC(O)$R^{r1}$, —OS(O)$_2$$R^{s1}$, —S(O)$_m$$R^{t1}$, —S(O)$_2$N($R^{u1}$)$R^{v1}$, heterocycloalkyl optionally substituted by one or more substituents selected from W¹, aryl optionally substituted by one or more substituents selected from W², heteroaryl optionally substituted by one or more substituents selected from W², or =O;

each Y³ independently represents halogen, —$R^{a1}$, —CN, —C(O)$R^{b1}$, —C(O)N($R^{c1}$)$R^{d1}$, —C(O)O$R^{e1}$, —N($R^{f1}$)$R^{g1}$, —N($R^{h1}$)C(O)$R^{i1}$, —N($R^{j1}$)C(O)O$R^{k1}$, —N($R^{l1}$)C(O)N($R^{m1}$)$R^{n1}$, —N($R^{o1}$)S(O)$_2$$R^{p1}$, —O$R^{q1}$, —OC(O)$R^{r1}$, —OS(O)$_2$$R^{s1}$, —S(O)$_m$$R^{t1}$, —S(O)$_2$N($R^{u1}$)$R^{v1}$, heterocycloalkyl optionally substituted by one or more substituents selected from W¹, aryl optionally substituted by one or more substituents selected from W², heteroaryl optionally substituted by one or more substituents selected from W², or =O;

each $R^{a1}$, $R^{b1}$, $R^{c1}$, $R^{d1}$, $R^{e1}$, $R^{f1}$, $R^{h1}$, $R^{i1}$, $R^{j1}$, $R^{l1}$, $R^{m1}$, $R^{n1}$, $R^{o1}$, $R^{q1}$, $R^{r1}$, $R^{t1}$, $R^{u1}$ and $R^{v1}$ independently represents hydrogen, $C_{1-6}$ alkyl optionally substituted by one or more substituents selected from W¹, heterocycloalkyl optionally substituted by one or more substituents selected from W², aryl optionally substituted by one or more substituents selected from W³, or heteroaryl optionally substituted by one or more substituents selected from W³; or any two $R^{c1}$ and $R^{d1}$, $R^{f1}$ and $R^{g1}$, $R^{m1}$ and $R^{n1}$ and/or $R^{u1}$ and $R^{v1}$ are linked together to form, along with the nitrogen atom to which they are attached, a 3- to 8-membered monocyclic or bicyclic ring, which ring optionally contains one or two heteroatoms and which ring optionally is substituted by one or more substituents selected from W², $C_{1-3}$alkyl optionally substituted by one or more substituents selected from W¹, and =O;

each $R^{g1}$, $R^{k1}$, $R^{p1}$ and $R^{s1}$ independently represents —$C_{1-6}$ alkyl optionally substituted by one or more substituents selected from W¹, heterocycloalkyl optionally substituted by one or more substituents selected from W², aryl optionally substituted by one or more substituents selected from W³, or heteroaryl optionally substituted by one or more substituents selected from W³;

each Z¹ independently represents halogen, —CN, —C(O)$R^{b2}$, —C(O)N($R^{c2}$)$R^{d2}$, —C(O)O$R^{e2}$, —N($R^{f2}$)$R^{g2}$, —N($R^{h2}$)C(O)$R^{i2}$, —N($R^{j2}$)C(O)O$R^{k2}$, —N($R^{l2}$)C(O)N($R^{m2}$)$R^{n2}$, —N($R^{o2}$)S(O)$_2$$R^{p2}$, —O$R^{q2}$, —OC(O)$R^{r2}$, —OS(O)$_2$$R^{s2}$, —S(O)$_m$$R^{t2}$, —S(O)$_2$N($R^{u2}$)$R^{v2}$, heterocycloalkyl optionally substituted by one or more substituents selected from W⁵, aryl represented by

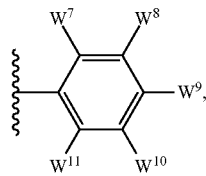

heteroaryl having 1 to 3 nitrogen atoms, one oxygen atom and/or one sulfur atom and optionally substituted by one or more substituents selected from W⁶, or =O;

each Z² and Z³ independently represents halogen, —$R^{a2}$, —CN, —C(O)$R^{b2}$, —C(O)N($R^{c2}$)$R^{d2}$, —C(O)O$R^{e2}$, —N($R^{f2}$)$R^{g2}$, —N($R^{h2}$)C(O)$R^{i2}$, —N($R^{j2}$)C(O)O$R^{k2}$, —N($R^{l2}$)C(O)N($R^{m2}$)$R^{n2}$, —N($R^{o2}$)S(O)$_2$$R^{p2}$, —O$R^{q2}$, —OC(O)$R^{r2}$, —OS(O)$_2$$R^{s2}$, —S(O)$_m$$R^{t2}$, —S(O)$_2$N($R^{u2}$)$R^{v2}$, heterocycloalkyl optionally substituted by one or more substituents selected from W⁵, aryl optionally substituted by one or more substituents selected from W⁶, or heteroaryl optionally substituted by one or more substituents selected from W⁶;

each Z⁴ independently represents halogen, —CN, —C(O)$R^{b2}$, —C(O)N($R^{c2}$)$R^{d2}$, —C(O)O$R^{e2}$, —N($R^{f2}$)$R^{g2}$, —N($R^{h2}$)C(O)$R^{i2}$, —N($R^{j2}$)C(O)O$R^{k2}$, —N($R^{l2}$)C(O)N($R^{m2}$)$R^{n2}$, —N($R^{o2}$)S(O)$_2$$R^{p2}$, —O$R^{q2}$, —OC(O)$R^{r2}$, —OS(O)$_2$$R^{s2}$, —S(O)$_m$$R^{t2}$, —S(O)$_2$N($R^{u2}$)$R^{v2}$, heterocycloalkyl optionally substituted by one or more substituents selected from W⁵, aryl optionally substituted by one or more substituents selected from W⁶, heteroaryl optionally substituted by one or more substituents selected from W⁶, or =O;

each $R^{a2}$, $R^{b2}$, $R^{c2}$, $R^{d2}$, $R^{e2}$, $R^{f2}$, $R^{h2}$, $R^{i2}$, $R^{j2}$, $R^{l2}$, $R^{m2}$, $R^{n2}$, $R^{o2}$, $R^{q2}$, $R^{r2}$, $R^{t2}$, $R^{u2}$ and $R^{v2}$ independently represents hydrogen, $C_{1-6}$ alkyl optionally substituted by one or more substituents selected from W⁴, heterocycloalkyl optionally substituted by one or more substituents selected from W⁵, aryl optionally substituted by one or more substituents selected from W⁶, or heteroaryl optionally substituted by one or more substituents selected from W⁶; or any two $R^{c2}$ and $R^{d2}$, $R^{f2}$ and $R^{g2}$, $R^{m2}$ and $R^{n2}$ and/or $R^{u2}$ and $R^{v2}$ are linked together to form, along with the nitrogen atom to which they are attached, a 3- to 8-membered monocyclic or bicyclic ring, which ring optionally contains one or two heteroatoms and which ring optionally is substituted by one or more substituents selected from W⁵, $C_{1-3}$alkyl optionally substituted by one or more substituents selected from W⁴), and =O;

each $R^{g2}$, $R^{k2}$, $R^{p2}$ and $R^{s2}$ independently represents $C_{1-6}$ alkyl optionally substituted by one or more substituents selected from W⁴, heterocycloalkyl optionally substituted by one or more substituents selected from W⁵, aryl optionally substituted by one or more substituents selected from W⁶, or heteroaryl optionally substituted by one or more substituents selected from W⁶;

each W¹ and W⁴ independently represents halogen, —CN, —N(V)$R^{g3}$, —N($R^{h3}$)C(O)$R^{i3}$, —N($R^{j3}$)C(O)O$R^{k3}$, —N($R^{l3}$)C(O)N($R^{m3}$)$R^{n3}$, —N($R^{o3}$)S(O)$_2$$R^{p3}$, —O$R^{q3}$, —OC(O)$R^{r3}$, —OS(O)$_2$$R^{s3}$, —S(O)$_m$$R^{t3}$, —S(O)$_2$N($R^{u3}$)$R^{v3}$, heterocycloalkyl optionally substituted by one or more substituents selected from G¹, aryl optionally substituted by one or more substituents selected from G², heteroaryl optionally substituted by one or more substituents selected from G², or =O;

each W², W³, W⁵ and W⁶ independently represents halogen, —$R^{a3}$, —CN, —C(O)$R^{b3}$, —C(O)N($R^{c3}$)$R^{d3}$, —C(O)O$R^{e3}$, —N($R^{f3}$)$R^{g3}$, —N($R^{h3}$)C(O)$R^{i3}$, —N($R^{j3}$)C(O)

$OR^{k3}$, $-N(R^{l3})C(O)N(R^{m3})R^{n3}$, $-N(R^{o3})S(O)_2R^{p3}$, $-OR^{q3}$, $-OC(O)R^{r3}$, $-OS(O)_2R^{s3}$, $-S(O)_mR^{t3}$, $-S(O)_2N(R^{u3})R^{v3}$, heterocycloalkyl optionally substituted by one or more substituents selected from $G^1$, aryl optionally substituted by one or more substituents selected from $G^2$, heteroaryl (optionally substituted by one or more substituents selected from $G^2$, or =O;

each $W^7$, $W^8$, $W^9$, $W^{10}$ and $W^{11}$ independently represents hydrogen, halogen, $-R^{a3}$, $-CN$, $-C(O)R^{b3}$, $-C(O)N(R^{c3})R^{d3}$, $-C(O)OR^{e3}$, $-N(R^{f3})R^{g3}$, $-N(R^{h3})C(O)R^{i3}$, $-N(R^{j3})C(O)OR^{k3}$, $-N(R^{l3})C(O)N(R^{m3})R^{n3}$, $-N(R^{o3})S(O)_2R^{p3}$, $-OR^{q3}$, $-OC(O)R^{r3}$, $-OS(O)_2R^{s3}$, $-S(O)_mR^{t3}$, $-S(O)_2N(R^{u3})R^{v3}$, heterocycloalkyl optionally substituted by one or more substituents selected from $G^1$, aryl optionally substituted by one or more substituents selected from $G^2$, or heteroaryl optionally substituted by one or more substituents selected from $G^2$;

each $R^{a3}$, $R^{b3}$, $R^{c3}$, $R^{d3}$, $R^{e3}$, $R^{f3}$, $R^{h3}$, $R^{i3}$, $R^{j3}$, $R^{l3}$, $R^{m3}$, $R^{n3}$, $R^{o3}$, $R^{q3}$, $R^{r3}$, $R^{t3}$, $R^{u3}$ and $R^{v3}$ independently represents hydrogen or $C_{1-6}$ alkyl optionally substituted by one or more $G^3$; or any two $R^{c3}$ and $R^{d3}$, $R^{f3}$ and $R^{g3}$, $R^{m3}$ and $R^{n3}$ and/or $R^{u3}$ and $R^{v3}$ are linked together to form, along with the nitrogen atom to which they are attached, a 4- to 6-membered ring, which ring optionally contains one heteroatom and which ring optionally is substituted by one or more $G^2$;

each $R^{g3}$, $R^{k3}$, $R^{p3}$, $R^{q3}$ and $R^{s3}$ independently represents $C_{1-6}$ alkyl optionally substituted by one or more $G^3$;

each $G^1$ and $G^2$ independently represents halogen, $-R^{a4}$, $-CN$, $-C(O)R^{b4}$, $-C(O)N(R^{c4})R^{d4}$, $-C(O)OR^{e4}$, $-N(R^{f4})R^{g4}$, $-N(R^{h4})C(O)R^{i4}$, $-N(R^{j4})C(O)OR^{k4}$, $-N(R^{l4})C(O)N(R^{m4})R^{n4}$, $-N(R^{o4})S(O)_2R^{p4}$, $-OR^{q4}$, $-OC(O)R^{r4}$, $-OS(O)_2R^{s4}$, $-S(O)_mR^{t4}$, $-S(O)_2N(R^{u4})R^{v4}$, or =O;

$G^3$ represents halogen, $-CN$, $-C(O)R^{b4}$, $-C(O)N(R^{c4})R^{d4}$, $-C(O)OR^{e4}$, $-N(R^{f4})R^{g4}$, $-N(R^{h4})C(O)R^{i4}$, $-N(R^{j4})C(O)OR^{k4}$, $-N(R^{l4})C(O)N(R^{m4})R^{n4}$, $-N(R^{o4})S(O)_2R^{p4}$, $-OR^{q4}$, $-OC(O)R^{r4}$, $-OS(O)_2R^{s4}$, $-S(O)_mR^{t4}$, $-S(O)_2N(R^{u4})R^{v4}$, or =O;

each $R^{a4}$, $R^{b4}$, $R^{c4}$, $R^{d4}$, $R^{e4}$, $R^{f4}$, $R^{h4}$, $R^{i4}$, $R^{j4}$, $R^{l4}$, $R^{m4}$, $R^{n4}$, $R^{o4}$, $R^{q4}$, $R^{r4}$, $R^{t4}$, $R^{u4}$ and $R^{v4}$ independently represents hydrogen or $C_{1-6}$ alkyl optionally substituted by one or more $-F$; or any two $R^{c4}$ and $R^{d4}$, $R^{f4}$ and $R^{g4}$, $R^{m4}$ and $R^{n4}$ and/or $R^{u4}$ and $R^{v4}$ are linked together to form, along with the nitrogen atom to which they are attached, a 3- to 6-membered ring, which ring optionally substituted by one or more $-F$, $-CH_3$, $-CH_2CH_3$, $-CHF_2$, $-CF_3$, $-CH_2CF_3$, or =O;

each $R^{g4}$, $R^{k4}$, $R^{p4}$ and $R^{s4}$ independently represent $C_{1-6}$ alkyl optionally substituted by one or more $-F$;

each m independently represents 0, 1 or 2;

provided that formula I does not represent $N^4$-cyclopropyl-6-(4-methoxy-2-methylphenyl)-2,4-pyrimidinediamine or a pharmaceutically acceptable salt thereof;

which compounds may be referred to herein as "the compounds of the invention".

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin. For the avoidance of doubt, solvates are also included within the scope of the invention.

Compounds of the invention may contain double bonds and may thus exist as E (entgegen) and Z (zusammen) geometric isomers about each individual double bond. All such isomers and mixtures thereof are included within the scope of the invention.

Compounds of the invention may also exhibit tautomerism. All tautomeric forms and mixtures thereof are included within the scope of the invention.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

Unless otherwise specified, $C_{1-q}$ alkyl groups (where q is the upper limit of the range) defined herein may be straight-chain or, when there is a sufficient number (i.e. a minimum of two or three, as appropriate) of carbon atoms, be branched-chain, and/or cyclic (so forming a $C_{3-q}$-cycloalkyl group). When there is a sufficient number (i.e. a minimum of four) of carbon atoms, such groups may also be part cyclic. Such alkyl groups may also be saturated or, when there is a sufficient number (i.e. a minimum of two) of carbon atoms, be unsaturated (forming, for example, a $C_{2-q}$ alkenyl or a $C_{2-q}$ alkynyl group).

Unless otherwise specified, $C_{1-q}$ alkylene groups (where q is the upper limit of the range) defined herein may (in a similar manner to the definition of $C_{1-q}$ alkyl) be straight-chain or, when there is a sufficient number (i.e. a minimum of two or three, as appropriate) of carbon atoms, be branched-chain, and/or cyclic (so forming a $C_{3-q}$-cycloalkylene group). When there is a sufficient number (i.e. a minimum of four) of carbon atoms, such groups may also be part cyclic. Such alkylene groups may also be saturated or, when there is a sufficient number (i.e. a minimum of two) of carbon atoms, be unsaturated (forming, for example, a $C_{2-q}$alkenylene or a $C_{2-q}$alkynylene group). Particular alkylene groups that may be mentioned include those that are straight-chained and saturated.

The term "halo", when used herein, includes fluoro, chloro, bromo and iodo (for example, fluoro and chloro).

Heterocycloalkyl groups that may be mentioned include non-aromatic monocyclic and bicyclic heterocycloalkyl groups (which groups may further be bridged) in which at least one (e.g. one to four) of the atoms in the ring system is other than carbon (i.e. a heteroatom), and in which the total number of atoms in the ring system is between three and twelve (e.g. between five and ten and, most preferably, between three and eight, e.g. a 5- or 6-membered heterocycloalkyl group). Further, such heterocycloalkyl groups may be saturated or unsaturated containing one or more double and/or triple bonds, forming for example a $C_{2-q}$ (e.g. $C_{4-q}$ heterocycloalkenyl (where q is the upper limit of the range) or a $C_{7-q}$ heterocycloalkynyl group. $C_{2-q}$ heterocycloalkyl groups that may be mentioned include 7-azabicyclo-[2.2.1] heptanyl, 6-azabicyclo[3.1.1]heptanyl, 6-azabicyclo[3.2.1]-octanyl, 8-azabicyclo[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo-[2.2.1]heptanyl, 6-oxabicyclo[3.2.1]-octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuryl, tetrahydropyridyl (such as 1,2,3,4-tetrahydropyridyl and 1,2,3,6-tetrahydropyridyl), thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom. Further, in the case where the substituent is another cyclic compound, then the cyclic compound may be attached through a single atom on the heterocycloalkyl group, forming a so-called "spiro"-compound. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form. At each occurrence when mentioned herein, a heterocycloalkyl group is preferably a 3- to 8-membered heterocycloalkyl group (e.g. a 5- or 6-membered heterocycloalkyl group).

The term "aryl", when used herein, includes $C_{6-14}$ (e.g. $C_{6-10}$ aromatic groups. Such groups may be monocyclic or bicyclic and, when bicyclic, be either wholly or partly aromatic. $C_{6-10}$ aryl groups that may be mentioned include phenyl, naphthyl, 1,2,3,4-tetrahydronaphthyl, indanyl, and the like (e.g. phenyl, naphthyl and the like). For the avoidance of doubt, the point of attachment of substituents on aryl groups may be via any carbon atom of the ring system.

The term "heteroaryl" (or heteroaromatic), when used herein, includes 5- to 10-membered heteroaromatic groups containing one or more heteroatoms selected from oxygen, nitrogen and/or sulfur. Such heteroaryl group may comprise one, or two rings, of which at least one is aromatic. Substituents on heteroaryl/heteroaromatic groups may, where appropriate, be located on any atom in the ring system including a heteroatom. The point of attachment of heteroaryl/heteroaromatic groups may be via any atom in the ring system including (where appropriate) a heteroatom. Bicyclic heteroaryl/heteroaromatic groups may comprise a benzene ring fused to one or more further aromatic or non-aromatic heterocyclic rings, in which instances, the point of attachment of the polycyclic heteroaryl/heteroaromatic group may be via any ring including the benzene ring or the heteroaryl/heteroaromatic or heterocycloalkyl ring. Examples of heteroaryl/heteroaromatic groups that may be mentioned include pyridinyl, pyrrolyl, furanyl, thiophenyl, oxadiazolyl, thiadiazolyl, thiazolyl, oxazolyl, pyrazolyl, triazolyl, tetrazolyl, isoxazolyl, isothiazolyl, imidazolyl, imidazopyrimidinyl, pyrimidinyl, indolyl, azaindolyl, pyrazinyl, indazolyl, pyrimidinyl, quinolinyl, isoquinolinyl, benzofuranyl, benzothiophenyl, benzoimidazolyl, benzoxazolyl, benzothiazolyl and benzotriazolyl. The oxides of heteroaryl/heteroaromatic groups are also embraced within the scope of the invention (e.g. the N-oxide). As stated above, heteroaryl includes polycyclic (e.g. bicyclic) groups in which one ring is aromatic (and the other may or may not be aromatic). Hence, other heteroaryl groups that may be mentioned include e.g. benzo[1,3]dioxolyl, benzo[1,4]dioxinyl, indolinyl, 5H,6H,7H-pyrrolo[1,2-b]pyrimidinyl, 1,2,3,4-tetra-hydroquinolinyl and the like.

Heteroatoms that may be mentioned include phosphorus, silicon, boron and, preferably, oxygen, nitrogen and sulfur.

For the avoidance of doubt, in cases in which the identity of two or more substituents in a compound of the invention may be the same, the actual identities of the respective substituents are not in any way interdependent.

For the avoidance of doubt, when $R^1$ is defined as

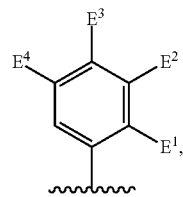

it is connected to the rest of formula I by the bond interrupted by the wiggly line, and formula I can thus be represented by

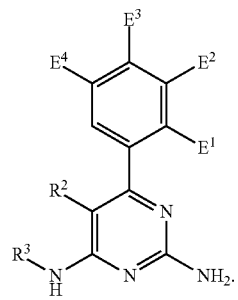

Likewise, when $R^3$ is —$C_{1-12}$ alkyl substituted by $Z^1$, and $Z^1$ is represented by

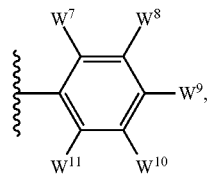

then, if e.g. $R^3$ is $C_2$alkyl, then formula I can be represented by

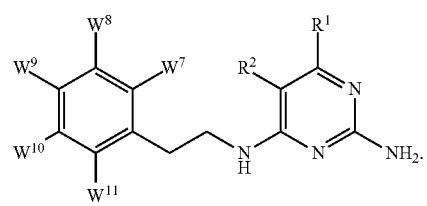

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Hence, the compounds of the invention also include deuterated compounds, i.e. in which one or more hydrogen atoms are replaced by the hydrogen isotope deuterium.

All individual features (e.g. preferred features) mentioned herein may be taken in isolation or in combination with any other feature (including preferred features) mentioned herein (hence, preferred features may be taken in conjunction with other preferred features, or independently of them).

The skilled person will appreciate that compounds of the invention that are the subject of this invention include those that are stable. That is, compounds of the invention include those that are sufficiently robust to survive isolation from e.g. a reaction mixture to a useful degree of purity.

Particular compounds of formula I that may be mentioned include those in which:
$R^2$ represents hydrogen or —$C_{1-12}$alkyl optionally substituted by one or more $Z^1$; and
$R^3$ represents —$C_{1-12}$alkyl optionally substituted by one or more $Z^1$ or heterocycloalkyl optionally substituted by one or more $Z^2$.

For example, compounds of formula I that may be mentioned include those in which $R^2$ represents methyl, or preferably, hydrogen and $R^3$ represents:
(a) —$C_{1-12}$alkyl (for example —$C_{1-6}$alkyl) optionally substituted by two, or preferably, one $Z^1$ or
(b) —$C_{2-6}$alkyl optionally substituted by two, or preferably, one $Z^1$ or heterocycloalkyl optionally substituted by two, or preferably, one $Z^2$; or
(c) —$C_{1-2}$alkyl optionally substituted with one or more —F; or
(d)

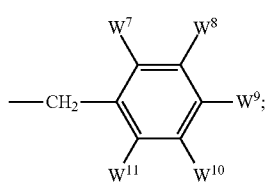

(e) —$C_{1-12}$alkyl (for example —$C_{1-6}$alkyl) substituted by heteroaryl having 1 to 3 nitrogen atoms, one oxygen atom and/or one sulfur atom and which heteroaryl is optionally substituted by one or more substituents selected from $W^3$; or
(f) a —$C_{3-6}$alkyl or a heterocycloalkyl selected from cyclopropyl, cyclobutyl, cyclopentyl, cyclohexyl, cyclopropylmethyl, cyclobutylmethyl, cyclopentylmethyl, cyclopropylethyl, cyclobutylethyl, cyclopropylpropyl, oxetanyl, tetrahydrofuryl, tetrahydropyranyl, azetidinyl, pyrrolidinyl, piperidinyl, piperazinyl or morpholinyl wherein the $C_{3-6}$alkyl is optionally substituted by two, or preferably, one $Z^1$ and the heterocycloalkyl is optionally substituted by two, or preferably, one $Z^2$.

Particular compounds of formula I that may be mentioned include those in which: $R^2$ and $R^3$ are linked together to form, along with the atoms to which they are attached, a 5- to 8-membered (e.g. a 5- to 6 membered) non-aromatic ring, wherein the link formed by $R^2$ and $R^3$ is optionally substituted by one or more substituents selected from $Z^3$ or —$C_{1-9}$alkyl optionally substituted by one or more $Z^4$.

For example, compounds of formula I that may be mentioned include those in which $R^2$ and $R^3$ are linked together to form, along with the atoms to which they are attached, a 5- to 6-membered non-aromatic ring, wherein the non-aromatic ring is:
(a) unsubstituted; or
(b) substituted by one or more substituents selected from $Z^3$; or
(c) substituted by —$C_{1-9}$alkyl optionally substituted by one or more $Z^4$; or
(d) substituted by one or more substituents selected from $Z^3$ and substituted by —$C_{1-9}$alkyl optionally substituted by one or more $Z^4$.

Particular compounds of formula I that may be mentioned include those in which:
$R^1$ represents

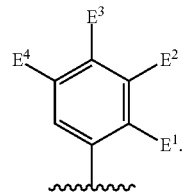

Preferred compounds of formula I that may be mentioned include those in which $E^1$ represents $Y^{1a}$ or —$C_{1-6}$alkyl optionally substituted by one or more $Y^2$; and at least one of $E^2$, $E^3$ and $E^4$ (preferably at least one of $E^2$ and $E^4$) represents $Y^{1b}$ or —$C_{1-6}$alkyl optionally substituted by one or more $Y^2$.

Particular compounds of formula I that may be mentioned include those in which $R^1$ represents heteroaryl.

Preferred compounds of formula I where $R^1$ represents heteroaryl that may be mentioned are those where $R^1$ represents benzofuranyl, benzothiophenyl, dihydrobenzofuranyl, indazolyl, indolyl, isoquinolinyl, isoxazolyl, pyridinyl, pyrrolyl and quinolinyl.

Particularly preferred compounds of formula I where $R^1$ represents heteroaryl that may be mentioned are those where $R^1$ represents benzofuran-3-yl, benzothiophen-3-yl, dihydrobenzofuran-7-yl, indol-3-yl, indol-4-yl, indol-5-yl, isoquinolin-4-yl, isoxazol-4-yl, pyridin-3-yl, pyridin-4-yl, pyrrol-2-yl and quinolin-5-yl.

For example, compounds of formula I that may be mentioned include those in which $R^1$ represents indolyl, e.g. indol-3-yl, indol-4-yl or indol-5-yl, where the indolyl is optionally substituted on the nitrogen with —$S(O)_2Ar^x$, where $Ar^x$ is aryl or heteroaryl, preferably optionally substituted phenyl, e.g. unsubstituted phenyl or phenyl substituted in the 4-position by —F, —Cl, —$CH_3$ or —$CF_3$.

Particular compounds of formula I that may be mentioned include those in which $R^1$ is represented by

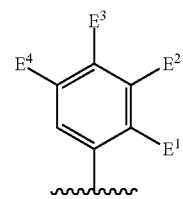

where:
E³ and E⁴ represent hydrogen; and
E¹ represents —F and E² represent —F, —Cl, —CH₃ or —CF₃; or
E¹ represents —Cl and E² represents —F, —Cl, —CH₃ or —CF₃; or
E¹ represents —CH₃ and E² represents —F, —Cl, —CH₃, —CF₃, —CN or —N(H)C(O)CH=CH₂; or
E² and E⁴ represent hydrogen; and
E¹ represents —F and E³ represents —F or phenyl; or
E¹ represents —Cl and E³ represents —F or —Cl; or
E¹ represents —CH₃ and E³ represents —Cl or —OCH₂phenyl; or
E¹ represents —OCH₃ and E³ represents —F; or
E² and E³ represent hydrogen; and
E¹ represents —F and E⁴ represents —Cl, —CH₃ or —CN; or
E¹ represents —Cl and E⁴ represent —F, —Cl, —CH₃, —CF₃ or —OCH₃; or
E¹ represents —CH₃ and E⁴ represent —F, —Cl, —CH₃, —CF₃, —CN, —N(H)C(O)CH=CH₂ or —S(O)₂(4-morpholinyl); or
E¹ represents —CF₃ and E⁴ represents —F or —CF₃; or
E¹ represents —CN and E⁴ represents —Cl; or
E¹ represents —OCH₃ and E⁴ represents —F, —Cl, Br, —CH₃, —CH(CH₃)₂, —C(CH₃)₃, —CN or —OCH₃; or
E¹ and E⁴ represent hydrogen; and
E² represents —F and E³ represents —F, —Cl, —OH or —OCH₃; or
E² represents —Cl and E³ represents —F or —C(O)(4-morpholinyl); or
E² represents —CH₃ and E³ represents —F or —OCH₃; or
E¹ represents —OCH₃ and E³ represents —OH; or
E¹ represents -CH₂OCH₃ and E³ represents (piperidin-4-yl)methoxy or ((1-tertbutoxycarbonyl)piperidin-4-yl)methoxy; or
E¹ and E³ represent hydrogen; and
E² and E⁴ represent —F; or
E² and E⁴ represent —CF₃; or
E⁴ represents hydrogen; and
E¹, E² and E³ represent —F; or
E¹ and E² represent —Cl and E³ represents —Cl, —OH or —OCH₃; or
E¹ and E² represent —CH₃ and E³ represents —F or —OCH₃; or
E² and E³ represent —Cl and E¹ represents —CH₃; or
E² represents hydrogen; and
E¹, E³ and E⁴ represent —F; or
E³ and E⁴ represent —Cl and E¹ represents —CH₃; or
E¹ and E⁴ represent —Cl and E¹ represents —OCH₃; or
E¹ and E⁴ represent —CH₃ and E³ represents —F, —CH₃ or —OCH₃; or
E¹ represents —F, E³ represents —CH₃ and E⁴ represents —Cl; or
E¹ represents —Cl, E³ represents —F and E⁴ represents —CH₃; or
E¹ represents —Cl, E³ represents —CH₃ and E⁴ represents —F; or
E¹ and E⁴ represent —CH₃ and E³ represents —F; or
E¹ represents —CH₃, E⁴ represents —Cl and E³ represents —CF₃ or —OCH₃; or
E¹ represents hydrogen; and
E² and E⁴ represent —CH₃ and E³ represents —OH; or
E³ represents hydrogen; and
E¹ and E² represent —Cl and E⁴ represents —CH₃.

Preferred particular compounds of formula I that may be mentioned include those in which R¹ is represented by

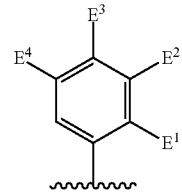

where:
E³ and E⁴ represent hydrogen; and
E¹ represents —F and E² represents —F, —Cl, or —CF₃; or
E¹ represents —Cl and E² represents —Cl, —CH₃ or —CF₃; or
E¹ represents —CH₃ and E² represents —Cl, —CH₃, —CN or —N(H)C(O)CH=CH₂; or
E² and E⁴ represent hydrogen; and
E¹ and E³ represent —F; or
E¹ represents —Cl and E³ represents —F or —Cl; or
E¹ represents —CH₃ and E³ represents —Cl; or
E² and E³ represent hydrogen; and
E¹ represents —F and E⁴ represents —Cl, —CH₃ or —CN; or
E¹ represents —Cl and E⁴ represents —F, —Cl, —CH₃ or —CF₃; or
E¹ represents —CH₃ and E⁴ represent, —Cl, —CH₃, —CF₃, —CN or —N(H)C(O)CH=CH; or
E¹ represents —CF₃ and E⁴ represents —F or —CF₃; or
E¹ represents —CN and E⁴ represents —Cl; or
E⁴ represents hydrogen; and
E¹, E² and E³ represent —F; or
E¹ and E² represent —CH₃ and E³ represents —F₃; or
E² and E³ represent —Cl and E¹ represents —CH₃; or
E² represents hydrogen; and
E¹, E³ and E⁴ represent —F; or
E³ and E⁴ represent —Cl and E¹ represents —CH₃; or
E¹ and E⁴ represent —CH₃ and E³ represents —F or —CH₃; or
E¹ represents —F, E³ represents —CH₃ and E⁴ represents —Cl; or
E¹ represents —Cl, E³ represents —F and E⁴ represents —CH₃; or
E¹ represents —Cl, E³ represents —CH₃ and E⁴ represents —F; or
E¹ and E⁴ represent —CH₃ and E³ represents —F; or
E¹ represents —CH₃, E³ represents —CF₃ and E⁴ represents —Cl; or
E¹ represents hydrogen; and
E² and E⁴ represent —CH₃ and E³ represents —OH; or
E³ represents hydrogen; and
E¹ and E² represent —Cl and E⁴ represents —CH₃.

Preferred compounds of formula I that may be mentioned include those in which:
(a) Z¹ is not present or is selected from —F, —CN, —C(O)R$^{b2}$, —C(O)N(R$^{c2}$)R$^{d2}$, —C(O)OR$^{e2}$, —N(R$^{f2}$)R$^{g2}$, —N(R$^{h2}$)C(O)R$^{i2}$, —N(R$^{j2}$)C(O)OR$^{k2}$, —N(R$^{l2}$)C(O)N(R$^{m2}$)R$^{n2}$, —N(R$^{o2}$)S(O)₂R$^{p2}$, —OR$^{q2}$, —S(O)$_m$R$^{r2}$, —S(O)₂N(R$^{u2}$)R$^{v2}$, heterocycloalkyl optionally substituted by one or more substituents selected from W⁵, aryl represented by

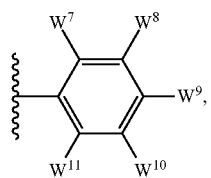

or heteroaryl having 1 to 3 nitrogen atoms, one oxygen atom and/or one sulfur atom and optionally substituted by one or more substituents selected from $W^6$; or (b) $Z^2$ is not present or is selected from —F, —$R^{a2}$, —C(O)N($R^{c2}$)$R^{d2}$, —N($R^{f2}$)$R^{g2}$, —N($R^{h2}$)C(O)$R^{i2}$, —N($R^{j2}$)C(O)O$R^{k2}$, —N($R^{l2}$)C(O)N($R^{m2}$)$R^{n2}$, —N($R^{o2}$)S(O)$_2$$R^{p2}$, —O$R^{q2}$, —S(O)$_m$$R^{r2}$, —S(O)$_2$N($R^{u2}$)$R^{v2}$, heterocycloalkyl optionally substituted by one or more substituents selected from $W^5$, aryl optionally substituted by one or more substituents selected from $W^6$, or heteroaryl optionally substituted by one or more substituents selected from $W^6$.

Other preferred compounds of formula I that may be mentioned include those in which:

(a) $Z^3$ is not present or is selected from —F, —$R^{a2}$, —C(O)N($R^{c2}$)$R^{d2}$, —N($R^{f2}$)$R^{g2}$, —N($R^{h2}$)C(O)$R^{i2}$, —N($R^{j2}$)C(O)O$R^{k2}$, —N($R^{l2}$)C(O)N($R^{m2}$)$R^{n2}$, —N($R^{o2}$)S(O)$_2$$R^{p2}$, —O$R^{q2}$, —S(O)$_m$$R^{r2}$, —S(O)$_2$N($R^{u2}$)$R^{v2}$, heterocycloalkyl optionally substituted by one or more substituents selected from $W^5$, aryl optionally substituted by one or more substituents selected from $W^6$, or heteroaryl optionally substituted by one or more substituents selected from $W^6$; and/or (b) $Z^4$ is not present or is selected from —F, —C(O)N($R^{c2}$)$R^{d2}$, —N($R^{f2}$)$R^{g2}$, —N($R^{h2}$)C(O)$R^{i2}$, —N($R^{j2}$)C(O)O$R^{k2}$, —N($R^{l2}$)C(O)N($R^{m2}$)$R^{n2}$, —N($R^{o2}$)S(O)$_2$$R^{p2}$, —O$R^{q2}$, —S(O)$_m$$R^{r2}$, —S(O)$_2$N($R^{u2}$)$R^{v2}$, heterocycloalkyl optionally substituted by one or more substituents selected from $W^5$, aryl optionally substituted by one or more substituents selected from $W^6$, or heteroaryl optionally substituted by one or more substituents selected from $W^6$.

Particularly preferred compounds of formula I that may be mentioned include those in which $Z^1$ represents —F, —CN, —C(O)NH$_2$, —C(O)N($R^{c2}$)$R^{d2}$, —C(O)-(4-morpholinyl), —C(O)OEt, —N(H)C(O)Me, —N(H)C(O)$R^{i2}$, —N(H)C(O)CH$_2$NMe$_2$, —N(H)C(O)OCMe$_3$, —N(H)C(O)OCH$_2$Ph, —N(Me)C(O)OCMe$_3$, —N(H)C(O)N(H)Me, —N(H)C(O)N(H)CHMe$_2$, —N(H)S(O)$_2$Me, —OMe, —OCF$_3$ and —OEt.

Preferred compounds of formula I where $Z^1$ represents heterocycloalkyl that may be mentioned are those where $Z^1$ represents dihydropyridinyl, imidazolinyl, morpholinyl, oxanyl, piperazinyl, piperidinyl, pyrrolidinyl and quinuclidinyl, wherein the heterocycloalkyl is optionally substituted by one or more substituents selected from $W^5$.

Preferred compounds of formula I where $Z^1$ represents

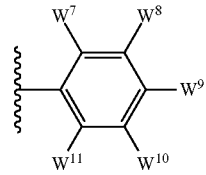

that may be mentioned are those where each $W^7$, $W^{10}$ and $W^{11}$ independently represents hydrogen, halogen, —$R^{a3}$ or —CN; and one of $W^8$ and $W^9$ represents hydrogen, halogen, —$R^{a3}$ or —CN and the other represents halogen, —$R^{a3}$, —CN, —C(O)$R^{b3}$, —C(O)N($R^{c3}$)$R^{d3}$, —C(O)O$R^{e3}$, —N($R^{f3}$)$R^{g3}$, —N($R^{h3}$)C(O)$R^{i3}$, —N($R^{j3}$)C(O)O$R^{k3}$, —N($R^{l3}$)C(O)N($R^{m3}$)$R^{n3}$, —N($R^{o3}$)S(O)$_2$$R^{p3}$, —O$R^{q3x}$, —OC(O)$R^{r3}$, —OS(O)$_2$$R^{s3}$, —S(O)$_m$$R^{t3}$, —S(O)$_2$N($R^{u3}$)$R^{v3}$, heterocycloalkyl optionally substituted by one or more substituents selected from $G^1$, aryl optionally substituted by one or more substituents selected from $G^2$, or heteroaryl optionally substituted by one or more substituents selected from $G^2$.

Particularly preferred compounds of formula I where $Z^1$ represents

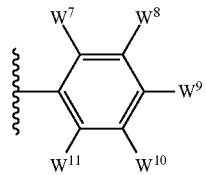

that may be mentioned are those where each $W^7$, $W^{10}$ and $W^{11}$ independently represents —F, —Cl, —CH$_3$, —CF$_3$, or more preferably, hydrogen; and one of $W^8$ and $W^9$ (preferably $W^8$) represents —F, —Cl, —CH$_3$, —CF$_3$, or more preferably, hydrogen, and the other (preferably $W^9$) represents halogen, —$R^{a3}$, —CN, —C(O)$R^{b3}$, —C(O)N($R^{c3}$)$R^{d3}$, —C(O)O$R^{e3}$, —N($R^{f3}$)$R^{g3}$, —N($R^{h3}$)C(O)$R^{i3}$, —N($R^{j3}$)C(O)O$R^{k3}$, —N($R^{l3}$)C(O)N($R^{m3}$)$R^{n3}$, —N($R^{o3}$)S(O)$_2$$R^{p3}$, —O$R^{q3x}$, —OC(O)$R^{r3}$, —OS(O)$_2$$R^{s3}$, —S(O)$_m$$R^{t3}$, —S(O)$_2$N($R^{u3}$)$R^{v3}$, heterocycloalkyl optionally substituted by one or more substituents selected from $G^1$, aryl optionally substituted by one or more substituents selected from $G^2$, or heteroaryl optionally substituted by one or more substituents selected from $G^2$.

For example, particular compounds of formula I that may be mentioned include those wherein:

(a) $W^8$, $W^9$, $W^{10}$ and $W^{11}$ represents hydrogen and $W^7$ represents —Cl or —S(O)$_2$CH$_3$; or (b) $W^7$, $W^9$, $W^{10}$ and $W^{11}$ represents hydrogen and $W^8$ represents —F, —Br, —CN, —N(H)C(O)CH$_3$, —OCH$_3$ or —S(O)$_2$CH$_3$; or (a) $W^7$, $W^{10}$ and $W^{11}$ represents hydrogen and:
  $W^8$ and $W^9$ represents —F or —Cl; or
  (ii) $W^8$ represents —F and $W^9$ represents —CH$_3$.

More particularly preferred compounds of formula I where $Z^1$ represents

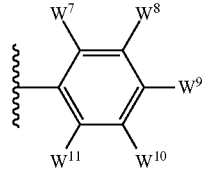

that may be mentioned are those where $W^7$, $W^8$, $W^{10}$ and $W^{11}$ are hydrogen and $W^9$ represents halogen, —$R^{a3}$, —CN, —C(O)$R^{b3}$, —C(O)N($R^{c3}$)$R^{d3}$, —C(O)O$R^{e3}$, —N($R^{f3}$)$R^{g3}$, —N($R^{h3}$)C(O)$R^{i3}$, —N($R^{j3}$)C(O)O$R^{k3}$, —N($R^{j3}$)C(O)N($R^{m3}$)$R^{n3}$, —N($R^{o3}$)S(O)$_2$$R^{p3}$, —O$R^{q3x}$, —S(O)$_m$$R^{t3}$, —S(O)$_2$N(R$^{u3}$)R$^{v3}$, heterocycloalkyl optionally substituted by one or more substituents selected from G$^1$, aryl optionally substituted by one or more substituents selected from G$^2$, or heteroaryl optionally substituted by one or more substituents selected from G$^2$.

For example, more particularly preferred compounds of formula I that may be mentioned are those where W$^7$, W$^8$, W$^{10}$ and W$^{11}$ are hydrogen and W$^9$ represents —F, —Cl, —CH$_3$, cyclopropyl, —CF$_3$, —CN, —NH$_2$, —N(CH$_3$)$_2$, —N(H)C(O)CH$_3$, —N(H)C(O)OC(CH$_3$)$_3$, —SO$_2$CH$_3$, —SO$_2$NH$_2$, —S(O)$_2$N(CH$_3$)$_2$, —S(O)$_2$-4-morpholinyl, 4-methylpiperazin-1-yl, 4-methylpiperidin-1-ylmethyl and 1,2,3-thiadiazol-4-yl.

Preferred compounds of formula I where Z$^1$ represents heteroaryl that may be mentioned are those where Z$^1$ represents benzimidazolyl, benzodioxinyl, benzoxazolyl, furanyl, imidazolyl, imidazopyridinyl, indolyl, isoquinolinyl, oxadiazolyl, oxazolyl, pyrazinyl, pyrazolyl, pyridyl, pyrrolopyridinyl, quinolinyl, thiazolyl, thiophenyl and triazolyl, wherein the heteroaryl is optionally substituted by one or more substituents selected from W$^6$.

Particularly preferred compounds of formula I where Z$^1$ represents heteroaryl that may be mentioned are those where Z$^1$ represents benzimidazol-2-yl, 1,4-benzodioxin-2-yl, benzoxazol-2-yl, furan-2-yl, imidazol-1-yl, imidazol-4-yl, imidazo-[1,2-a]pyridin-2-yl, indol-3-yl, indol-5-yl, isoquinolin-4-yl, 1,3,4-oxadiazol-2-yl, 1,2-oxazol-4-yl, pyrazin-3-yl, pyrazol-1-yl, pyrazol-4-yl, pyridin-2-yl, pyridin-3-yl, pyridin-4-yl, 5H,6H,7H-pyrrolo[3,4-b]pyridin-5-yl, thiazol-5-yl, thiophen-2-yl, 1,2,3-triazol-4-yl and 1,2,4-triazol-3-yl, wherein the heteroaryl is optionally substituted by one or more substituents selected from W$^6$.

More particularly preferred compounds of formula I that may be mentioned are those where W$^6$ represents —F, —Cl, —Br, —CH$_3$, cyclopropyl, —CF$_3$, —CN, —NH$_2$, —N(CH$_3$)$_2$, —SO$_2$CH$_3$, —SO$_2$NH$_2$ and —SO)$_2$N(CH$_3$)$_2$.

In one embodiment, the compound according to the invention is selected from the compounds of Examples 1-454

As discussed hereinbefore, compounds of the invention are indicated as pharmaceuticals. According to a further aspect of the invention there is provided a compound of the invention, as hereinbefore defined, for use as a pharmaceutical.

In another aspect of the invention the use of a compound of the invention, as hereinbefore defined, is provided for the manufacture of a medicament for the treatment of cancer.

Although compounds of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the "active" compounds to which they are metabolised) may therefore be described as "prodrugs" of compounds of the invention.

By "prodrug of a compound of the invention", we include compounds that form a compound of the invention, in an experimentally-detectable amount, within a predetermined time, following enteral or parenteral administration (e.g. oral or parenteral administration). All prodrugs of the compounds of the invention are included within the scope of the invention.

Furthermore, certain compounds of the invention may possess no or minimal pharmacological activity as such, but may be administered parenterally or orally, and thereafter be metabolised in the body to form compounds of the invention that possess pharmacological activity as such. Such compounds (which also includes compounds that may possess some pharmacological activity, but that activity is appreciably lower than that of the "active" compounds of the invention to which they are metabolised), may also be described as "prodrugs".

Thus, the compounds of the invention are useful because they possess pharmacological activity, and/or are metabolised in the body following oral or parenteral administration to form compounds, which possess pharmacological activity.

It is stated herein that the compounds of the invention may be useful in the treatment of cancer. For the purposes of this specification, and for the avoidance of doubt, the term "treatment" includes treatment per se, prevention and prophylaxis.

In an alternative embodiment, compounds of the invention may be useful in the the treatment of cancer.

Preferably the cancer is selected from the group comprising: Soft Tissue Cancers: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood and bone marrow (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Kaposi's sarcoma, moles dysplastic nevi, lipoma, angioma, dermatofibroma, keloids; neurofibromatosis and Adrenal glands: neuroblastoma. The term "cancerous cell" as provided herein, includes a cell afflicted by any one of the above identified conditions.

In certain embodiments of the present invention, the cancer is a solid tumor cancer.

In certain embodiments of the present invention, the cancer is selected from pancreatic cancer, ovarian cancer and colorectal cancer.

In certain embodiments of the present invention, the cancer is selected from colorectal cancer (including Ras mutations), small cell lung cancer, non-small cell lung cancer, and glioma.

In certain embodiments of the present invention, the cancer is selected from non-small cell lung cancer, ovarian cancer, metastatic breast cancer, pancreatic cancer, hepatobiliary cancer (including hepatocellular cancer, bile duct cancer and cholangiocarcinoma), and gastric cancer.

In certain embodiments of the present invention, the cancer is selected from colorectal cancer (including Ras mutations), small cell lung cancer, non-small cell lung cancer, ovarian cancer, hepatobiliary cancer (including hepatocellular cancer, bile duct cancer and cholangiocarcinoma), gastric cancer, testicular cancer, and head and neck squamous cell carcinoma.

In certain embodiments of the present invention, the cancer is selected from leukemia (including acute myeloid leukemia, acute lymphoblastic leukemia, chronic myeloid leukemia, and chronic lymphoid leukemia), lymphoma (including mantle cell lymphoma, Hodgkin's lymphoma and non-Hodgkin's lymphoma), and prostate cancer Compounds of the invention will normally be administered orally, intravenously, subcutaneously, buccally, rectally, dermally, nasally, tracheally, bronchially, sublingually, intranasally, topically, by any other parenteral route or via inhalation, in a pharmaceutically acceptable dosage form.

Compounds of the invention may be administered alone, but are preferably administered by way of known pharmaceutical compositions/formulations, including tablets, capsules or elixirs for oral administration, suppositories for rectal administration, sterile solutions or suspensions for parenteral or intramuscular administration, and the like.

Compounds of the invention (i.e. compounds that inhibit MTH1) may be administered in the form of tablets or capsules, e.g., time-release capsules that are taken orally. Alternatively, the compounds of the invention may be in a liquid form and may be taken orally or by injection. The compounds of the invention may also be in the form of suppositories, or, creams, gels, and foams e.g. that can be applied to the skin. In addition, they may be in the form of an inhalant that is applied nasally.

Such compositions/formulations may be prepared in accordance with standard and/or accepted pharmaceutical practice.

According to a further aspect of the invention there is thus provided a pharmaceutical composition/formulation including a compound of the invention, as hereinbefore defined, optionally in admixture with a pharmaceutically acceptable adjuvant, diluent and/or carrier. Such compositions/formulations may be of use in the treatment, prevention and/or prophylaxis of cancer and diseases which benefit by inhibition of MTH1.

Depending on e.g. potency and physical characteristics of the compound of the invention (i.e. active ingredient), pharmaceutical formulations that may be mentioned include those in which the active ingredient is present in at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The invention further provides a process for the preparation of a pharmaceutical formulation, as hereinbefore defined, which process comprises bringing into association a compound of the invention, as hereinbefore defined, or a pharmaceutically acceptable salt thereof with a pharmaceutically-acceptable adjuvant, diluent or carrier.

In yet another aspect the present invention provides methods for the treatment of cancer comprising administering a therapeutically effective amount of a compound of the invention to a subject (e.g. patient) in need of such treatment.

"Patients" include mammalian (including human) patients.

The term "effective amount" refers to an amount of a compound, which confers a therapeutic effect on the treated patient. The effect may be objective (i.e. measurable by some test or marker) or subjective (i.e. the subject gives an indication of or feels an effect).

Compounds of the invention may also be combined with other therapeutic agents that are useful in the treatment of cancer.

According to a further aspect of the invention, there is provided a combination product comprising:

(A) a compound of the invention, as hereinbefore defined; and (B) another therapeutic agent that is useful in the in the treatment of cancer, wherein each of components (A) and (B) is formulated in admixture with a pharmaceutically-acceptable adjuvant, diluent or carrier.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:

(1) a pharmaceutical formulation including a compound of the invention, as hereinbefore defined, another therapeutic agent that is useful in the treatment of cancer, and a pharmaceutically-acceptable adjuvant, diluent or carrier; and (2) a kit of parts comprising components:

(a) a pharmaceutical formulation including a compound of the invention, as hereinbefore defined, in admixture with a pharmaceutically-acceptable adjuvant, diluent or carrier; and (b) a pharmaceutical formulation including another therapeutic agent that is useful in the treatment of cancer in admixture with a pharmaceutically-acceptable adjuvant, diluent or carrier, which components (a) and (b) are each provided in a form that is suitable for administration in conjunction with the other.

The invention further provides a process for the preparation of a combination product as hereinbefore defined, which process comprises bringing into association a compound of the invention, as hereinbefore defined, or a pharmaceutically acceptable salt thereof with the other therapeutic agent that is useful in the treatment of cancer, and at least one pharmaceutically-acceptable adjuvant, diluent or carrier.

By "bringing into association", we mean that the two components are rendered suitable for administration in conjunction with each other.

Thus, in relation to the process for the preparation of a kit of parts as hereinbefore defined, by bringing the two components "into association with" each other, we include that the two components of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Compounds of the invention may be administered at varying doses. Oral, pulmonary and topical dosages (and subcutaneous dosages, although these dosages may be relatively lower) may range from between about 0.01 mg/kg of body weight per day (mg/kg/day) to about 100 mg/kg/day, preferably about 0.01 to about 10 mg/kg/day, and more preferably about 0.1 to about 5.0 mg/kg/day. For e.g. oral administration, the compositions typically contain between about 0.01 mg to about 2000 mg, for example between about 0.1 mg to about 500 mg, or between 1 mg to about 100 mg, of the active ingredient. Intravenously, the most preferred doses will range from about 0.001 to about 10 mg/kg/hour during constant rate infusion. Advantageously, compounds may be administered in a single daily dose, or the total daily dosage may be administered in divided doses of two, three or four times daily.

In any event, the physician, or the skilled person, will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. The above-mentioned dosages are exemplary of the average case; there can, of course, be individual instances where higher or lower dosage ranges are merited, and such are within the scope of this invention.

Compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise. In particular, compounds of the invention may have the advantage that they are more efficacious and/or exhibit advantageous properties in vivo.

It is contemplated that any method or composition described herein can be implemented with respect to any other method or composition described herein.

Unless otherwise defined, all technical and scientific terms used herein have the same meaning as commonly understood by one of ordinary skill in the art to which this invention pertains.

EXAMPLES

The invention is illustrated by way of the following examples, in which the following abbreviations may be employed.
aq aqueous
DMF dimethylformamide
DMSO dimethyl sulfoxide
EtOAc ethyl acetate
EtOH ethanol
MeOH methanol
MeCN acetonitrile
Pd—C palladium on carbon
sat. saturated
TFA trifluoroacetic acid
THF tetrahydrofuran
min. minutes
h. hours
Hunigs base N,N-diisopropylethylamine
DCM dichloromethane
n-BuOH butan-1-ol
iPrOH propan-2-ol
NEt$_3$ triethylamine
Boc tert-butoxycarbonyl
HATU (1-[Bis(dimethylamino)methylene]-1H-1,2,3-triazolo-[4,5-b]pyridinium 3-oxid hexafluorophosphate
NMP N-methylpyrrolidine
LCMS liquid-chromatography electrospray mass spectroscopy
NMR nuclear magnetic resonance
NCS N-chlorosuccinimide
Pd(PPh$_3$)$_4$ tetrakis(triphenylphosphine)palladium (0)
B(OMe)$_3$ trimethylborate
n-BuLi n-butyl lithium
MeI iodomethane
NaOMe sodium methoxide
CHCl$_3$ chloroform
MgSO$_4$ anhydrous magnesium sulphate
K$_2$CO$_3$ anhydrous potassium carbonate
NH$_4$OH ammonium hydroxide
Ac$_2$O acetic anhydride
POCl$_3$ phosphorus oxychloride Starting materials and chemical reagents specified in the syntheses described below are commercially available, e.g. from Sigma-Aldrich, Fine Chemicals Combi-Blocks and other vendors.

In the event that there is a discrepancy between nomenclature and any compounds depicted graphically, then it is the latter that presides (unless contradicted by any experimental details that may be given or unless it is clear from the context). Final compounds were named using Marvin software version 6.1.

Purification of compounds may be carried out using silica gel column chromatography or preparative reverse phase HPLC (ACE column, acidic gradients with MeCN—H$_2$O containing 0.1% TFA or XBridge column, basic gradients using MeCN—H$_2$O containing ammonium bicarbonate) to give the products as their free bases or trifluoroacetic acid salts.

Intermediate 1

(7-chloro-2H-1,3-benzodioxol-5-yl)boronic Acid

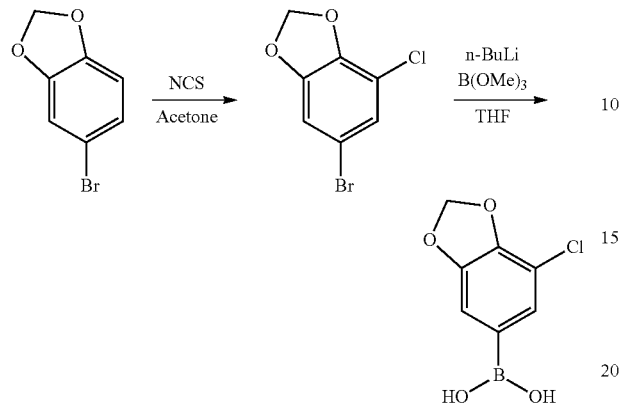

Step 1: 6-bromo-4-chloro-2H-1,3-benzodioxole:

To a solution of 5-bromo-2H-1,3-benzodioxole (60 µL, 0.50 mmol, 1 eq.) in acetonitrile (1 mL) was added 1-chloropyrrolidine-2,5-dione (73 mg, 0.55 mmol, 1.1 eq.). The reaction was stirred overnight at room temperature. After completion of the reaction, the reaction mixture was concentrated and purified by column chromatography (Heptane/EtOAc 100%→5:1) to afford the desired product as a colourless solid (104 mg, 89%). LCMS [M+H]$^+$ 234; $^1$H NMR (400 MHz, CD$_3$OD) $\delta_H$ 7.05 (1H, s), 6.93 (1H, s), 2.78 (2H, s).

Step 2: (7-chloro-2H-1,3-benzodioxol-5-yl)boronic Acid:

To a solution of 6-bromo-4-chloro-2H-1,3-benzodioxole (104 mg, 0.44 mmol, 1 eq.) in THF (5.8 mL) was added, at −78° C., n-BuLi (2.5 M in hexanes, 265 µL, 0.66 mmol, 1.5 eq.). The reaction mixture was stirred at this temperature for 30 min, before addition of B(OMe)$_3$ (248 µL, 2.21 mmol, 5 eq.). The reaction was slowly allowed to warm up to rt, 2N HCl was added, and stirring was continued for 1 h. The reaction mixture was extracted with EtOAc, and the organic layer was dried over MgSO$_4$ and evaporated under reduced pressure. The crude product was purified by column chromatography (Pentane/EtOAc 100%→3:1) to afford the desired product as a white solid (22 mg, 25%). LCMS [M+H]$^+$ 201; $^1$H NMR (400 MHz, DMSO-d$_6$) $\delta_H$ 7.34 (1H, s), 6.81 (1H, s), 5.99 (2H, s).

Intermediate 2

2,3-dichloro-4-(tetramethyl-1,3,2-dioxaborolan-2-yl)phenol

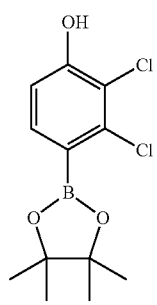

To a solution of 4-bromo-2,3-dichlorophenol (250 mg, 1.03 mmol, 1 eq.) in THF (10 mL) was added, at −78° C., n-BuLi (2.5 M in hexanes, 1.25 mL, 3.10 mmol, 3 eq.). The reaction mixture was stirred at this temperature for 30 min, before addition of 2-isopropoxy-4,4,5,5-tetramethyl-1,3,2-dioxaborolane (316 µL, 1.55 mmol, 1.5 eq.). The reaction was slowly allowed to warm up to rt, 2N HCl was added, and stirring was continued for 1 h. The reaction mixture was extracted with EtOAc, and the organic layer was dried over MgSO$_4$ and evaporated under reduced pressure. The crude product was purified by column chromatography (Pentane/EtOAc 100%→4:1) to afford the desired product as a white solid (102 mg, 34%). LCMS [M+H]$^+$ 289; $^1$H NMR (400 MHz, CD$_3$OD) $\delta_H$ 7.47 (1H, d, J=8.1 Hz), 6.85 (1H, d, J=8.1 Hz), 1.36 (12H, s).

Intermediate 3

(2,3-dichloro-4-methoxyphenyl)boronic Acid

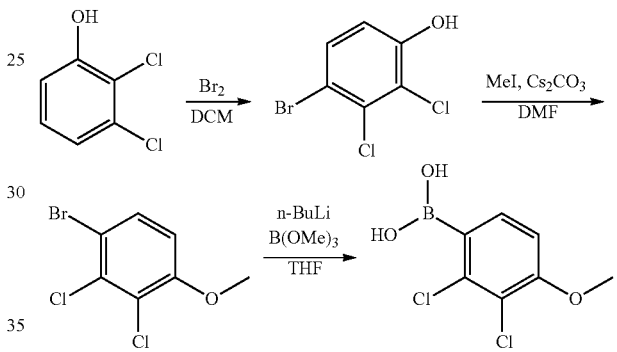

Step 1: 4-Bromo-2,3-dichlorophenol.

To a solution of 2,3-dichlorophenol (1.0 g, 6.13 mmol, 1 eq.) in DCM (4 mL) was added, at 0° C., bromine (348 µL, 6.75 mmol, 1.1 eq.) over 15 min. The reaction was allowed to warm up to rt over 12 hours. NMR showed unreacted starting material, bromine (0.33 eq.) was added at 0° C. and the reaction was allowed to warm up to rt over 12 hours. The reaction was stopped by addition of Na$_2$S$_2$O$_3$, the organic layer was washed with brine, dried with MgSO$_4$ and concentrated under reduced pressure. The crude product was purified by column chromatography (Pentane/EtOAc 100%→25:1) to afford the desired product as a white solid (685 mg, 46%). LCMS [M+H]$^+$ 239; $^1$H NMR (400 MHz, DMSO-d$_6$) $\delta_H$ 10.98 (1H, s), 7.54 (1H, d, J=8.8 Hz), 6.91 (1H, d, J=8.8 Hz).

Step 2: 1-Bromo-2,3-dichloro-4-methoxybenzene.

To a solution of 4-bromo-2,3-dichlorophenol (200 mg, 0.83 mmol, 1 eq.) in DMF (3 mL) was added Cs$_2$CO$_3$ (538 mg, 1.65 mmol, 2 eq.) followed by iodomethane (208 µL, 3.3 mmol, 4 eq.). The reaction mixture was stirred at 70° C. for 3 h. The reaction was stopped by addition of H$_2$O, extracted with DCM, dried with MgSO$_4$ and concentrated under reduced pressure. The crude product was purified by column chromatography (Pentane/EtOAc 100%→20:1) to afford the desired product as a white solid (190 mg, 89%). LCMS [M+H]$^+$ 256; $^1$H NMR (400 MHz, CDCl$_3$) $\delta_H$ 7.47 (1H, d, J=9.0 Hz), 6.73 (1H, d, J=8.8 Hz), 3.88 (3H, s).

Step 3: (2,3-dichloro-4-methoxyphenyl)boronic Acid.

To a solution of 1-bromo-2,3-dichloro-4-methoxybenzene (100 mg, 0.39 mmol, 1 eq.) in THF (5 mL) was added, at −78° C., n-BuLi (2.5 M in hexanes, 234 μL, 0.59 mmol, 1.5 eq.). The reaction mixture was stirred at this temperature for 30 min, before addition of B(OMe)$_3$ (218 μL, 1.95 mmol, 5 eq.). The reaction was slowly allowed to warm up to rt, 2N HCl was added, and stirring was continued for 1 h. The reaction mixture was extracted with EtOAc, and the organic layer was dried over MgSO$_4$ and evaporated under reduced pressure. The crude product was purified by column chromatography (Pentane/EtOAc 100%→3:1) to afford the desired product as a white solid (52 mg, 59%). LCMS [M+H]$^+$ 221; $^1$H NMR (400 MHz, DMSO-d$_6$) δ$_H$ 8.25 (1H, s), 7.35 (1H, d, J=8.1 Hz), 7.10 (1H, d, J=8.1 Hz), 3.87 (3H, s).

Intermediate 4

(2,3-dichloro-5-methoxyphenyl)boronic Acid

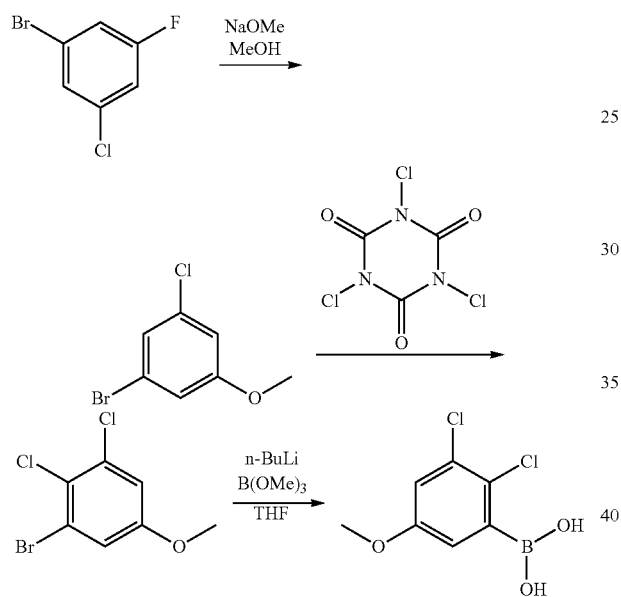

Step 1: 1-Bromo-3-chloro-5-methoxybenzene.

1-Bromo-3-chloro-5-fluorobenzene (1 g, 4.77 mmol, 1 eq.) was treated at 0° C. with sodium methoxide (25% in MeOH, 1.2 mL, 5.71 mmol, 1.2 eq.). The reaction mixture was stirred at 100° C. for 3 h. The solution was concentrated under reduced pressure, the crude product was extracted with DCM, washed with H$_2$O, brine, dried over MgSO$_4$ and concentrated. The product was obtained as a white solid (747 mg, 71%). LCMS [M+H]$^+$ 220; $^1$H NMR (400 MHz, CD$_3$Cl) δ$_H$ 7.09 (1H, t, J=1.7 Hz), 6.94-6.92 (1H, m), 6.83-6.80 (1H, m), 3.77 (3H, s).

Step 2: 1-Bromo-2,3-dichloro-5-methoxybenzene.

To a solution of 1-bromo-3-chloro-5-methoxybenzene (300 mg, 1.35 mmol, 1 eq.) in DMF (5 mL) was added trichloro-1,3,5-triazinane-2,4,6-trione (115 mg, 0.49 mmol, 0.36 eq.) and the reaction was stirred at 50° C. for 3 h. The reaction mixture was concentrated and the crude product was purified by column chromatography (Heptane/EtOAc 100%→20:1) to afford the desired product as a white solid (253 mg, 73%). LCMS [M+H]$^+$ 254; $^1$H NMR (400 MHz, CD$_3$Cl) δ$_H$ 7.09 (1H, d, J=3.0 Hz), 6.97 (1H, d, J=3.0 Hz), 3.77 (3H, s).

Step 3: (2,3-dichloro-5-methoxyphenyl)boronic Acid.

To a solution of 1-bromo-2,3-dichloro-5-methoxybenzene (87 mg, 0.34 mmol, 1 eq.) in THF (4.5 mL) was added, at −78° C., n-BuLi (2.5 M in hexanes, 205 μL, 0.51 mmol, 1.5 eq.). The reaction mixture was stirred at this temperature for 30 min, before addition of B(OMe)$_3$ (191 μL, 1.70 mmol, 5 eq.). The reaction was slowly allowed to warm up to rt, 2N HCl was added, and stirring was continued for 1 h. The reaction mixture was extracted with EtOAc, and the organic layer was dried over MgSO$_4$ and evaporated under reduced pressure to afford the desired product as a white solid (75 mg, 100%). LCMS [M+H]$^+$ 221.

Intermediate 5

4-chloro-5H,6H,7H,8H-pyrido[2,3-d]pyrimidin-2-amine

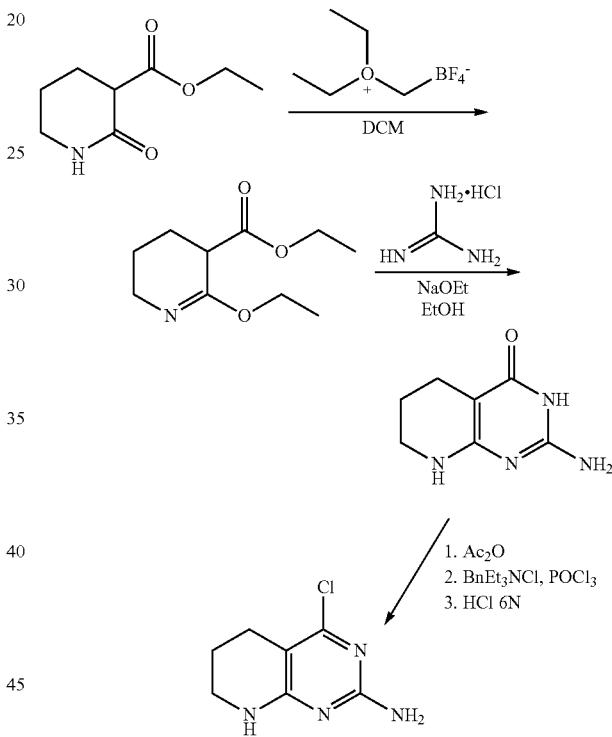

Step 1: ethyl 2-ethoxy-3,4,5,6-tetrahydropyridine-3-carboxylate.

To a solution of ethyl 2-oxopiperidine-3-carboxylate (1.5 g, 8.76 mmol, 1 eq.) in DCM (6.5 mL) under N$_2$ was added a solution of triethyloxonium tetrafluoroborate (2.0 g, 10.51 mmol, 1.2 eq.) in DCM (6.5 mL). The reaction mixture was stirred at room temperature overnight. The solution was poured in water (5 mL) and allowed to stand for 30 min. The organic layer was washed with NaHCO$_3$, H$_2$O, dried over Na$_2$SO$_4$ and concentrated under reduced pressure to afford the desired product as a colourless oil (1.2 g, 66%). $^1$H NMR (400 MHz, CDCl$_3$) δ$_H$ 4.15 (2H, q, J=7.2 Hz), 4.00-3.98 (2H, m), 3.46-3.44 (2H, m), 3.18-3.16 (1H, m), 1.97-1.95 (2H, m), 1.68-1.66 (1H, m), 1.49-1.47 (1H, m), 1.25 (3H, t, J=7.1 Hz), 1.20 (3H, t, J=7.0 Hz).

Step 2: 2-amino-3H,4H,5H,6H,7H,8H-pyrido[2,3-d]pyrimidin-4-one.

A solution of sodium ethoxide (21% in EtOH, 197 μL, 2.51 mmol, 2.5 eq.) was added to the mixture of ethyl 2-ethoxy-3,4,5,6-tetrahydropyridine-3-carboxylate (200 mg, 1 mmol, 1 eq.) and guanidine hydrochloride (96 mg, 1 mmol, 1 eq.) in EtOH (2 mL). The reaction mixture was stirred a reflux overnight. The solvent were removed under vacuum and the obtained solid was dried to afford the desired product as a light yellow solid (116 mg, 70% yield). $^1$H NMR (400 MHz, CDCl$_3$) $\delta_H$ 9.89 (1H, br s), 6.18 (1H, br s), 6.10 (2H, br s), 3.10-3.08 (2H, m), 2.20-2.18 (2H, m), 1.61-1.59 (2H, m).

Step 3: 4-chloro-5H,6H,7H,8H-pyrido[2,3-d]pyrimidin-2-amine.

A mixture of 2-amino-5,6,7,8-tetrahydropyrido[2,3-d]pyrimidin-4(3H)-one and acetic anhydride was heated at reflux for 1 h until completion of the reaction as monitored by LCMS. The solvent was removed under reduced pressure and the obtained residue was treated with benzyltriethylammonium chloride (547 mg, 2.4 mmol, 2 eq.) and POCl$_3$ (671 μL, 7.2 mmol, 6 eq.) and heated at reflux for 1 h. After evaporation of the solvents, ice water was added to the residue and HCl (6N, 5.5 mL) was added. The reaction mixture was heated at 50° C. overnight. After evaporation of the solvents, the residue is diluted in EtOAc and washed with NaHCO$_3$, brine and dried over Na$_2$SO$_4$. The combined organic layers were then evaporated, and the crude product was purified by column chromatography (DCM/MeOH 98/2 200 mL, 95/5 100 mL). The pure product was obtained as a yellow powder (45 mg, 20%). LCMS [M+H]$^+$ 185. $^1$H NMR (400 MHz, CDCl$_3$) $\delta_H$ 8.09-8.03 (1H, br s), 3.28-3.26 (2H, m), 2.53-2.51 (2H, m), 1.81-1.79 (2H, m).

Intermediate 6

4-chloro-6-phenylpyrimidin-2-amine

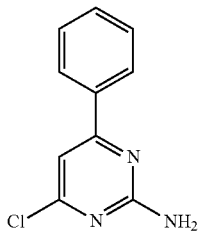 [SMILES: Nc1nc(Cl)cc(-c2ccccc2)n1]

A mixture of 2-amino-4,6-dichloropyrimidine (3 g, 18.29 mmol, 1 eq.), phenylboronic acid (2.45 g, 20.12 mmol, 1.1 eq.), K$_2$CO$_3$ (5.06 g, 36.6 mmol, 2 eq.) and Pd(PPh$_3$)$_4$ (700 mg, 0.6 mmol, 0.03 eq.) in 1,4-dioxane (15 mL) and water (1 mL) was heated in a sealed tube at 95° C. for 12 h. The mixture was run through a plug of silica using EtOAc as eluent, concentrated and purified by column chromatography (1:4 EtOAc/pentane) to give the desired product as a white solid (2.2 g, 60%). LCMS [M+H]$^+$ 206; $^1$H NMR (400 MHz, CDCl$_3$) $\delta_H$ 8.27-8.20 (2H, m), 8.16-8.05 (3H, m), 7.19 (2H, s), 6.76 (1H, s).

Intermediate 7

6-chloro-4-N-propylpyrimidine-2,4-diamine

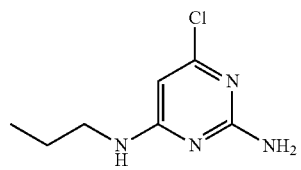

A solution of 4,6-dichloropyrimidin-2-amine (820 mg, 5.0 mmol, 1 eq.) in EtOH (40 mL) was treated with propan-1-amine (5.0 ml). The reaction mixture was stirred at 85° C. for 48 h. The mixture was cooled, concentrated by evaporation then flash-chromatographed over silica to afford the product as a colorless solid (705 mg; 76%). LCMS [M+H]$^+$ 187.

Intermediate 8

4-N-tert-butyl-6-chloropyrimidine-2,4-diamine

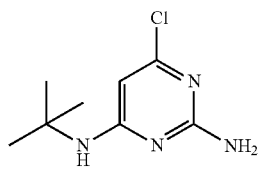

To a solution of 4,6-dichloropyrimidin-2-amine (820 mg, 5.0 mmol, 1 eq.) in n-BuOH (20 mL) was added tert-butylamine (365 mg, 5.0 mmol, 1 eq.) and Hünig's base (645 mg, 5.0 mmol, 1 eq.). The reaction mixture was stirred overnight at 95° C. The mixture was cooled and some unreacted starting material removed by filtration. The filtrate was concentrated and the residue flash-chromatographed over silica to afford the product (0.27 g; 27%). LCMS [M+H]$^+$ 201.

Intermediate 9

6-chloro-4-N-(oxan-4-yl)pyrimidine-2,4-diamine

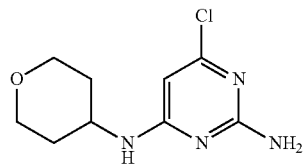 [SMILES: Nc1nc(Cl)cc(NC2CCOCC2)n1]

To a solution of 4,6-dichloropyrimidin-2-amine (492 mg, 3.0 mmol, 1 eq.) in n-BuOH (20 mL) was added tetrahydro-2H-pyran-4-amine (303 mg, 3.0 mmol, 1 eq.) and Hünig's base (387 mg, 3.0 mmol, 1 eq.). The reaction mixture was stirred overnight at 95° C. The mixture was cooled the precipitated solid was collected and washed with water to give the product (0.42 g; 37%). LCMS [M+H]$^+$ 229.

Intermediate 10

6-chloro-4-N-cyclopropylpyrimidine-2,4-diamine

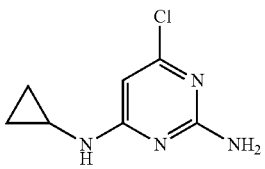 [SMILES: Nc1nc(Cl)cc(NC2CC2)n1]

To a solution of 4,6-dichloropyrimidin-2-amine (164 mg, 1.0 mmol, 1 eq.) in n-BuOH (5 mL) were added cyclopropanamine (80 μL, 1.1 mmol, 1.1 eq.) and Hünig's base (260 μL, 1.5 mmol, 1.5 eq.). The reaction mixture was stirred overnight at 95° C. The solvent was removed in vacuo. The crude product was diluted in EtOAc and washed with H₂O, brine, dried over MgSO₄ and concentrated to afford the desired product as an off-white solid (152 mg, 82%). LCMS [M+H]⁺ 185; ¹H NMR (400 MHz, DMSO-d₆) $\delta_H$ 7.29 (1H, s), 6.38 (2H, s), 5.85 (1H, s), 3.52 (1H, s), 0.73-0.64 (2H, m), 0.53-0.35 (2H, m).

Intermediate 11

6-chloro-4-N-(1-methoxybutan-2-yl)pyrimidine-2,4-diamine

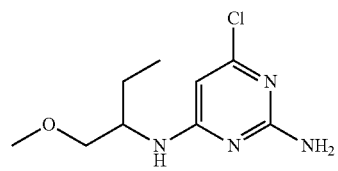

To a solution of 4,6-dichloropyrimidin-2-amine (500 mg, 3.1 mmol, 1 eq.) in n-BuOH (10 mL) were added 1-methoxybutan-2-amine (315 mg, 3.1 mmol, 1 eq.) and Hünig's base (531 μL, 3.1 mmol, 1 eq.). The reaction mixture was stirred overnight at 95° C. The solvent was removed in vacuo. The crude product was diluted in EtOAc and washed with H₂O, brine, dried over MgSO₄ and concentrated to afford the desired product as an off-white solid (592 mg, 84%). LCMS [M+H]⁺ 231.

Intermediate 12

6-chloro-4-N-(2,2,2-trifluoroethyl)pyrimidine-2,4-diamine

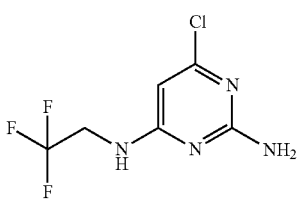 [SMILES: Nc1nc(Cl)cc(NCC(F)(F)F)n1]

To a solution of 4,6-dichloropyrimidin-2-amine (164 mg, 1.00 mmol, 1 eq.) in n-BuOH (5 mL) were added 2,2,2-trifluoroethanamine hydrochloride (149 mg, 1.1 mmol, 1.1 eq.) and NEt₃ (202 mg, 2.0 mmol, 2 eq.). The reaction mixture was stirred overnight at 90° C. The solvent was removed in vacuo. The crude product was diluted in EtOAc and washed with H₂O, brine, dried over MgSO₄ and concentrated to afford the desired product as a yellow solid (59 mg, 26%). LCMS [M+H]⁺ 227.

Intermediate 13

6-chloro-4-N-(2,2-difluoroethyl)pyrimidine-2,4-diamine

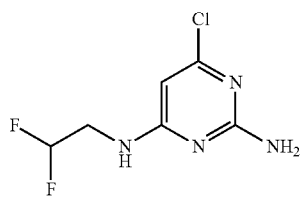 [SMILES: Nc1nc(Cl)cc(NCC(F)F)n1]

To a solution of 4,6-dichloropyrimidin-2-amine (164 mg, 1.00 mmol, 1 eq.) in n-BuOH (5 mL) were added 2,2-difluoroethanamine hydrochloride (129 mg, 1.1 mmol, 1.1 eq.) and triethylamine (202 mg, 2.0 mmol, 2 eq.). The reaction mixture was stirred overnight at 90° C. The solvent was removed in vacuo. The crude product was diluted in EtOAc and washed with H₂O, brine, dried over MgSO₄ and concentrated to afford the desired product as a yellow solid (80 mg, 38%). LCMS [M+H]⁺ 209.

Intermediate 14

6-chloro-4-N-(prop-2-en-1-yl)pyrimidine-2,4-diamine

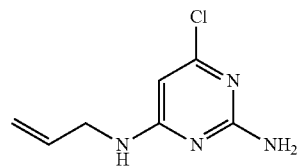

To a solution of 4,6-dichloropyrimidin-2-amine (500 mg, 3.04 mmol, 1 eq.) in n-BuOH (10 mL) were added 2,2-difluoroethanamine hydrochloride (229 μL, 3.04 mmol, 1 eq.) and Hünig's base (584 μL, 3.35 mmol, 1.1 eq.). The reaction mixture was stirred overnight at 95° C. The solvent was removed in vacuo. The crude product was diluted in EtOAc and washed with H₂O, brine, dried over MgSO₄ and concentrated to afford the desired product as a yellow solid (471 mg, 84%). LCMS [M+H]⁺ 185.

Intermediate 15

6-chloro-4-N-cyclopentylpyrimidine-2,4-diamine

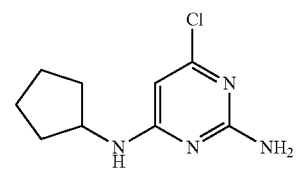 [SMILES: Nc1nc(Cl)cc(NC2CCCC2)n1]

To a solution of 4,6-dichloropyrimidin-2-amine (500 mg, 3.04 mmol, 1 eq.) in n-BuOH (10 mL) were added cyclopentanamine (301 μL, 3.04 mmol, 1 eq.) and Hünig's base (584 µL, 3.35 mmol, 1.1 eq.). The reaction mixture was stirred overnight at 95° C. The solvent was removed in vacuo. The crude product was diluted in EtOAc and washed with H$_2$O, brine, dried over MgSO$_4$ and concentrated to afford the desired product as a brown foam (620 mg, quantitative). LCMS [M+H]$^+$ 213.

Intermediate 16

6-chloro-4-N-cyclobutylpyrimidine-2,4-diamine

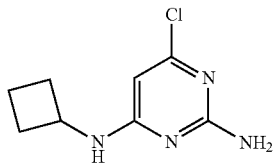 [SMILES: Nc1nc(Cl)cc(NC2CCC2)n1]

To a solution of 4,6-dichloropyrimidin-2-amine (250 mg, 1.52 mmol, 1 eq.) in n-BuOH (5 mL) were added cyclobutanamine (130 µL, 1.52 mmol, 1 eq.) and Hünig's base (292 µL, 1.72 mmol, 1.1 eq.). The reaction mixture was stirred overnight at 95° C. The solvent was removed in vacuo. The crude product was diluted in EtOAc and washed with H$_2$O, brine, dried over MgSO$_4$ and concentrated to afford the desired product as a white solid (248 mg, 80%). LCMS [M+H]$^+$ 199.

Intermediate 17

6-iodo-4-N-methylpyrimidine-2,4-diamine

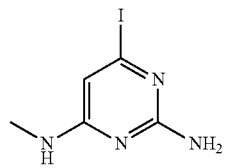

To a suspension of 6-Chloro-4-N-methylpyrimidine-2,4-diamine (1.5 g, 9.43 mmol, 1 eq.) in acetone (6.2 mL) was added sodium iodide (7.9 g, 52.8 mmol, 5.6 eq.) and hydrogen iodide (15 mL). The reaction mixture was stirred at 60° C. for 12 h. The solid was filtered off, dissolved in EtOAc, washed with NaHCO$_3$, brine, dried over MgSO$_4$ and concentrated under reduced pressure to afford the desired compound as an orange solid (1.7 g, 73%). LCMS [M+H]$^+$ 251; $^1$H NMR (400 MHz, CDCl$_3$) $\delta_H$ 6.27 (1H, s), 2.80 (3H, s).

Intermediate 18

6-chloro-4-N-(2-phenylethyl)pyrimidine-2,4-diamine

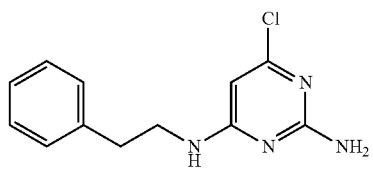 [SMILES: Nc1nc(Cl)cc(NCCc2ccccc2)n1]

To a solution of 4,6-dichloropyrimidin-2-amine (66 mg, 0.40 mmol, 1 eq.) in n-BuOH (2.5 mL) were added 2-phenylethanamine (75 µL, 0.60 mmol, 1.1 eq.) and Hünig's base (100 µg, 0.60 mmol, 1.1 eq.). The reaction mixture was stirred at 95° C. for 3 h. The solvent was removed in vacuo. The crude product was diluted in EtOAc and washed with H$_2$O, brine, dried over MgSO$_4$ and concentrated to afford the desired product as a yellow solid (88 mg, 88%). LCMS [M+H]$^+$ 249.

Intermediate 19

4-chloro-6-(2,3-dimethylphenyl)pyrimidin-2-amine

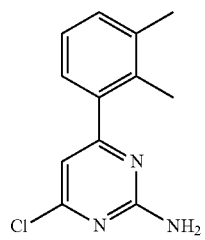

A mixture of 2-amino-4,6-dichloropyrimidine (0.82 g, 5.0 mmol, 1 eq.), 2,3-dimethylphenylboronic acid (0.75 g, 5.0 mmol, 1 eq.), K$_2$CO$_3$ (1.38 g, 10.0 mmol, 2 eq.) and palladium tetrakis(triphenylphosphine)palladium (0) (0.12 g, 0.10 mmol, 0.1 eq.) in 1,4-dioxane (20 mL) and water (5 mL) was heated in a sealed tube at 90° C. for 2.5 hours. The mixture was run through a plug of silica using EtOAc as eluent, concentrated and purified by column chromatography (1:4 EtOAc/pentane) to give the desired product as a white solid (0.76 g, 65%). LCMS [M+H]$^+$ 234; $^1$H NMR (400 MHz, CD$_3$OD) $\delta_H$ 7.21-7.29 (1H, m), 7.20-7.09 (2H, m), 6.70 (1H, s), 2.34 (3H, s), 2.23 (3H, s).

Intermediate 20

6-chloro-4-N-methylpyrimidine-2,4-diamine

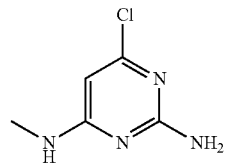

A mixture of 4,6-dichloropyrimidin-2-amine (3.28 g, 20.0 mmol), methanamine (12.0 mL, 24.0 mmol; as a 2 M solution in methanol) and Hunig's base in n-butanol (20 mL) was heated at 95° C. overnight. The mixture was concentrated and the crude was taken up in EtOAc (300 mL) and washed with water (3×150 mL). The organic layer was dried over MgSO4, filtered and concentrated to give the desired product as a buff solid (2.90 g, 91%). LCMS [M+H]$^+$159.

Intermediate 21

4-chloro-6-(2,3-dichlorophenyl)pyrimidin-2-amine

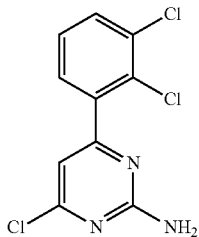 [SMILES: Nc1nc(Cl)cc(-c2cccc(Cl)c2Cl)n1]

A mixture of 4,6-dichloropyrimidin-2-amine (0.50 g, 3.05 mmol), (2,3-dichlorophenyl)boronic acid (0.64 g, 3.35 mmol), sodium carbonate (0.65 g, 6.10 mmol) and palladium tetrakis(triphenylphosphine)palladium (0) (0.088 g, 0.076 mmol) in 1,4-dioxane/water (30 ml; 4:1) was heated in a sealed tube at 95° C. for 2 h. The reaction mixture was run through a plug of silica (EtOAc) and then concentrated. Purification by column chromatography (1:4 →1:3 EtOAc/hexane) afforded the desired product as a white solid (0.26 g, 31%). LCMS [M+H]$^+$274; $^1$H NMR (400 MHz, DMSO-d$_6$) $\delta_H$ 6.89 (1 H, s)7.33 (2H, br s) 7.44- 7.52 (2H, m) 7.71- 7.81 (1H, m).

Intermediate 22

6-Chloro-4-N-[2-(4-chlorophenyl)ethyl]pyrimidine-2,4-diamine

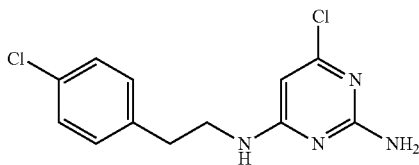 [SMILES: Nc1nc(Cl)cc(NCCc2ccc(Cl)cc2)n1]

A mixture of 4,6-dichloropyrimidin-2-amine (0.50 g, 3.05 mmol), 2-(4-chlorophenyl)ethan-1-amine (0.56 mL, 3.96 mmol) and Hünig's base (0.80 mL, 4.57 mmol) in n-butanol (5 mL) was heated in a sealed tube at 95° C. overnight. The mixture was concentrated and the crude was taken up in EtOAc (50 mL) and washed with water (3×40 mL). The organic layer was dried over MgSO4, filtered and concentrated to give the desired product as a buff solid (0.61 g, 71%). LCMS [M+H]$^+$ 283.

Intermediate 23

1-{3-[(2-amino-6-chloropyrimidin-4-yl)amino]propyl}pyrrolidin-2-one

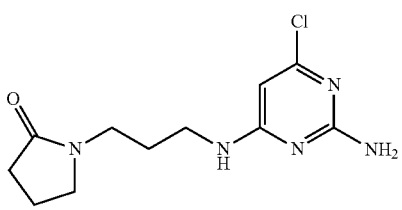 [SMILES: Nc1nc(Cl)cc(NCCCN2CCCC2=O)n1]

A mixture of 4,6-dichloropyrimidin-2-amine (1.64 g, 10.0 mmol), 1-(3-aminopropyl)pyrrolidin-2-one (1.96 mL, 14.0 mmol) and Hünig's base (2.61 mL, 15.0 mmol) in n-butanol (20 mL) was heated in a sealed tube at 110° C. overnight. The mixture was concentrated and the crude was taken up in EtOAc (300 mL) and washed with water (3×150 mL). The aqueous layers were combined and extracted with EtOAc (2×200 mL). The combined organic layers were dried over MgSO4, filtered and concentrated to give the desired product as a buff solid (1.63 g, 60%). LCMS [M+H]$^+$ 270.

Intermediate 24

4-chloro-6-(3-chloro-2-methyl phenyl)pyrimidin-2-amine

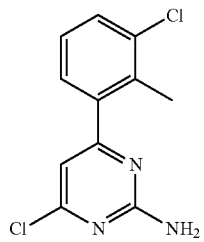 [SMILES: Cc1c(Cl)cccc1-c1cc(Cl)nc(N)n1]

A stirred mixture of 2-amino-4,6-dichloropyrimidine (0.50 g, 3.1 mmol), 3-chloro-2-methylphenylboronic acid (0.57 g, 3.4 mmol), Na$_2$CO$_3$ (1.0 g, 9.8 mmol), palladium tetrakis(triphenylphosphine)palladium (0) (88 mg, 0.076 mmol), dioxane (22 mL) and water (8 mL) were heated in a sealed tube at 90° C. for 2 hours. The solvents were removed in vacuo and the remaining solid was added EtOAc (20 mL) and washed with water. The organic phase was dried over MgSO$_4$ and removed in vacuo. The crude material was purified by flash chromatography (1:4 EtOAc/petroleum ether) to give the desired product as a white solid (365 mg, 47%). LCMS [M+H]$^+$ 254; $^1$H NMR (400 MHz, DMSO-d$_6$) $\delta_H$ ppm 7.52-7.56 (1 H, dd, J$_1$=6.5 Hz, J$_2$=2.5 Hz) 7.30-7.33 (2 H, m) 7.26 (2 H, s) 6.79 (1 H, s) 2.32 (3 H, s).

Intermediate 25

4-{2-[(2-amino-6-chloropyrimidin-4-0amino]ethyl}benzene-1-sulfonamide

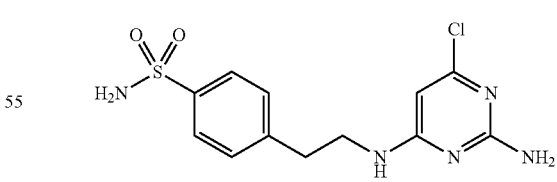

To a suspension of 4,6-dichloropyrimidin-2-amine (800 mg, 4.9 mmol) and 4-(2-aminoethyl)benzenesulfonamide (980 mg, 4.9 mmol) in 2-propanol (10 mL), was added Hünig's base (1.0 mL, 5.7 mmol) and the resulting mixture was heated at reflux for 15 h. The mixture was then poured into NaHCO$_3$ (aq) and extracted three times with DCM. The combined organic layers were dried and concentrated and the crude mixture was purified by column chromatography to afford the title compound. LCMS [M+H]⁺ 328; ¹H NMR (400 MHz, CD₃OD) $\delta_H$ ppm 7.80-7.85 (m, 2 H), 7.41 (d, J=8.6 Hz, 2 H), 5.76-5.81 (m, 1 H), 3.54-3.64 (m, 2 H), 2.95 (t, J=7.1 Hz, 2 H).

Intermediate 26

4-chloro-6-(2,3,4-trichlorophenyl)pyrimidin-2-amine

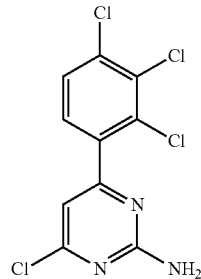 [SMILES: Nc1nc(Cl)cc(-c2ccc(Cl)c(Cl)c2Cl)n1]

A mixture of 4,6-dichloropyrimidin-2-amine (82 mg, 0.50 mmol), (2,3,4-trichlorophenyl)-boronic acid (113 mg, 0.50 mmol), potassium carbonate (138 mg, 1.0 mmol) and palladium tetrakis(triphenylphosphine)palladium (0) (14 mg, 0.013 mmol) in 1,4-dioxane/water (8 mL; 4:1) was heated in a sealed tube at 90° C. for 2 h. The reaction mixture was run through a plug of silica (EtOAc) and then concentrated and purified by preparative HPLC. LCMS [M+H]⁺ 308.

Intermediate 27

6-chloro-4-N-ethylpyrimidine-2,4-diamine

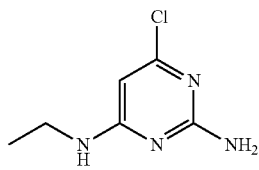

To a solution of 4,6-dichloropyrimidin-2-amine (1 g, 6.09 mmol, 1 eq.) in n-BuOH (18 mL) were added ethaneamine (2M, 3.0 mL, 6.09 mmol, 1 eq.) and Hünig's base (1.17 mL, 6.70 mmol, 1.1 eq.). The reaction mixture was stirred overnight at 95° C. Ethaneamine (1 eq) was added and the reaction was stirred overnight at 95° C. until complete consumption of starting material (2 additions). The solvent was removed in vacuo. The crude product was taken up in EtOAc and H₂O. The aqueous layer was extracted twice with EtOAc and once with CHCl₃/ⁱPrOH (3:1). The combined organic layers were washed with brine, dried over MgSO₄ and concentrated to afford the desired product as a white solid. LCMS [M+H]⁺ 173; ¹H NMR (400 MHz, CDCl₃) $\delta_H$ 5.76 (1 H, s), 4.79 (3 H, br s), 3.26 (2 H, br s), 1.20 (3 H, t, J=7.2 Hz).

Intermediate 28

6-chloro-4-N-cyclohexylpyrimidine-2,4-diamine

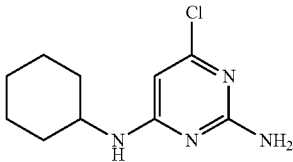 [SMILES: Nc1nc(Cl)cc(NC2CCCCC2)n1]

To a solution of 4,6-dichloropyrimidin-2-amine (1 g, 6.09 mmol, 1 eq.) in n-BuOH (18 mL) were added cyclohexanamine (698 µL, 6.09 mmol, 1 eq.) and Hünig's base (1.17 mL, 6.70 mmol, 1.1 eq.). The reaction mixture was stirred overnight at 95° C. Cyclohexanamine (1 eq) was added and the reaction was stirred overnight at 95° C. until complete consumption of starting material (2 additions). The solvent was removed in vacuo. The crude product was taken up in EtOAc and H₂O. The aqueous layer was extracted twice with EtOAc and once with CHCl₃/ⁱPrOH (3:1). The combined organic layers were washed with brine, dried over MgSO₄ and concentrated to afford the desired product as a white solid. LCMS [M+H]⁺ 227; ¹H NMR (400 MHz, CDCl₃) $\delta_H$ 5.73 (1H, s), 4.97 (2H, s), 4.79 (1H, br s), 3.45 (1H, br s), 1.97-1.92 (2H, m), 1.74-1.69 (2H, m), 1.63-1.58 (1H, m), 1.39-1.32 (2H, m), 1.22-1.10 (2H, m).

Intermediate 29

6-chloro-4-N-(cyclopropylmethyl)pyrimidine-2,4-diamine

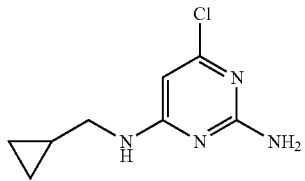 [SMILES: Nc1nc(Cl)cc(NCC2CC2)n1]

To a solution of 4,6-dichloropyrimidin-2-amine (250 mg, 1.52 mmol, 1 eq.) in n-BuOH (4.5 mL) were added cyclopropylmethanamine (131 µL, 6.09 mmol, 1 eq.) and Hünig's base (292 µL, 6.70 mmol, 1.1 eq.). The reaction mixture was stirred overnight at 95° C. The solvent was removed in vacuo. The crude product was taken up in EtOAc and H₂O. The aqueous layer was extracted twice with EtOAc and once with CHCl₃/ⁱPrOH (3:1). The combined organic layers were washed with brine, dried over MgSO₄ and concentrated to afford the desired product as a white solid. LCMS [M+H]⁺ 199; ¹H NMR (400 MHz, CDCl₃) $\delta_H$ 5.75 (1H, s), 4.92 (3H, br s), 3.07 (2H, s), 1.04-0.96 (1H, m), 0.55-0.49 (2H, m), 0.23-0.19 (2H, m).

Intermediate 30

6-chloro-4-N-[(1R)-1-cyclopropylethyl]pyrimidine-2,4-diamine

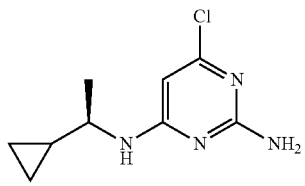

To a solution of 4,6-dichloropyrimidin-2-amine (250 mg, 1.52 mmol, 1 eq.) in n-BuOH (4.5 mL) were added (1R)-1-cyclopropylethan-1-amine (141 µL, 6.09 mmol, 1 eq.) and Hünig's base (292 µL, 6.70 mmol, 1.1 eq.). The reaction mixture was stirred overnight at 95° C. The solvent was removed in vacuo. The crude product was taken up in EtOAc and H₂O. The aqueous layer was extracted twice with EtOAc and once with CHCl₃/ⁱPrOH (3:1). The combined organic layers were washed with brine, dried over MgSO₄ and concentrated to afford the desired product as a colourless oil (321 mg, 99%). LCMS [M+H]⁺ 213; ¹H NMR (400 MHz, CDCl₃) $\delta_H$ 5.71 (1H, s), 4.97 (2H, s), 4.86 (1H, br s), 3.23 (1H, s), 1.19 (3H, d, J=6.4 Hz), 0.89-0.81 (1H, m), 0.52-0.41 (2H, m), 0.31-0.25 (1H, m), 0.23-0.18 (1H, m).

Intermediate 31

6-chloro-4-N-(propan-2-yl)pyrimidine-2,4-diamine

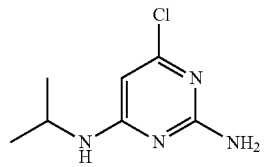

To a solution of 4,6-dichloropyrimidin-2-amine (500 mg, 3.05 mmol, 1 eq.) in n-BuOH (9 mL) were added propan-2-amine (262 µL, 6.09 mmol, 1 eq.) and Hünig's base (584 µL, 6.70 mmol, 1.1 eq.). The reaction mixture was stirred overnight at 95° C. The solvent was removed in vacuo. The crude product was taken up in EtOAc and H₂O. The aqueous layer was extracted twice with EtOAc and once with CHCl₃/ⁱPrOH (3:1). The combined organic layers were washed with brine, dried over MgSO₄ and concentrated to afford the desired product as a white solid (569 mg, 99%). LCMS [M+H]⁺ 187; ¹H NMR (400 MHz, CDCl₃) $\delta_H$ 5.74 (1H, s), 4.76 (2H, s), 4.60 (1H, br s), 3.85 (1H, br s), 1.19 (3H, s), 1.18 (3H, s).

Intermediate 32

6-chloro-4-N-[(1S)-1-cyclopropylethyl]pyrimidine-2,4-diamine

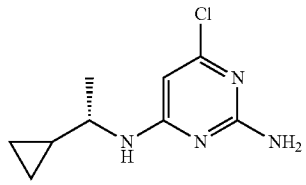

To a solution of 4,6-dichloropyrimidin-2-amine (250 mg, 1.52 mmol, 1 eq.) in n-BuOH (4.5 mL) were added (1S)-1-cyclopropylethan-1-amine (141 µL, 6.09 mmol, 1 eq.) and Hünig's base (292 µL, 6.70 mmol, 1.1 eq.). The reaction mixture was stirred overnight at 95° C. The solvent was removed in vacuo. The crude product was taken up in EtOAc and H₂O. The aqueous layer was extracted twice with EtOAc and once with CHCl₃/ⁱPrOH (3:1). The combined organic layers were washed with brine, dried over MgSO₄ and concentrated to afford the desired product as a colourless oil (296 mg, 91%). LCMS [M+H]⁺ 213; ¹H NMR (400 MHz, CDCl₃) $\delta_H$ 5.71 (1H, s), 4.99 (2H, s), 4.89 (1H, br s), 3.23 (1H, s), 1.19 (3H, d, J=6.4 Hz), 0.88-0.81 (1H, m), 0.50-0.40 (2H, m), 0.31-0.25 (1H, m), 0.23-0.17 (1H, m).

Intermediate 33

6-chloro-4-N-[2-(4-methanesulfonylphenyl)ethyl]pyrimidine-2,4-diamine

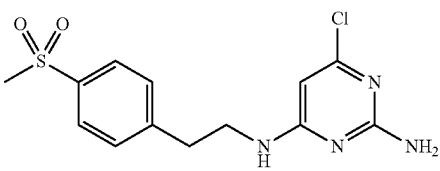 [SMILES: CS(=O)(=O)c1ccc(CCNc2cc(Cl)nc(N)n2)cc1]

A mixture of 4,6-dichloropyrimidin-2-amine (500 mg, 3.0 mmol), 2-(4-methylsulfonylphenyl)ethanamine (600 mg, 3.0 mmol) and Hünig's base (0.63 mL, 3.6 mmol) in 2-propanol (10 mL) was heated at reflux for 15 h. The reaction mixture was poured into NaHCO₃ (aq) and extracted three times with DCM. The combined organic layers were dried and concentrated. The crude mixture was purified by column chromatography which afforded the title compound. LCMS [M+H]+ 327; ¹H NMR (400 MHz, CDCl3) δ ppm 7.90 (d, J=8.3 Hz, 2 H), 7.41 (d, J=8.3 Hz, 2 H), 5.77 (s, 1 H), 4.80-4.89 (m, 2 H), 4.69-4.79 (m, 1 H), 3.56-3.67 (m, 2 H), 3.07 (s, 3 H), 3.00 (t, J=6.8 Hz, 2 H).

Intermediate 34

6-chloro-4-N-(2,2-dimethylpropyl)pyrimidine-2,4-diamine

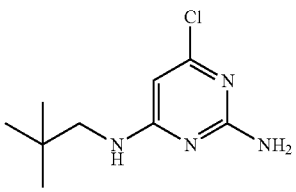

To a solution of 4,6-dichloropyrimidin-2-amine (250 mg, 1.52 mmol, 1 eq.) in n-BuOH (9 mL) were added 2,2-dimethylpropan-1-amine (6.09 mmol, 1 eq.) and Hünig's base (292 µL, 6.70 mmol, 1.1 eq.). The reaction mixture was stirred overnight at 95° C. The solvent was removed in vacuo. The crude product was taken up in EtOAc and H₂O. The aqueous layer was extracted twice with EtOAc and once with CHCl₃/ⁱPrOH (3:1). The combined organic layers were washed with brine, dried over MgSO₄ and concentrated to afford the desired product as a white solid. LCMS [M+H]⁺ 215; ¹H NMR (400 MHz, CDCl₃) $\delta_H$ 5.94 (1H, s), 3.24 (2H, br s), 0.98 (9H, s).

Intermediate 35

4-N-(2-aminoethyl)-6-(2,3-dimethylphenyl)pyrimidine-2,4-diamine

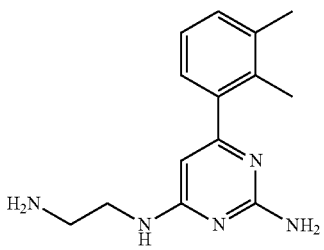 [SMILES: Cc1cccc(-c2cc(NCCN)nc(N)n2)c1C]

Step 1: To a suspension of 4,6-dichloropyrimidin-2-amine (500 mg, 3.05 mmol) and Hünig's base (0.80 mL) in 2-propanol (3.0 mL) was added tert-butyl N-(2-aminoethyl) carbamate (586 mg, 3.66 mmol) and the mixture was stirred at 150° C. for 15 min. The crude mixture was poured into NaHCO3 (aq) and extracted three times with DCM. The combined organic layers were dried and concentrated. Purification by column chromatography (0→10% MeOH in DCM) afforded tert-butyl N-[2-[(2-amino-6-chloro-pyrimidin-4-yl)amino]ethyl]carbamate (850 mg, 2.95 mmol).

Step 2: tert-Butyl N-[2-[(2-amino-6-chloro-pyrimidin-4-yl)amino]ethyl]carbamate (850 mg, 2.95 mmol), (2,3-dimethylphenyl)boronic acid (532 mg, 3.55 mmol), palladium tetrakis(triphenylphosphine)palladium (0) (34 mg, 0.030 mmol), and $K_2CO_3$ (1020 mg, 7.39 mmol) were suspended in 1,4-dioxane (10 ml) and $H_2O$ (2.0 ml). The vial was flushed with nitrogen and the resulting mixture was stirred at 90° C. for 16 h. The crude mixture was poured into NaHCO3 (aq) and extracted three times with DCM. The combined organic layers were dried and concentrated. Purification by column chromatography (0→10% MeOH in DCM) afforded tert-butyl N-[2-[[2-amino-6-(2,3-dimethylphenyl)pyrimidin-4-yl]amino]ethyl]carbamate (770 mg, 2.15 mmol).

Step 3: tert-Butyl N-[2-[[2-amino-6-(2,3-dimethylphenyl)pyrimidin-4-yl]amino]ethyl]carbamate (770 mg, 2.15 mmol) was dissolved in TFA (6 mL) and the resulting mixture was stirred for 1 h at rt, after which the TFA was distilled off. Purification by column chromatography (5→30% MeOH [containing 1 v/v % $NH_4OH$] in DCM) afforded 4-N-(2-aminoethyl)-6-(2,3-dimethylphenyl)pyrimidine-2,4-diamine (500 mg, 1.94 mmol). LCMS $[M+H]^+$ 258.

Intermediate 36

4-N-(3-aminopropyl)-6-(2,3-dimethylphenyl)pyrimidine-2,4-diamine

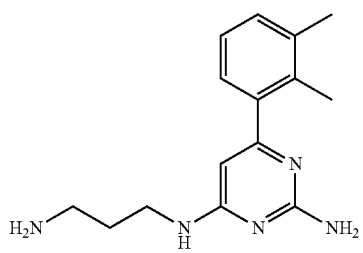 [SMILES: Cc1cccc(-c2cc(NCCCN)nc(N)n2)c1C]

Step 1: A vial was charged with 4,6-dichloropyrimidin-2-amine (500 mg, 3.0 mmol) and tert-butyl N-(2-aminopropyl)carbamate (640 mg, 3.7 mmol). Then 2-propanol (3.0 ml) and Hünig's base (0.80 ml) were added and the resulting mixture was heated at 150° C. using microwave irradiation for 15 min. The mixture was then concentrated and purified by column chromatography (2→10% MeOH in DCM) to afford tert-butyl N-[3-[(2-amino-6-chloro-pyrimidin-4-yl)amino]propyl]-carbamate (788 mg, 2.61 mmol).

Step 2: tert-Butyl N-[3-[(2-amino-6-chloro-pyrimidin-4-yl)amino]propyl]carbamate (790 mg, 2.6 mmol), (2,3-dimethylphenyl)boronic acid (470 mg, 3.1 mmol), palladium tetrakis(triphenylphosphine)palladium (0) (60 mg, 0.050 mmol), and $K_2CO_3$ (720 mg 5.2 mmol) were suspended in 1,4-dioxane (6.0 ml) and $H_2O$ (1.5 ml). The resulting mixture was heated at 90° C. for 16 h and then poured into $H_2O$ and extracted three times with DCM. The combined organic layers were dried and concentrated. Purification by column chromatography (1→10% MeOH in DCM) afforded tert-butyl N-[3-[[2-amino-6-(2,3-dimethylphenyl)pyrimidin-4-yl]amino]propyl]carbamate (800 mg, 2.1 mmol).

Step 3: tert-Butyl N-[3-[[2-amino-6-(2,3-dimethylphenyl)pyrimidin-4-yl]amino]propyl]carbamate (800 mg, 2.1 mmol) was dissolved in TFA and heated at reflux for 1 h. The TFA was evaporated and the crude residue was purified by column chromatography (2→30% MeOH [containing 1 v/v % $NH_4OH$] in DCM) to afford 4-N-(3-aminopropyl)-6-(2,3-dimethylphenyl)pyrimidine-2,4-diamine (540 mg, 2.0 mmol). LCMS $[M+H]^+$ 272.

Intermediate 37

4-chloro-6-(2-chloro-3-methylphenyl)pyrimidin-2-amine

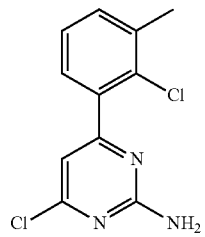 [SMILES: Cc1cccc(-c2cc(Cl)nc(N)n2)c1Cl]

To a suspension of 4,6-dichloropyrimidin-2-amine (250 mg, 1.52 mmol, 1 eq) in dioxane/$H_2O$ (5 mL, 4:1) was added (2-chloro-3-methylphenyl)boronic acid (260 mg, 1.52 mmol, 1 eq) followed by potassium carbonate (421 mg, 3.05 mmol, 2 eq) and Pd(PPh$_3$)$_4$ (44 mg, 0.04 mmol, 0.025 eq). The resulting mixture was stirred at 90° C. for 12 hrs. The solvent was removed in vacuo. The residue was taken up in DMF and purified by preparative to afford the desired product as an off-white solid (166 mg, 43%). LCMS $[M+H]^+$ 254; $^1$H NMR (400 MHz, CDCl$_3$) $\delta_H$ 7.32-7.28 (2H, m), 7.25-7.21 (1H, m), 6.92 (1H, s), 5.31 (2H, br s), 2.42 (3H, 5).

Intermediate 38

4-chloro-6-(quinolin-5-yl)pyrimidin-2-amine

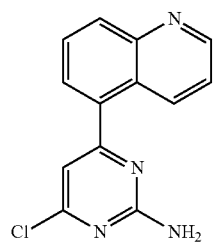 [SMILES: Nc1nc(Cl)cc(-c2cccc3ncccc23)n1]

To a suspension of 4,6-dichloropyrimidin-2-amine (150 mg, 0.91 mmol, 1 eq) in dioxane/H$_2$O (5 mL, 4:1) was added (quinolin-5-yl)boronic acid (158 mg, 0.91 mmol, 1 eq) followed by potassium carbonate (253 mg, 1.83 mmol, 2 eq) and Pd(PPh$_3$)$_4$ (26 mg, 0.020 mmol, 0.025 eq). The resulting mixture was stirred at 90° C. for 12 hrs. The solvent was removed in vacuo and the residue was purified by preparative HPLC to afford the desired product as a yellow solid (63 mg, 27%). LCMS [M+H]$^+$ 257; $^1$H NMR (400 MHz, CDCl$_3$) $\delta_H$ 9.21-9.19 (2H, m), 8.62 (1H, d, J=8.8 Hz), 8.30-7.99 (1H, m), 7.92 (1H, dd, J=7.2 and 0.8 Hz), 7.81-7.77 (1H, m), 6.98 (1H, s), 5.40 (2H, br s).

Intermediate 39

4-chloro-6-(1H-indol-4-yl)pyrimidin-2-amine

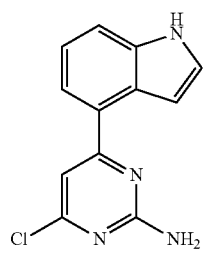 [SMILES: Nc1nc(Cl)cc(-c2cccc3[nH]ccc23)n1]

To a suspension of 4,6-dichloropyrimidin-2-amine (150 mg, 0.91 mmol, 1 eq) in dioxane/H$_2$O (5 mL, 4:1) was added (1H-indol-4-yl)boronic acid (147 mg, 0.91 mmol, 1 eq) followed by potassium carbonate (253 mg, 1.83 mmol, 2 eq) and Pd(PPh$_3$)$_4$ (26 mg, 0.02 mmol, 0.025 eq). The resulting mixture was stirred at 90° C. for 12 hrs. The solvent was removed in vacuo and the residue was purified by preparative HPLC to afford the desired product as a yellow solid (111 mg, 50%). LCMS [M+H]$^+$ 245; $^1$H NMR (400 MHz, CDCl$_3$) $\delta_H$ 8.45 (1H, br s), 7.57 (1H, d, J=7.2 Hz), 7.51 (1H, d, J=8.0 Hz), 7.35 (1H, t, J=4.0 Hz), 7.27 (1H, d, J=7.6 Hz), 7.18 (1H, s), 7.00-6.99 (1H, m), 5.90 (2H, br s).

Intermediate 40

4-chloro-6-(5-chloro-2-methylphenyl)pyrimidin-2-amine

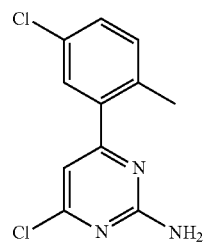 [SMILES: Cc1ccc(Cl)cc1-c1cc(Cl)nc(N)n1]

To a suspension of 4,6-dichloropyrimidin-2-amine (150 mg, 0.91 mmol, 1 eq) in dioxane/H$_2$O (5 mL, 4:1) was added (5-chloro-2-methylphenyl)boronic acid (155 mg, 0.91 mmol, 1 eq) followed by potassium carbonate (253 mg, 1.83 mmol, 2 eq) and Pd(PPh$_3$)$_4$ (26 mg, 0.02 mmol, 0.025 eq). The resulting mixture was stirred at 90° C. for 12 hrs. The solvent was removed in vacuo and the residue was purified by preparative HPLC to afford the desired product as an off-white solid (98 mg, 42%). LCMS [M+H]$^+$ 254; $^1$H NMR (400 MHz, CDCl$_3$) $\delta_H$ 7.35 (1H, d, J=2.0 Hz), 7.28 (1H, dd, J=8.4 and 2.4 Hz), 7.18 (1H, d, J=8.4 Hz), 6.72 (1H, s), 5.30 (2H, br s), 2.34 (3H, s).

Intermediate 41

6-(3-aminophenyl)-4-N-methylpyrimidine-2,4-diamine

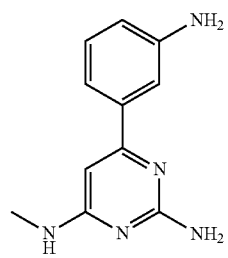 [SMILES: CNc1cc(-c2cccc(N)c2)nc(N)n1]

Tetrakis(triphenylphosphine)palladium (0) (5 mol %) was added to a stirred mixture of 6-chloro-4-N-methylpyrimidine-2,4-diamine (1.00 mmol), (3-aminophenyl)boronic acid (1.3 eq.), sodium carbonate (3.2 eq.), 1,4-dioxane (4 mL) and water (1 mL) in a tube. The tube was sealed and the reaction was heated at 90° C. for 5 h and then concentrated. The crude material was taken up in ethyl acetate and washed with water. The organic phase was dried over magnesium sulfate, concentrated and purified by flash chromatography (0→15% MeOH in DCM) to give the title compound. LCMS [M+H]$^+$ 216.

Intermediate 42

6-(3-amino-2-methylphenyl)-4-N-methylpyrimidine-2,4-diamine

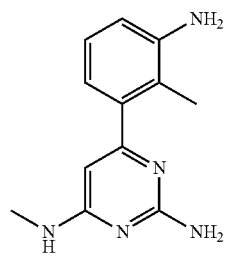

Tetrakis(triphenylphosphine)palladium (0) (5 mol %) was added to a stirred mixture of 6-chloro-4-N-methylpyrimidine-2,4-diamine (3.00 mmol), (3-amino-2-methylphenyl)boronic acid (1.3 eq.), sodium carbonate (3.2 eq.), 1,4-dioxane (4 mL) and water (1 mL). The tube was sealed and the reaction was heated at 90° C. for 5 h. The mixture was concentrated and purified by column chromatography (13% MeOH in DCM) to give the title compound. LCMS [M+H]$^+$ 230; $^1$H NMR (400 MHz, DMSO-d$_6$) δ ppm 6.88 (1 H, t, J=7.71 Hz), 6.71-6.81 (1 H, m), 6.61 (1 H, dd, J=7.96, 1.14 Hz), 6.44 (1 H, dd, J=7.58, 1.01 Hz), 5.90 (2 H, br. s.), 5.64 (1 H, s), 4.83 (2 H, s), 2.75 (3 H, d, J=4.55 Hz), 1.98 (3 H, s).

Intermediate 43

6-(5-amino-2-methylphenyl)-4-N-methylpyrimidine-2,4-diamine

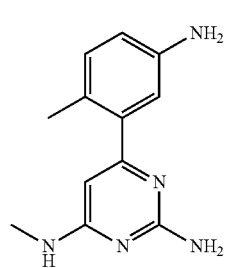 [SMILES: CNc1cc(-c2cc(N)ccc2C)nc(N)n1]

Tetrakis(triphenylphosphine)palladium (0) (5 mol %) was added to a stirred mixture of 6-chloro-4-N-methylpyrimidine-2,4-diamine (3.0 mmol), (5-amino-2-methylphenyl)boronic acid (1.3 eq.), sodium carbonate (3.2 eq.), 1,4-dioxane (4 mL) and water (1 mL) in a tube. The tube was sealed and the reaction was heated at 90° C. for 5 h. The mixture was concentrated and purified by column chromatography (13% MeOH in DCM) to give the title compound. LCMS [M+H]$^+$ 230.

Intermediate 44

6-(4-aminophenyl)-4-N-methylpyrimidine-2,4-diamine

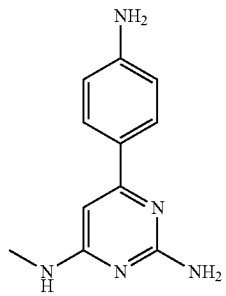 [SMILES: CNc1cc(-c2ccc(N)cc2)nc(N)n1]

Tetrakis(triphenylphosphine)palladium (0) (5 mol %) was added to a stirred mixture of 6-chloro-4-N-methylpyrimidine-2,4-diamine (1.0 mmol), 4-(tetramethyl-1,3,2-dioxaborolan-2-yl)aniline (1.3 eq.), sodium carbonate (3.2 eq.), 1,4-dioxane (4 mL) and water (1 mL) in a tube. The tube was sealed and the reaction was heated at 90° C. for 5 h and then concentrated. The crude material was taken up in ethyl acetate and washed with water. The organic phase was dried over magnesium sulfate, concentrated and purified by flash chromatography (0→15% MeOH/DCM) to give the title compound. LCMS [M+H]$^+$ 216; $^1$H NMR (400 MHz, CDCl$_3$) δ$_H$ ppm 7.64 (2 H, d, J=8.53 Hz), 6.50-6.62 (3 H, m), 6.03 (1 H, s), 5.74 (2 H, s), 5.37 (2 H, s), 2.76 (3 H, d, J=4.77 Hz).

General procedures

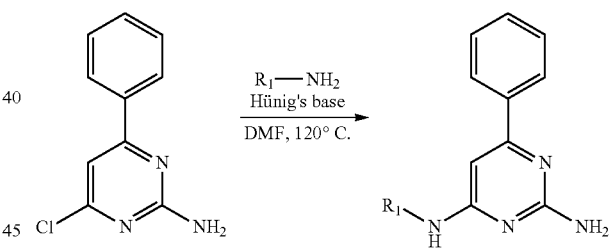

General Procedure 1: To a mixture of 4-chloro-6-phenylpyrimidin-2-amine (1 equiv.) is added Hünig's base (3.4 equiv.) and an appropriate amine (1.6 equiv.) in DMF (500 µL). The mixture is heated at 120° C. overnight. The crude mixture is purified by preparative HPLC to afford the desired product.

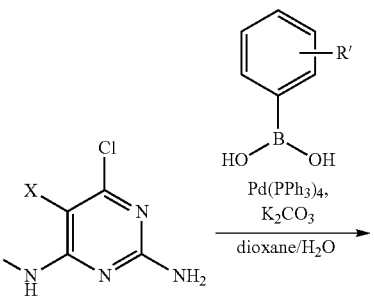

-continued

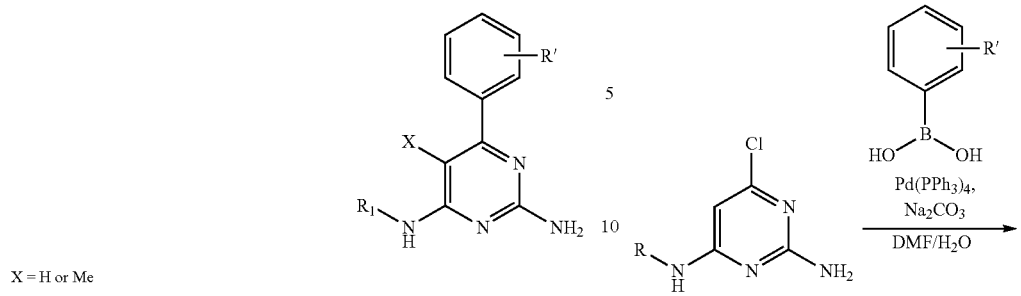

X = H or Me

General Procedure 2: To a mixture of a suitable chloropyrimidine derivative (1 equiv.) in 1,4-dioxane/water (4:1) is added the appropriate boronic acid (or boronic ester) derivative (1.3 equiv.), $K_2CO_3$ (2 equiv.) and $Pd(PPh_3)_4$ (0.1 equiv.). The mixture is heated at 95° C. overnight or in a microwave reactor until the reaction is complete as shown by LCMS. The crude mixture is purified by preparative HPLC to afford the desired product.

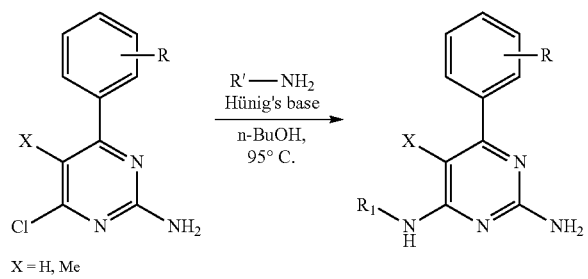

X = H, Me

General Procedure 3: To a mixture of a suitable chloropyrimidine derivative (1 equiv.) is added Hünig's base (3.4 equiv.) and an appropriate amine (1.6 equiv.) in n-BuOH (500 µL). The mixture is heated at 95° C. overnight. The crude mixture was purified by preparative HPLC to afford the desired product.

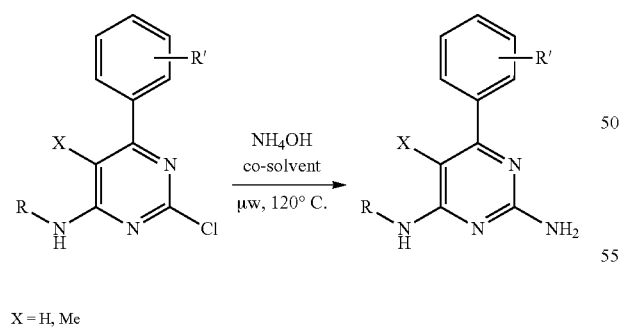

X = H, Me

General Procedure 4: A solution of an appropriate chloropyrimidine derivative (1 equiv.) in ammonium hydroxide (25% aq.) is heated in the microwave at 120° C. until completion of the reaction as monitored by LCMS. The solvent is then evaporated and the product is dried under vacuum. Further purification by preparative HPLC is performed when required.

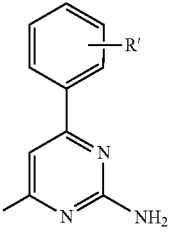

General Procedure 5: To a mixture of a suitable chloropyrimidine derivative (1 equiv.) in DMF/water (9:1) is added the appropriate boronic acid (or boronic ester) derivative (1.1 equiv.), $Na_2CO_3$ (2 equiv.) and $Pd(PPh_3)_4$ (0.1 equiv.). The mixture is heated at 120° C. overnight or in the microwave until the reaction is complete as shown by LCMS. The crude mixture is then purified by preparative HPLC to afford the desired product.

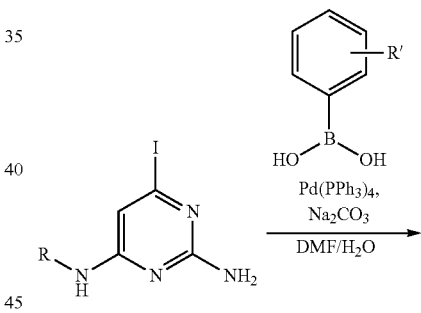

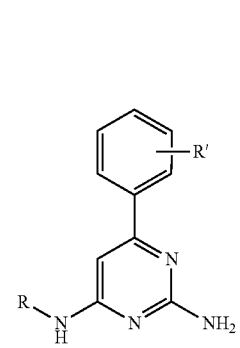

General Procedure 6: To a mixture of a suitable iodopyrimidine derivative (1 equiv.) in DMF/water (20:1) is added the appropriate boronic acid (or boronic ester) derivative (1.3 equiv.), $Na_2CO_3$ (2 equiv.) and $Pd(PPh_3)_4$ (0.1 equiv.). The mixture is heated at 120° C. overnight or in a microwave reactor until the reaction is complete as shown by LCMS. The crude mixture is then purified by HPLC to afford the desired product.

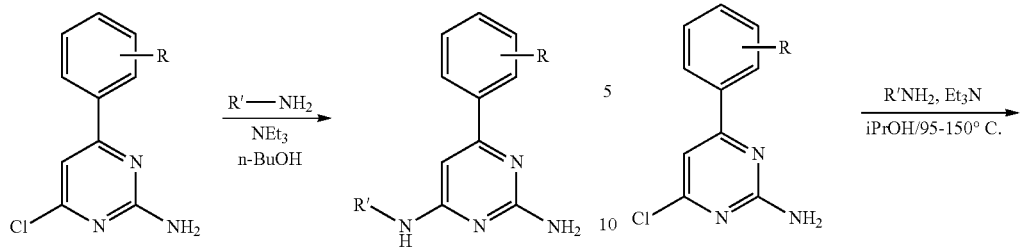

General Procedure 7: A mixture of a suitable 6-aryl-4-chloropyrimidin-2-amine (1 equiv.), a suitable amine (1.5 equiv.) and triethylamine (2 equiv.) in n-butanol (1.5 mL) is heated in a sealed tube at 95° C. overnight. Concentrated and purified by preparative HPLC to give the desired product.

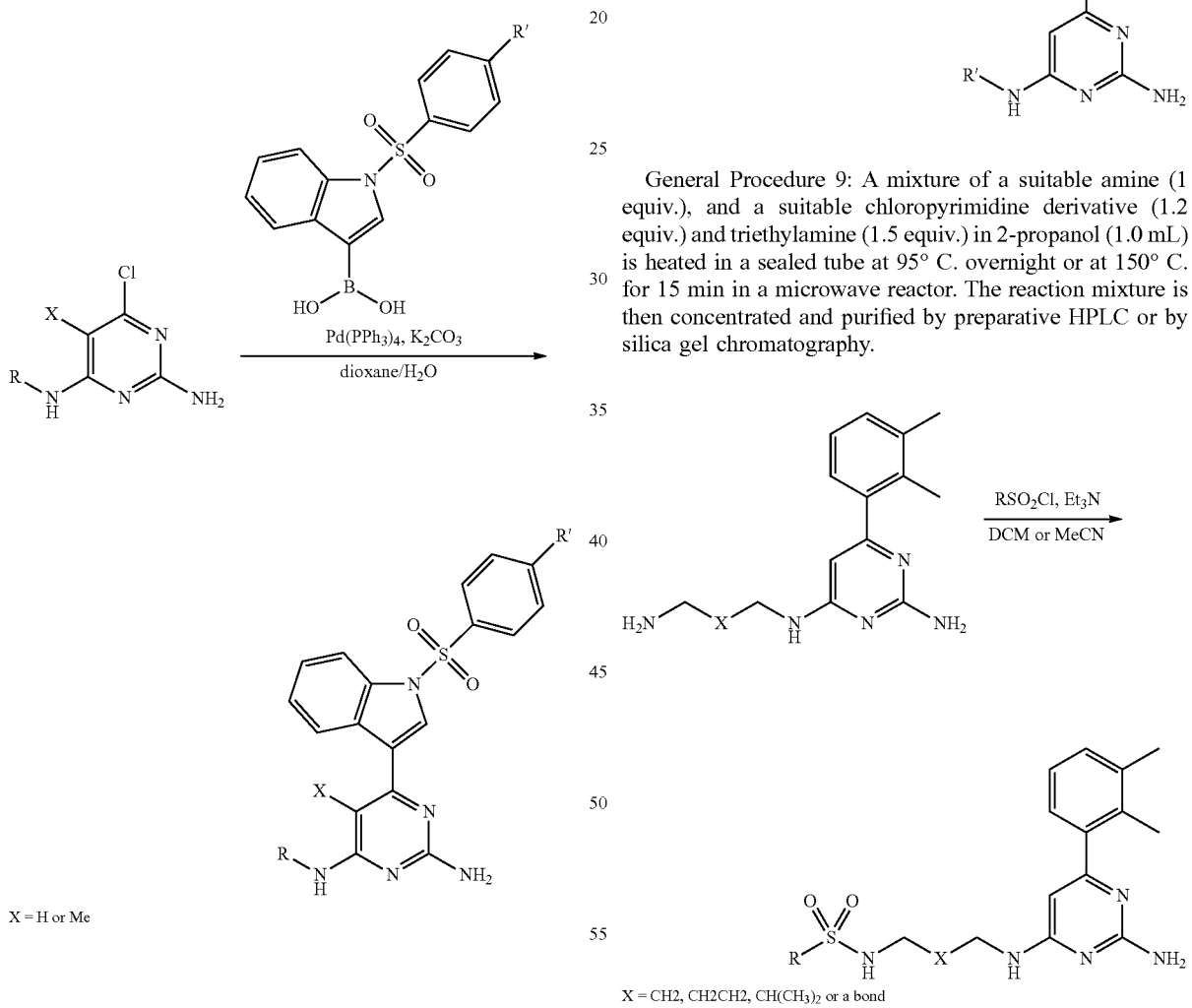

General Procedure 8: To a mixture of a suitable 4-chloropyrimidin-2-amine (1 equiv.) in 1,4-dioxane/water (4:1) is added the desired boronic acid (or boronic ester) (1.3 equiv.), $K_2CO_3$ (2 equiv.) and $Pd(PPh_3)_4$ (0.1 equiv.). The mixture is heated at 95° C. overnight or in a microwave until the reaction is complete as shown by LCMS. The crude mixture is purified by HPLC to afford the desired product.

General Procedure 9: A mixture of a suitable amine (1 equiv.), and a suitable chloropyrimidine derivative (1.2 equiv.) and triethylamine (1.5 equiv.) in 2-propanol (1.0 mL) is heated in a sealed tube at 95° C. overnight or at 150° C. for 15 min in a microwave reactor. The reaction mixture is then concentrated and purified by preparative HPLC or by silica gel chromatography.

General Procedure 10: A mixture of an 4-N-(aminoalkyl)-6-(2,3-dimethylphenyl)pyrimidine-2,4-diamine (1.0 equiv.), a suitable sulfonyl chloride (1.2 equiv.), and triethylamine (1.5 equiv.) in DCM or MeCN (1.0 mL) is stirred in a sealed tube at rt or 50° C. After completion the crude mixture is concentrated and purified by preparative HPLC or by silica gel chromatography.

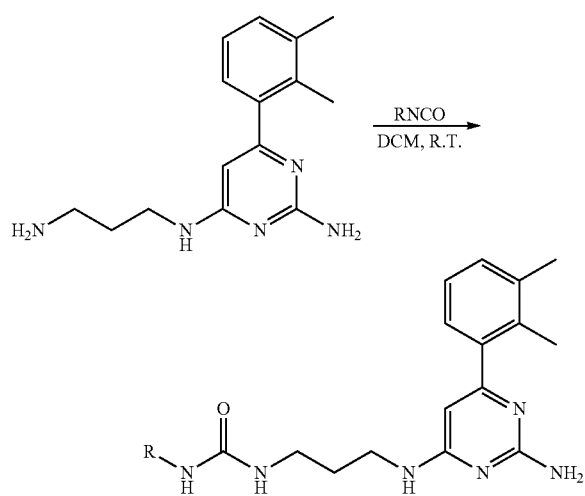

General Procedure 11: A mixture of 4-N-(3-aminopropyl)-6-(2,3-dimethylphenyl)pyrimidine-2,4-diamine (1.0 eq.) and the corresponding isocyanate (1.05 eq.) is dissolved in DCM. The resulting reaction mixture is stirred at rt until completion according to LCMS. The mixture is then concentrated and purified by preparative HPLC or by silica gel chromatography.

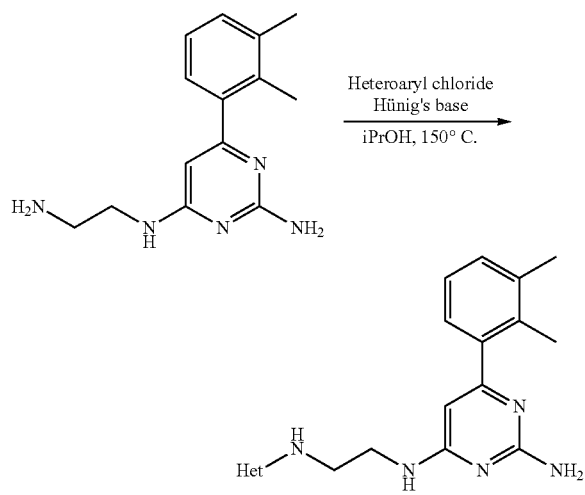

General Procedure 12: A mixture of 4-N-(2-aminoethyl)-6-(2,3-dimethylphenyl)pyrimidine-2,4-diamine (1.0 equiv.) and the corresponding heteroaryl chloride (1.5 equiv.), and Hünig's base (1.5 equiv.) in 2-propanol (0.5 mL) is stirred in a sealed tube at 150° C. in a microwave reactor for 30 min. The crude mixture is then concentrated and purified by preparative HPLC or by silica gel chromatography.

EXAMPLES

The utility of the compounds of the present invention can be illustrated, for example, by their activity in vitro in the cancer cell clonogenic and/or viability assay described below. The link between activity in tumor cell clonogenic assay and anti-tumor activity in the clinical setting has been well established in the art (e.g. see ref Silverstini et al Stem Cells 1993, 11(6), 258-35).

Example 1

4-N-cyclohexyl-6-phenylpyrimidine-2,4-diamine

Prepared according to general procedure 1 from cyclohexanamine and 4-chloro-6-phenylpyrimidin-2-amine. LCMS [M+H]$^+$ 269; $^1$H NMR (400 MHz, DMSO-d$_6$) $\delta_H$ 8.79-8.61 (1H, m), 7.78-7.67 (2H, m), 7.66-7.55 (3H, m), 6.33 (1H, s), 4.05-3.85 (1H, m), 2.00-1.83 (2H, m), 1.80-1.70 (2H, m), 1.41-1.10 (6H, m).

Example 2

4-N-ethyl-6-phenylpyrimidine-2,4-diamine

Prepared according to general procedure 1 from ethanamine and 4-chloro-6-phenylpyrimidin-2-amine. LCMS [M+H]$^+$ 215; $^1$H NMR (400 MHz, DMSO-d$_6$) $\delta_H$ 8.82 (1H, s), 7.74-7.71 (2H, m), 7.67-7.57 (3H, m), 6.33 (1H, s), 3.53-3.41 (2H, m), 1.18 (3H, t, J=7.1 Hz).

Example 3

4-N-(3-ethoxypropyl)-6-phenylpyrimidine-2,4-diamine

Prepared according to general procedure 1 from 3-ethoxypropan-1-amine and 4-chloro-6-phenylpyrimidin-2-amine. LCMS [M+H]$^+$ 273; $^1$H NMR (400 MHz, DMSO-d$_6$) $\delta_H$ 8.82 (1H, s), 7.74-7.71 (2H, m), 7.63-7.59 (3H, m), 6.37 (1H, s), 3.45-3.41 (6H, m), 1.80 (2H, q, J=6.5 Hz), 1.11 (3H, t, J=6.5 Hz).

Example 4

6-phenyl-4-N-propylpyrimidine-2,4-diamine

Prepared according to general procedure 2 from phenylboronic acid and 6-chloro-4-N-propylpyrimidine-2,4-diamine. LCMS [M+H]$^+$ 229.

Example 5

6-(4-methanesulfonylphenyl)-4-N-propylpyrimidine-2,4-diamine

Prepared according to general procedure 2 from (4-methane-sulfonylphenyl)boronic acid and 6-chloro-4-N-propylpyrimidine-2,4-diamine. LCMS [M+H]$^+$ 307; $^1$H NMR (400 MHz, DMSO-d$_6$) $\delta_H$ 8.21-8.11 (2H, m), 8.05-7.92 (2H, m), 6.42 (1H, s), 3.50-3.40 (2H, m), 3.31 (3H, s), 1.68-1.51 (2H, m), 0.94 (3H, t, J=7.1 Hz).

Example 6

4-N-(cyclopropylmethyl)-6-phenylpyrimidine-2,4-diamine

Prepared according to general procedure 1 from cyclopropylmethanamine and 4-chloro-6-phenylpyrimidin-2-amine. LCMS [M+H]$^+$ 241; $^1$H NMR (400 MHz, DMSO-d$_6$)

δ$_H$ 8.92 (1H, s), 7.83-7.50 (5H, m), 6.39 (1H, s), 3.33-3.20 (2H, m), 1.15-0.95 (1H, m), 0.51 (1H, d, J=5.8 Hz), 0.27 (1H, d, J=5.8 Hz).

Example 7

4-N-(oxan-4-yl)-6-phenylpyrimidine-2,4-diamine

Prepared according to general procedure 1 from oxan-4-amine and 4-chloro-6-phenylpyrimidin-2-amine. LCMS [M+H]$^+$ 271.

Example 8

4-N-(furan-2-ylmethyl)-6-phenylpyrimidine-2,4-diamine

Prepared according to general procedure 1 from furan-2-ylmethanamine and 4-chloro-6-phenylpyrimidin-2-amine. LCMS [M+H]$^+$ 267.

Example 9

4-N-(pentan-3-yl)-6-phenylpyrimidine-2,4-diamine

Prepared according to general procedure 1 from pentan-3-amine and 4-chloro-6-phenylpyrimidin-2-amine. LCMS [M+H]$^+$ 257.

Example 10

6-phenyl-4-N-(propan-2-yl)pyrimidine-2,4-diamine

Prepared according to general procedure 1 from propan-2-amine and 4-chloro-6-phenylpyrimidin-2-amine. LCMS [M+H]$^+$ 229.

Example 11

4-N-benzyl-6-phenylpyrimidine-2,4-diamine

Prepared according to general procedure 1 from phenylmethanamine and 4-chloro-6-phenylpyrimidin-2-amine. LCMS [M+H]$^+$ 277; $^1$H NMR (400 MHz, DMSO-d$_6$) δ$_H$ 7.92-7.84 (2H, m), 7.48-7.40 (4H, m), 7.37-7.27 (4H, m), 7.27-7.20 (1H, m), 6.29 (1H, s), 6.06 (2H, s), 4.54 (2H, d, J=5.9 Hz).

Example 12

4-N-[2-(morpholin-4-yl)ethyl]-6-phenylpyrimidine-2,4-diamine

Prepared according to general procedure 1 from 2-(morpholin-4-yl)ethan-1-amine and 4-chloro-6-phenylpyrimidin-2-amine. LCMS [M+H]$^+$ 300.

Example 13

6-(4-chlorophenyl)-4-N-cyclopropylpyrimidine-2,4-diamine

Prepared according to general procedure 1 from cyclopropanamine and 4-chloro-6-phenylpyrimidin-2-amine. LCMS [M+H]$^+$ 261.

Example 14

4-N-tert-butyl-6-(4-chlorophenyl)pyrimidine-2,4-diamine

Prepared according to general procedure 2 from (4-chlorophenyl)boronic acid and 4-N-tert-butyl-6-chloropyrimidine-2,4-diamine. LCMS [M+H]$^+$ 277; $^1$H NMR (400 MHz, DMSO-d$_6$) δ$_H$ 8.38 (1H, s), 7.75-7.66 (4H, m), 6.38 (1H, s), 1.46 (9H, s).

Example 15

6-(4-chlorophenyl)-4-N-(oxan-4-yl)pyrimidine-2,4-diamine

Prepared according to general procedure 2 from (4-chlorophenyl)boronic acid and 6-chloro-4-N-(oxan-4-yl)pyrimidine-2,4-diamine. LCMS [M+H]$^+$ 305.

Example 16

4-N-cyclopropyl-6-[3-(trifluoromethyl)phenyl]pyrimidine-2,4-diamine

Prepared according to general procedure 2 from [3-(trifluoromethyl)phenyl]-boronic acid and 6-chloro-4-N-cyclopropylpyrimidine-2,4-diamine. LCMS [M+H]$^+$ 295.

Example 17

4-N-tert-butyl-6-(4-methoxyphenyl)pyrimidine-2,4-diamine

Prepared according to general procedure 2 from (4-methoxyphenyl)boronic acid and 4-N-tert-butyl-6-chloropyrimidine-2,4-diamine. LCMS [M+H]$^+$ 273; $^1$H NMR (400 MHz, DMSO-d$_6$) δ$_H$ 7.65 (2H, d, J=9.4 Hz), 7.15 (2H, d, J=9.4 Hz), 6.35 (1H, s), 3.85 (3H, s), 1.45 (9H, s).

Example 18

4-N-cyclopropyl-6-(4-methoxyphenyl)pyrimidine-2,4-diamine

Prepared according to general procedure 2 from (4-methoxyphenyl)boronic acid and 6-chloro-4-N-cyclopropylpyrimidine-2,4-diamine. LCMS [M+H]$^+$ 257; $^1$H NMR (400 MHz, DMSO-d$_6$) δ$_H$ 7.79-7.72 (2H, m), 7.17-7.15 (2H, m), 6.24 (1H, s), 3.85 (4H, s), 0.83-0.81 (2H, m), 0.62-0.60 (2H, m).

Example 19

6-(3-chlorophenyl)-4-N-cyclopropylpyrimidine-2,4-diamine

Prepared according to general procedure 2 from (3-chlorophenyl)boronic acid and 6-chloro-4-N-cyclopropylpyrimidine-2,4-diamine. LCMS [M+H]$^+$ 261; $^1$H NMR (400

MHz, CD$_3$OD) δ$_H$ 7.78-7.76 (1H, m), 7.64-7.57 (3H, m), 6.27 (1H, s), 0.89-0.87 (2H, m), 0.70-0.63 (3H, m).

Example 20

4-N-tert-butyl-6-[3-(trifluoromethyl)phenyl]pyrimidine-2,4-diamine

Prepared according to general procedure 2 from [3-(trifluoromethyl)phenyl]boronic acid and 4-N-tert-butyl-6-chloropyrimidine-2,4-diamine. LCMS [M+H]$^+$ 311.

Example 21

6-(3-chlorophenyl)-4-N-(oxan-4-yl)pyrimidine-2,4-diamine

Prepared according to general procedure 2 from (3-chlorophenyl)boronic acid and 6-chloro-4-N-(oxan-4-yl)pyrimidine-2,4-diamine. LCMS [M+H]$^+$ 305; $^1$H NMR (400 MHz, CD$_3$OD) δ$_H$ 7.78-7.76 (1H, m), 7.65-7.63 (2H, m), 7.59-7.57 (1H, m), 6.30 (1H, s), 4.30-4.28 (1H, m), 4.02-3.98 (2H, m), 3.53-3.51 (2H, m), 2.01-2.00 (2H, m), 1.65-1.63 (2H, m).

Example 22

4-N-tert-butyl-6-(3-chlorophenyl)pyrimidine-2,4-diamine

Prepared according to general procedure 2 from (3-chlorophenyl)boronic acid and 4-N-tert-butyl-6-chloropyrimidine-2,4-diamine. LCMS [M+H]$^+$ 277; $^1$H NMR (400 MHz, CD$_3$OD) δ$_H$ 7.75-7.73 (1H, m), 7.65-7.62 (2H, m), 7.59-7.55 (2H, m), 1.52 (9H, s).

Example 23

4-N-methyl-6-[1-(4-methylbenzenesulfonyl)-1H-indol-3-yl]pyrimidine-2,4-diamine

Prepared according to general procedure 8 from [1-(4-methylbenzenesulfonyl)-1H-indol-3-yl]boronic acid and 6-chloro-4-N-methylpyrimidine-2,4-diamine. LCMS [M+H]$^+$ 394; $^1$H NMR (400 MHz, CD$_3$OD) δ$_H$ 8.36 (1H, s), 8.07 (1H, d, J=8.3 Hz), 7.93 (2H, d, J=8.3 Hz), 7.83 (1H, d, J=7.9 Hz), 7.51-7.44 (1H, m), 7.43-7.31 (3H, m), 6.46 (1H, s), 3.04 (3H, s), 2.37 (3H, s).

Example 24

6-(2,3-dichlorophenyl)-4-N-(2,2,2-trifluoroethyl)pyrimidine-2,4-diamine

Prepared according to general procedure 2 from (2,3-dichlorophenyl)boronic acid and 6-chloro-4-N-(2,2,2-trifluoroethyl)pyrimidine-2,4-diamine. LCMS [M+H]$^+$ 337.

Example 25

6-(3-chlorophenyl)-4-N-(2,2,2-trifluoroethyl)pyrimidine-2,4-diamine

Prepared according to general procedure 2 from (3-chlorophenyl)boronic acid and 6-chloro-4-N-(2,2,2-trifluoroethyl)pyrimidine-2,4-diamine. LCMS [M+H]$^+$ 303.

Example 26

6-[1-(benzenesulfonyl)-1H-indol-3-yl]-4-N-methylpyrimidine-2,4-diamine

Prepared according to general procedure 8 from [1-(benzenesulfonyl)-1H-indol-3-yl]boronic acid and 6-chloro-4-N-methylpyrimidine-2,4-diamine. LCMS [M+H]$^+$ 380; $^1$H NMR (400 MHz, DMSO-d$_6$) δ$_H$ 8.43-8.25 (2H, m), 8.10-8.03 (2H, m), 8.01-7.95 (1H, m), 7.77-7.68 (1H, m), 7.66-7.56 (2H, m), 7.46-7.26 (2H, m), 6.74 (1H, br s), 6.32 (1H, s), 6.02 (2H, s), 2.81 (3H, d, J=5.0 Hz).

Example 27

4-N-cyclopropyl-6-[1-(4-methylbenzenesulfonyl)-1H-indol-3-yl]pyrimidine-2,4-diamine Prepared according to general procedure 8 from [1-(4-methylbenzenesulfonyl)-1H-indol-3-yl]boronic acid and 6-chloro-4-N-cyclopropylpyrimidine-2,4-diamine. LCMS [M+H]$^+$ 420; $^1$H NMR (400 MHz, CD$_3$OD) δ$_H$ 8.14 (1H, s), 8.07 (1H, d, J=7.9 Hz), 8.01 (1H, d, J=8.2 Hz), 7.86 (2H, d, J=8.2 Hz), 7.43-7.23 (4H, m), 6.43 (1H, s), 2.65 (1H, s), 2.34 (3H, s), 0.88-0.74 (2H, m), 0.65-0.48 (2H, m).

Example 28

6-[1-(benzenesulfonyl)-1H-indol-3-yl]-4-N-cyclopropylpyrimidine-2,4-diamine

Prepared according to general procedure 8 from [1-(benzenesulfonyl)-1H-indol-3-yl]boronic acid and 6-chloro-4-N-cyclopropylpyrimidine-2,4-diamine. LCMS [M+H]$^+$ 406; $^1$H NMR (400 MHz, CD$_3$OD) δ$_H$ 8.16 (1H, s), 8.10-7.98 (4H, m), 7.66-7.58 (1H, m), 7.56-7.46 (2H, m), 7.43-7.25 (2H, m), 6.43 (1H, s), 2.66 (1H, s), 0.84-0.81 (2H, m), 0.58-0.55 (2H, m).

Example 29

6-[1-(benzenesulfonyl)-1H-pyrrolo[2,3-b]pyridin-3-yl]-4-N-methylpyrimidine-2,4-diamine Prepared according to general procedure 8 from [1-(benzenesulfonyl)-1H-pyrrolo[2,3-b]pyridin-3-yl]boronic acid and 6-chloro-4-N-methylpyrimidine-2,4-diamine. LCMS [M+H]$^+$ 381; $^1$H NMR (400 MHz, CD$_3$OD) δ$_H$ 8.55 (1H, d, J=8.2 Hz), 8.41-8.30 (2H, m), 8.22-8.11 (2H, m), 7.71-7.61 (1H, m), 7.57-7.50 (2H, m), 7.37-7.28 (1H, m), 6.27 (1H, s), 2.92 (3H, s).

Example 30

6-[1-(benzenesulfonyl)-1H-indol-4-yl]-4-N-methylpyrimidine-2,4-diamine

Prepared according to general procedure 8 from [1-(benzenesulfonyl)-1H-indol-4-yl]boronic acid and 6-chloro-4-N-methylpyrimidine-2,4-diamine and 6-chloro-4-N-methylpyrimidine-2,4-diamine. LCMS [M+H]$^+$ 380; $^1$H NMR (400 MHz, CD$_3$OD) δ$_H$ 8.08 (1H, d, J=8.2 Hz), 7.97-7.89 (2H, m), 7.73 (1H, d, J=3.8 Hz), 7.65-7.56 (1H, m), 7.53-7.45 (3H, m), 7.39 (1H, t, J=8.2 Hz), 7.10 (1H, d, J=3.8 Hz), 6.10 (1H, s), 2.89 (3H, s).

Example 31

6-[1-(benzenesulfonyl)-1H-indol-5-yl]-4-N-methyl-pyrimidine-2,4-diamine

Prepared according to general procedure 8 from [1-(benzenesulfonyl)-1H-indol-5-yl]boronic acid and 6-chloro-4-N-methylpyrimidine-2,4-diamine. LCMS [M+H]$^+$ 380; $^1$H NMR (400 MHz, CD$_3$OD) $\delta_H$ 8.07-7.99 (2H, m), 7.98-7.89 (2H, m), 7.83-7.74 (1H, m), 7.71 (1H, d, J=4.0 Hz), 7.64-7.55 (1H, m), 7.54-7.45 (2H, m), 6.80 (1H, d, J=4.0 Hz), 6.21 (1H, s), 2.90 (3H, s).

Example 32

6-(2-methoxyphenyl)-4-N-methylpyrimidine-2,4-diamine

Prepared according to general procedure 2 from (2-methoxyphenyl)boronic acid and 6-chloro-4-N-methylpyrimidine-2,4-diamine. LCMS [M+H]$^+$ 231; $^1$H NMR (400 MHz, CD$_3$OD) $\delta_H$ 7.50 (1H, dd, J=7.5 and 1.7 Hz), 7.41-7.36 (1H, m), 7.08 (1H, d, J=8.3 Hz), 7.01 (1H, td, J=7.5 and 1.0 Hz), 6.17 (1H, s), 3.84 (3H, s), 2.89 (3H, s).

Example 33

6-(4-methoxyphenyl)-4-N-methylpyrimidine-2,4-diamine

Prepared according to general procedure 2 from (4-methoxyphenyl)boronic acid and 6-chloro-4-N-methylpyrimidine-2,4-diamine. LCMS [M+H]$^+$ 231.

Example 34

6-[3,5-bis(trifluoromethyl)phenyl]-4-N-methylpyrimidine-2,4-diamine

Prepared according to general procedure 2 from [3,5-bis(trifluoromethyl)phenyl]boronic acid and 6-chloro-4-N-methylpyrimidine-2,4-diamine. LCMS [M+H]$^+$ 337; $^1$H NMR (400 MHz, CD$_3$OD) $\delta_H$ 8.31 (2H, s), 8.17 (1H, s), 7.55-7.20 (3H, br s), 6.45 (1H, s), 3.02 (3H, s).

Example 35

6-(isoquinolin-4-yl)-4-N-methylpyrimidine-2,4-diamine

Prepared according to general procedure 2 from (isoquinolin-4-yl)boronic acid and 6-chloro-4-N-methylpyrimidine-2,4-diamine. LCMS [M+H]$^+$ 252; $^1$H NMR (400 MHz, CD$_3$OD) $\delta_H$ 9.17 (1H, s), 8.78 (1H, s), 8.17 (1H, d, J=8.4 Hz), 8.12 (1H, d, J=8.1 Hz), 7.98-7.94 (1H, m), 7.80-7.77 (1H, m), 6.54 (1H, s), 3.10 (3H, s).

Example 36

4-N-methyl-6-[4-(trifluoromethyl)phenyl]pyrimidine-2,4-diamine

Prepared according to general procedure 2 from [4-(trifluoromethyl)phenyl]boronic acid and 6-chloro-4-N-methylpyrimidine-2,4-diamine. LCMS [M+H]$^+$ 269; $^1$H NMR (400 MHz, CD$_3$OD) $\delta_H$ 7.93-7.87 (4H, m), 6.38 (1H, s), 3.04 (3H, s).

Example 37

4-N-methyl-6-[3-(trifluoromethyl)phenyl]pyrimidine-2,4-diamine

Prepared according to general procedure 2 from [3-(trifluoromethyl)phenyl]boronic acid and 6-chloro-4-N-methylpyrimidine-2,4-diamine. LCMS [M+H]$^+$ 269; $^1$H NMR (400 MHz, CD$_3$OD) $\delta_H$ 8.05 (1H, s), 7.99 (1H, d, J=8.0 Hz), 7.92 (1H, d, J=8.0 Hz), 7.79 (1H, t, J=8.0 Hz), 6.38 (1H, s), 3.05 (3H, s).

Example 38

6-(2,3-dichlorophenyl)-4-N-methylpyrimidine-2,4-diamine

Prepared according to general procedure 3 from methanamine and 4-chloro-6-(2,3-dichlorophenyl)pyrimidin-2-amine. LCMS [M+H]$^+$ 269; $^1$H NMR (400 MHz, CD$_3$OD) $\delta_H$ 7.79-7.77 (1H, m), 7.50-7.49 (2H, m), 6.12 (1H, s), 3.04 (3H, s).

Example 39

6-(2H-1,3-benzodioxol-5-yl)-4-N-methylpyrimidine-2,4-diamine

Prepared according to general procedure 2 from (2H-1,3-benzodioxol-5-yl)boronic acid and 6-chloro-4-N-methylpyrimidine-2,4-diamine. LCMS [M+H]$^+$ 245; $^1$H NMR (400 MHz, CD$_3$OD) $\delta_H$ 7.42-7.39 (1H, m), 7.36-7.35 (1H, m), 6.89 (1H, d, J=8.0 Hz), 6.15 (1H, s), 6.02 (1H, s), 2.92 (3H, s).

Example 40

3-[2-amino-6-(methylamino)pyrimidin-4-yl]benzonitrile

Prepared according to general procedure 2 from (3-cyanophenyl)boronic acid and 6-chloro-4-N-methylpyrimidine-2,4-diamine. LCMS [M+H]$^+$ 226; $^1$H NMR (400 MHz, CD$_3$OD) $\delta_H$ 8.15 (1H, s), 8.05-8.03 (1H, m), 7.95-7.92 (1H, m), 7.74 (1H, t, J=8.5 Hz), 6.35 (1H, s), 3.02 (3H, s).

Example 41

N-{3-[2-amino-6-(methylamino)pyrimidin-4-yl]phenyl}acetamide

Prepared according to general procedure 2 from (3-acetamidophenyl)boronic acid and 6-chloro-4-N-methylpyrimidine-2,4-diamine. LCMS [M+H]$^+$ 258; $^1$H NMR (400 MHz, CD$_3$OD) $\delta_H$ 8.20 (1H, s), 7.56-7.52 (2H, m), 7.45-7.43 (1H, m), 6.31 (1H, s), 3.06 (3H, s), 2.19 (3H, s).

Example 42

4-N-methyl-6-[4-(morpholine-4-sulfonyl)phenyl]pyrimidine-2,4-diamine

Prepared according to general procedure 2 from [4-(morpholine-4-sulfonyl)phenyl]boronic acid and 6-chloro-4-N-methylpyrimidine-2,4-diamine. LCMS [M+H]$^+$ 350;

¹H NMR (400 MHz, CD₃OD) δ$_H$ 7.99 (4H, s), 6.42 (1H, s), 3.76-3.72 (4H, m), 3.07 (3H, s), 3.06-3.03 (4H, m).

Example 43

6-(4-methanesulfonylphenyl)-4-N-methylpyrimidine-2,4-diamine

Prepared according to general procedure 2 from (4-methanesulfonyl-phenyl)boronic acid and 6-chloro-4-N-methylpyrimidine-2,4-diamine. LCMS [M+H]⁺ 279; ¹H NMR (400 MHz, CD₃OD) δ$_H$ 8.20-8.17 (2H, m), 8.00-7.97 (2H, m), 6.41 (1H, s), 3.22 (3H, s), 3.08 (3H, s).

Example 44

4-N-methyl-6-[3-(morpholine-4-carbonyl)phenyl]pyrimidine-2,4-diamine

Prepared according to general procedure 2 from [3-(morpholine-4-carbonyl)phenyl]boronic acid and 6-chloro-4-N-methylpyrimidine-2,4-diamine. LCMS [M+H]⁺ 314; ¹H NMR (400 MHz, CD₃OD) δ$_H$ 8.00-7.96 (1H, m), 7.92 (1H, s), 7.57 (1H, t, J=7.8 Hz), 7.52 (1H, dt, J=7.8 and 1.4 Hz), 6.27 (1H, s), 3.79-3.50 (8H, m), 2.94 (3H, s).

Example 45

4-[2-amino-6-(methylamino)pyrimidin-4-yl]-N-(furan-2-ylmethyl)benzamide

Prepared according to general procedure 2 from {4-[(furan-2-ylmethyl)carbamoyl]phenyl}boronic acid and 6-chloro-4-N-methylpyrimidine-2,4-diamine. LCMS [M+H]⁺ 324; ¹H NMR (400 MHz, CD₃OD) δ$_H$ 7.93-7.90 (4H, m), 7.46-7.44 (1H, m), 6.39-6.37 (1H, m), 6.34-6.32 (1H, m), 6.28 (1H, s), 4.60 (2H, s), 2.94 (3H, s).

Example 46

N-{4-[2-amino-6-(methylamino)pyrimidin-4-yl]phenyl}methanesulfonamide

Prepared according to general procedure 2 from (4-methanesulfon-amidophenyl)boronic acid and 6-chloro-4-N-methylpyrimidine-2,4-diamine. LCMS [M+H]⁺ 294; ¹H NMR (400 MHz, CD₃OD) δ$_H$ 7.72-7.70 (2H, m), 7.43-7.40 (2H, m), 6.29 (1H, s), 3.06 (3H, s), 3.03 (3H, s).

Example 47

N-{4-[2-amino-6-(methylamino)pyrimidin-4-yl]phenyl}acetamide

Prepared according to general procedure 2 from (4-acetamidophenyl)boronic acid and 6-chloro-4-N-methylpyrimidine-2,4-diamine. LCMS [M+H]⁺ 258; ¹H NMR (400 MHz, CD₃OD) δ$_H$ 7.82-7.80 (2H, m), 7.75-7.73 (2H, m), 6.31 (1H, s), 3.03 (3H, s), 2.18 (3H, d, J=2.5 Hz).

Example 48

4-N-methyl-6-(pyridin-4-yl)pyrimidine-2,4-diamine

Prepared according to general procedure 2 from (pyridin-4-yl)boronic acid and 6-chloro-4-N-methylpyrimidine-2,4-diamine. LCMS [M+H]⁺ 202; ¹H NMR (400 MHz, CD₃OD) δ$_H$ 8.79 (2H, dd, J=4.7 and 1.6 Hz), 7.76 (2H, d, J=4.7 Hz), 6.47 (1H, s), 3.07 (3H, s).

Example 49

6-(6-methoxypyridin-3-yl)-4-N-methylpyrimidine-2,4-diamine

Prepared according to general procedure 2 from (6-methoxypyridin-3-yl)boronic acid and 6-chloro-4-N-methylpyrimidine-2,4-diamine. LCMS [M+H]⁺ 232; ¹H NMR (400 MHz, CD₃OD) δ$_H$ 8.57 (1H, s), 8.03 (1H, d, J=7.3 Hz), 6.98 (1H, d, J=7.3 Hz), 6.30 (1H, s), 4.02 (3H, s), 3.07 (3H, s).

Example 50

6-(2-fluoro-4-phenylphenyl)-4-N-methylpyrimidine-2,4-diamine

Prepared according to general procedure 2 from (2-fluoro-4-phenylphenyl)boronic acid and 6-chloro-4-N-methylpyrimidine-2,4-diamine. LCMS [M+H]⁺ 295; ¹H NMR (400 MHz, CD₃OD) δ$_H$ 7.75-7.61 (5H, m), 7.54-7.44 (3H, m), 6.41 (1H, s), 6.30 (1H, s), 3.06 (3H, s).

Example 51

4-[2-amino-6-(methylamino)pyrimidin-4-yl]benzonitrile

Prepared according to general procedure 2 from (4-cyanophenyl)boronic acid and 6-chloro-4-N-methylpyrimidine-2,4-diamine. LCMS [M+H]⁺ 226; ¹H NMR (400 MHz, CD₃OD) δ$_H$ 8.03 (2H, d, J=8.2 Hz), 7.84-7.80 (2H, m), 6.29 (1H, s), 2.93 (3H, s).

Example 52

4-N-methyl-6-(quinolin-5-yl)pyrimidine-2,4-diamine

Prepared according to general procedure 2 from (quinolin-5-yl)boronic acid and 6-chloro-4-N-methylpyrimidine-2,4-diamine. LCMS [M+H]⁺ 252; ¹H NMR (400 MHz, CD₃OD) δ$_H$ 8.98 (1H, dd, J=4.2 and 1.9 Hz), 8.49 (1H, d, J=8.6 Hz), 8.26 (1H, d, J=8.6 Hz), 7.95-7.91 (1H, m), 7.82 (1H, d, J=7.2 Hz), 7.67 (1H, dd, J=8.6 and 4.2 Hz), 6.23 (1H, s), 3.08 (3H, s).

Example 53

6-(4-chlorophenyl)-4-N-(prop-2-en-1-yl)pyrimidine-2,4-diamine

Prepared according to general procedure 2 from (4-chlorophenyl)boronic acid and 6-chloro-4-N-(prop-2-en-1-yl)pyrimidine-2,4-diamine. LCMS [M+H]⁺ 261; ¹H NMR (400 MHz, CD₃OD) δ$_H$ 7.75-7.73 (2H, m), 7.64-7.62 (2H, m), 6.36 (1H, s), 6.02-5.92 (1H, m), 5.33-5.31 (1H, m), 5.23-5.20 (1H, m), 4.18-4.16 (2H, m).

Example 54

6-(4-methoxyphenyl)-4-N-(prop-2-en-1-yl)pyrimidine-2,4-diamine

Prepared according to general procedure 2 from (4-methoxyphenyl)boronic acid and 6-chloro-4-N-(prop-2-en-1-yl)pyrimidine-2,4-diamine. LCMS [M+H]$^+$ 257.

Example 55

6-(4-chlorophenyl)-4-N-cyclopentylpyrimidine-2,4-diamine

Prepared according to general procedure 2 from (4-chlorophenyl)boronic acid and 6-chloro-4-N-cyclopentylpyrimidine-2,4-diamine. LCMS [M+H]$^+$ 289; $^1$H NMR (400 MHz, CD$_3$OD) $\delta_H$ 7.60 (2H, d, J=8.8 Hz), 7.51-7.49 (2H, m), 6.17 (1H, s), 4.36 (1H, s), 2.00-1.93 (2H, m), 1.73-1.65 (2H, m), 1.61-1.53 (2H, m), 1.50-1.43 (2H, m).

Example 56

4-N-cyclopentyl-6-(4-methoxyphenyl)pyrimidine-2,4-diamine

Prepared according to general procedure 2 from 6-chloro-4-N-cyclopentylpyrimidine-2,4-diamine and (4-methoxyphenyl)boronic acid. LCMS [M+H]$^+$ 285; $^1$H NMR (400 MHz, CD$_3$OD) $\delta_H$ 7.68 (2H, d, J=9.2 Hz), 7.12 (2H, d, J=9.2 Hz), 6.27 (1H, s), 4.47 (1H, q, J=6.7 Hz), 3.89 (3H, s), 2.10-2.03 (2H, m), 1.82-1.79 (2H, m), 1.72-1.63 (2H, m), 1.62-1.53 (2H, m).

Example 57

4-N-cyclopentyl-6-[3-(trifluoromethyl)phenyl]pyrimidine-2,4-diamine

Prepared according to general procedure 2 from [3-(trifluoromethyl)-phenyl]boronic acid and 6-chloro-4-N-cyclopentylpyrimidine-2,4-diamine. LCMS [M+H]$^+$ 323; $^1$H NMR (400 MHz, CD$_3$OD) $\delta_H$ 8.17 (1H, s), 8.08 (1H, d, J=7.9 Hz), 7.74 (1H, d, J=7.9 Hz), 7.65 (1H, t, J=7.9 Hz), 6.28 (1H, s), 4.29 (1H, s), 2.09-1.99 (2H, m), 1.75-1.74 (2H, m), 1.71-1.62 (2H, m), 1.60-1.49 (2H, m).

Example 58

6-(4-chlorophenyl)-4-N-cyclobutylpyrimidine-2,4-diamine

Prepared according to general procedure 2 from (4-chlorophenyl)boronic acid and 6-chloro-4-N-cyclobutylpyrimidine-2,4-diamine. LCMS [M+H]$^+$ 275; $^1$H NMR (400 MHz, CD$_3$OD) $\delta_H$ 7.83 (2H, d, J=8.4 Hz), 7.45 (2H, d, J=8.4 Hz), 6.17 (1H, s), 4.42 (1H, s), 2.44-2.38 (2H, m), 2.02-1.94 (2H, m), 1.83-1.76 (2H, m).

Example 59

4-N-cyclobutyl-6-(4-methoxyphenyl)pyrimidine-2,4-diamine

Prepared according to general procedure 2 from (4-methoxyphenyl)boronic acid and 6-chloro-4-N-cyclobutylpyrimidine-2,4-diamine. LCMS [M+H]$^+$ 271; $^1$H NMR (400 MHz, CD$_3$OD) $\delta_H$ 7.68 (2H, d, J=8.5 Hz), 7.14 (2H, d, J=8.5 Hz), 6.22 (1H, s), 4.64 (1H, q, J=7.9 Hz), 3.90 (3H, s), 2.46-2.38 (2H, m), 2.12-2.01 (2H, m), 1.87-1.78 (2H, m).

Example 60

4-N-cyclobutyl-6-[3-(trifluoromethyl)phenyl]pyrimidine-2,4-diamine

Prepared according to general procedure 2 from [3-(trifluoromethyl)phenyl]boronic acid and 6-chloro-4-N-cyclobutylpyrimidine-2,4-diamine. LCMS [M+H]$^+$ 309; $^1$H NMR (400 MHz, CD$_3$OD) $\delta_H$ 7.68 (2H, d, J=8.5 Hz), 7.14 (2H, d, J=8.5 Hz), 6.22 (1H, s), 4.64 (1H, q, J=7.9 Hz), 3.90 (3H, s), 2.46-2.38 (2H, m), 2.12-2.01 (2H, m), 1.87-1.78 (2H, m).

Example 61

6-(2,3-dichlorophenyl)-4-N-pentylpyrimidine-2,4-diamine

Prepared according to general procedure 3 from pentan-1-amine and 4-chloro-6-(2,3-dichlorophenyl)pyrimidin-2-amine. LCMS [M+H]$^+$ 325; $^1$H NMR (400 MHz, CD$_3$OD) $\delta_H$ 7.80-7.78 (1H, m), 7.52-7.50 (2H, m), 6.12 (1H, s), 3.54-3.50 (2H, m), 1.69-1.65 (2H, m), 1.42-1.39 (4H, m), 0.98-0.95 (3H, m).

Example 62

4-N-cyclopropyl-6-(2,3-dichlorophenyl)pyrimidine-2,4-diamine

Prepared according to general procedure 3 from cyclopropanamine and 4-chloro-6-(2,3-dichlorophenyl)pyrimidin-2-amine. LCMS [M+H]$^+$ 295; $^1$H NMR (400 MHz, CDCl$_3$) $\delta_H$ 7.51 (1H, dd, J=7.9 and 1.6 Hz), 7.41 (1H, dd, J=7.9 and 1.6 Hz), 7.28 (1H, t, J=7.9 Hz), 6.35 (1H, s), 5.21 (1H, s), 4.78 (2H, s), 2.63-2.47 (1H, m), 0.86-0.78 (2H, m), 0.64-0.57 (2H, m).

Example 63

4-N-tert-butyl-6-(2,3-dichlorophenyl)pyrimidine-2,4-diamine

Prepared according to general procedure 3 from 2-methylpropan-2-amine and 4-chloro-6-(2,3-dichlorophenyl)pyrimidin-2-amine. LCMS [M+H]$^+$ 311.

Example 64

4-N-cyclobutyl-6-(2,3-dichlorophenyl)pyrimidine-2,4-diamine

Prepared according to general procedure 3 from cyclobutanamine and 4-chloro-6-(2,3-dichlorophenyl)pyrimidin-2-amine. LCMS [M+H]$^+$ 309; $^1$H NMR (400 MHz, CD$_3$OD) $\delta_H$ 7.60-7.58 (1H, m), 7.37-7.34 (2H, m), 5.89 (1H, s), 4.46 (1H, s), 3.37 (2H, s), 2.43-2.35 (2H, m), 2.01-1.94 (2H, m), 1.80-1.72 (2H, m).

Example 65

4-N-cyclopentyl-6-(2,3-dichlorophenyl)pyrimidine-2,4-diamine

Prepared according to general procedure 3 from cyclopentanamine and 4-chloro-6-(2,3-dichlorophenyl)pyrimidin-2-amine. LCMS [M+H]⁺ 323; ¹H NMR (400 MHz, CD₃OD) $\delta_H$ 7.62-7.56 (1H, m), 7.40-7.34 (2H, m), 5.93 (1H, s), 3.37 (1H, s), 2.09-1.98 (2H, m), 1.82-1.72 (2H, m), 1.71-1.61 (2H, m), 1.58-1.48 (2H, m).

Example 66

6-(2,3-dichlorophenyl)-4-N-ethylpyrimidine-2,4-diamine

Prepared according to general procedure 3 from ethanamine and 4-chloro-6-(2,3-dichlorophenyl)pyrimidin-2-amine. LCMS [M+H]⁺ 283; ¹H NMR (400 MHz, CD₃OD) $\delta_H$ 7.62-7.57 (1H, m), 7.40-7.35 (2H, m), 5.92 (1H, s), 3.44-3.36 (2H, m), 1.24 (3H, t, J=7.1 Hz).

Example 67

6-(2,3-dichlorophenyl)-4-N-(oxolan-3-yl)pyrimidine-2,4-diamine

Prepared according to general procedure 3 from oxolan-3-amine and 4-chloro-6-(2,3-dichlorophenyl)pyrimidin-2-amine. LCMS [M+H]⁺ 325; ¹H NMR (400 MHz, CD₃OD) $\delta_H$ 7.63-7.58 (1H, m), 7.39-7.35 (2H, m), 5.98 (1H, s), 4.59 (1H, s), 4.02-3.94 (2H, m), 3.90-3.82 (1H, m), 3.73-3.67 (1H, m), 2.36-2.26 (1H, m), 1.99-1.89 (1H, m).

Example 68

6-(3,4-dichlorophenyl)-4-N-methylpyrimidine-2,4-diamine

Prepared according to general procedure 2 from (3,4-dichlorophenyl)boronic acid and 6-chloro-4-N-methylpyrimidine-2,4-diamine. LCMS [M+H]⁺ 269; ¹H NMR (400 MHz, CD₃OD) $\delta_H$ 7.96 (1H, d, J=2.0 Hz), 7.77 (1H, d, J=8.5 Hz), 7.70-7.55 (2H, m), 6.35 (1H, s), 3.06 (3H, s).

Example 69

6-(4-tert-butylphenyl)-4-N-methyl pyrimidine-2,4-diamine

Prepared according to general procedure 5 from (4-tert-butylphenyl)boronic acid and 6-chloro-4-N-methylpyrimidine-2,4-diamine. LCMS [M+H]⁺ 257; ¹H NMR (400 MHz, CD₃OD) $\delta_H$ 7.77 (2H, d, J=8.7 Hz), 7.53-7.48 (2H, m), 6.22 (1H, s), 2.93 (3H, s), 1.38 (9H, s).

Example 70

4-N-methyl-6-(4-methylphenyl)pyrimidine-2,4-diamine

Prepared according to general procedure 5 from (4-methylphenyl)boronic acid and 6-chloro-4-N-methylpyrimidine-2,4-diamine. LCMS [M+H]⁺ 215; ¹H NMR (400 MHz, CD₃OD) $\delta_H$ 7.73 (2H, d, J=8.9 Hz), 7.28 (2H, d, J=8.9 Hz), 6.20 (1H, s), 2.93 (3H, s), 2.41 (3H, s).

Example 71

6-(2,4-dichlorophenyl)-4-N-methylpyrimidine-2,4-diamine

Prepared according to general procedure 5 from (2,4-dichlorophenyl)boronic acid and 6-chloro-4-N-methylpyrimidine-2,4-diamine. LCMS [M+H]⁺ 269; ¹H NMR (400 MHz, CD₃OD) $\delta_H$ 7.57 (1H, d, J=1.9 Hz), 7.48-7.41 (2H, m), 5.98 (1H, s), 2.92 (3H, s).

Example 72

4-N-methyl-6-(2,4,5-trifluorophenyl)pyrimidine-2,4-diamine

Prepared according to general procedure 5 from (2,4,5-trifluorophenyl)boronic acid and 6-chloro-4-N-methylpyrimidine-2,4-diamine. LCMS [M+H]⁺ 255; ¹H NMR (400 MHz, CD₃OD) $\delta_H$ 7.86-7.75 (1H, m), 7.31-7.24 (1H, m), 6.25 (1H, s), 2.91 (3H, s).

Example 73

6-(4-fluoro-2-methoxyphenyl)-4-N-methylpyrimidine-2,4-diamine

Prepared according to general procedure 5 from (4-fluoro-2-methoxyphenyl)-boronic acid and 6-chloro-4-N-methylpyrimidine-2,4-diamine. LCMS [M+H]⁺ 249; ¹H NMR (400 MHz, CD₃OD) $\delta_H$ 7.57 (1H, dd, J=8.5 and 6.3 Hz), 6.89 (1H, dd, J=11.4 and 2.5 Hz), 6.76 (1H, td, J=8.5 and 2.5 Hz), 6.19 (1H, s), 3.87 (3H, s), 2.90 (3H, s).

Example 74

6-(5-chloro-2-methylphenyl)-4-N-methylpyrimidine-2,4-diamine

Prepared according to general procedure 5 from (5-chloro-2-methylphenyl)-boronic acid and 6-chloro-4-N-methylpyrimidine-2,4-diamine. LCMS [M+H]⁺ 249; ¹H NMR (400 MHz, CD₃OD) $\delta_H$ 7.33-7.23 (3H, m), 5.85 (1H, s), 2.92 (3H, s), 2.32 (3H, s).

Example 75

6-(2,4-difluorophenyl)-4-N-methylpyrimidine-2,4-diamine

Prepared according to general procedure 5 from (2,4-difluorophenyl)boronic acid and 6-chloro-4-N-methylpyrimidine-2,4-diamine. LCMS [M+H]⁺ 237; ¹H NMR (400 MHz, CD₃OD) $\delta_H$ 7.88-7.79 (1H, m), 7.10-7.00 (2H, m), 6.19 (1H, d, J=2.0 Hz), 2.92 (3H, s).

Example 76

6-(5-fluoro-2-methoxyphenyl)-4-N-methylpyrimidine-2,4-diamine

Prepared according to general procedure 5 from (5-fluoro-2-methoxyphenyl)-boronic acid and 6-chloro-4-N-methylpyrimidine-2,4-diamine. LCMS [M+H]⁺ 249; ¹H NMR (400 MHz, CD₃OD) $\delta_H$ 7.36 (1H, dd, J=9.4 and 3.1 Hz), 7.15-7.04 (2H, m), 6.28 (1H, s), 3.85 (3H, s), 2.91 (3H, s).

Example 77

6-(2-chlorophenyl)-4-N-methylpyrimidine-2,4-diamine

Prepared according to general procedure 5 from (2-chlorophenyl)boronic acid and 6-chloro-4-N-methylpyrimidine- 2,4-diamine. LCMS [M+H]$^+$ 235; $^1$H NMR (400 MHz, CD$_3$OD) δ$_H$ 7.51-7.44 (1H, m), 7.42-7.36 (2H, m), 5.98 (1H, s), 2.92 (3H, s).

Example 78

4-N-methyl-6-(pyridin-2-yl)pyrimidine-2,4-diamine

To a solution of 6-iodo-4-N-methylpyrimidine-2,4-diamine (1 eq.) and 2-(tributylstannyl)pyridine (1.3 eq.) in toluene (1 mL) were added CuI (0.25 eq.) and Pd(PPh$_3$)$_4$ (0.05 eq.). The reaction mixture was heated at 120° C. for 1 hour. The crude mixture was purified by HPLC. LCMS [M+H]$^+$ 202.

Example 79

6-(4-methoxy-3-methylphenyl)-4-N-methylpyrimidine-2,4-diamine

Prepared according to general procedure 6 from (4-methoxy-3-methylphenyl)-boronic acid and 6-iodo-4-N-methylpyrimidine-2,4-diamine. LCMS [M+H]$^+$ 245; $^1$H NMR (400 MHz, CD$_3$OD) δ$_H$ 7.72-7.62 (2H, m), 6.99 (1H, d, J=8.3 Hz), 6.18 (1H, s), 3.91 (3H, s), 2.94 (3H, s), 2.28 (3H, s).

Example 80

6-(3-chloro-4-fluorophenyl)-4-N-methylpyrimidine-2,4-diamine

Prepared according to general procedure 6 from (3-chloro-4-fluorophenyl)boronic acid and 6-iodo-4-N-methylpyrimidine-2,4-diamine. LCMS [M+H]$^+$ 253; $^1$H NMR (400 MHz, CD$_3$OD) δ$_H$ 8.05-7.99 (1H, m), 7.87-7.79 (1H, m), 7.33 (1H, t, J=8.2 Hz), 6.23 (1H, s), 2.94 (3H, s).

Example 81

4-N-methyl-6-[4-(trifluoromethoxy)phenyl]pyrimidine-2,4-diamine

Prepared according to general procedure 6 from [4-(trifluoromethoxy)phenyl]boronic acid and 6-iodo-4-N-methylpyrimidine-2,4-diamine. LCMS [M+H]$^+$ 285; $^1$H NMR (400 MHz, CD$_3$OD) δ$_H$ 7.98-7.92 (2H, m), 7.38-7.32 (2H, m), 6.23 (1H, s), 2.93 (3H, s).

Example 82

6-(3-fluoro-4-methoxyphenyl)-4-N-methylpyrimidine-2,4-diamine

Prepared according to general procedure 6 from (3-fluoro-4-methoxyphenyl)-boronic acid and 6-iodo-4-N-methylpyrimidine-2,4-diamine. LCMS [M+H]$^+$ 249; $^1$H NMR (400 MHz, CD$_3$OD) δ$_H$ 7.97-7.60 (2H, m), 7.21-7.12 (1H, m), 6.20 (1H, s), 3.95 (3H, s), 2.94 (3H, s).

Example 83

6-(3,4-difluorophenyl)-4-N-methylpyrimidine-2,4-diamine

Prepared according to general procedure 6 from (3,4-difluorophenyl)boronic acid and 6-iodo-4-N-methylpyrimidine-2,4-diamine. LCMS [M+H]$^+$ 237; $^1$H NMR (400 MHz, CD$_3$OD) δ$_H$ 7.86-7.77 (1H, m), 7.74-7.66 (1H, m), 7.40-7.30 (1H, m), 6.23 (1H, s), 2.94 (3H, s).

Example 84

4-N-methyl-6-[4-(propan-2-yloxy)phenyl]pyrimidine-2,4-diamine

Prepared according to general procedure 6 from [4-(propan-2-yloxy)phenyl]boronic acid and 6-iodo-4-N-methylpyrimidine-2,4-diamine. LCMS [M+H]$^+$ 259.

Example 85

6-[2-fluoro-3-(trifluoromethyl)phenyl]-4-N-methylpyrimidine-2,4-diamine

Prepared according to general procedure 6 from [2-fluoro-3-(trifluoromethyl)phenyl]boronic acid and 6-iodo-4-N-methylpyrimidine-2,4-diamine. LCMS [M+H]$^+$ 287; $^1$H NMR (400 MHz, CD$_3$OD) δ$_H$ 7.98 (1H, t, J=7.0 Hz), 7.87 (1H, t, J=7.0 Hz), 7.52 (1H, t, J=8.0 Hz), 6.27 (1H, d, J=1.5 Hz), 3.00 (3H, s).

Example 86

6-(2,3-dimethylphenyl)-4-N-methylpyrimidine-2,4-diamine

Prepared according to general procedure 6 from (2,3-dimethylphenyl)boronic acid and 6-iodo-4-N-methylpyrimidine-2,4-diamine. LCMS [M+H]$^+$ 229; $^1$H NMR (400 MHz, CD$_3$OD) δ$_H$ 7.24-7.18 (1H, m), 7.17-7.05 (2H, m), 5.82 (1H, s), 2.92 (3H, s), 2.35 (3H, s), 2.22 (3H, s).

Example 87

6-(3-chloro-2-fluorophenyl)-4-N-methylpyrimidine-2,4-diamine

Prepared according to general procedure 6 from (3-chloro-2-fluorophenyl)boronic acid and 6-iodo-4-N-methylpyrimidine-2,4-diamine. LCMS [M+H]$^+$ 253; $^1$H NMR (400 MHz, CD$_3$OD) δ$_H$ 7.71-7.65 (1H, m), 7.58-7.53 (1H, m), 7.30-7.22 (1H, m), 6.18 (1H, d, J=2.1 Hz), 2.93 (3H, s).

Example 88

6-(4-chloro-3-fluorophenyl)-4-N-methylpyrimidine-2,4-diamine

Prepared according to general procedure 6 from (4-chloro-3-fluorophenyl)boronic acid and 6-iodo-4-N-methylpyrimidine-2,4-diamine. LCMS [M+H]$^+$ 253; $^1$H NMR (400 MHz, CD$_3$OD) δ$_H$ 7.73-7.65 (2H, m), 7.62-7.55 (1H, m), 6.34 (1H, s), 3.03 (3H, s).

Example 89

4-N-methyl-6-[2-(trifluoromethyl)phenyl]pyrimidine-2,4-diamine

Prepared according to general procedure 6 from [2-(trifluoromethyl)-phenyl]boronic acid and 6-iodo-4-N-methylpyrimidine-2,4-diamine. LCMS [M+H]$^+$ 269; $^1$H NMR (400 MHz, CD$_3$OD) $\delta_H$ 7.80 (1H, d, J=8.1 Hz), 7.70 (1H, t, J=7.7 Hz), 7.61 (1H, t, J=7.7 Hz), 7.48 (1H, d, J=8.1 Hz), 5.88 (1H, s), 2.92 (3H, s).

Example 90

4-N-methyl-6-(1-methyl-1H-indazol-4-yl)pyrimidine-2,4-diamine

Prepared according to general procedure 6 from (1-methyl-1H-indazol-4-yl)boronic acid and 6-iodo-4-N-methylpyrimidine-2,4-diamine. LCMS [M+H]$^+$ 255; $^1$H NMR (400 MHz, CD$_3$OD) $\delta_H$ 8.42 (1H, s), 7.69-7.63 (1H, m), 7.60-7.50 (2H, m), 6.33 (1H, s), 4.14 (3H, s), 2.97 (3H, s).

Example 91

6-[2-chloro-3-(trifluoromethyl)phenyl]-4-N-methylpyrimidine-2,4-diamine

Prepared according to general procedure 6 from [2-chloro-3-(trifluoromethyl)phenyl]boronic acid and 6-iodo-4-N-methylpyrimidine-2,4-diamine. LCMS [M+H]$^+$ 303; $^1$H NMR (400 MHz, CD$_3$OD) $\delta_H$ 7.90-7.85 (1H, m), 7.71-7.66 (1H, m), 7.62-7.55 (1H, m), 5.95 (1H, s), 2.94 (3H, s).

Example 92

6-(2-chloro-3-fluorophenyl)-4-N-methylpyrimidine-2,4-diamine

Prepared according to general procedure 6 from (2-chloro-3-fluorophenyl)boronic acid and 6-iodo-4-N-methylpyrimidine-2,4-diamine. LCMS [M+H]$^+$ 253; $^1$H NMR (400 MHz, CD$_3$OD) $\delta_H$ 7.46-7.38 (1H, m), 7.35-7.28 (2H, m), 5.98 (1H, s), 2.93 (3H, s).

Example 93

6-(2,3-difluorophenyl)-4-N-methylpyrimidine-2,4-diamine

Prepared according to general procedure 6 from (2,3-difluorophenyl)boronic acid and 6-iodo-4-N-methylpyrimidine-2,4-diamine. LCMS [M+H]$^+$ 237; $^1$H NMR (400 MHz, CD$_3$OD) $\delta_H$ 7.58-7.51 (1H, m), 7.34-7.31 (1H, m), 7.29-7.22 (1H, m), 6.20 (1H, s), 2.93 (3H, s).

Example 94

6-(3-chloro-2-methylphenyl)-4-N-methylpyrimidine-2,4-diamine

Prepared according to general procedure 6 from (3-chloro-2-methylphenyl)boronic acid and 6-iodo-4-N-methylpyrimidine-2,4-diamine. LCMS [M+H]$^+$ 249; $^1$H NMR (400 MHz, CD$_3$OD) $\delta_H$ 7.47-7.41 (1H, m), 7.27-7.21 (2H, m), 5.85 (1H, s), 2.93 (3H, s), 2.36 (3H, s).

Example 95

6-(2,3-dichlorophenyl)-4-N,5-dimethylpyrimidine-2,4-diamine

Step 1: 4-chloro-6-(2,3-dichlorophenyl)-5-methylpyrimidin-2-amine was prepared according to general procedure 2 from 4,6-dichloro-5-methylpyrimidin-2-amine and (2,3-dichlorophenyl)boronic acid (and using DMF instead of dioxane).

Step 2: 6-(2,3-dichlorophenyl)-4-N,5-dimethylpyrimidine-2,4-diamine was prepared according to general procedure 3 from methanamine and 4-chloro-6-(2,3-dichlorophenyl)-5-methylpyrimidin-2-amine (prepared in step 1 above). LCMS [M+H]$^+$ 283; $^1$H NMR (400 MHz, CD$_3$OD) $\delta_H$ 7.62 (1H, dd, J=7.9 and 1.9 Hz), 7.41 (1H, t, J=7.9 Hz), 7.27 (1H, dd, J=7.9 and 1.9 Hz), 3.01 (3H, s), 1.71 (3H, s).

Example 96

4-N-cyclopropyl-6-(2,3-dichlorophenyl)-5-methylpyrimidine-2,4-diamine

Was prepared according to general procedure 3 from cyclopropanamine and 4-chloro-6-(2,3-dichlorophenyl)-5-methylpyrimidin-2-amine (prepared in example 95, step 1 above). LCMS [M+H]$^+$ 309; $^1$H NMR (400 MHz, CD$_3$OD) $\delta_H$ 7.83 (1H, dd, J=7.7 and 1.2 Hz), 7.56 (1H, t, J=7.8 Hz), 7.48 (1H, dd, J=7.8 and 1.2 Hz), 3.17-3.09 (1H, m), 1.79 (3H, s), 0.96-0.90 (2H, m), 0.82-0.75 (2H, m).

Example 97

6-(7-chloro-2H-1,3-benzodioxol-5-yl)-4-N-methylpyrimidine-2,4-diamine

Prepared according to general procedure 6 from (7-chloro-2H-1,3-benzodioxol-5-yl)boronic acid and 6-iodo-4-N-methylpyrimidine-2,4-diamine. LCMS [M+H]$^+$ 279; $^1$H NMR (400 MHz, CD$_3$OD) $\delta_H$ 7.11 (1H, s), 7.04 (1H, s), 6.13 (2H, s), 6.10 (1H, s), 3.04 (3H, s).

Example 98

6-(2,3-dichloro-4-methoxyphenyl)-4-N-methylpyrimidine-2,4-diamine

Step 1: 4-chloro-6-(2,3-dichloro-5-methoxyphenyl)pyrimidin-2-amine was prepared according to general procedure 2 from 4,6-dichloropyrimidin-2-amine and 2,3-dichloro-4-methoxyphenyl)boronic acid.

Step 2: Prepared according to general procedure 3 from methanamine and 4-chloro-6-(2,3-dichloro-5-methoxyphenyl)pyrimidin-2-amine (prepared in step 1 above). LCMS [M+H]$^+$ 299; $^1$H NMR (400 MHz, CD$_3$OD) $\delta_H$ 7.49 (1H, d, J=8.6 Hz), 7.24 (1H, d, J=8.6 Hz), 6.11 (1H, s), 4.01 (3H, s), 3.09 (3H, s).

Example 99

6-(2,3-dichloro-5-methoxyphenyl)-4-N-methylpyrimidine-2,4-diamine

Prepared according to general procedure 6 from (2,3-dichloro-5-methoxyphenyl)boronic acid and 6-iodo-4-N-methylpyrimidine-2,4-diamine. LCMS [M+H]$^+$ 299; $^1$H NMR (400 MHz, CD$_3$OD) $\delta_H$ 7.38 (1H, d, J=2.9 Hz), 7.12 (1H, d, J=2.9 Hz), 6.13 (1H, s), 3.88 (3H, s), 3.05 (3H, s).

Example 100

4-[2-amino-6-(methylamino)pyrimidin-4-yl]phenol

Prepared according to general procedure 6 from (4-hydroxyphenyl)boronic acid and 6-iodo-4-N-methylpyrimidine-2,4-diamine. LCMS [M+H]⁺ 217; ¹H NMR (400 MHz, CD₃OD) $\delta_H$ 7.69 (2H, d, J=8.5 Hz), 6.85 (2H, d, J=8.5 Hz), 6.15 (1H, s), 4.59 (1H, s), 2.93 (3H, s).

Example 101

{3-[2-amino-6-(methylamino)pyrimidin-4-yl]phenyl}methanol

Prepared according to general procedure 6 from [3-(hydroxymethyl) phenyl]boronic acid and 6-iodo-4-N-methylpyrimidine-2,4-diamine. LCMS [M+H]⁺ 231; ¹H NMR (400 MHz, CD₃OD) $\delta_H$ 7.83 (1H, s), 7.76-7.70 (1H, m), 7.45-7.41 (2H, m), 6.22 (1H, s), 4.68 (2H, s), 2.92 (3H, s).

Example 102

4-[2-amino-6-(methylamino)pyrimidin-4-yl]benzoic acid

Prepared according to general procedure 6 from 4-(dihydroxyboranyl)benzoic acid and 6-iodo-4-N-methylpyrimidine-2,4-diamine. LCMS [M+H]⁺ 245.

Example 103 methyl 4-[2-amino-6-(methylamino)pyrimidin-4-yl]benzoate

Prepared according to general procedure 6 from [4-(methoxycarbonyl)-phenyl]boronic acid and 6-iodo-4-N-methylpyrimidine-2,4-diamine. LCMS [M+H]⁺ 259; ¹H NMR (400 MHz, CD₃OD) $\delta_H$ 8.12-8.06 (2H, m), 7.95 (2H, d, J=8.2 Hz), 6.28 (1H, s), 3.94 (3H, s), 2.93 (3H, s).

Example 104

6-[3-chloro-4-(morpholine-4-carbonyl)phenyl]-4-N-methylpyrimidine-2,4-diamine

Prepared according to general procedure 6 from [3-chloro-4-(morpholine-4-carbonyl)phenyl]boronic acid and 6-iodo-4-N-methylpyrimidine-2,4-diamine. LCMS [M+H]⁺ 348; ¹H NMR (400 MHz, CD₃OD) $\delta_H$ 7.90 (1H, d, J=1.8 Hz), 7.75 (1H, dd, J=7.9 and 1.8 Hz), 7.59 (1H, d, J=7.9 Hz), 6.35 (1H, s), 3.85-3.74 (6H, m), 3.69-3.60 (2H, m), 3.04 (3H, s).

Example 105

4-[2-amino-6-(methylamino)pyrimidin-4-yl]-2,3-dichlorophenol

Prepared according to general procedure 6 from 2,3-dichloro-4-(tetramethyl-1,3,2-dioxaborolan-2-yl)phenol and 6-iodo-4-N-methylpyrimidine-2,4-diamine.
LCMS [M+H]⁺ 285; ¹H NMR (400 MHz, CD₃OD) $\delta_H$ 7.32 (1H, d, J=8.7 Hz), 7.04 (1H, d, J=8.7 Hz), 6.09 (1H, s), 3.04 (3H, s).

Example 106 methyl (2E)-3-{4-[2-amino-6-(methylamino)pyrimidin-4-yl]phenyl}prop-2-enoate

Prepared according to general procedure 6 from {4-[(1E)-3-methoxy-3-oxoprop-1-en-1-yl]phenyl}boronic acid and 6-iodo-4-N-methylpyrimidine-2,4-diamine. LCMS [M+H]⁺ 285; ¹H NMR (400 MHz, CD₃OD) $\delta_H$ 7.82 (4H, s), 7.76 (1H, d, J=16.0 Hz), 6.69 (1H, d, J=16.0 Hz), 6.36 (1H, s), 3.83 (3H, s), 3.04 (3H, s).

Example 107 methyl (2E)-3-{3-[2-amino-6-(methylamino)pyrimidin-4-yl]phenyl}prop-2-enoate

Prepared according to general procedure 6 from {3-[(1E)-3-methoxy-3-oxoprop-1-en-1-yl]phenyl}boronic acid and 6-iodo-4-N-methylpyrimidine-2,4-diamine. LCMS [M+H]⁺ 285; ¹H NMR (400 MHz, CD₃OD) $\delta_H$ 7.99-7.95 (1H, m), 7.92-7.86 (1H, m), 7.83-7.73 (2H, m), 7.69-7.63 (1H, m), 6.72 (1H, d, J=16.0 Hz), 6.37 (1H, s), 3.83 (3H, s), 3.07 (3H, s).

Example 108

4-[2-amino-6-(methylamino)pyrimidin-4-yl]benzaldehyde

Prepared according to general procedure 6 from (4-formylphenyl)boronic acid and 6-iodo-4-N-methylpyrimidine-2,4-diamine. LCMS [M+H]⁺ 229.

Example 109

1-(4-(2-Amino-6-(methylamino)pyrimidin-4-yl)phenyl)ethanone

Prepared according to general procedure 6 from (4-acetylphenyl)boronic acid and 6-iodo-4-N-methylpyrimidine-2,4-diamine. LCMS [M+H]⁺ 243; ¹H NMR (400 MHz, CD₃OD) $\delta_H$ 8.22-8.15 (2H, m), 7.88-7.82 (2H, m), 6.38 (1H, s), 3.05 (3H, s), 2.67 (3H, s).

Example 110

4-[2-amino-6-(methylamino)pyrimidin-4-yl]-N-methylbenzamide

Prepared according to general procedure 6 from [4-(methylcarbamoyl)phenyl]boronic acid and 6-iodo-4-N-methylpyrimidine-2,4-diamine. LCMS [M+H]⁺ 258; ¹H NMR (400 MHz, CD₃OD) $\delta_H$ 8.02 (2H, d, J=8.5 Hz), 7.83 (2H, d, J=8.5 Hz), 6.38 (1H, s), 3.06 (3H, s), 2.97 (3H, s).

Example 111

6-(4-ethenylphenyl)-4-N-methylpyrimidine-2,4-diamine

Prepared according to general procedure 6 from (4-ethenylphenyl)boronic acid and 6-iodo-4-N-methylpyrimidine-2,4-diamine.
LCMS [M+H]⁺ 227; ¹H NMR (400 MHz, CD₃OD) $\delta_H$ 7.75-7.63 (4H, m), 6.84 (1H, dd, J=17.5 and 10.7 Hz), 6.34 (1H, s), 5.98 (1H, d, J=17.5 Hz), 5.43 (1H, d, J=10.7 Hz), 3.06 (3H, s).

Example 112

6-(2,3-dimethylphenyl)-4-N-[2-(piperidin-1-yl)ethyl]pyrimidine-2,4-diamine

Prepared according to general procedure 7 from 2-(piperidin-1-yl)ethan-1-amine and 4-chloro-6-(2,3-dimethylphenyl)pyrimidin-2-amine. LCMS [M+H]$^+$ 326.

Example 113

6-(2,3-dimethylphenyl)-4-N-[2-(morpholin-4-yl)ethyl]pyrimidine-2,4-diamine

Prepared according to general procedure 7 from 2-(morpholin-4-yl)ethan-1-amine and 4-chloro-6-(2,3-dimethylphenyl)pyrimidin-2-amine. LCMS [M+H]$^+$ 328.

Example 114

4-N-cyclopropyl-6-(2,3-dimethylphenyl)pyrimidine-2,4-diamine

Prepared according to general procedure 2 from (2,3-dimethylphenyl)boronic acid and 6-chloro-4-N-cyclopropylpyrimidine-2,4-diamine. LCMS [M+H]$^+$ 255; $^1$H NMR (400 MHz, CD$_3$OD) $\delta_H$ 7.42-7.31 (1H, m), 7.29-7.12 (2H, m), 6.44 (0.3H, s), 5.95 (0.7H, s), 3.13. (0.7H, s), 2.68 (0.3H, s), 2.36 (3H, s), 2.25 (3H, s), 0.95-0.79 (2H, m), 0.72-0.55 (2H, m).

Example 115

3-[2-amino-6-(methylamino)pyrimidin-4-yl]-N-(4-methylphenyl)benzamide

Step 1: A mixture of 6-chloro-4-N-methylpyrimidine-2,4-diamine (48 mg, 0.30 mmol), 3-(dihydroxyboranyl)benzoic acid (60 mg, 0.36 mmol), K$_2$CO$_3$ (104 mg, 0.75 mmol) and palladium tetrakis(triphenylphosphine)palladium (0) (17 mg, 0.015 mmol) in 1,4-dioxane (3 mL) and water (1 mL) was heated in a sealed tube at 90° C. for 15 h. Concentrated and purified by preparative HPLC. LCMS [M+H]$^+$ 245.

Step 2: To a mixture of 3-(2-amino-6-(methylamino)pyrimidin-4-yl)benzoic acid (50 mg, 0.47 mmol) and p-toluidine (150 mg, 1.4 mmol) in DMF (2.5 mL) were added HATU (266 mg, 0.70 mmol) and NEt$_3$ (200 µL, 1.4 mmol). The mixture was stirred at rt overnight. The crude reaction mixture was purified by HPLC. LCMS [M+H]$^+$ 334.

Example 116

6-(1H-indol-3-yl)-4-N-methylpyrimidine-2,4-diamine

To a solution of 4-N-methyl-6-[1-(4-methylbenzenesulfonyl)-1H-indol-3-yl]pyrimidine-2,4-diamine (1 eq.; prepared in example 23) in MeOH (2 mL) was added 10% NaOH (1 mL). The reaction mixture was heated at 50° C. overnight and the crude product was purified by HPLC. LCMS [M+H]$^+$ 240; $^1$H NMR (400 MHz, CD$_3$OD) $\delta_H$ 8.04 (1H, d, J=7.7 Hz), 7.82 (1H, s), 7.46-7.36 (1H, m), 7.21-7.09 (2H, m), 6.29 (1H, s), 2.92 (3H, s).

Example 117

6-phenyl-4-N-(2-phenylethyl)pyrimidine-2,4-diamine

Prepared according to general procedure 2 from phenylboronic acid and 6-chloro-4-N-(2-phenylethyl)pyrimidine-2,4-diamine. LCMS [M+H]$^+$ 291; $^1$H NMR (400 MHz, CD$_3$OD) $\delta_H$ 7.83-7.73 (2H, m), 7.47-7.37 (3H, m), 7.31-7.22 (4H, m), 7.21-7.15 (1H, m), 6.17 (1H, s), 3.60 (2H, t, J=7.3 Hz), 2.91 (2H, t, J=7.3 Hz).

Example 118

6-(2,3-dimethylphenyl)-4-N-(2-phenylethyl)pyrimidine-2,4-diamine

Prepared according to general procedure 2 from (2,3-dimethylphenyl)boronic acid and 6-chloro-4-N-(2-phenylethyl)pyrimidine-2,4-diamine. LCMS [M+H]$^+$ 319; $^1$H NMR (400 MHz, CD$_3$OD) $\delta_H$ 7.31-7.23 (4H, m), 7.21-7.15 (2H, m), 7.10 (1H, t, J=7.0 Hz), 7.05 (1H, d, J=7.0 Hz), 5.77 (1H, s), 3.64-3.50 (2H, m), 2.90 (2H, t, J=7.6 Hz), 2.31 (3H, s), 2.19 (3H, s).

Example 119

6-(3-chlorophenyl)-4-N-(2,2-difluoroethyl)pyrimidine-2,4-diamine

Prepared according to general procedure 2 from (3-chlorophenyl)boronic acid and 6-chloro-4-N-(2,2-difluoroethyl)pyrimidine-2,4-diamine. LCMS [M+H]$^+$ 285.

Example 120

6-(3-chloro-2-methoxypyridin-4-yl)-4-N-methylpyrimidine-2,4-diamine

Prepared according to general procedure 2 from (3-chloro-2-methoxypyridin-4-yl)boronic acid and 6-chloro-4-N-methylpyrimidine-2,4-diamine. LCMS [M+H]$^+$ 266.

Example 121

4-(2,3-dimethylphenyl)-5H,6H,7H,8H-pyrido[2,3-d]pyrimidin-2-amine. To a solution of 4-chloro-5,6,7,8-tetrahydropyrido[2,3-d]pyrimidin-2-amine (10 mg, 0.054 mmol, 1 eq.) in DMF/water (9:1) is added 2,3-dimethylphenylboronic acid (8.9 mg, 0.060 mmol, 1.1 eq.), Na$_2$CO$_3$ (11.5 mg, 0.11 mmol, 2 eq.) and Pd(PPh$_3$)$_4$ (3.1 mg, 0.002 mmol, 0.05 eq.). The mixture is heated at 120° C. in a microwave reactor until the reaction is complete as shown by LCMS. The crude mixture is then purified by HPLC to afford the desired product. LCMS [M+H]$^+$ 255; $^1$H NMR (400 MHz, DMSO-d$_6$) $\delta_H$ 12.05 (1H, br s), 8.88 (1H, br s), 7.37 (1H, d, J=6.9 Hz), 7.29 (1H, t, J=7.6 Hz), 7.17 (1H, d, J=6.3 Hz), 3.34-3.32 (2H, m), 2.32 (3H, s), 2.28-2.26 (2H, m), 2.09 (3H, s), 1.76-1.74 (2H, m).

Example 122

4-(2,3-dichlorophenyl)-5H,6H,7H,8H-pyrido[2,3-d]pyrimidin-2-amine

To a solution of 4-chloro-5,6,7,8-tetrahydropyrido[2,3-d]pyrimidin-2-amine (10 mg, 0.054 mmol, 1 eq.) in DMF/ water (9:1) is added 2,3-dichlorophenylboronic acid (11.3 mg, 0.060 mmol, 1.1 eq.), Na$_2$CO$_3$ (11.5 mg, 0.11 mmol, 2 eq.) and Pd(PPh$_3$)$_4$ (3.1 mg, 0.002 mmol, 0.05 eq.). The mixture is heated at 120° C. in a microwave reactor until the reaction is complete as shown by LCMS. The crude mixture is then purified by HPLC to afford the desired product. LCMS [M+H]$^+$ 295.

Example 123

4-[1-(benzenesulfonyl)-1H-indol-3-yl]-5H,6H,7H, 8H-pyrido[2,3-d]pyrimidin-2-amine To a solution of 4-chloro-5,6,7,8-tetrahydropyrido[2,3-d]pyrimidin-2-amine (10 mg, 0.054 mmol, 1 eq.) in DMF/water (9:1) is added (1-(phenylsulfonyl)-1H-indol-3-yl)boronic acid (18.0 mg, 0.060 mmol, 1.1 eq.), Na$_2$CO$_3$ (11.5 mg, 0.11 mmol, 2 eq.) and Pd(PPh$_3$)$_4$ (3.1 mg, 0.002 mmol, 0.05 eq.). The mixture is heated at 120° C. in a microwave reactor until the reaction is complete as shown by LCMS. The crude mixture is then purified by HPLC to afford the desired product. LCMS [M+H]$^+$ 406; $^1$H NMR (400 MHz, DMSO-d$_6$) $\delta_H$ 12.03 (1H, br s), 8.03 (1H, br s), 8.36 (1H, s), 8.09 (2H, dd, J=8.6 Hz and 1.2 Hz), 8.04 (1H, d, J=8.3 Hz), 7.78-7.76 (1H, m), 7.68-7.66 (2H, m), 7.61 (1H, d, J=7.8 Hz), 7.48 (1H, ddd, J=8.4 Hz, 7.3 Hz and 1.1 Hz), 7.38 (1H, ddd, J=8.0 Hz, 7.2 Hz and 1.0 Hz), 3.38-3.36 (2H, m), 2.48-2.46 (2H, m), 1.76-1.74 (2H, m).

Example 124

6-(3,5-difluorophenyl)-4-N-methylpyrimidine-2,4-diamine

Prepared according to general procedure 2 from (3,5-difluorophenyl)boronic acid and 6-chloro-4-N-methylpyrimidine-2,4-diamine. LCMS [M+H]$^+$ 237.

Example 125

6-(2,3-dimethylphenyl)-4-N-[2-(4-methoxyphenyl)ethyl]pyrimidine-2,4-diamine

Prepared according to general procedure 7 from 2-(4-methoxyphenyl)ethan-1-amine and 4-chloro-6-(2,3-dimethylphenyl)pyrimidin-2-amine. LCMS [M+H]$^+$ 349.

Example 126

6-(2,3-dimethylphenyl)-4-N-[2-(2-methoxyphenyl)ethyl]pyrimidine-2,4-diamine

Prepared according to general procedure 7 from 2-(2-methoxyphenyl)ethan-1-amine and 4-chloro-6-(2,3-dimethylphenyl)pyrimidin-2-amine. LCMS [M+H]$^+$ 349.

Example 127

6-(2,3-dimethylphenyl)-4-N-[2-(4-methylphenyl)ethyl]pyrimidine-2,4-diamine

Prepared according to general procedure 7 from 2-(4-methylphenyl)ethan-1-amine and 4-chloro-6-(2,3-dimethylphenyl)pyrimidin-2-amine. LCMS [M+H]$^+$ 333.

Example 128

4-N-[2-(4-chlorophenyl)ethyl]-6-(2,3-dimethylphenyl)pyrimidine-2,4-diamine

Prepared according to general procedure 7 from 2-(4-chlorophenyl)ethan-1-amine and 4-chloro-6-(2,3-dimethylphenyl)pyrimidin-2-amine. LCMS [M+H]$^+$ 353.

Example 129

6-(2,3-dimethylphenyl)-4-N-[2-(pyridin-2-yl)ethyl]pyrimidine-2,4-diamine

Prepared according to general procedure 7 from 2-(pyridin-2-yl)ethan-1-amine and 4-chloro-6-(2,3-dimethylphenyl)pyrimidin-2-amine. LCMS [M+H]$^+$ 320.

Example 130

6-(2,3-dimethylphenyl)-4-N-(2-phenylpropyl)pyrimidine-2,4-diamine

Prepared according to general procedure 7 from 2-phenylpropan-1-amine and 4-chloro-6-(2,3-dimethylphenyl)pyrimidin-2-amine. LCMS [M+H]$^+$ 333.

Example 131

6-(2,3-dimethylphenyl)-4-N-(3-phenylpropyl)pyrimidine-2,4-diamine

Prepared according to general procedure 7 from 3-phenylpropan-1-amine and 4-chloro-6-(2,3-dimethylphenyl)pyrimidin-2-amine. LCMS [M+H]$^+$ 333.

Example 132

6-(2,3-dimethylphenyl)-4-N-(2-phenoxyethyl)pyrimidine-2,4-diamine

Prepared according to general procedure 7 from (2-aminoethoxy)benzene and 4-chloro-6-(2,3-dimethylphenyl)pyrimidin-2-amine. LCMS [M+H]$^+$ 335.

Example 133

6-(2,3-dimethylphenyl)-4-N-[2-(phenylamino)ethyl]pyrimidine-2,4-diamine

Prepared according to general procedure 7 from N-(2-aminoethyl)aniline and 4-chloro-6-(2,3-dimethylphenyl)pyrimidin-2-amine. LCMS [M+H]$^+$ 334.

Example 134

6-(2,3-dimethylphenyl)-4-N-[2-(1H-indol-3-yl)ethyl]pyrimidine-2,4-diamine

Prepared according to general procedure 7 from 2-(1H-indol-3-yl)ethan-1-amine and 4-chloro-6-(2,3-dimethylphenyl)pyrimidin-2-amine. LCMS [M+H]$^+$ 358.

Example 135

6-(2,3-dimethylphenyl)-4-N-pentylpyrimidine-2,4-diamine

Prepared according to general procedure 7 from pentan-1-amine and 4-chloro-6-(2,3-dimethylphenyl)pyrimidin-2-amine. LCMS [M+H]$^+$ 285.

Example 136

1-(2-{[2-amino-6-(2,3-dimethylphenyl)pyrimidin-4-yl]amino}ethyl)imidazolidin-2-one Prepared according to general procedure 7 from 1-(2-aminoethyl)imidazolidin-2-one and 4-chloro-6-(2,3-dimethylphenyl)pyrimidin-2-amine. LCMS [M+H]$^+$ 327.

Example 137

1-(3-{[2-amino-6-(2,3-dimethylphenyl)pyrimidin-4-yl]amino}propyl)pyrrolidin-2-one Prepared according to general procedure 7 from 1-(3-aminopropyl)pyrrolidin-2-one and 4-chloro-6-(2,3-dimethylphenyl)pyrimidin-2-amine. LCMS [M+H]$^+$ 340.

Example 138

4-[2-amino-6-(methylamino)pyrimidin-4-yl]-2,6-dimethylphenol

Prepared according to general procedure 6 from (4-hydroxy-3,5-dimethylphenyl)boronic acid. LCMS [M+H]$^+$ 245; $^1$H NMR (400 MHz, CD$_3$OD) $\delta_H$ 7.44 (2H, s), 6.12 (1H, s), 2.91 (3H, s), 2.27 (6H, s).

Example 139

4-[2-amino-6-(methylamino)pyrimidin-4-yl]-2-methoxyphenol

Prepared according to general procedure 6 from (4-hydroxy-3-methoxyphenyl)boronic acid and 6-iodo-4-N-methylpyrimidine-2,4-diamine. LCMS [M+H]$^+$ 247; $^1$H NMR (400 MHz, CD$_3$OD) $\delta_H$ 7.46 (1H, s), 7.33 (1H, d, J=8.4 Hz), 6.86 (1H, d, J=8.0 Hz), 6.17 (1H, s), 3.34 (3H, s), 2.92 (3H, s).

Example 140

4-[2-amino-6-(methylamino)pyrimidin-4-yl]-2-fluorophenol

Prepared according to general procedure 6 from (3-fluoro-4-hydroxyphenyl)boronic acid and 6-iodo-4-N-methylpyrimidine-2,4-diamine. LCMS [M+H]$^+$ 235.

Example 141

5-[2-amino-6-(methylamino)pyrimidin-4-yl]pyridin-2-ol

Prepared according to general procedure 6 from (6-hydroxypyridin-3-yl)boronic acid and 6-iodo-4-N-methylpyrimidine-2,4-diamine. LCMS [M+H]$^+$ 218; $^1$H NMR (400 MHz, CD$_3$OD) $\delta_H$ 7.99 (1H, s), 7.86 (1H, d, J=9.6 Hz), 6.68 (1H, dd, J=9.6 and 0.4 Hz), 6.21 (1H, s), 3.04 (3H, s).

Example 142

{4-[2-amino-6-(methylamino)pyrimidin-4-yl]phenyl}methanol

Prepared according to general procedure 6 from [4-(hydroxymethyl)phenyl]boronic acid and 6-iodo-4-N-methylpyrimidine-2,4-diamine. LCMS [M+H]$^+$ 231; $^1$H NMR (400 MHz, CD$_3$OD) $\delta_H$ 7.79 (2H, d, J=8.0 Hz), 7.43 (2H, d, J=8.4 Hz), 6.21 (1H, s), 4.65 (2H, s), 2.91 (3H, s).

Example 143

4-N-methyl-6-(2-methylphenyl)pyrimidine-2,4-diamine

Prepared according to general procedure 6 from (2-methylphenyl)boronic acid and 6-iodo-4-N-methylpyrimidine-2,4-diamine. LCMS [M+H]$^+$ 215; $^1$H NMR (400 MHz, CD$_3$OD) $\delta_H$ 7.29-7.23 (4H, m), 5.83 (1H, s), 2.90 (3H, s), 2.33 (3H, s).

Example 144

6-[1-(4-chlorobenzenesulfonyl)-1H-indol-3-yl]-4-N-methylpyrimidine-2,4-diamine

Prepared according to general procedure 8 from [1-(4-chlorobenzenesulfonyl)-1H-indol-3-yl]boronic acid and 6-chloro-4-N-methylpyrimidine-2,4-diamine. LCMS [M+H]$^+$ 414; $^1$H NMR (400 MHz, CD$_3$OD) $\delta_H$ 8.15 (1H, s), 8.08 (1H, d, J=8.0 Hz), 8.04 (1H, d, J=8.0 Hz), 8.00-7.98 (2H, m), 7.57-7.55 (2H, m), 7.41 (1H, td, J=8.4 and 1.2 Hz), 7.35 (1H, td, J=8.0 and 0.8 Hz), 6.28 (1H, s), 2.29 (3H, s).

Example 145

4-N-methyl-6-(4-methyl-1H-indazol-5-yl)pyrimidine-2,4-diamine

Prepared according to general procedure 6 from (4-methyl-1H-indazol-5-yl)boronic acid and 6-iodo-4-N-methylpyrimidine-2,4-diamine. LCMS [M+H]$^+$ 255.

Example 146

4-N-methyl-6-(6-methyl-1H-indazol-5-yl)pyrimidine-2,4-diamine

Prepared according to general procedure 6 from (6-methyl-1H-indazol-5-yl)boronic acid and 6-iodo-4-N-methylpyrimidine-2,4-diamine. LCMS [M+H]$^+$ 255; $^1$H NMR (400 MHz, CD$_3$OD) $\delta_H$ 8.12 (1H, d, J=0.8 Hz), 7.88 (1H, s), 7.56 (1H, d, J=0.8 Hz), 6.09 (1H, s), 3.07 (3H, s), 2.50 (3H, d, J=0.8 Hz).

Example 147

4-N-methyl-6-(3-methylphenyl)pyrimidine-2,4-diamine

Prepared according to general procedure 6 from (3-methylphenyl)boronic acid. LCMS [M+H]$^+$ 215; $^1$H NMR (400

MHz, CD$_3$OD) δ$_H$ 7.56 (1H, s), 7.51-7.47 (3H, m), 6.32 (1H, s), 3.06 (3H, s), 2.47 (3H, s).

Example 148

6-(1H-indol-5-yl)-4-N-methylpyrimidine-2,4-diamine

Prepared according to general procedure 6 from (1H-indol-5-yl)boronic acid and 6-iodo-4-N-methylpyrimidine-2,4-diamine. LCMS [M+H]$^+$ 240; $^1$H NMR (400 MHz, CD$_3$OD) δ$_H$ 8.00 (1H, dd, J=1.6 and 0.4 Hz), 7.59 (1H, td, J=8.4 and 0.8 Hz), 7.47 (1H, dd, J=8.4 and 1.6 Hz), 7.42 (1H, d, J=3.2 Hz), 6.63 (1H, dd, J=3.2 and 1.2 Hz), 6.35 (1H, s), 3.06 (3H, s).

Example 149

6-(3-chloropyridin-4-yl)-4-N-methylpyrimidine-2,4-diamine

Prepared according to general procedure 6 from (3-chloropyridin-4-yl)boronic acid and 6-iodo-4-N-methylpyrimidine-2,4-diamine. LCMS [M+H]$^+$ 236; $^1$H NMR (400 MHz, CD$_3$OD) δ$_H$ 8.83 (1H, s), 8.71 (1H, d, J=5.2 Hz), 7.62 (1H, d, J=4.8 Hz), 6.24 (1H, s), 3.07 (3H, s).

Example 150

{5-[2-amino-6-(methylamino)pyrimidin-4-yl]pyridin-2-yl}methanol

Prepared according to general procedure 6 from [6-(hydroxymethyl)pyridin-3-yl]boronic acid and 6-iodo-4-N-methylpyrimidine-2,4-diamine. LCMS [M+H]$^+$ 232.

Example 151

4-N-cyclobutyl-6-(2,3-dimethylphenyl)pyrimidine-2,4-diamine

Prepared according to general procedure 2 from (2,3-dimethylphenyl)boronic acid and 6-chloro-4-N-cyclobutylpyrimidine-2,4-diamine. LCMS [M+H]$^+$ 269; $^1$H NMR (400 MHz, CD$_3$OD) δ$_H$ 7.20 (1H, d, J=7.2 Hz), 7.13 (1H, t, J=7.2 Hz), 7.08 (1H, d, J=7.2 Hz), 5.77 (1H, s), 4.44 (1H, br s), 2.44-2.36 (2H, m), 2.34 (3H, s), 2.21 (3H, s), 2.04-1.94 (m, 2H), 1.82-1.73 (m, 2H).

Example 152

4-N-cyclobutyl-6-[1-(4-methylbenzenesulfonyl)-1H-indol-3-yl]pyrimidine-2,4-diamine Prepared according to general procedure 8 from [1-(4-methylbenzenesulfonyl)-1H-indol-3-yl]boronic acid and 6-chloro-4-N-cyclobutylpyrimidine-2,4-diamine. LCMS [M+H]$^+$ 434; $^1$H NMR (400 MHz, CD$_3$OD) δ$_H$ 8.39 (1H, s), 8.09 (1H, d, J=8.4 Hz), 7.96-7.94 (2H, m), 7.84 (1H, d, J=8.0 Hz), 7.50 (1H, td, J=7.2 and 0.8 Hz), 7.35 (1H, td, J=7.2 and 0.8 Hz), 7.41-7.39 (2H, m), 6.44 (1H, s), 4.66 (1H, quintet, J=8.4 Hz), 2.47-2.41 (2H, m), 2.39 (3H, s), 2.14-2.04 (2H, m), 1.89-1.82 (2H, m).

Example 153

4-N-cyclopentyl-6-(2,3-dimethylphenyl)pyrimidine-2,4-diamine

Prepared according to general procedure 2 from (2,3-dimethylphenyl)boronic acid and 6-chloro-4-N-cyclopentylpyrimidine-2,4-diamine. LCMS [M+H]$^+$ 283; $^1$H NMR (400 MHz, CD$_3$OD) δ$_H$ 7.19 (1H, d, J=7.2 Hz), 7.13 (1H, t, J=7.6 Hz), 7.08 (1H, dd, J=7.6 and 1.6 Hz), 5.81 (1H, s), 4.25 (1H, br s), 2.33 (3H, s), 2.22 (3H, s), 2.06-2.00 (2H, m), 1.81-1.74 (2H, m), 1.71-1.63 (2H, m), 1.58-1.51 (2H, m).

Example 154

4-N-cyclopentyl-6-[1-(4-methylbenzenesulfonyl)-1H-indol-3-yl]pyrimidine-2,4-diamine Prepared according to general procedure 8 from [1-(4-methylbenzenesulfonyl)-1H-indol-3-yl]boronic acid and 6-chloro-4-N-cyclopentylpyrimidine-2,4-diamine. LCMS [M+H]$^+$ 448; $^1$H NMR (400 MHz, CD$_3$OD) δ$_H$ 8.38 (1H, s), 8.10 (1H, d, J=8.4 Hz), 7.96-7.94 (2H, m), 7.84 (1H, d, J=8.0 Hz), 7.50 (1H, td, J=7.2 and 1.2 Hz), 7.42 (1H, td, J=7.2 and 0.8 Hz), 7.41-7.39 (2H, m), 6.48 (1H, s), 4.51 (1H, quintet, J=6.8 Hz), 2.39 (3H, s), 2.14-2.05 (2H, m), 1.84-1.78 (2H, m), 1.75-1.66 (2H, m), 1.63-1.57 (2H, m).

Example 155

4-N-methyl-6-{1-[4-(trifluoromethyl)benzenesulfonyl]-1H-indol-3-yl}pyrimidine-2,4-diamine Prepared according to general procedure 8 from {1-[4-(trifluoromethyl)benzenesulfonyl]-1H-indol-3-yl}boronic acid and 6-chloro-4-N-methylpyrimidine-2,4-diamine. LCMS [M+H]$^+$ 448; $^1$H NMR (400 MHz, CD$_3$OD) δ$_H$ 8.19 (2H, d, J=8.4 Hz), 8.16 (1H, s), 8.08-8.04 (2H, m), 7.84 (2H, d, J=8.4 Hz), 7.41 (1H, td, J=7.6 and 0.8 Hz), 7.34 (1H, td, J=8.0 and 0.8 Hz), 6.26 (1H, s), 2.92 (s, 3H).

Example 156

4-N-cyclohexyl-6-(2,3-dimethylphenyl)pyrimidine-2,4-diamine

Prepared according to general procedure 2 from (2,3-dimethylphenyl)boronic acid and 6-chloro-4-N-cyclohexylpyrimidine-2,4-diamine. LCMS [M+H]$^+$ 297; $^1$H NMR (400 MHz, CD$_3$OD) δ$_H$ 7.19 (1H, d, J=7.2 Hz), 7.12 (1H, t, J=7.6 Hz), 7.08 (1H, dd, J=7.6 and 1.6 Hz), 5.78 (1H, s), 3.82 (1H, br s), 2.33 (3H, s), 2.21 (3H, s), 2.03-1.99 (2H, m), 1.83-1.78 (2H, m), 1.71-1.66 (1H, m), 1.48-1.37 (2H, m), 1.31-1.21 (3H, m).

Example 157

4-N-cyclohexyl-6-[1-(4-methylbenzenesulfonyl)-1H-indol-3-yl]pyrimidine-2,4-diamine Prepared according to general procedure 8 from [1-(4-methylbenzenesulfonyl)-1H-indol-3-yl]boronic acid and 6-chloro-4-N-cyclohexylpyrimidine-2,4-diamine. LCMS

[M+H]⁺ 462; ¹H NMR (400 MHz, CD₃OD) δ_H 8.36 (1H, s), 8.08 (1H, d, J=8.0 Hz), 7.95-7.93 (2H, m), 7.83 (1H, d, J=8.0 Hz), 7.48 (1H, td, J=7.2 and 0.8 Hz), 7.41 (1H, td, J=8.0 and 1.2 Hz), 7.40-7.38 (2H, m), 6.46 (1H, s), 4.11-4.05 (1H, m), 2.38 (3H, s), 2.04-2.00 (2H, m), 1.86-1.82 (2H, m), 1.72-1.68 (1H, m), 1.48-1.26 (5H, m).

Example 158

6-(2,3-dimethylphenyl)-4-N-ethylpyrimidine-2,4-diamine

Prepared according to general procedure 2 from (2,3-dimethylphenyl)boronic acid and 6-chloro-4-N-ethylpyrimidine-2,4-diamine. LCMS [M+H]⁺ 243; ¹H NMR (400 MHz, CD₃OD) δ_H 7.19 (1H, d, J=7.2 Hz), 7.13 (1H, t, J=7.6 Hz), 7.08 (1H, dd, J=7.6 and 1.2 Hz), 5.80 (1H, s), 3.41-3.36 (2H, m), 2.33 (3H, s), 2.21 (3H, s), 1.23 (3H, t, J=7.2 Hz).

Example 159

4-N-ethyl-6-[1-(4-methyl benzenesulfonyl)-1H-indol-3-yl]pyrimidine-2,4-diamine

Prepared according to general procedure 8 from [1-(4-methylbenzenesulfonyl)-1H-indol-3-yl]boronic acid and 6-chloro-4-N-ethylpyrimidine-2,4-diamine. LCMS [M+H]⁺ 408; ¹H NMR (400 MHz, CD₃OD) δ_H 8.12 (1H, s), 8.05-8.01 (2H, m), 7.87-7.85 (2H, m), 7.37 (1H, td, J=7.2 and 1.2 Hz), 7.34-7.32 (2H, m), 7.30 (1H, td, J=8.0 and 1.2 Hz), 6.26 (1H, s), 3.39 (2H, q, J=7.2 Hz), 2.34 (3H, s), 1.24 (3H, t, J=7.2 Hz).

Example 160

4-N-tert-butyl-6-(2,3-dimethylphenyl)pyrimidine-2,4-diamine

Prepared according to general procedure 2 from (2,3-dimethylphenyl)boronic acid and 4-N-tert-butyl-6-chloropyrimidine-2,4-diamine. LCMS [M+H]⁺ 271; ¹H NMR (400 MHz, CD₃OD) δ_H 7.18 (1H, d, J=7.2 Hz), 7.12 (1H, t, J=7.6 Hz), 7.07 (1H, dd, J=7.6 and 1.6 Hz), 5.81 (1H, s), 2.33 (3H, s), 2.21 (3H, s), 1.49 (9H, s).

Example 161

4-N-tert-butyl-6-[1-(4-methylbenzenesulfonyl)-1H-indol-3-yl]pyrimidine-2,4-diamine Prepared according to general procedure 8 from [1-(4-methylbenzenesulfonyl)-1H-indol-3-yl]boronic acid and 4-N-tert-butyl-6-chloropyrimidine-2,4-diamine. LCMS [M+H]⁺ 436; ¹H NMR (400 MHz, CD₃OD) δ_H 8.36 (1H, s), 8.08 (1H, d, J=8.4 Hz), 7.95-7.93 (2H, m), 7.84 (1H, d, J=7.6 Hz), 7.48 (1H, td, J=7.2 and 1.2 Hz), 7.40 (1H, td, J=8.4 and 1.2 Hz), 7.40-7.38 (2H, m), 6.52 (1H, s), 2.38 (3H, s), 1.54 (9H, s).

Example 162

6-(2,3-dimethylphenyl)-4-N-(propan-2-yl)pyrimidine-2,4-diamine

Prepared according to general procedure 2 (2,3-dimethylphenyl)boronic acid and 6-chloro-4-N-(propan-2-yl)pyrimidine-2,4-diamine. LCMS [M+H]⁺ 257; ¹H NMR (400 MHz, CD₃OD) δ_H 7.36 (1H, d, J=7.2 Hz), 7.25 (1H, t, J=7.6 Hz), 7.19 (1H, d, J=7.2 Hz), 5.96 (1H, s), 4.39 (1H, septet, J=6.4 Hz), 2.37 (3H, s), 2.26 (3H, s), 1.29 (3H, s), 1.27 (3H, s).

Example 163

6-[1-(4-methylbenzenesulfonyl)-1H-indol-3-yl]-4-N-(propan-2-yl)pyrimidine-2,4-diamine Prepared according to general procedure 8 from [1-(4-methylbenzenesulfonyl)-1H-indol-3-yl]boronic acid and 6-chloro-4-N-(propan-2-yl)pyrimidine-2,4-diamine. LCMS [M+H]⁺ 422; ¹H NMR (400 MHz, CD₃OD) δ_H 8.12 (1H, s), 8.05-8.02 (2H, m), 7.89-7.86 (2H, m), 7.40-7.30 (4H, m), 6.25 (1H, s), 4.19 (1H, br s), 2.36 (3H, s), 1.26 (3H, s), 1.24 (3H, s).

Example 164

4-N-(cyclopropylmethyl)-6-(2,3-dimethylphenyl)pyrimidine-2,4-diamine

Prepared according to general procedure 2 from (2,3-dimethylphenyl)boronic acid and 6-chloro-4-N-(cyclopropylmethyl)pyrimidine-2,4-diamine. LCMS [M+H]⁺ 269.

Example 165

4-N-(cyclopropylmethyl)-6-[1-(4-methylbenzenesulfonyl)-1H-indol-3-yl]pyrimidine-2,4-diamine Prepared according to general procedure 8 from [1-(4-methylbenzenesulfonyl)-1H-indol-3-yl]boronic acid and 6-chloro-4-N-(cyclopropylmethyl)pyrimidine-2,4-diamine. LCMS [M+H]⁺ 434; ¹H NMR (400 MHz, CD₃OD) δ_H 8.14 (1H, s), 8.06-8.02 (2H, m), 7.88-7.86 (2H, m), 7.40-7.30 (5H, m), 6.31 (1H, s), 3.25 (2H, d, J=6.8 Hz), 1.14-1.11 (1H, m), 0.57-0.55 (2H, m), 0.30-0.28 (2H, m).

Example 166

4-N-[(1R)-1-cyclopropylethyl]-6-(2,3-dimethylphenyl)pyrimidine-2,4-diamine

Prepared according to general procedure 2 from (2,3-dimethylphenyl)boronic acid and 6-chloro-4-N-[(1R)-1-cyclopropylethyl]pyrimidine-2,4-diamine. LCMS [M+H]⁺ 283; ¹H NMR (400 MHz, CD₃OD) δ_H 7.19 (1H, d, J=6.8 Hz), 7.13 (1H, t, J=7.6 Hz), 7.09 (1H, dd, J=7.6 and 1.2 Hz), 5.80 (1H, s), 3.58 (1H, br s), 2.34 (3H, s), 2.22 (3H, s), 1.28 (3H, d, J=6.4 Hz), 0.99-0.92 (1H, m), 0.57-0.45 (2H, m), 0.44-0.38 (1H, m), 0.29-0.23 (1H, m).

Example 167

4-N-[(1R)-1-cyclopropylethyl]-6-[1-(4-methylbenzenesulfonyl)-1H-indol-3-yl]pyrimidine-2,4-diamine Prepared according to general procedure 8 from [1-(4-methylbenzenesulfonyl)-1H-indol-3-yl]boronic acid and 6-chloro-4-N-[(1R)-1-cyclopropylethyl]pyrimidine-2,4-diamine. LCMS [M+H]⁺ 448; ¹H NMR (400 MHz, CD₃OD) δ_H 8.37 (1H, s), 8.08 (1H, d, J=8.0 Hz), 7.95-7.93 (2H, m), 7.84 (1H, d, J=7.6 Hz), 7.49 (1H, dt, J=7.6 and 1.2 Hz), 7.42 (1H, dt, J=8.0 and 0.8 Hz), 7.40-7.38 (2H, m), 6.47 (1H, s), 3.78-3.71 (1H, m), 2.38 (3H, s), 1.33 (3H, d, J=6.8 Hz), 1.04-0.99 (1H, m), 0.64-0.57 (1H, m), 0.56-0.49 (1H, m), 0.47-0.41 (1H, m), 0.33-0.27 (1H, m).

Example 168

4-N-[(1S)-1-cyclopropylethyl]-6-(2,3-dimethylphenyl)pyrimidine-2,4-diamine

Prepared according to general procedure 2 from (2,3-dimethylphenyl)boronic acid and 6-chloro-4-N-[(1S)-1-cyclopropylethyl]pyrimidine-2,4-diamine. LCMS [M+H]$^+$ 283; $^1$H NMR (400 MHz, CD$_3$OD) $\delta_H$ 7.18 (1H, d, J=6.8 Hz), 7.11 (1H, t, J=7.6 Hz), 7.07 (1H, dd, J=7.6 and 1.6 Hz), 5.78 (1H, s), 3.56 (1H, br s), 2.32 (3H, s), 2.20 (3H, s), 1.27 (3H, d, J=6.4 Hz), 0.98-0.91 (1H, m), 0.56-0.43 (2H, m), 0.42-0.36 (1H, m), 0.27-0.21 (1H, m).

Example 169

4-N-[(1S)-1-cyclopropylethyl]-6-[1-(4-methyl benzenesulfonyl)-1H-indol-3-yl]pyrimidine-2,4-diamine Prepared according to general procedure 8 from [1-(4-methylbenzenesulfonyl)-1H-indol-3-yl]boronic acid and 6-chloro-4-N-[(1S)-1-cyclopropylethyl]pyrimidine-2,4-diamine. LCMS [M+H]$^+$ 448; $^1$H NMR (400 MHz, CD$_3$OD) $\delta_H$ 8.37 (1H, s), 8.09 (1H, d, J=8.4 Hz), 7.96-7.94 (2H, m), 7.85 (1H, d, J=8.0 Hz), 7.49 (1H, dt, J=7.6 and 1.2 Hz), 7.42 (1H, dt, J=8.0 and 1.2 Hz), 7.41-7.39 (2H, m), 6.47 (1H, s), 3.78-3.71 (1H, m), 2.39 (3H, s), 1.33 (3H, d, J=6.8 Hz), 1.05-0.98 (1H, m), 0.63-0.58 (1H, m), 0.57-0.50 (1H, m), 0.48-0.42 (1H, m), 0.33-0.27 (1H, m).

Example 170

6-(1-benzofuran-3-yl)-4-N-methylpyrimidine-2,4-diamine

Prepared according to general procedure 6 from (1-benzofuran-3-yl)boronic acid and 6-iodo-4-N-methylpyrimidine-2,4-diamine. LCMS [M+H]$^+$ 241; $^1$H NMR (400 MHz, CD$_3$OD) $\delta_H$ 8.27 (1H, s), 8.07 (1H, dd, J=8.0 and 1.2 Hz), 7.58-7.56 (1H, m), 7.35 (2H, dt, J=7.6 and 1.2 Hz), 6.32 (1H, s), 2.95 (3H, s).

Example 171

6-(2-chloro-5-methylphenyl)-4-N-methylpyrimidine-2,4-diamine

Prepared according to general procedure 2 from (2-chloro-5-methylphenyl)boronic acid and 6-chloro-4-N-methylpyrimidine-2,4-diamine. LCMS [M+H]$^+$ 249; $^1$H NMR (400 MHz, CD$_3$OD) $\delta_H$ 7.35 (1H, d, J=8.0 Hz), 7.28 (1H, d, J=2.0 Hz), 7.23-7.20 (1H, m), 5.97 (1H, s), 2.92 (3H, s), 2.38 (3H, s).

Example 172

6-(1-benzothiophen-3-yl)-4-N-methylpyrimidine-2,4-diamine

Prepared according to general procedure 2 from (1-benzothiophen-3-yl)boronic acid and 6-chloro-4-N-methylpyrimidine-2,4-diamine. LCMS [M+H]$^+$ 257; $^1$H NMR (400 MHz, CD$_3$OD) $\delta_H$ 8.27 (1H, d, J=7.2 Hz), 7.97-7.94 (1H, m), 7.92 (1H, s), 7.45 (1H, dt, J=7.2 and 1.6 Hz), 7.41 (1H, dt, J=7.2 and 1.6 Hz), 6.20 (1H, s), 2.95 (3H, s).

Example 173

2-{4-[2-amino-6-(methylamino)pyrimidin-4-yl]phenyl}propan-2-ol

Prepared according to general procedure 2 from [4-(2-hydroxypropan-2-yl)phenyl]boronic acid and 6-chloro-4-N-methylpyrimidine-2,4-diamine. LCMS [M+H]$^+$ 259; $^1$H NMR (400 MHz, CD$_3$OD) $\delta_H$ 7.82-7.80 (2H, m), 7.60-7.57 (2H, m), 6.23 (1H, s), 2.94 (3H, s), 1.58 (6H, s).

Example 174

6-(1H-indol-4-yl)-4-N-methylpyrimidine-2,4-diamine

Prepared according to general procedure 2 from (1H-indol-4-yl)boronic acid and 6-chloro-4-N-methylpyrimidine-2,4-diamine. LCMS [M+H]$^+$ 240; $^1$H NMR (400 MHz, CD$_3$OD) $\delta_H$ 7.50-7.48 (1H, m), 7.38 (1H, dd, J=7.6 and 0.8 Hz), 7.34 (1H, d, J=3.2 Hz), 7.21 (1H, t, J=7.6 Hz), 6.80 (1H, dd, J=3.2 and 0.8 Hz), 6.31 (1H, s), 2.96 (3H, s).

Example 175

4-N-cyclohexyl-6-(2,3-dichlorophenyl)pyrimidine-2,4-diamine

Prepared according to general procedure 3 from cyclohexanamine and 4-chloro-6-(2,3-dichlorophenyl)pyrimidin-2-amine. LCMS [M+H]$^+$ 337; $^1$H NMR (400 MHz, CD$_3$OD) $\delta_H$ 7.63-7.61 (1H, m), 7.40 (1H, d, J=2.0 Hz), 7.39 (1H, s), 5.93 (1H, s), 3.88 (1H, br s), 2.06-2.02 (2H, m), 1.86-1.81 (2H, m), 1.73-1.69 (1H, m), 1.50-1.40 (2H, m), 1.34-1.25 (3H, m).

Example 176

6-(2,3-dichlorophenyl)-4-N-(propan-2-yl)pyrimidine-2,4-diamine

Prepared according to general procedure 3 from propan-2-amine and 4-chloro-6-(2,3-dichlorophenyl)pyrimidin-2-amine. LCMS [M+H]$^+$ 297; $^1$H NMR (400 MHz, CD$_3$OD) $\delta_H$ 7.61-7.59 (1H, m), 7.38 (1H, d, J=2.0 Hz), 7.37 (1H, s), 5.92 (1H, s), 4.17 (1H, br s), 1.25 (3H, s), 1.24 (3H, s).

Example 177

4-N-(cyclopropylmethyl)-6-(2,3-dichlorophenyl)pyrimidine-2,4-diamine

Prepared according to general procedure 3 from cyclopropylmethanamine and 4-chloro-6-(2,3-dichlorophenyl)pyrimidin-2-amine. LCMS [M+H]$^+$ 309.

Example 178

4-N-[(1S)-1-cyclopropylethyl]-6-(2,3-dichlorophenyl)pyrimidine-2,4-diamine

Prepared according to general procedure 3 from (1S)-1-cyclopropylethan-1-amine and 4-chloro-6-(2,3-dichlorophenyl)pyrimidin-2-amine. LCMS [M+H]$^+$ 323; $^1$H NMR (400

MHz, CD$_3$OD) δ$_H$ 7.61-7.59 (1H, m), 7.38 (1H, d, J=2.0 Hz), 7.37 (1H, s), 5.92 (1H, s), 3.59 (1H, br s), 1.28 (3H, d, J=6.8 Hz), 0.99-0.92 (2H, m), 0.53-0.48 (2H, m), 0.46-0.38 (1H, m), 0.29-0.23 (1H, m).

Example 179

4-N-[(1R)-1-cyclopropylethyl]-6-(2,3-dichlorophenyl)pyrimidine-2,4-diamine

Prepared according to general procedure 3 from (1R)-1-cyclopropylethan-1-amine and 4-chloro-6-(2,3-dichlorophenyl)pyrimidin-2-amine. LCMS [M+H]$^+$ 323; $^1$H NMR (400 MHz, CD$_3$OD) δ$_H$ 7.61-7.59 (1H, m), 7.38 (1H, d, J=2.0 Hz), 7.37 (1H, s), 5.92 (1H, s), 3.59 (1H, br s), 1.28 (3H, d, J=6.8 Hz), 0.99-0.92 (2H, m), 0.58-0.47 (2H, m), 0.46-0.38 (1H, m), 0.29-0.23 (1H, m).

Example 180

6-(2,3-dichlorophenyl)-4-N-(2,2-dimethylpropyl)pyrimidine-2,4-diamine

Prepared according to general procedure 3 from 2,2-dimethylpropan-1-amine and 4-chloro-6-(2,3-dichlorophenyl)pyrimidin-2-amine. LCMS [M+H]$^+$ 325; $^1$H NMR (400 MHz, CD$_3$OD) δ$_H$ 7.61-7.58 (1H, m), 7.38 (1H, d, J=2.0 Hz), 7.36 (1H, s), 6.01 (1H, s), 3.27 (2H, br s), 0.98 (9H, s).

Example 181

6-(2,3-dimethylphenyl)-4-N-(2,2-dimethylpropyl)pyrimidine-2,4-diamine

Prepared according to general procedure 5 from (2,3-dimethylphenyl)boronic acid and 6-chloro-4-N-(2,2-dimethylpropyl)pyrimidine-2,4-diamine. LCMS [M+H]$^+$ 285; $^1$H NMR (400 MHz, CD$_3$OD) δ$_H$ 7.20 (1H, d, J=6.8 Hz), 7.14 (1H, t, J=7.6 Hz), 7.10 (1H, dd, J=7.6 and 1.6 Hz), 5.90 (1H, s), 2.34 (3H, s), 2.22 (3H, s), 1.00 (9H, s).

Example 182

4-N-(2,2-dimethylpropyl)-6-[1-(4-methylbenzenesulfonyl)-1H-indol-3-yl]pyrimidine-2,4-diamine Prepared according to general procedure 8 from [1-(4-methylbenzenesulfonyl)-1H-indol-3-yl]boronic acid and 6-chloro-4-N-(2,2-dimethylpropyl)pyrimidine-2,4-diamine. LCMS [M+H]$^+$ 450; $^1$H NMR (400 MHz, CD$_3$OD) δ$_H$ 8.14 (1H, s), 8.08 (1H, d, J=7.6), 8.04 (1H, dt, J=8.0 and 1.2 Hz), 7.90-7.88 (2H, m), 7.39 (1H, td, J=7.2 and 1.2 Hz), 7.37-7.34 (2H, m), 7.33 (1H, td, J=7.2 and 1.2 Hz), 6.38 (1H, s), 3.27 (2H, s), 2.37 (3H, s), 1.02 (9H, s).

Example 183

6-(5-bromo-2-methoxyphenyl)-4-N-methylpyrimidine-2,4-diamine

Prepared according to general procedure 6 from (5-bromo-2-methoxyphenyl)boronic acid and 6-iodo-4-N-methylpyrimidine-2,4-diamine. LCMS [M+H]$^+$ 310; $^1$H NMR (400 MHz, CD$_3$OD) δ$_H$ 7.72 (1H, d, J=2.4 Hz), 7.52 (1H, dd, J=8.8 and 2.8 Hz), 7.04 (1H, d, J=9.2 Hz), 6.25 (1H, s), 3.87 (3H, s), 2.91 (s, 3H).

Example 184

6-(2,5-dimethylphenyl)-4-N-methylpyrimidine-2,4-diamine

Prepared according to general procedure 6 from (2,5-dimethylphenyl)boronic acid and 6-iodo-4-N-methylpyrimidine-2,4-diamine. LCMS [M+H]$^+$ 229; $^1$H NMR (400 MHz, CD$_3$OD) δ$_H$ 7.16-7.13 (2H, m), 7.11 (1H, s), 5.84 (1H, s), 2.92 (3H, s), 2.35 (3H, s), 2.29 (3H, s).

Example 185

4-N-methyl-6-[2-(trifluoromethyl)pyridin-3-yl]pyrimidine-2,4-diamine

Prepared according to general procedure 6 from [2-(trifluoromethyl)pyridin-3-yl]boronic acid and 6-iodo-4-N-methylpyrimidine-2,4-diamine. LCMS [M+H]$^+$ 270.

Example 186

4-N-methyl-6-(pyrimidin-5-yl)pyrimidine-2,4-diamine

Prepared according to general procedure 6 from (pyrimidin-5-yl)boronic acid and 6-iodo-4-N-methylpyrimidine-2,4-diamine. LCMS [M+H]$^+$ 203.

Example 187

6-[4-(benzyloxy)-2-methylphenyl]-4-N-methylpyrimidine-2,4-diamine.

Prepared according to general procedure 6 from [4-(benzyloxy)-2-methylphenyl]boronic acid and 6-iodo-4-N-methylpyrimidine-2,4-diamine. LCMS [M+H]$^+$ 321; $^1$H NMR (400 MHz, CD$_3$OD) δ$_H$ 7.47-7.46 (2H, m), 7.41-7.38 (2H, m), 7.35-7.32 (1H, m), 7.24 (1H, d, J=8.4 Hz), 6.92-6.87 (2H, m), 5.84 (1H, s), 5.14 (2H, s), 2.91 (3H, s), 2.34 (3H, s).

Example 188

6-(4-methoxy-2,5-dimethylphenyl)-4-N-methylpyrimidine-2,4-diamine

Prepared according to general procedure 6 from (4-methoxy-2,5-dimethylphenyl)boronic acid and 6-iodo-4-N-methylpyrimidine-2,4-diamine. LCMS [M+H]$^+$ 259; $^1$H NMR (400 MHz, CD$_3$OD) δ$_H$ 7.08 (1H, s), 6.79 (1H, s), 5.83 (1H, s), 3.86 (3H, s), 2.91 (3H, s), 2.34 (3H, s), 2.19 (3H, s).

Example 189

4-N-methyl-6-(2,4,5-trimethylphenyl)pyrimidine-2,4-diamine

Prepared according to general procedure 6 from (2,4,5-trimethylphenyl)boronic acid and 6-iodo-4-N-methylpyrimidine-2,4-diamine. LCMS [M+H]$^+$ 243; $^1$H NMR (400 MHz, CD$_3$OD) δ$_H$ 7.07 (1H, s), 7.03 (1H, s), 5.83 (1H, s), 2.91 (3H, s), 2.28 (9H, s).

Example 190

2-[2-amino-6-(methylamino)pyrimidin-4-yl]-4-chlorobenzonitrile

Prepared according to general procedure 6 from (5-chloro-2-cyanophenyl)boronic acid and 6-iodo-4-N-methylpyrimidine-2,4-diamine. LCMS [M+H]$^+$ 260.

Example 191

6-(4,5-dichloro-2-methylphenyl)-4-N-methylpyrimidine-2,4-diamine

Prepared according to general procedure 6 from (4,5-dichloro-2-methylphenyl)boronic acid and 6-iodo-4-N-methylpyrimidine-2,4-diamine. LCMS [M+H]$^+$ 283; $^1$H NMR (400 MHz, CD$_3$OD) $\delta_H$ 7.62 (1H, s), 7.61 (1H, s), 6.06 (1H, s), 3.04 (3H, s), 2.36 (3H, s).

Example 192

6-(2,5-dichloro-4-methoxyphenyl)-4-N-methylpyrimidine-2,4-diamine

Prepared according to general procedure 6 from (2,5-dichloro-4-methoxyphenyl)boronic acid and 6-iodo-4-N-methylpyrimidine-2,4-diamine. LCMS [M+H]$^+$ 299; $^1$H NMR (400 MHz, CD$_3$OD) $\delta_H$ 7.52 (1H, s), 7.22 (1H, s), 6.03 (1H, s), 3.96 (3H, s), 2.92 (3H, s).

Example 193

6-(4-fluoro-2,5-dimethylphenyl)-4-N-methylpyrimidine-2,4-diamine

Prepared according to general procedure 6 from (4-fluoro-2,5-dimethylphenyl)boronic acid and 6-iodo-4-N-methylpyrimidine-2,4-diamine. LCMS [M+H]$^+$ 247; $^1$H NMR (400 MHz, CD$_3$OD) $\delta_H$ 7.16 (1H, d, J=8.0 Hz), 6.95 (1H, d, J=10.8 Hz), 5.83 (1H, s), 2.91 (3H, s), 2.30 (3H, s), 2.27 (3H, s).

Example 194

4-N-methyl-6-[2-methyl-5-(trifluoromethyl)phenyl]pyrimidine-2,4-diamine

Prepared according to general procedure 6 from [2-methyl-5-(trifluoromethyl)phenyl]boronic acid and 6-iodo-4-N-methylpyrimidine-2,4-diamine. LCMS [M+H]$^+$ 283; $^1$H NMR (400 MHz, CD$_3$OD) $\delta_H$ 7.78-7.73 (2H, m), 7.61 (1H, d, J=8.0 Hz), 6.08 (1H, s), 3.05 (3H, s), 2.46 (3H, s).

Example 195

6-[5-chloro-2-methyl-4-(trifluoromethyl)phenyl]-4-N-methylpyrimidine-2,4-diamine Prepared according to general procedure 6 from [5-chloro-2-methyl-4-(trifluoromethyl)phenyl]boronic acid and 6-iodo-4-N-methylpyrimidine-2,4-diamine. LCMS [M+H]$^+$ 317; $^1$H NMR (400 MHz, CD$_3$OD) $\delta_H$ 7.69 (1H, s), 7.53 (1H, s), 5.89 (1H, s), 2.93 (3H, s), 2.40 (3H, s).

Example 196

6-[2,5-bis(trifluoromethyl)phenyl]-4-N-methylpyrimidine-2,4-diamine

Prepared according to general procedure 6 from [2,5-bis(trifluoromethyl)phenyl]boronic acid and 6-iodo-4-N-methylpyrimidine-2,4-diamine. LCMS [M+H]$^+$ 337; $^1$H NMR (400 MHz, CD$_3$OD) $\delta_H$ 8.20-8.15 (2H, m), 8.10 (1H, s), 6.15 (1H, s), 3.08 (3H, s).

Example 197

6-(5-tert-butyl-2-methoxyphenyl)-4-N-methylpyrimidine-2,4-diamine

Prepared according to general procedure 6 from (5-tert-butyl-2-methoxyphenyl)boronic acid and 6-iodo-4-N-methylpyrimidine-2,4-diamine. LCMS [M+H]$^+$ 287; $^1$H NMR (400 MHz, CD$_3$OD) $\delta_H$ 7.64 (1H, dd, J=8.8 and 2.4 Hz), 7.51 (1H, s), 7.17 (1H, d, J=8.8 Hz), 6.25 (1H, s), 3.94 (3H, s), 3.05 (3H, s), 1.37 (9H, s).

Example 198

6-[2-methoxy-5-(propan-2-yl)phenyl]-4-N-methylpyrimidine-2,4-diamine

Prepared according to general procedure 6 from [2-methoxy-5-(propan-2-yl)phenyl]boronic acid and 6-iodo-4-N-methylpyrimidine-2,4-diamine. LCMS [M+H]$^+$ 273; $^1$H NMR (400 MHz, CD$_3$OD) $\delta_H$ 7.49 (1H, dd, J=8.4 and 2.0 Hz), 7.39 (1H, s), 7.17 (1H, d, J=8.8 Hz), 6.28 (1H, s), 3.95 (3H, s), 3.06 (3H, s), 2.98 (1H, sept, J=6.8 Hz), 1.31 (3H, s), 1.30 (3H, s).

Example 199

6-[2-chloro-5-(trifluoromethyl)phenyl]-4-N-methylpyrimidine-2,4-diamine

Prepared according to general procedure 6 from [2-chloro-5-(trifluoromethyl)phenyl]boronic acid and 6-iodo-4-N-methylpyrimidine-2,4-diamine. LCMS [M+H]$^+$ 303; $^1$H NMR (400 MHz, CD$_3$OD) $\delta_H$ 7.87 (1H, br s), 7.82 (1H, d, J=2.0 Hz), 7.81 (1H, s), 6.14 (1H, s), 3.03 (3H, s).

Example 200

6-(2-fluoro-5-methylphenyl)-4-N-methylpyrimidine-2,4-diamine

Prepared according to general procedure 6 from (2-fluoro-5-methylphenyl)boronic acid and 6-iodo-4-N-methylpyrimidine-2,4-diamine. LCMS [M+H]$^+$ 233; $^1$H NMR (400 MHz, CD$_3$OD) $\delta_H$ 7.58 (1H, dd, J=7.2 and 2.0 Hz), 7.28-7.25 (1H, m), 7.10-7.06 (1H, m), 6.02 (1H, d, J=1.6 Hz), 2.94 (3H, s), 2.40 (3H, s).

Example 201

6-(5-chloro-2-methoxyphenyl)-4-N-methylpyrimidine-2,4-diamine

Prepared according to general procedure 6 from (5-chloro-2-methoxyphenyl)boronic acid and 6-iodo-4-N-methylpyrimidine-2,4-diamine. LCMS [M+H]$^+$ 265; $^1$H NMR (400 MHz, CD$_3$OD) $\delta_H$ 7.58-7.57 (1H, m), 7.56 (1H, d, J=2.8 Hz), 7.23 (1H, d, J=9.6 Hz), 6.27 (1H, s), 3.96 (3H, s), 3.05 (3H, s).

Example 202

6-(5-fluoro-2-methylphenyl)-4-N-methylpyrimidine-2,4-diamine

Prepared according to general procedure 6 from (5-fluoro-2-methylphenyl)boronic acid and 6-iodo-4-N-methylpyrimidine-2,4-diamine. LCMS [M+H]$^+$ 233; $^1$H NMR (400 MHz, CD$_3$OD) $\delta_H$ 7.31-7.27 (1H, m), 7.08-7.04 (2H, m), 5.87 (1H, s), 2.94 (3H, s), 2.33 (3H, s).

Example 203

6-(2,5-dimethoxyphenyl)-4-N-methylpyrimidine-2,4-diamine

Prepared according to general procedure 6 from (2,5-dimethoxyphenyl)boronic acid and 6-iodo-4-N-methylpyrimidine-2,4-diamine. LCMS [M+H]$^+$ 261; $^1$H NMR (400 MHz, CD$_3$OD) $\delta_H$ 7.18 (1H, d, J=3.2 Hz), 7.04 (1H, d, J=9.2 Hz), 6.98 (1H, dd, J=8.8 and 3.2 Hz), 6.27 (1H, s), 3.83 (6H, s), 2.93 (3H, s).

Example 204

6-(2-methoxy-5-methylphenyl)-4-N-methylpyrimidine-2,4-diamine

Prepared according to general procedure 6 from (2-methoxy-5-methylphenyl)boronic acid and 6-iodo-4-N-methylpyrimidine-2,4-diamine. LCMS [M+H]$^+$ 245; $^1$H NMR (400 MHz, CD$_3$OD) $\delta_H$ 7.36 (1H, s), 7.20 (1H, d, J=8.8 Hz), 6.98 (1H, d, J=8.8 Hz), 6.20 (1H, s), 3.83 (3H, s), 2.91 (3H, s), 2.33 (3H, s).

Example 205

6-(2-chloro-5-fluorophenyl)-4-N-methylpyrimidine-2,4-diamine

Prepared according to general procedure 6 from (2-chloro-5-fluorophenyl)boronic acid and 6-iodo-4-N-methylpyrimidine-2,4-diamine. LCMS [M+H]$^+$ 253; $^1$H NMR (400 MHz, CD$_3$OD) $\delta_H$ 7.54-7.50 (1H, m), 7.25 (1H, dd, J=9.2 and 3.2 Hz), 7.19 (1H, td, J=8.8 and 3.2 Hz), 6.01 (1H, s), 2.93 (3H, s).

Example 206

3-[2-amino-6-(methylamino)pyrimidin-4-yl]-4-fluorobenzonitrile

Prepared according to general procedure 6 from (5-cyano-2-fluorophenyl)boronic acid and 6-iodo-4-N-methylpyrimidine-2,4-diamine. LCMS [M+H]$^+$ 244; $^1$H NMR (400 MHz, CD$_3$OD) $\delta_H$ 8.26 (1H, dd, J=6.8 and 2.0 Hz), 7.87-7.84 (1H, m), 7.45-7.40 (1H, m), 6.27 (1H, d, J=2.0 Hz), 2.93 (3H, s).

Example 207

6-(2-chloro-5-methoxyphenyl)-4-N-methylpyrimidine-2,4-diamine

Prepared according to general procedure 6 from (2-chloro-5-methoxyphenyl)boronic acid and 6-iodo-4-N-methylpyrimidine-2,4-diamine. LCMS [M+H]$^+$ 265; $^1$H NMR (400 MHz, CD$_3$OD) $\delta_H$ 7.39 (1H, d, J=8.8 Hz), 7.02 (1H, d, J=3.2 Hz), 6.98 (1H, dd, J=8.8 and 3.2 Hz), 5.99 (1H, s), 3.84 (3H, s), 2.92 (3H, s).

Example 208

6-[5-fluoro-2-(trifluoromethyl)phenyl]-4-N-methylpyrimidine-2,4-diamine

Prepared according to general procedure 6 from [5-fluoro-2-(trifluoromethyl)phenyl]boronic acid and 6-iodo-4-N-methylpyrimidine-2,4-diamine. LCMS [M+H]$^+$ 287; $^1$H NMR (400 MHz, CD$_3$OD) $\delta_H$ 7.87-7.83 (1H, m), 7.39-7.34 (1H, m), 7.25 (1H, dd, J=9.2 and 2.8 Hz), 5.89 (1H, s), 2.92 (3H, s).

Example 209

6-(2,5-dichlorophenyl)-4-N-methylpyrimidine-2,4-diamine

Prepared according to general procedure 6 from (2,5-dichlorophenyl)boronic acid and 6-iodo-4-N-methylpyrimidine-2,4-diamine. LCMS [M+H]$^+$ 269; $^1$H NMR (400 MHz, CD$_3$OD) $\delta_H$ 7.51-7.49 (2H, m), 7.42 (1H, dd, J=8.4 and 2.4 Hz), 6.01 (1H, s), 2.92 (3H, s).

Example 210

6-(5-chloro-2-fluorophenyl)-4-N-methylpyrimidine-2,4-diamine

Prepared according to general procedure 6 from (5-chloro-2-fluorophenyl)boronic acid and 6-iodo-4-N-methylpyrimidine-2,4-diamine. LCMS [M+H]$^+$ 253; $^1$H NMR (400 MHz, CD$_3$OD) $\delta_H$ 7.75-7.23 (1H, m), 7.69-7.65 (1H, m), 7.40 (1H, m), 6.31 (1H, s), 3.07 (3H, s).

Example 211

3-[2-amino-6-(methylamino)pyrimidin-4-yl]-4-methylbenzonitrile

Prepared according to general procedure 6 from (5-cyano-2-methylphenyl)boronic acid and 6-iodo-4-N-methylpyrimidine-2,4-diamine. LCMS [M+H]$^+$ 240; $^1$H NMR (400 MHz, CD$_3$OD) $\delta_H$ 7.68-7.66 (2H, m), 7.48 (1H, d, J=7.6 Hz), 5.88 (1H, s), 2.93 (3H, s), 2.44 (3H, s).

Example 212

3-[2-amino-6-(methylamino)pyrimidin-4-yl]-4-methoxybenzonitrile

Prepared according to general procedure 6 from (5-cyano-2-methoxyphenyl)boronic acid and 6-iodo-4-N-methylpyrimidine-2,4-diamine. LCMS [M+H]$^+$ 256; $^1$H NMR (400 MHz, CD$_3$OD) $\delta_H$ 7.95 (1H, d, J=2.4 Hz), 7.98 (1H, dd, J=8.8 and 2.0 Hz), 7.27 (1H, d, J=8.8 Hz), 6.26 (1H, s), 3.97 (3H, s), 2.92 (3H, s).

Example 213

6-(2-chloro-5-fluoro-4-methylphenyl)-4-N-methylpyrimidine-2,4-diamine

Prepared according to general procedure 6 from (2-chloro-5-fluoro-4-methylphenyl)boronic acid and 6-iodo- 4-N-methylpyrimidine-2,4-diamine. LCMS [M+H]+ 267; 1H NMR (400 MHz, CD3OD) δ$_H$ 7.39 (1H, d, J=6.8 Hz), 7.19 (1H, d, J=9.6 Hz), 6.02 (1H, s), 2.92 (3H, s), 2.32 (3H, d, J=1.6 Hz).

Example 214

6-(5-chloro-2-fluoro-4-methylphenyl)-4-N-methyl-pyrimidine-2,4-diamine

Prepared according to general procedure 6 from (5-chloro-2-fluoro-4-methylphenyl)boronic acid and 6-iodo-4-N-methylpyrimidine-2,4-diamine. LCMS [M+H]+ 267; 1H NMR (400 MHz, CD3OD) δ$_H$ 7.72 (1H, d, J=6.8 Hz), 7.19 (1H, d, J=11.2 Hz), 6.31 (1H, s), 3.05 (3H, s), 2.48 (3H, s).

Example 215

6-(2-chloro-4-fluoro-5-methylphenyl)-4-N-methyl-pyrimidine-2,4-diamine

Prepared according to general procedure 6 from (2-chloro-4-fluoro-5-methylphenyl)boronic acid. and 6-iodo-4-N-methylpyrimidine-2,4-diamine LCMS [M+H]+ 267; 1H NMR (400 MHz, CD3OD) δ$_H$ 7.36 (1H, d, J=8.4 Hz), 7.23 (1H, d, J=9.6 Hz), 5.96 (1H, s), 2.91 (3H, s), 2.29 (3H, d, J=1.6 Hz).

Example 216

4-N-cyclopropyl-6-(4-fluoro-2,5-dimethylphenyl)pyrimidine-2,4-diamine

Prepared according to general procedure 2 from (4-fluoro-2,5-dimethylphenyl)boronic acid and 6-chloro-4-N-cyclopropylpyrimidine-2,4-diamine. LCMS [M+H]+ 273; 1H NMR (400 MHz, CD3OD) δ$_H$ 7.19 (1H, d, J=8.0 Hz), 6.97 (1H, d, J=10.4 Hz), 6.03 (1H, s), 2.63 (1H, br s), 2.33 (3H, s), 2.28 (3H, s), 0.84-0.79 (2H, m), 0.60-0.56 (2H, m).

Example 217

4-N-cyclopropyl-6-(4-methoxy-2,5-dimethylphenyl)pyrimidine-2,4-diamine.

Prepared according to general procedure 2 from (4-methoxy-2,5-dimethylphenyl)boronic acid and 6-chloro-4-N-cyclopropylpyrimidine-2,4-diamine. LCMS [M+H]+ 285.

Example 218

4-N-cyclopropyl-6-(2,5-dimethylphenyl)pyrimidine-2,4-diamine

Prepared according to general procedure 2 from (2,5-dimethylphenyl)boronic acid and 6-chloro-4-N-cyclopropylpyrimidine-2,4-diamine. LCMS [M+H]+ 255; 1H NMR (400 MHz, CD3OD) δ$_H$ 7.30-7.28 (2H, m), 7.23 (1H, s), 6.00 (1H, s), 3.06 (1H, br s), 2.40 (3H, s), 2.36 (3H, s), 0.93-0.88 (2H, m), 0.69-0.66 (2H, m).

Example 219

6-(5-chloro-2-methylphenyl)-4-N-cyclopropylpyrimidine-2,4-diamine

Prepared according to general procedure 2 from (5-chloro-2-methylphenyl)boronic acid and 6-chloro-4-N-cyclopropylpyrimidine-2,4-diamine. LCMS [M+H]+ 275; 1H NMR (400 MHz, CD3OD) δ$_H$ 7.33-7.27 (3H, m), 6.05 (1H, s), 2.65 (1H, br s), 0.84-0.79 (2H, m), 0.60-0.56 (2H, m).

Example 220

6-(5-chloro-2-methylphenyl)-4-N-cyclobutylpyrimidine-2,4-diamine

Prepared according to general procedure 2 from (5-chloro-2-methylphenyl)boronic acid and 6-chloro-4-N-cyclobutylpyrimidine-2,4-diamine. LCMS [M+H]+ 289; 1H NMR (400 MHz, CD3OD) δ$_H$ 7.33-7.26 (3H, m), 5.81 (1H, s), 4.45 (1H, br s), 2.44-2.37 (2H, m), 2.32 (3H, s), 2.05-1.95 (2H, m), 1.83-1.74 (2H, m).

Example 221

6-(5-chloro-2-methylphenyl)-4-N-ethylpyrimidine-2,4-diamine

Prepared according to general procedure 2 from (5-chloro-2-methylphenyl)boronic acid and 6-chloro-4-N-ethylpyrimidine-2,4-diamine. LCMS [M+H]+ 263; 1H NMR (400 MHz, CD3OD) δ$_H$ 7.51-7.46 (2H, m), 7.41 (1H, d, J=8.4 Hz), 6.05 (1H, s), 3.57 (2H, q, J=6.8 Hz), 2.37 (3H, s), 1.28 (3H, t, J=7.2 Hz).

Example 222

6-(5-chloro-2-methylphenyl)-4-N-[2-(4-chlorophenyl)ethyl]pyrimidine-2,4-diamine.

Prepared according to general procedure 2 from (5-chloro-2-methylphenyl)boronic acid and 6-chloro-4-N-[2-(4-chlorophenyl)ethyl]pyrimidine-2,4-diamine. LCMS [M+H]+ 374; 1H NMR (400 MHz, CD3OD) δ$_H$ 7.32-7.26 (7H, m), 5.81 (1H, s), 3.64-3.60 (2H, m), 2.92 (2H, t, J=7.6 Hz), 2.31 (3H, s).

Example 223

4-N-[2-(4-chlorophenyl)ethyl]-6-(4-fluoro-2,5-dimethylphenyl)pyrimidine-2,4-diamine Prepared according to general procedure 2 from (4-fluoro-2,5-dimethylphenyl)boronic acid and 6-chloro-4-N-[2-(4-chlorophenyl)ethyl]pyrimidine-2,4-diamine. LCMS [M+H]+ 371; 1H NMR (400 MHz, CD3OD) δ$_H$ 7.32-7.26 (4H, m), 7.14 (1H, d, J=8.0 Hz), 6.94 (1H, d, J=10.8 Hz), 5.79 (1H, s), 3.63-3.59 (2H, m), 2.92 (2H, t, J=7.2 Hz), 2.30 (3H, s), 2.27 (3H, s).

Example 224

4-N-[2-(4-chlorophenyl)ethyl]-6-(2,5-dimethylphenyl)pyrimidine-2,4-diamine

Prepared according to general procedure 2 from (2,5-dimethylphenyl)boronic acid and 6-chloro-4-N-[2-(4-chlorophenyl)ethyl]pyrimidine-2,4-diamine. LCMS [M+H]+ 353; 1H NMR (400 MHz, CD3OD) δ$_H$ 7.32-7.26 (4H, m), 7.16-7.09 (3H, m), 5.80 (1H, s), 3.61 (2H, t, J=6.4 Hz), 2.92 (2H, t, J=7.2 Hz), 2.35 (3H, s), 2.28 (3H, s).

Example 225

1-(3-{[2-amino-6-(quinolin-5-yl)pyrimidin-4-yl]amino}propyl)pyrrolidin-2-one

Prepared according to general procedure 2 from (quinolin-5-yl)boronic acid and 1-{3-[(2-amino-6-chloropyrimidin-4-yl)amino]propyl}pyrrolidin-2-one. LCMS [M+H]$^+$ 363; $^1$H NMR (400 MHz, CD$_3$OD) $\delta_H$ 8.90 (1H, dd, J=4.0 and 1.6 Hz), 8.64 (1H, d, J=8.8 Hz), 8.12 (1H, d, J=8.4 Hz), 7.88-7.84 (1H, m), 7.71 (1H, d, J=7.2 Hz), 7.59-7.56 (1H, m), 6.07 (1H, s), 3.53 (2H, t, J=6.8 Hz), 3.42 (4H, t, J=6.8 Hz), 2.42 (2H, t, J=8.0 Hz), 2.12-2.05 (2H, m), 1.93-1.86 (2H, m).

Example 226

6-(2-chloro-3-methylphenyl)-4-N-methylpyrimidine-2,4-diamine

Prepared according to general procedure 3 from methanamine and 4-chloro-6-(2-chloro-3-methylphenyl)pyrimidin-2-amine. LCMS [M+H]$^+$ 249; $^1$H NMR (400 MHz, CD$_3$OD) $\delta_H$ 7.56-7.54 (1H, m), 7.42-7.37 (2H, m), 6.11 (1H, s), 3.05 (3H, s), 2.49 (3H, s).

Example 227

6-(2-chloro-3-methylphenyl)-4-N-cyclopropylpyrimidine-2,4-diamine

Prepared according to general procedure 3 from cyclopropanamine and 4-chloro-6-(2-chloro-3-methylphenyl)pyrimidin-2-amine. LCMS [M+H]$^+$ 275; $^1$H NMR (400 MHz, CD$_3$OD) $\delta_H$ 7.56 (1H, d, J=5.6 Hz), 7.42-7.39 (2H, m), 6.07 (1H, s), 3.09 (1H, br s), 2.50 (3H, s), 0.92-0.90 (2H, m), 0.68 (2H, br s).

Example 228

6-(2-chloro-3-methylphenyl)-4-N-[2-(4-chlorophenyl)ethyl]pyrimidine-2,4-diamine

Prepared according to general procedure 3 from 2-(4-chlorophenyl)ethan-1-amine and 4-chloro-6-(2-chloro-3-methylphenyl)pyrimidin-2-amine. LCMS [M+H]$^+$ 373; $^1$H NMR (400 MHz, CD$_3$OD) $\delta_H$ 7.57-7.55 (1H, m), 7.41 (1H, t, J=7.6 Hz), 7.37 (1H, dd, J=8.0 and 2.0 Hz), 7.34-7.28 (4H, m), 6.08 (1H, s), 3.79 (2H, t, J=7.2 Hz), 2.97 (2H, t, J=7.2 Hz), 2.49 (3H, s).

Example 229

1-(3-{[2-amino-6-(2-chloro-3-methylphenyl)pyrimidin-4-yl]amino}propyl)pyrrolidin-2-one Prepared according to general procedure 3 from 1-(3-aminopropyl)pyrrolidin-2-one and 4-chloro-6-(2-chloro-3-methylphenyl)pyrimidin-2-amine. LCMS [M+H]$^+$ 360; $^1$H NMR (400 MHz, CD$_3$OD) $\delta_H$ 7.57-7.55 (1H, m), 7.44-7.38 (2H, m), 6.13 (1H, s), 3.55 (2H, t, J=5.6 Hz), 3.52 (2H, t, J=7.2 Hz), 3.41 (2H, t, J=6.8 Hz), 2.49 (3H, s), 2.42 (2H, t, J=8.0 Hz), 2.09 (2H, quintet, J=7.6 Hz), 1.92 (2H, quintet, J=7.2 Hz).

Example 230

4-N-cyclopropyl-6-(1H-indol-4-yl)pyrimidine-2,4-diamine

Prepared according to general procedure 3 from cyclopropanamine and 4-chloro-6-(1H-indol-4-yl)pyrimidin-2-amine. LCMS [M+H]$^+$ 266; $^1$H NMR (400 MHz, CD$_3$OD) $\delta_H$ 7.67 (1H, d, J=7.6 Hz), 7.50 (1H, s), 7.33 (2H, d, J=7.2 Hz), 6.71 (1H, s), 6.43 (1H, s), 3.10 (1H, br s), 0.92 (2H, br s), 0.69 (2H, br s).

Example 231

4-N-[2-(4-chlorophenyl)ethyl]-6-(1H-indol-4-yl)pyrimidine-2,4-diamine

Prepared according to general procedure 3 from 2-(4-chlorophenyl)ethan-1-amine and 4-chloro-6-(1H-indol-4-yl)pyrimidin-2-amine. LCMS [M+H]$^+$ 364; $^1$H NMR (400 MHz, CD$_3$OD) $\delta_H$ 7.67-7.66 (1H, m), 7.52-7.46 (1H, m), 7.35-7.29 (6H, m), 6.86 (1H, s), 6.44 (1H, s), 3.80 (2H, t, J=7.2 Hz), 2.95 (2H, t, J=6.8 Hz).

Example 232

4-N-cyclopropyl-6-(quinolin-5-yl)pyrimidine-2,4-diamine

Prepared according to general procedure 3 from cyclopropanamine and 4-chloro-6-(quinolin-5-yl)pyrimidin-2-amine. LCMS [M+H]$^+$ 278; $^1$H NMR (400 MHz, CD$_3$OD) $\delta_H$ 8.91 (1H, dd, J=4 and 1.6 Hz), 8.66 (1H, d, J=8.4 Hz), 8.14 (1H, d, J=8.4 Hz), 7.89-7.85 (1H, m), 7.74 (1H, d, J=6.8 Hz), 7.59-7.56 (1H, m), 6.26 (1H, s), 2.69 (1H, br s), 0.85-0.80 (2H, m), 0.62-0.59 (2H, m).

Example 233

(2E)-3-{4-[2-amino-6-(methylamino)pyrimidin-4-yl]phenyl}prop-2-enoic acid

Prepared according to general procedure 6 from (2E)-3-[4-(dihydroxyboranyl)phenyl]prop-2-enoic acid and 6-iodo-4-N-methylpyrimidine-2,4-diamine. LCMS [M+H]$^+$ 271.

Example 234 tert-butyl 3-({[2-amino-6-(2,3-dimethylphenyl)pyrimidin-4-yl]amino}methyl)-azetidine-1-carboxylate Prepared according to general procedure 3 from tert-butyl 3-(aminomethyl)azetidine-1-carboxylate and 4-chloro-6-(2,3-dimethylphenyl)-pyrimidin-2-amine. LCMS [M+H]$^+$ 384; $^1$H NMR (400 MHz, CD$_3$OD) $\delta_H$ 7.19 (1H, d, J=7.6 Hz), 7.12 (1H, t, J=7.6 Hz), 7.07 (1H, d, J=7.6 Hz), 5.82 (s, 1H), 4.05-4.00 (2H, m), 3.73-3.69 (2H, m), 3.60-3.59 (2H, m), 2.92-2.82 (1H, m), 2.33 (3H, s), 2.21 (3H, s), 1.45 (9H, s).

Example 235

4-N-cyclopropyl-6-(1H-indol-5-yl)pyrimidine-2,4-diamine

Prepared according to general procedure 2 from (1H-indol-5-yl)boronic acid and 6-chloro-4-N-cyclopropylpyrimidine-2,4-diamine. LCMS [M+H]$^+$ 266.

Example 236

1-(3-{[2-amino-6-(1H-indol-5-yl)pyrimidin-4-yl]amino}propyl)pyrrolidin-2-one Prepared according to general procedure 2 from (2,3-dimethylphenyl)boronic acid and 1-{3-[(2-amino-6-chloropyrimidin-4-yl)amino]propyl}pyrrolidin-2-one. LCMS [M+H]$^+$ 351; $^1$H NMR (400 MHz, CD$_3$OD) $\delta_H$ 8.02 (1H, d, J=1.6 Hz), 7.59 (1H, d, J=8.4 Hz), 7.48 (1H, dd, J=8.4 and 2.0 Hz), 7.42 (1H, d, J=3.2 Hz), 6.64 (1H, d, J=3.2 Hz), 6.37 (1H, s), 3.57-3.51 (4H, m), 3.42 (2H, t, J=7.2 Hz), 2.43 (2H, t, J=8.0 Hz), 2.10 (2H, quintet, J=8.4 Hz), 1.93 (2H, quintet, J=7.2 Hz).

Example 237 tert-Butyl 4-((2-amino-6-(2,3-dimethylphenyl)pyrimidin-4-yl)amino)piperidine-1-carboxylate Prepared according to general procedure 3 from 4-chloro-6-(3-chloro-2-methylphenyl)pyrimidin-2-amine and tert-butyl 4-aminopiperidine-1-carboxylate. LCMS [M+H]$^+$ 398; $^1$H NMR (400 MHz, CD$_3$OD) $\delta_H$ 7.19 (1H, d, J=6.8 Hz), 7.13 (1H, t, J=7.6 Hz), 7.08 (1H, dd, J=7.2 and 0.8 Hz), 5.82 (1H, s), 4.07-4.05 (2H, m), 2.99 (2H, m), 2.33 (3H, s), 2.22 (3H, s), 2.03-1.99 (2H, s), 1.49 (9H, s), 1.42-1.39 (2H, m).

Example 238

Ethyl 4-((2-amino-6-(2,3-dimethylphenyl)pyrimidin-4-yl)amino)piperidine-1-carboxylate Prepared according to general procedure 3 from 4-chloro-6-(3-chloro-2-methylphenyl)pyrimidin-2-amine and ethyl 4-aminopiperidine-1-carboxylate. LCMS [M+H]$^+$ 370; $^1$H NMR (400 MHz, CD$_3$OD) $\delta_H$ 7.19 (1H, d, J=7.2 Hz), 7.11 (1H, t, J=7.2 Hz), 7.08 (1H, d, J=7.6 Hz), 5.82 (1H, s), 4.15 (2H, q, J=7.2 Hz), 4.15-4.09 (3H, m), 3.07-2.98 (2H, m), 2.33 (3H, s), 2.21 (3H, s), 2.04-2.01 (2H, m), 1.48-1.39 (2H, m), 1.29 (4H, t, J=7.2 Hz).

Example 239 tert-Butyl (3-((2-amino-6-(2,3-dimethylphenyl)pyrimidin-4-yl)amino)-2,2-dimethyl-propyl)carbamate Prepared according to general procedure 3 from 4-chloro-6-(3-chloro-2-methylphenyl)pyrimidin-2-amine and tert-butyl N-(3-amino-2,2-dimethylpropyl)carbamate. LCMS [M+H]$^+$ 400.

Example 240

6-(5-chloro-4-methoxy-2-methylphenyl)-4-N-methylpyrimidine-2,4-diamine

Prepared according to general procedure 6 from (5-chloro-4-methoxy-2-methylphenyl)boronic acid and 6-iodo-4-N-methylpyrimidine-2,4-diamine. LCMS [M+H]$^+$ 279.

Example 241

6-(3-chloro-2-methylphenyl)-4-N-[(1R)-1-phenylethyl]pyrimidine-2,4-diamine

4-Chloro-6-(3-chloro-2-methylphenyl)pyrimidin-2-amine (25 mg, 0.098 mmol) and (+)1-phenylethan-1-amine (0.050 mL) were stirred neat at 150° C. for 1 hour. The crude material was dissolved in MeOH (2 mL) and purified by preparative HPLC to give the desired product. LCMS [M+H]$^+$ 339; $^1$H NMR (400 MHz, DMSO-d$_6$) $\delta_H$ ppm 9.25 (1 H, d, J=8.08 Hz) 7.62-7.71 (1 H, m) 7.24-7.47 (7 H, m) 6.23 (0.1 H, s) 6.09 (0.9 H, s) 5.35 (1 H, quin, J=7.26 Hz) 2.31 (2.7 H, s) 2.13 (0.3 H, s) 1.46-1.57 (3 H, m).

Example 242

6-(3-chloro-2-methylphenyl)-4-N-(2-phenylpropan-2-yl)pyrimidine-2,4-diamine

4-Chloro-6-(3-chloro-2-methylphenyl)pyrimidin-2-amine (25 mg, 0,098 mmol) and 2-phenylpropan-2-amine (0.050 mL) were stirred neat at 150° C. for 24 hours. The crude material was dissolved in MeOH (2 mL) and purified by preparative HPLC to give the desired product. LCMS [M+H]$^+$ 353; $^1$H NMR (400 MHz, DMSO-d$_6$) $\delta_H$ ppm 12.45 (1 H, br. s.) 8.96 (1 H, br. s.) 7.12-7.79 (8 H, m) 6.22 (1 H, s) 2.31 (3 H, s) 1.79 (6 H, br. s.)

Example 243

6-(3-chloro-2-methylphenyl)-4-N-[1-(1H-indol-3-yl)propan-2-yl]pyrimidine-2,4-diamine 4-Chloro-6-(3-chloro-2-methylphenyl)pyrimidin-2-amine (25 mg, 0.098 mmol) and 1-(1H-indol-3-yl)propan-2-amine (0.050 mL) were stirred neat at 150° C. for 1 hour. The crude material was dissolved in MeOH (2 mL) and purified by preparative HPLC to give the desired product. LCMS [M+H]$^+$ 392; $^1$H NMR (400 MHz, DMSO-d$_6$) $\delta_H$ ppm 12.34 (1 H, br. s.) 10.90 (0.9 H, s) 10.85 (0.1 H, br. s.) 8.79 (0.9 H, d, J=7.83 Hz) 8.63 (0.1 H, d, J=9.09 Hz) 7.66 (0.9 H, dd, J=7.20, 2.15 Hz) 7.62 (0.1 H, d, J=7.58 Hz) 7.54 (1 H, d, J=7.83 Hz) 7.28-7.43 (3 H, m) 7.20 (0.9 H, d, J=2.27 Hz) 6.95-7.13 (2 H, m) 6.89-6.95 (0.1 H, m) 5.99 (0.9 H, s) 5.93 (0.1 H, s) 4.39-4.50 (1 H, m) 2.86-3.03 (2 H, m) 2.30 (2.7H, s) 2.14 (0.3 H, s) 1.27 (0.3 H, d, J=6.32 Hz) 1.20 (2.7 H, d, J=6.57 Hz).

Example 244

4-N-{bicyclo[2.2.1]heptan-2-yl}-6-(3-chloro-2-methylphenyl)pyrimidine-2,4-diamine 4-Chloro-6-(3-chloro-2-methylphenyl)pyrimidin-2-amine (25 mg, 0.098 mmol) and bicyclo[2.2.1]heptan-2-amine (0.050 mL) were stirred neat at 150° C. for 1 hour. The crude material was dissolved in MeOH (~2 mL) and purified by preparative HPLC to give the desired product. LCMS [M+H]$^+$ 329; $^1$H NMR (400 MHz, DMSO-d$_6$) $\delta_H$ ppm 8.66 (1 H, br. s.) 7.62-7.69 (1 H, m) 7.35-7.44 (2 H, m) 5.99 (1 H, s) 3.87 (1 H, br. s.) 2.30 (3 H, s) 2.27-2.35 (1 H, m) 2.24 (1 H, d, J=3.28 Hz) 1.70-1.80 (1 H, m) 1.33-1.60 (4 H, m) 1.09-1.26 (3 H, m)

Example 245

6-(3-chloro-2-methylphenyl)-4-N-ethylpyrimidine-2,4-diamine

4-Chloro-6-(3-chloro-2-methylphenyl)pyrimidin-2-amine (25 mg, 0.098 mmol), 70% ethanamine (0.050 mL) and n-butanol (2 mL) were stirred in a sealed tube at 120° C. for 8 hours. The solvent was removed in vacuo and the crude material was dissolved in MeOH (2 mL) and purified by preparative HPLC to give the desired product. LCMS [M+H]+ 263; $^1$H NMR (400 MHz, DMSO-d$_6$) $\delta_H$ ppm 12.49 (1 H, br. s.) 8.86 (0.9H, t, J=5.18 Hz) 8.63-8.73 (0.1 H, m) 7.60-7.70 (1 H, m) 7.34-7.45 (2 H, m) 6.34 (0.1 H, br. s.) 6.02 (0.9 H, s) 3.23-3.58 (2 H, m) 2.33 (0.3 H, s) 2.30 (2.7 H, s) 1.18 (2.7 H, t, J=7.20 Hz) 1.08-1.14 (0.3 H, m)

Example 246

6-(3-chloro-2-methylphenyl)-4-N-(propan-2-yl)pyrimidine-2,4-diamine

4-Chloro-6-(3-chloro-2-methylphenyl)pyrimidin-2-amine (25 mg, 0.098 mmol), propan-2-amine (0.050 mL) and n-butanol (2 mL) were stirred in a sealed tube at 120° C. for 8 hours. The solvent was removed in vacuo and the crude material was dissolved in MeOH (2 mL) and purified by preparative HPLC to give the desired product. LCMS [M+H]+ 277.

Example 247

4-N-[2-(2-chlorophenoxy)ethyl]-6-(2,3-dimethylphenyl)pyrimidine-2,4-diamine

4-Chloro-6-(2,3-dimethylphenyl)pyrimidin-2-amine (13 mg, 0.054 mmol) and 1-(2-aminoethoxy)-2-chlorobenzene (18 mg, 0.11 mmol) were stirred neat at 150° C. for 1 h. The crude material was dissolved in MeOH (1 mL) and purified by preparative HPLC to give the desired product. LCMS [M+H]+ 369

Example 248

4-N-[2-(5-chloro-1H-1,3-benzodiazol-2-yl)ethyl]-6-(2,3-dimethylphenyl)pyrimidine-2,4-diamine 4-Chloro-6-(3-chloro-2-methylphenyl)pyrimidin-2-amine (23 mg, 0.10 mmol), 2-(5-chloro-1H-1,3-benzodiazol-2-yl)ethan-1-amine (20 mg, 0.10 mmol), Et$_3$N (0.040 mL, 0.30 mmol) and 1-butanol (0.20 mL) were stirred at 100° C. for 20 hours.
MeOH (1 mL) was added and the mixture was purified by preparative HPLC to give the desired product. LCMS [M+H]+ 393.

Example 249

4-N-[2-(2,5-dimethyl-1H-indol-3-yl)ethyl]-6-(2,3-dimethylphenyl)pyrimidine-2,4-diamine 4-Chloro-6-(2,3-dimethylphenyl)pyrimidin-2-amine (12 mg, 0.050 mmol) and 2-(2,5-dimethyl-1H-indol-3-yl)ethan-1-amine (0.020 mL) were stirred neat at 150° C. for 1 hour. The crude material was dissolved in MeOH (1 mL) and purified by preparative HPLC to give the desired product. LCMS [M+H]+ 386; $^1$H NMR (400 MHz, DMSO-d$_6$) $\delta$ ppm 12.30 (1 H, br. s.) 10.65 (0.9 H, s) 10.60 (0.1 H, s) 8.82 (0.9 H, t, J=5.56 Hz) 8.56-8.67 (0.1 H, m) 7.06-7.41 (5 H, m) 6.70-6.85 (1 H, m) 5.97 (0.9 H, s) 5.76 (0.1 H, s) 3.58 (1.8 H, q, J=6.65 Hz) 3.48 (0.2 H, d, J=6.32 Hz) 2.93 (0.8 H, t, J=7.07 Hz) 2.80-2.89 (0.2 H, m) 2.23-2.38 (9 H, m) 2.17 (2.7 H, s) 2.06 (0.3 H, s)

Example 250

6-(2,3-dimethylphenyl)-4-N-[2-(pyridin-3-yloxy)propyl]pyrimidine-2,4-diamine

4-Chloro-6-(2,3-dimethylphenyl)pyrimidin-2-amine (12 mg, 0,050 mmol) and 3-[(1-aminopropan-2-yl)oxy]pyridine (15 mg, 0.10 mmol) were stirred neat at 150° C. for 1 h. The crude material was dissolved in MeOH (1 mL) and purified by preparative HPLC to give the desired product. LCMS [M+H]+ 350.

Example 251

6-(2,3-dimethylphenyl)-4-N-(1H-indazol-5-ylmethyl)pyrimidine-2,4-diamine

4-Chloro-6-(2,3-dimethylphenyl)pyrimidin-2-amine (12 mg, 0.050 mmol), 1H-indazol-5-ylmethanamine (15 mg, 0.10 mmol), Et$_3$N (0.040 mL, 0.30 mmol) and 1-butanol (0.20 mL) were stirred at 100° C. for 20 hours. MeOH (1 mL) was added and the mixture was purified by preparative HPLC to give the desired product. LCMS [M+H]+ 345.

Example 252

6-(2,3-dimethylphenyl)-4-N-(1H-indazol-6-ylmethyl)pyrimidine-2,4-diamine

4-Chloro-6-(2,3-dimethylphenyl)pyrimidin-2-amine (12 mg, 0.050 mmol), 1H-indazol-6-ylmethanamine (15 mg, 0.10 mmol), Et3N (0.040 mL), 0.30 mmol) and 1-butanol (0.20 mL) were stirred at 100° C. for 20 h. MeOH (1 mL) was added and the mixture was purified by preparative HPLC to give the desired product. LCMS [M+H]+ 345

Example 253

6-(2,3-dimethylphenyl)-4-N-[(2-methoxypyridin-4-yl)methyl]pyrimidine-2,4-diamine 4-Chloro-6-(2,3-dimethylphenyl)pyrimidin-2-amine (12 mg, 0.050 mmol), (2-methoxypyridin-4-yl)methanamine (14 mg, 0.10 mmol), Et$_3$N (0.040 mL, 0.30 mmol) and 1-butanol (0.20 mL) were stirred at 100° C. for 20 hours. MeOH (1 mL) was added and the mixture was purified by preparative HPLC to give the desired product. LCMS [M+H]+ 336.

Example 254

4-N-[(5-chloropyrazin-2-yl)methyl]-6-(2,3-dimethylphenyl)pyrimidine-2,4-diamine

4-Chloro-6-(2,3-dimethylphenyl)pyrimidin-2-amine (12 mg, 0.050 mmol), (5-chloropyrazin-2-yl)methanamine (14 mg, 0.10 mmol), Et$_3$N (0.040 mL, 0.30 mmol) and 1-butanol (0.20 mL) were stirred at 100° C. for 20 hours. MeOH (1 mL) was added and the mixture was purified by preparative HPLC to give the desired product. LCMS [M+H]+ 341.

Example 255

6-(2,3-dimethylphenyl)-4-N-{imidazo[1,2-a]pyridin-2-ylmethyl}pyrimidine-2,4-diamine 4-Chloro-6-(2,3-dimethylphenyl)pyrimidin-2-amine (12 mg, 0.050 mmol), imidazo[1,2-a]pyridin-2-ylmethanamine (14 mg, 0.10 mmol), Et₃N (0.040 mL, 0.30 mmol) and 1-butanol (0.20 mL) were stirred at 100° C. for 20 hours. MeOH (1 mL) was added and the mixture was purified by preparative HPLC to give the desired product. LCMS [M+H]⁺ 345.

Example 256 tert-butyl 4-{4-[2-amino-6-(methylamino)pyrimidin-4-yl]-2-(methoxymethyl)phenoxymethyl}piperidine-1-carboxylate A mixture of 6-chloro-4-N-methylpyrimidine-2,4-diamine (24 mg, 0.15 mmol), tert-butyl 4-[4-(dimethoxyboranyl)-2-(methoxymethyl)phenoxymethyl]piperidine-1-carboxylate (67 mg, 0.17 mmol), potassium carbonate (41 mg, 0.30 mmol) and palladium tetrakis(triphenylphosphine)palladium (0) (9 mg, 0.008 mmol) in 1,4-dioxane (5 mL) and water (1.5 mL) was heated in a sealed tube at 90° C. overnight. The reaction mixture was concentrated and purified by preparative HPLC. LCMS [M+H]⁺ 458.

Example 257

6-[3-(methoxymethyl)-4-(piperidin-4-ylmethoxy)phenyl]-4-N-methylpyrimidine-2,4-diamine hydrochloride A solution of tert-butyl 4-{4-[2-amino-6-(methylamino)pyrimidin-4-yl]-2-(methoxymethyl)-phenoxymethyl}piperidine-1-carboxylate (45 mg, 0.10 mmol; Example 256) in methanol (3 mL) was treated with 4M HCl in 1,4-dioxane (1 mL). The mixture was stirred at r.t. for 3 h, concentrated and dried in vacuo to give the desired product. LCMS [M+H]⁺ 358.

Example 258

3-[2-amino-6-(methylamino)pyrimidin-4-yl]-2-methylbenzonitrile

A mixture of 6-chloro-4-N-methylpyrimidine-2,4-diamine (24 mg, 0.15 mmol), (3-cyano-2-methylphenyl)boronic acid (29 mg, 0.18 mmol), potassium carbonate (41 mg, 0.30 mmol) and palladium tetrakis(triphenylphosphine)palladium (0) (9 mg, 0.008 mmol) in 1,4-dioxane (3 mL) and water (1 mL) was heated in a sealed tube at 90° C. overnight. The reaction mixture was concentrated and purified by preparative HPLC. LCMS [M+H]⁺ 240.

Example 259

6-(4-methoxy-2,3-dimethylphenyl)-4-N-methylpyrimidine-2,4-diamine

A mixture of 6-chloro-4-N-methylpyrimidine-2,4-diamine (24 mg, 0.15 mmol), (4-methoxy-2,3-dimethylphenyl)boronic acid (32 mg, 0.18 mmol), potassium carbonate (41 mg, 0.30 mmol) and tetrakis(triphenylphosphine)palladium (0) (9 mg, 0.008 mmol) in 1,4-dioxane (3 mL) and water (1 mL) was heated in a sealed tube at 90° C. overnight. The reaction mixture was concentrated and purified by preparative HPLC. LCMS [M+H]⁺ 259.

Example 260

6-(4-fluoro-2,3-dimethylphenyl)-4-N-methylpyrimidine-2,4-diamine

A mixture of 6-chloro-4-N-methylpyrimidine-2,4-diamine (24 mg, 0.15 mmol), (4-fluoro-2,3-dimethylphenyl)boronic acid (30 mg, 0.18 mmol), potassium carbonate (41 mg, 0.30 mmol) and tetrakis(triphenylphosphine)palladium (0) (9 mg, 0.008 mmol) in 1,4-dioxane (3 mL) and water (1 mL) was heated in a sealed tube at 90° C. overnight. The reaction mixture was concentrated and purified by preparative HPLC. LCMS [M+H]⁺ 247.

Example 261

6-(2,3-dihydro-1-benzofuran-7-yl)-4-N-methylpyrimidine-2,4-diamine

A mixture of 6-chloro-4-N-methylpyrimidine-2,4-diamine (24 mg, 0.15 mmol), (2,3-dihydro-1-benzofuran-7-yl)boronic acid (30 mg, 0.18 mmol), potassium carbonate (41 mg, 0.30 mmol) and tetrakis(triphenylphosphine)palladium (0) (9 mg, 0.008 mmol) in 1,4-dioxane (3 mL) and water (1 mL) was heated in a sealed tube at 90° C. overnight. The reaction mixture was concentrated and purified by preparative HPLC. LCMS [M+H]⁺ 243.

Example 262

4-N-methyl-6-[2-methyl-5-(morpholine-4-sulfonyl)phenyl]pyrimidine-2,4-diamine

A mixture of 6-chloro-4-N-methylpyrimidine-2,4-diamine (24 mg, 0.15 mmol), [2-methyl-5-(morpholine-4-sulfonyl)phenyl]boronic acid (51 mg, 0.18 mmol), potassium carbonate (41 mg, 0.30 mmol) and tetrakis(triphenylphosphine)-palladium (0) (9 mg, 0.008 mmol) in 1,4-dioxane (3 mL) and water (1 mL) was heated in a sealed tube at 90° C. overnight. The reaction mixture was concentrated and purified by preparative HPLC. LCMS [M+H]⁺ 364.

Example 263

4-N-[2-(4-chlorophenyl)ethyl]-6-(2,3-dichlorophenyl)pyrimidine-2,4-diamine

A mixture of 4-chloro-6-(2,3-dichlorophenyl)pyrimidin-2-amine (28 mg, 0.10 mmol), 2-(4-chlorophenyl)ethan-1-amine (22 mg, 0.14 mmol) and Hünig's base (36 μL, 0.20 mmol) in n-butanol (2 mL) was heated in a sealed tube at 85° C. overnight. The reaction mixture was concentrated and purified by preparative HPLC. LCMS [M+H]⁺ 393. 1H NMR (400 MHz, DMSO-d6) $\delta_H$ ppm 12.56 (br. s., 1 H), 8.90 (br. s., 1 H), 7.83-7.89 (m, 1 H), 7.51-7.59 (m, 2 H), 7.35-7.41 (m, 2 H), 7.28-7.34 (m, 2 H), 6.11 (s, 1 H), 3.63 (q, J=6.4 Hz, 2 H), 2.89 (t, J=7.1 Hz, 2 H).

Example 264

4-N-[2-(4-chlorophenyl)ethyl]-6-(2-methylphenyl)pyrimidine-2,4-diamine

A mixture of 6-chloro-4-N-[2-(4-chlorophenyl)ethyl]pyrimidine-2,4-diamine (34 mg, 0.12 mmol), (2-methylphenyl)boronic acid (20 mg, 0.14 mmol), potassium carbonate (33 mg, 0.24 mmol) and palladium tetrakis(triphenylphosphine)-palladium (0) (7 mg, 0.006 mmol) in 1,4-dioxane/water (4 mL; 4:1) was heated in a sealed tube at 90° C. overnight. The reaction mixture was concentrated and purified by preparative HPLC. LCMS [M+H]+ 339.

Example 265

4-N-[2-(4-chlorophenyl)ethyl]-6-[3-(trifluoromethyl)phenyl]pyrimidine-2,4-diamine A mixture of 6-chloro-4-N-[2-(4-chlorophenyl)ethyl]pyrimidine-2,4-diamine (34 mg, 0.12 mmol), [3-(trifluoromethyl)phenyl]boronic acid (27 mg, 0.14 mmol), potassium carbonate (33 mg, 0.24 mmol) and palladium tetrakis(triphenylphosphine)palladium (0) (7 mg, 0.006 mmol) in 1,4-dioxane/water (4 mL; 4:1) was heated in a sealed tube at 90° C. overnight. The reaction mixture was concentrated and purified by preparative HPLC. LCMS [M+H]+ 393.

Example 266

4-N-[2-(4-chlorophenyl)ethyl]-6-(quinolin-5-yl)pyrimidine-2,4-diamine

A mixture of 6-chloro-4-N-[2-(4-chlorophenyl)ethyl]pyrimidine-2,4-diamine (34 mg, 0.12 mmol), (quinolin-5-yl)boronic acid (25 mg, 0.14 mmol), potassium carbonate (33 mg, 0.24 mmol) and palladium tetrakis(triphenylphosphine)palladium (0) (7 mg, 0.006 mmol) in 1,4-dioxane/water (4 mL; 4:1) was heated in a sealed tube at 90° C. overnight. The reaction mixture was concentrated and purified by preparative HPLC. LCMS [M+H]+ 376.

Example 267

4-N-[2-(4-chlorophenyl)cyclopropyl]-6-(2,3-dimethylphenyl)pyrimidine-2,4-diamine A mixture of 4-chloro-6-(2,3-dimethylphenyl)pyrimidin-2-amine (28 mg, 0.12 mmol), 2-(4-chlorophenyl)cyclopropan-1-amine (43 mg, 0.26 mmol) and Hünig's base (90 µL, 0.52 mmol) in n-butanol (2 mL) was heated in a sealed tube at 85° C. overnight. The reaction mixture was concentrated and purified by preparative HPLC. LCMS [M+H]+ 365.

Example 268

6-(2,3-dimethylphenyl)-4-N-[2-(pyridin-3-yl)ethyl]pyrimidine-2,4-diamine

A mixture of 4-chloro-6-(2,3-dimethylphenyl)pyrimidin-2-amine (28 mg, 0.12 mmol), 2-(pyridin-3-yl)ethan-1-amine (21 mg, 0.17 mmol) and Hünig's base (42 µL, 0.24 mmol) in n-butanol (2 mL) was heated in a sealed tube at 85° C. overnight. The reaction mixture was concentrated and purified by preparative HPLC. LCMS [M+H]+ 320.

Example 269

3-(2-{[2-amino-6-(2,3-dimethylphenyl)pyrimidin-4-yl]amino}ethyl)phenol

A mixture of 4-chloro-6-(2,3-dimethylphenyl)pyrimidin-2-amine (28 mg, 0.12 mmol), 3-(2-aminoethyl)phenol (23 mg, 0.17 mmol) and Hünig's base (42 µL, 0.24 mmol) in n-butanol (2 mL) was heated in a sealed tube at 85° C. overnight. The reaction mixture was concentrated and purified by preparative HPLC. LCMS [M+H]+ 335.

Example 270

6-(2,3-dimethylphenyl)-4-N-[3-(morpholin-4-yl)propyl]pyrimidine-2,4-diamine

A mixture of 4-chloro-6-(2,3-dimethylphenyl)pyrimidin-2-amine (28 mg, 0.12 mmol), 3-(morpholin-4-yl)propan-1-amine (24 mg, 0.17 mmol) and Hünig's base (42 µL, 0.24 mmol) in n-butanol (2 mL) was heated in a sealed tube at 85° C. overnight. The reaction mixture was concentrated and purified by preparative HPLC. LCMS [M+H]+ 342.

Example 271 tert-butyl N-(2-{[2-amino-6-(2,3-dimethylphenyl)pyrimidin-4-yl]amino}ethyl)-carbamate A mixture of 4-chloro-6-(2,3-dimethylphenyl)pyrimidin-2-amine (28 mg, 0.12 mmol), tert-butyl N-(2-aminoethyl)carbamate (27 mg, 0.17 mmol) and Hünig's base (42 µL, 0.24 mmol) in n-butanol (2 mL) was heated in a sealed tube at 85° C. overnight. The reaction mixture was concentrated and purified by preparative HPLC. LCMS [M+H]+ 358.

Example 272

N-(2-{[2-amino-6-(2,3-dimethylphenyl)pyrimidin-4-yl]amino}ethyl)acetamide

A mixture of 4-chloro-6-(2,3-dimethylphenyl)pyrimidin-2-amine (28 mg, 0.12 mmol), N-(2-aminoethyl)acetamide (17 mg, 0.17 mmol) and Hünig's base (42 µL, 0.24 mmol) in n-butanol (2 mL) was heated in a sealed tube at 85° C. overnight. The reaction mixture was concentrated and purified by preparative HPLC. LCMS [M+H]+ 300.

Example 273 benzyl N-(2-{[2-amino-6-(2,3-dimethylphenyl)pyrimidin-4-yl]amino}ethyl)-carbamate A mixture of 4-chloro-6-(2,3-dimethylphenyl)pyrimidin-2-amine (28 mg, 0.12 mmol), benzyl N-(2-aminoethyl)carbamate hydrochloride (39 mg, 0.17 mmol) and Hünig's base (42 µL, 0.24 mmol) in n-butanol (2 mL) was heated in a sealed tube at 85° C. overnight. The reaction mixture was concentrated and purified by preparative HPLC. LCMS [M+H]+ 392.

Example 274 tert-butyl N-(2-{[2-amino-6-(2,3-dimethylphenyl)pyrimidin-4-yl]amino}ethyl)-N-methylcarbamate A mixture of 4-chloro-6-(2,3-dimethylphenyl)pyrimidin-2-amine (28 mg, 0.12 mmol), tert-butyl N-(2-aminoethyl)-N-methylcarbamate (29 mg, 0.17 mmol) and Hünig's base (42 µL, 0.24 mmol) in n-butanol (2 mL) was heated in a sealed tube at 85° C. overnight. The reaction mixture was concentrated and purified by preparative HPLC. LCMS [M+H]+ 372.

Example 275 tert-butyl N-(3-{[2-amino-6-(2,3-dimethylphenyl) pyrimidin-4-yl]amino}propyl)-carbamate A mixture of 4-chloro-6-(2,3-dimethylphenyl)pyrimidin-2-amine (28 mg, 0.12 mmol), tert-butyl N-(3-aminopropyl) carbamate (29 mg, 0.17 mmol) and Hünig's base (42 µL, 0.24 mmol) in n-butanol (2 mL) was heated in a sealed tube at 85° C. overnight. The reaction mixture was concentrated and purified by preparative HPLC. LCMS [M+H]+ 372.

Example 276

6-(2,3-dimethylphenyl)-4-N-[3-(5-methyl-1H-pyrazol-3-yl)propyl]pyrimidine-2,4-diamine A mixture of 4-chloro-6-(2,3-dimethylphenyl)pyrimidin-2-amine (28 mg, 0.12 mmol), 3-(5-methyl-1H-pyrazol-4-yl) propan-1-amine (23 mg, 0.17 mmol) and Hünig's base (42 µL, 0.24 mmol) in n-butanol (2 mL) was heated in a sealed tube at 85° C. overnight. The reaction mixture was concentrated and purified by preparative HPLC. LCMS [M+H]+ 337.

Example 277

3-{[2-amino-6-(2,3-dimethylphenyl)pyrimidin-4-yl] amino}-1-(morpholin-4-yl)propan-1-one A mixture of 4-chloro-6-(2,3-dimethylphenyl)pyrimidin-2-amine (23 mg, 0.10 mmol), 3-amino-1-(morpholin-4-yl) propan-1-one (22 mg, 0.14 mmol) and Hünig's base (35 µL, 0.20 mmol) in n-butanol (1.5 mL) was heated in a sealed tube at 85° C. overnight. The reaction mixture was concentrated and purified by preparative HPLC.
LCMS [M+H]+ 356.

Example 278

4-N-[(4-benzylmorpholin-2-yl)methyl]-6-(2,3-dimethylphenyl)pyrimidine-2,4-diamine A mixture of 4-chloro-6-(2,3-dimethylphenyl)pyrimidin-2-amine (23 mg, 0.10 mmol), (4-benzylmorpholin-2-yl) methanamine (29 mg, 0.14 mmol) and Hünig's base (35 µL, 0.20 mmol) in n-butanol (1.5 mL) was heated in a sealed tube at 85° C. overnight. The reaction mixture was concentrated and purified by preparative HPLC.
LCMS [M+H]+ 404.

Example 279

6-(2,3-dimethylphenyl)-4-N-[(4-methanesulfonylphenyl)methyl]pyrimidine-2,4-diamine A mixture of 4-chloro-6-(2,3-dimethylphenyl)pyrimidin-2-amine (23 mg, 0.10 mmol), (4-methanesulfonylphenyl) methanamine hydrochloride (31 mg, 0.14 mmol) and Hünig's base (35 µL, 0.20 mmol) in n-butanol (1.5 mL) was heated in a sealed tube at 85° C. overnight. The reaction mixture was concentrated and purified by preparative HPLC. LCMS [M+H]+ 383.

Example 280

6-(2,3-dimethylphenyl)-4-N-{[4-(4-methylpiperazin-1-yl)phenyl]methyl}pyrimidine-2,4-diamine A mixture of 4-chloro-6-(2,3-dimethylphenyl)pyrimidin-2-amine (23 mg, 0.10 mmol), [4-(4-methylpiperazin-1-yl) phenyl]methanamine (29 mg, 0.14 mmol) and Hünig's base (35 µL, 0.20 mmol) in n-butanol (1.5 mL) was heated in a sealed tube at 85° C. overnight. The reaction mixture was concentrated and purified by preparative HPLC. LCMS [M+H]+ 403.

Example 281

4-N-[(3S)-1-azabicyclo[2.2.2]octan-3-yl]-6-(2,3-dimethylphenyl)pyrimidine-2,4-diamine A mixture of 4-chloro-6-(2,3-dimethylphenyl)pyrimidin-2-amine (23 mg, 0.10 mmol), (S)-quinuclidin-3-amine hydrochloride (29 mg, 0.14 mmol) and Hünig's base (35 µL, 0.20 mmol) in n-butanol (1.5 mL) was heated in a sealed tube at 85° C. overnight. The reaction mixture was concentrated and purified by preparative HPLC. LCMS [M+H]+ 324.

Example 282 tert-butyl 2-({[2-amino-6-(2,3-dimethylphenyl)pyrimidin-4-yl]amino}methyl)-pyrrolidine-1-carboxylate A mixture of 4-chloro-6-(2,3-dimethylphenyl)pyrimidin-2-amine (23 mg, 0.10 mmol), tert-butyl 2-(aminomethyl) pyrrolidine-1-carboxylate (28 mg, 0.14 mmol) and Hünig's base (35 µL, 0.20 mmol) in n-butanol (1.5 mL) was heated in a sealed tube at 85° C. overnight. The reaction mixture was concentrated and purified by preparative HPLC. LCMS [M+H]+ 398.

Example 283 tert-butyl 4-({[2-amino-6-(2,3-dimethylphenyl)pyrimidin-4-yl]amino}methyl)-piperidine-1-carboxylate A mixture of 4-chloro-6-(2,3-dimethylphenyl)pyrimidin-2-amine (23 mg, 0.10 mmol), tert-butyl 4-(aminomethyl) piperidine-1-carboxylate (30 mg, 0.14 mmol) and Hünig's base (35 µL, 0.20 mmol) in n-butanol (1.5 mL) was heated in a sealed tube at 85° C. overnight. The reaction mixture was concentrated and purified by preparative HPLC. LCMS [M+H]+ 412.

Example 284

1-(3-{[2-amino-6-(2,3-dichlorophenyl)pyrimidin-4-yl]amino}propyl)pyrrolidin-2-one A mixture of 4-chloro-6-(2,3-dichlorophenyl)pyrimidin-2-amine (19 mg, 0.070 mmol) and 1-(3-aminopropyl)pyrrolidin-2-one (49 µL, 0.35 mmol) in n-butanol (1 mL) was

Example 285

1-(3-{[2-amino-6-(3-chloro-2-methylphenyl)pyrimidin-4-yl]amino}propyl)pyrrolidin-2-one A mixture of 4-chloro-6-(3-chloro-2-methylphenyl)pyrimidin-2-amine (19 mg, 0.076 mmol) and 1-(3-aminopropyl)pyrrolidin-2-one (53 μL, 0.38 mmol) in n-butanol (1 mL) was heated in a sealed tube at 110° C. overnight. The reaction mixture was concentrated and purified by preparative HPLC. LCMS [M+H]$^+$ 360.

Example 286

1-(3-{[2-amino-6-(4-fluoro-2,3-dimethylphenyl)pyrimidin-4-yl]amino}propyl)pyrrolidin-2-one A mixture of 1-{3-[(2-amino-6-chloropyrimidin-4-yl)amino]propyl}pyrrolidin-2-one (27 mg, 0.10 mmol), (4-fluoro-2,3-dimethylphenyl)boronic acid (18 mg, 0.11 mmol), potassium carbonate (28 mg, 0.20 mmol) and palladium tetrakis(triphenylphosphine)palladium (0) (6 mg, 0.005 mmol) in 1,4-dioxane (4 mL) and water (1 mL) was heated in a sealed tube at 95° C. for 2 h. The reaction mixture was concentrated and purified by preparative HPLC. LCMS [M+H]$^+$ 358.

Example 287

1-(3-{[2-amino-6-(4-methoxy-2,3-dimethylphenyl)pyrimidin-4-yl]amino}propyl)pyrrolidin-2-one A mixture of 1-{3-[(2-amino-6-chloropyrimidin-4-yl)amino]propyl}pyrrolidin-2-one (27 mg, 0.10 mmol), (4-methoxy-2,3-dimethylphenyl)boronic acid (20 mg, 0.11 mmol), potassium carbonate (28 mg, 0.20 mmol) and palladium tetrakis(triphenylphosphine)palladium (0) (6 mg, 0.005 mmol) in 1,4-dioxane (4 mL) and water (1 mL) was heated in a sealed tube at 95° C. for 2 h. The reaction mixture was concentrated and purified by preparative HPLC. LCMS [M+H]$^+$ 370.

Example 288

1-(3-{[2-amino-6-(4-methyl-1H-indazol-5-yl)pyrimidin-4-yl]amino}propyl)pyrrolidin-2-one A mixture of 1-{3-[(2-amino-6-chloropyrimidin-4-yl)amino]propyl}pyrrolidin-2-one (27 mg, 0.10 mmol), (4-methyl-1H-indazol-5-yl)boronic acid (19 mg, 0.11 mmol), potassium carbonate (28 mg, 0.20 mmol) and palladium tetrakis(triphenylphosphine)palladium (0) (6 mg, 0.005 mmol) in 1,4-dioxane (4 mL) and water (1 mL) was heated in a sealed tube at 95° C. for 2 h. The reaction mixture was concentrated and purified by preparative HPLC. LCMS [M+H]$^+$ 366.

Example 289

1-[3-({2-amino-6-[2-methyl-5-(morpholine-4-sulfonyl)phenyl]pyrimidin-4-yl}amino)propyl]pyrrolidin-2-one A mixture of 1-{3-[(2-amino-6-chloropyrimidin-4-yl)amino]propyl}pyrrolidin-2-one (27 mg, 0.10 mmol), [2-methyl-5-(morpholine-4-sulfonyl)phenyl]boronic acid (31 mg, 0.11 mmol), potassium carbonate (28 mg, 0.20 mmol) and palladium tetrakis(triphenylphosphine)palladium (0) (6 mg, 0.005 mmol) in 1,4-dioxane (4 mL) and water (1 mL) was heated in a sealed tube at 95° C. for 2 h. The reaction mixture was concentrated and purified by preparative HPLC. LCMS [M+H]$^+$ 475.

Example 290

1-(3-{[2-amino-6-(2,3-dihydro-1-benzofuran-7-yl)pyrimidin-4-yl]amino}propyl)pyrrolidin-2-one A mixture of 1-{3-[(2-amino-6-chloropyrimidin-4-yl)amino]propyl}pyrrolidin-2-one (27 mg, 0.10 mmol), (2,3-dihydro-1-benzofuran-7-yl)boronic acid (18 mg, 0.11 mmol), potassium carbonate (28 mg, 0.20 mmol) and palladium tetrakis(triphenylphosphine)palladium (0) (6 mg, 0.005 mmol) in 1,4-dioxane (4 mL) and water (1 mL) was heated in a sealed tube at 95° C. for 2 h. The reaction mixture was concentrated and purified by preparative HPLC. LCMS [M+H]$^+$ 354.

Example 291

1-(3-{[2-amino-6-(2,5-dimethylphenyl)pyrimidin-4-yl]amino}propyl)pyrrolidin-2-one A mixture of 1-{3-[(2-amino-6-chloropyrimidin-4-yl)amino]propyl}pyrrolidin-2-one (27 mg, 0.10 mmol), (2,5-dimethylphenyl)boronic acid (17 mg, 0.11 mmol), potassium carbonate (28 mg, 0.20 mmol) and palladium tetrakis(triphenylphosphine)palladium (0) (6 mg, 0.005 mmol) in 1,4-dioxane (4 mL) and water (1 mL) was heated in a sealed tube at 95° C. for 2 h. The reaction mixture was concentrated and purified by preparative HPLC. LCMS [M+H]$^+$ 340.

Example 292

1-(3-{[2-amino-6-(5-chloro-2-methylphenyl)pyrimidin-4-yl]amino}propyl)pyrrolidin-2-one A mixture of 1-{3-[(2-amino-6-chloropyrimidin-4-yl)amino]propyl}pyrrolidin-2-one (27 mg, 0.10 mmol), (5-chloro-2-methylphenyl)boronic acid (19 mg, 0.11 mmol), potassium carbonate (28 mg, 0.20 mmol) and palladium tetrakis(triphenyl-phosphine)palladium (0) (6 mg, 0.005 mmol) in 1,4-dioxane (4 mL) and water (1 mL) was heated in a sealed tube at 95° C. for 2 h. The reaction mixture was concentrated and purified by preparative HPLC. LCMS [M+H]$^+$ 360.

Example 293

1-[3-({2-amino-6-[2-(trifluoromethyl)phenyl]pyrimidin-4-yl}amino)propyl]pyrrolidin-2-one A mixture of 1-{3-[(2-amino-6-chloropyrimidin-4-yl)amino]propyl}pyrrolidin-2-one (27 mg, 0.10 mmol), [2-(trifluoromethyl)phenyl]boronic acid (21 mg, 0.11 mmol), potassium carbonate (28 mg, 0.20 mmol) and palladium tetrakis-(triphenylphosphine)palladium (0) (6 mg, 0.005 mmol) in 1,4-dioxane (4 mL) and water (1 mL) was heated in a sealed tube at 95° C. for 2 h. The reaction mixture was concentrated and purified by preparative HPLC. LCMS [M+H]$^+$ 380.

Example 294

1-(3-{[2-amino-6-(1H-indol-4-yl)pyrimidin-4-yl]amino}propyl)pyrrolidin-2-one

A mixture of 1-{3-[(2-amino-6-chloropyrimidin-4-yl)amino]propyl}pyrrolidin-2-one (27 mg, 0.10 mmol), (1H-indol-4-yl)boronic acid (18 mg, 0.11 mmol), potassium carbonate (28 mg, 0.20 mmol) and palladium tetrakis(triphenylphosphine)-palladium (0) (6 mg, 0.005 mmol) in 1,4-dioxane (4 mL) and water (1 mL) was heated in a sealed tube at 95° C. for 2 h. The reaction mixture was concentrated and purified by preparative HPLC. LCMS [M+H]+ 351.

Example 295

4-N-{[1-(4-chlorophenyl)cyclopropyl]methyl}-6-(2,3-dimethylphenyl)pyrimidine-2,4-diamine A mixture of 4-chloro-6-(2,3-dimethylphenyl)pyrimidin-2-amine (47 mg, 0.20 mmol), [1-(4-chlorophenyl)cyclopropyl]methanamine hydrochloride (65 mg, 0.30 mmol) and Hünig's base (70 µL, 0.40 mmol) in n-butanol (1.5 mL) was heated in a sealed tube at 130° C. overnight. The reaction mixture was concentrated and purified by preparative HPLC. LCMS [M+H]+ 379.

Example 296

4-(2-{[2-amino-6-(2,3-dichlorophenyl)pyrimidin-4-yl]amino}ethyl)benzene-1-sulfonamide A mixture of 4-chloro-6-(2,3-dichlorophenyl)pyrimidin-2-amine (41 mg, 0.15 mmol), 4-(2-aminoethyl)benzene-1-sulfonamide (45 mg, 0.23 mmol) and Hünig's base (39 µL, 0.23 mmol) in n-butanol (2 mL) was heated in a sealed tube at 90° C. for 48 h. The reaction mixture was concentrated and purified by preparative HPLC. LCMS [M+H]+ 438.

Example 297

4-(2-{[2-amino-6-(3-chloro-2-methyl phenyl)pyrimidin-4-yl]amino}ethyl)benzene-1-sulfonamide A mixture of 4-chloro-6-(3-chloro-2-methylphenyl)pyrimidin-2-amine (38 mg, 0.15 mmol), 4-(2-aminoethyl)benzene-1-sulfonamide (45 mg, 0.23 mmol) and Hünig's base (39 µL, 0.23 mmol) in n-butanol (2 mL) was heated in a sealed tube at 90° C. for 48 h. The reaction mixture was concentrated and purified by preparative HPLC. LCMS [M+H]+ 418. 1H NMR (400 MHz, DMSO-d6) $\delta_H$ ppm 12.33 (br. s., 1 H), 8.89 (br. s., 1 H), 7.77 (d, J=8.1 Hz, 2 H), 7.64-7.68 (m, 1 H), 7.48 (d, J=8.1 Hz, 2 H), 7.37-7.41 (m, 2 H), 7.32 (s, 2 H), 6.03 (s, 1 H), 3.67 (q, J=6.7 Hz, 2 H), 2.98 (t, J=7.1 Hz, 2 H), 2.30 (s, 3 H).

Example 298

4-N-(Adamantan-1-yl)-6-(2,3-dichlorophenyl)pyrimidine-2,4-diamine

A mixture of the 4-chloro-6-(2,3-dichlorophenyl)pyrimidin-2-amine (25 mg) and adamantylamine (50 mg) was heated at 150° C. for 1 h. The mixture was cooled, diluted in methanol then purified by preparative HPLC. LCMS [M+H]+ 389.

Example 299

6-(2,3-dichlorophenyl)-4-N-[(1R,2R,3R,5S)-2,6,6-trimethylbicyclo[3.1.1]heptan-3-yl]pyrimidine-2,4-diamine A mixture of 4-chloro-6-(2,3-dichlorophenyl)pyrimidin-2-amine (25 mg) and (1R,2R,3R,5S)-2,6,6-trimethylbicyclo[3.1.1]heptan-3-amine (50 mg) was heated at 150° C. for 1 h. The mixture was cooled, diluted in methanol then purified by preparative HPLC. LCMS [M+H]+ 391.

Example 300

6-(2,3-Dichlorophenyl)-4-N-({3-[(4-methylpiperidin-1-yl)methyl]phenyl}methyl)-pyrimidine-2,4-diamine A mixture of 4-chloro-6-(2,3-dichlorophenyl)pyrimidin-2-amine (25 mg) and {3-[(4-methylpiperidin-1-yl)methyl]phenyl}methanamine (50 mg) was heated at 150° C. for 1 h. The mixture was cooled, diluted in methanol and then purified by preparative HPLC. LCMS [M+H]+ 456.

Example 301

4-(2-{[2-Amino-6-(2,3-dichlorophenyl)pyrimidin-4-yl]amino}ethyl)phenol

A mixture of 4-chloro-6-(2,3-dichlorophenyl)pyrimidin-2-amine (25 mg) and 4-(2-aminoethyl)phenol (50 mg) was heated at 150° C. for 1 h. The mixture was cooled, diluted in methanol then purified by preparative HPLC. LCMS [M+H]+ 375.

Example 302

Ethyl 4-{[2-amino-6-(2,3-dichlorophenyl)pyrimidin-4-yl]amino}piperidine-1-carboxylate A mixture of 4-chloro-6-(2,3-dichlorophenyl)pyrimidin-2-amine (25 mg) and ethyl 4-aminopiperidine-1-carboxylate (50 mg) was heated at 150° C. for 1 h. The mixture was cooled, diluted in methanol then purified by preparative HPLC. LCMS [M+H]+ 410.

Example 303

N-(4-{[2-Amino-6-(2,3-dichlorophenyl)pyrimidin-4-yl]amino}butyl)acetamide

A solution of 4-chloro-6-(2,3-dichlorophenyl)pyrimidin-2-amine (25 mg; 0.1 mmol) in n-BuOH (1.0 ml) was heated at 130° C. with N-(4-aminobutyl)acetamide (1 eq.) and triethylamine (1 eq). After 18 h the reaction was halted and evaporated. The residue was purified by preparative HPLC. LCMS [M+H]+ 368.

Example 304

6-(2,3-Dichlorophenyl)-4-N-{tricyclo[3.3.1.0$^{3,7}$]nonan-3-yl}pyrimidine-2,4-diamine A solution of 4-chloro-6-(2,3-dichlorophenyl)pyrimidin-2-amine (25 mg; 0.1 mmol) in n-BuOH (1.0 ml) was heated at 130° C. with tricyclo[3.3.1.0$^{3,7}$]nonan-3-amine (1 eq) and triethylamine (1 eq). After 18 h the reaction was halted and evaporated. The residue was purified by preparative HPLC. LCMS [M+H]$^+$ 375.

Example 305

6-(2,3-Dichlorophenyl)-4-N-{[4-(1,2,3-thiadiazol-4-yl)phenyl]methyl}pyrimidine-2,4-diamine A solution of 4-chloro-6-(2,3-dichlorophenyl)pyrimidin-2-amine (25 mg; 0.1 mmol) in n-BuOH (1.0 ml) was heated at 130° C. with [4-(1,2,3-thiadiazol-4-yl)phenyl]methanamine (1 eq) and triethylamine (1 eq). After 18 h the reaction was halted and evaporated. The residue was purified by preparative HPLC. LCMS [M+H]$^+$ 429.

Example 306

4-N-[2-(1-Benzylpiperidin-4-yl)ethyl]-6-(2,3-dichlorophenyl)pyrimidine-2,4-diamine A solution of 4-chloro-6-(2,3-dichlorophenyl)pyrimidin-2-amine (25 mg; 0.1 mmol) in n-BuOH (1.0 ml) was heated at 130° C. with 2-(1-benzylpiperidin-4-yl)ethan-1-amine (1 eq) and triethylamine (1 eq). After 18 h the reaction was halted and evaporated. The residue was purified by preparative HPLC. LCMS [M+H]$^+$ 456.

Example 307

6-(2,3-Dichlorophenyl)-4-N-(2,3-dihydro-1,4-benzodioxin-2-ylmethyl)pyrimidine-2,4-diamine A solution of 4-chloro-6-(2,3-dichlorophenyl)pyrimidin-2-amine (25 mg; 0.1 mmol) in n-BuOH (1.0 ml) was heated at 130 degrees with 2,3-dihydro-1,4-benzodioxin-2-ylmethanamine (1 eq) and triethylamine (1 eq). After 18 h the reaction was halted and evaporated. The residue was purified by preparative HPLC. LCMS [M+H]$^+$ 403.

Example 308

N-{3-[2-amino-6-(methylamino)pyrimidin-4-yl]phenyl}-3-hydroxypyridine-2-carboxamide Equimolar quantities of 3-hydroxypyridine-2-carboxylic acid (0.24 mmol) and 6-(3-aminophenyl)-4-N-methyl-pyrimidine-2,4-diamine were dissolved in 2 ml DMF followed by addition of hydroxybenzotriazole (1.0 eq) and N,N'-dicyclohexylcarbodiimide (1.5 eq). The solution was stirred at rt overnight. The mixture was then filtrated and purified by preparative HPLC.

LCMS [M+H]$^+$ 337; $^1$H NMR (400 MHz, DMSO-d$_6$) $\delta_H$ ppm 12.15 (1 H, br. s.), 11.17 (1 H, s), 8.86 (1 H, m, J=5.05 Hz), 8.25-8.35 (2 H, m), 8.03 (1 H, dd, J=8.08, 1.26 Hz), 7.59-7.68 (2 H, m), 7.52 (2 H, dd, J=8.46, 1.39 Hz), 6.36 (1 H, s), 2.95 (3 H, d, J=4.80 Hz).

Example 309

N-{3-[2-Amino-6-(methylamino)pyrimidin-4-yl]phenyl}prop-2-enamide

To a stirred suspension of 6-(3-aminophenyl)-4-N-methyl-pyrimidine-2,4-diamine (0.29 mmol) and triethylamine (1.5 eq.) in acetonitrile (2 mL) at 0° C. was slowly added prop-2-enoyl chloride (1.0 eq.). The mixture was allowed to warm to rt and stirred for 3 h. The mixture was concentrated and purified by preparative HPLC.

LCMS [M+H]$^+$ 270; $^1$H NMR (400 MHz, DMSO-d$_6$) $\delta_H$ ppm 10.35 (1 H, s), 8.23 (1 H, t, J=1.89 Hz), 7.79 (1 H, d, J=8.08 Hz), 7.56-7.69 (4 H, m), 7.34-7.52 (4 H, m), 6.88 (1 H, s), 6.84 (1 H, s), 6.18 (1 H, s), 5.98 (2 H, s), 2.80 (3 H, d, J=4.80 Hz).

Example 310

(2E)-N-{3-[2-Amino-6-(methylamino)pyrimidin-4-yl]phenyl}-3-phenylprop-2-enamide

To a suspension of the 6-(3-aminophenyl)-4-N-methyl-pyrimidine-2,4-diamine (0.25 mmol) and triethylamine (1.5 eq.) in acetonitrile (2 mL) at 0° C. was added drop wise, with stirring, the (E)-3-phenylprop-2-enoyl chloride (1.0 eq.). The mixture was allowed to warm to rt, and stirred for 3 h. The mixture was concentrated and purified by preparative HPLC. LCMS [M+H]$^+$ 346; $^1$H NMR (400 MHz, DMSO-d$_6$) $\delta_H$ ppm 10.35 (s, 1 H), 8.23 (t, J=1.89 Hz, 1 H), 7.79 (d, J=8.08 Hz, 1 H), 7.56-7.69 (m, 4 H), 7.34-7.52 (m, 4 H), 6.88 (s, 1 H), 6.84 (s, 1 H), 6.18 (s, 1 H), 5.98 (s, 2 H), 2.80 (d, J=4.80 Hz, 3 H).

Example 311

N-{3-[2-Amino-6-(methylamino)pyrimidin-4-yl]-2-methylphenyl}prop-2-enamide

To a suspension of 6-(3-amino-2-methyl-phenyl)-4-N-methyl-pyrimidine-2,4-diamine (0.39 mmol) and triethylamine (1.5 eq.) in acetonitrile (3 ml) at 0° C. was added drop wise, with stirring, prop-2-enoyl chloride (1.0 eq.). The mixture was allowed to warm to rt, and stirred for 3 h. The mixture was concentrated and purified by preparative HPLC. LCMS [M+H]$^+$ 284; $^1$H NMR (400 MHz, DMSO-d$_6$) $\delta_H$ ppm 9.57 (1 H, s), 7.41 (1 H, d, J=7.58 Hz), 7.20 (1 H, t, J=7.83 Hz), 7.10 (1 H, d, J=6.82 Hz), 6.83 (1 H, br. s.), 6.54 (1 H, dd, J=17.05, 10.23 Hz), 6.25 (1 H, dd, J=17.05, 2.15 Hz), 5.97 (2 H, s), 5.73-5.78 (1 H, m), 5.71 (1 H, s), 2.77 (3 H, d, J=4.55 Hz), 2.14 (3 H, s).

Example 312

(2E)-N-{3-[2-Amino-6-(methylamino)pyrimidin-4-yl]phenyl}-4-(dimethylamino)but-2-enamide To a solution of 6-(3-aminophenyl)-4-N-methylpyrimidine-2,4-diamine (0.29 mol) in acetonitrile (4 mL) was added successively (E)-4-(dimethylamino)but-2-enoic acid; hydrochloride (1.0 eq.), triethylamine (3.0 eq.) and n-propanephosphonic acid anhydride (T3P, 2.0 eq.). The resulting mixture was stirred at rt overnight. The solution was then filtrated and purified by preparative HPLC. LCMS [M+H]$^+$ 327; $^1$H NMR (400 MHz, DMSO-d$_6$) $\delta_H$ ppm 10.17 (1 H, s), 8.20 (1 H, t, J=1.77 Hz), 7.71 (1 H, d, J=8.08 Hz), 7.58 (1 H, d, J=7.83 Hz), 7.36 (1 H, t, J=7.83 Hz), 6.81-6.96 (1 H, m), 6.70-6.80 (1 H, m), 6.28 (1 H, dt, J=15.35, 1.55 Hz), 6.16 (1 H, s), 5.97 (2 H, s), 3.06 (2 H, dd, J=6.06, 1.52 Hz), 2.79 (3 H, d, J=4.80 Hz), 2.18 (6 H, s).

Example 313

N-{3-[2-amino-6-(methylamino)pyrimidin-4-yl]phenyl}ethene-1-sulfonamide

To a suspension of 6-(3-aminophenyl)-4-N-methyl-pyrimidine-2,4-diamine (0.20 mmol) and triethylamine (1.1 eq.) in acetonitrile (1.5 mL) at −60° C. was added drop wise, with stirring, ethenesulfonyl chloride (0.9 eq.) in 0.5 ml acetonitrile. The mixture was allowed to warm to rt, and stirred for 2 h. The solution was then filtrated and purified by preparative HPLC. LCMS [M+H]+ 306; $^1$H NMR (400 MHz, DMSO-d$_6$) δ$_H$ ppm 11.98 (1 H, br. s.), 10.38 (1 H, br. s.), 8.79 (1 H, br. s.), 7.31-7.60 (4 H, m), 6.85 (1 H, dd, J=16.42, 9.85 Hz), 6.25 (1 H, s), 6.18 (1 H, d, J=16.42 Hz), 6.08 (1 H, d, J=9.85 Hz), 2.93 (3 H, d, J=4.80 Hz).

Example 314

N-{3-[2-Amino-6-(methylamino)pyrimidin-4-yl] phenyl}prop-2-ynamide

To a solution of 6-(3-aminophenyl)-4-N-methyl-pyrimidine-2,4-diamine (0.30 mol) in acetonitrile (5 mL) at 0° C. was added successively prop-2-ynoic acid (1.0 eq.), triethylamine (2.0 eq.) and n-propanephosphonic acid anhydride (T3P, 1.7 eq.). The resulting mixture was stirred at rt overnight. The solution was then filtrated and purified by preparative HPLC. LCMS [M+H]+ 268; $^1$H NMR (400 MHz, DMSO-d$_6$) δ$_H$ ppm 8.19 (1 H, br. s.), 7.84 (1 H, d, J=7.83 Hz), 7.65 (1 H, d, J=7.83 Hz), 7.46 (1 H, d, J=13.39 Hz), 7.38 (1 H, t, J=7.83 Hz), 7.00 (1 H, d, J=13.89 Hz), 6.28 (1 H, br. s.), 5.97 (2 H, s), 2.78 (3 H, d, J=4.55 Hz).

Example 315

N-{3-[2-Amino-6-(methylamino)pyri midi n-4-yl] phenyl}-2-oxopropanamide

To a solution of 6-(3-aminophenyl)-4-N-methyl-pyrimidine-2,4-diamine (0.39 mol) in acetonitrile (4 mL) was added successively pyruvic acid (1.0 eq.), triethylamine (2.5 eq.) and n-propanephosphonic acid anhydride (T3P, 2.0 eq.). The resulting mixture was stirred at rt overnight. The solution was then filtrated and purified by preparative HPLC. LCMS [M+H]+ 286.

Example 316

N-{3-[2-Amino-6-(methylamino)pyrimidin-4-yl] phenyl}-2-oxo-2-phenylacetamide

To a solution of 6-(3-aminophenyl)-4-N-methyl-pyrimidine-2,4-diamine (0.42 mol) in acetonitrile (4 mL) was added successively 2-oxo-2-phenyl-acetic acid (0.9 eq.), triethylamine (2.5 eq.) and n-propanephosphonic acid anhydride (T3P, 2.0 eq.). The resulting mixture was stirred at rt overnight. The mixture was concentrated and purified by preparative HPLC. LCMS [M+H]+ 348; $^1$H NMR (400 MHz, DMSO-d$_6$) δ$_H$ ppm 8.30-8.36 (1 H, m), 8.00-8.11 (2 H, m), 7.66-7.84 (3 H, m), 7.59-7.66 (2 H, m), 7.45 (1 H, t, J=7.96 Hz), 6.90 (1 H, br. s.), 6.19 (1 H, s), 6.01 (2 H, s), 2.80 (3 H, d, J=4.80 Hz).

Example 317

N-{4-[2-Amino-6-(methylamino)pyrimidin-4-yl] phenyl}prop-2-enamide

To a suspension of 6-(4-aminophenyl)-4-N-methyl-pyrimidine-2,4-diamine (0.29 mmol) and triethylamine (1.5 eq.) in tetrahydrofuran (2 ml) at 0° C. was added drop wise, with stirring, prop-2-enoyl chloride (1.0 eq.). The mixture was allowed to warm to rt, and stirred for 3 h. The mixture was concentrated and purified by preparative HPLC. LCMS [M+H]+ 270; $^1$H NMR (400 MHz, DMSO-d6) δ$_H$ ppm 10.28 (1 H, s), 7.89 (2 H, d, J=8.8 Hz), 7.58-7.75 (2 H, m), 6.76 (1 H, br. s.), 6.40-6.49 (1 H, m), 6.24-6.30 (1 H, m), 6.17 (1 H, s), 5.94 (2 H, s), 5.58-5.80 (1 H, m), 2.79 (3 H, d, J=4.8 Hz).

Example 318

N-({4-[2-Amino-6-(methylamino)pyrimidin-4-yl] phenyl}methyl)prop-2-enamide

To a suspension of 6-[4-(aminomethyl)phenyl]-4-N-methyl-pyrimidine-2,4-diamine (0.29 mmol) and triethylamine (1.5 eq.) in tetrahydrofuran (2 ml) at 0° C. was added drop wise, with stirring, prop-2-enoyl chloride (1.0 eq.). The mixture was allowed to warm to rt and stirred for 3 h. The mixture was concentrated and purified by preparative HPLC. LCMS [M+H]+ 284.

Example 319

N-({3-[2-Amino-6-(methylamino)pyrimidin-4-yl] phenyl}methyl)prop-2-enamide

To a suspension of 6-[3-(aminomethyl)phenyl]-4-N-methyl-pyrimidine-2,4-diamine (0.16 mmol) and triethylamine (1.5 eq.) acetonitrile (4 mL) at 0° C. was added drop wise, with stirring, prop-2-enoyl chloride (1.0 eq.). The mixture was allowed to warm to room temperature, and stirred for 3 h. The mixture was concentrated and purified by preparative HPLC. LCMS [M+H]+ 284.

Example 320

N-{3-[2-Amino-6-(ethylamino)pyrimidin-4-yl]-4-methylphenyl}prop-2-enamide

To a suspension of 6-(5-amino-2-methyl-phenyl)-4-N-methyl-pyrimidine-2,4-diamine (0.48 mmol) and triethylamine (1.7 eq.) in acetonitrile (3 mL) at 0° C. was added drop wise, with stirring, prop-2-enoyl chloride (1.0 eq.). The mixture was allowed to warm to rt and stirred for 3 h. The mixture was concentrated and purified by preparative HPLC. LCMS [M+H]+ 284; $^1$H NMR (400 MHz, DMSO-d$_6$) δ$_H$ ppm 10.10 (1 H, s), 7.46-7.75 (2 H, m), 7.16 (1 H, d, J=8.34 Hz), 6.80 (1H, br. s.), 6.37-6.46 (1 H, m), 6.23 (1 H, dd, J=17.05, 2.15 Hz), 5.95 (2 H, s), 5.62-5.84 (2 H, m), 2.77 (3 H, d, J=4.55 Hz), 2.27 (3 H, s).

Example 321

N-{3-[2-Amino-6-(methylamino)pyrimidin-4-yl] phenyl}-5-chloro-2-hydroxybenzamide Equimolar quantities of 5-chloro-2-hydroxy-benzoic acid and 6-(3-aminophenyl)-4-N-methyl-pyrimidine-2,4-diamine (0.24 mmol) were dissolved in DMF (2 mL) followed by adding hydroxybenzotriazole (1.0 eq) and N,N'-dicyclohexylcarbodiimide (1.5 eq). The solution was stirred under rt overnight. The mixture was then filtrated and purified by preparative HPLC. LCMS [M+H]+ 370; $^1$H NMR (400 MHz, DMSO-d$_6$) δ$_H$ ppm 15.10 (1 H, br. s), 8.08-8.16 (1 H, m), 7.86 (1 H, d, J=7.58 Hz), 7.64 (1 H, d, J=3.03 Hz), 7.49 (1 H, d, J=7.33 Hz), 7.32 (1 H, t, J=7.96 Hz), 6.93 (1 H, dd, J=8.84, 3.03 Hz), 6.78-6.89 (1 H, m), 6.40 (1 H, d, J=8.84 Hz), 6.20 (1 H, s), 6.03 (2 H, s), 2.80 (3 H, d, J=4.55 Hz).

Example 322

N-{3-[2-Amino-6-(methylamino)pyrimidin-4-yl] phenyl}-2-hydroxyacetamide

Equimolar quantities of 2-hydroxyacetic acid and 6-(3-aminophenyl)-4-N-methyl-pyrimidine-2,4-diamine (0.24 mmol) were dissolved in 2 ml DMF followed by adding hydroxybenzotriazole (1.0 eq) in 1 mL DMF and N,N'-dicyclohexylcarbodiimide (1.5 eq, dissolved in xylene). The solution was stirred under room temperature overnight. The mixture was then filtrated and purified by preparative. LCMS [M+H]$^+$ 274; $^1$H NMR (400 MHz, DMSO-d$_6$) $\delta_H$ ppm 12.06 (1 H, br. s.), 9.75-10.10 (1 H, m), 8.83 (1 H, d, J=4.55 Hz), 8.22 (1 H, s), 7.84 (1 H, d, J=9.35 Hz), 7.54 (1 H, t, J=7.96 Hz), 7.40 (1 H, d, J=8.08 Hz), 6.30 (1 H, s), 5.61-5.97 (1 H, m), 4.03 (2 H, s), 2.94 (3 H, d, J=4.80 Hz).

Example 323

N-{3-[2-Amino-6-(methylamino)pyrimidin-4-yl] phenyl}-2-(4-chlorophenyl)-2-hydroxyacetamide Equimolar quantities of 6-(3-aminophenyl)-4-N-methyl-pyrimidine-2,4-diamine (0.24 mmol) and 2-(4-chlorophenyl)-2-hydroxy-acetic acid were dissolved in 2 ml DMF followed by adding hydroxybenzotriazole (1.0 eq) in 1 mL DMF and N,N'-dicyclohexylcarbodiimide (1.5 eq.; as a solution in xylene). The solution was stirred at rt overnight. The mixture was then filtrated and purified by preparative HPLC. LCMS [M+H]$^+$ 384; $^1$H NMR (400 MHz, DMSO-d$_6$) $\delta_H$ ppm 10.05 (1 H, s), 8.22 (1 H, t, J=1.89 Hz), 7.69 (1 H, d, J=8.59 Hz), 7.59 (1 H, d, J=6.57 Hz), 7.52-7.57 (2 H, m), 7.40-7.45 (2 H, m), 7.34 (1 H, t, J=7.96 Hz), 6.85 (1 H, br. s.), 6.14 (1 H, s), 6.04 (2 H, br. s.), 5.97 (1 H, s), 5.14 (1 H, s), 2.78 (3 H, d, J=4.80 Hz).

Example 324

N-{3-[2-Amino-6-(methylamino)pyrimidin-4-yl] phenyl}-2-hydroxy-2-phenylacetamide Equimolar quantities of 2-hydroxy-2-phenyl-acetic acid and 6-(3-aminophenyl)-4-N-methyl-pyrimidine-2,4-diamine (0.24 mmol) were dissolved in DMF (2 mL) followed by adding hydroxybenzotriazole (1.0 eq) in DMF (1 mL) and N,N'-dicyclohexylcarbodiimide (1.5 eq, dissolved in xylene). The solution was stirred under rt overnight. The mixture was then filtrated and purified by preparative HPLC. LCMS [M+H]$^+$ 350; $^1$H NMR (400 MHz, DMSO-d$_6$) $\delta_H$ ppm 11.86 (1 H, br. s.), 10.25 (2 H, s), 8.25 (1 H, s), 7.85 (1 H, d, J=8.59 Hz), 7.48-7.63 (3 H, m), 7.26-7.46 (4 H, m), 6.56 (1 H, d, J=4.29 Hz), 6.28 (1 H, s), 5.15 (1 H, d, J=3.79 Hz), 2.93 (3 H, d, J=4.80 Hz).

Example 325

N-{3-[2-Amino-6-(methylamino)pyrimidin-4-yl] phenyl}-4-oxo-4-(pyrrolidin-1-yl)butanamide Equimolar quantities of 4-oxo-4-pyrrolidin-1-yl-butanoic acid and 6-(3-aminophenyl)-4-N-methyl-pyrimidine-2,4-diamine (0.24 mmol) were dissolved in DMF (2 mL) followed by adding hydroxybenzotriazole (1.0 eq) in DMF (1 mL) and N,N'-dicyclohexylcarbodiimide (1.5 eq, dissolved in xylene). The solution was stirred at rt overnight. The mixture was then filtrated and purified by preparative HPLC. LCMS [M+H]$^+$ 369.

Example 326

N-{3-[2-Amino-6-(methylamino)pyrimidin-4-yl] phenyl}-2-hydroxybenzamide

Equimolar quantities of 2-hydroxybenzoic acid and 6-(3-aminophenyl)-4-N-methyl-pyrimidine-2,4-diamine (0.24 mmol) were dissolved in MeCN (2 mL) followed by adding N,N'-dicyclohexylcarbodiimide (1.25 eq). The solution was stirred at rt overnight. The mixture was then filtrated and purified by preparative HPLC. LCMS [M+H]$^+$ 336.

Example 327

1-{4-[2-Amino-6-(methylamino)pyrimidin-4-yl] phenyl}-2,2,2-trifluoroethan-1-one

Tetrakis(triphenylphosphine)palladium (0) (5 mol %) was added to a stirred mixture of 6-chloro-4-N-methylpyrimidine-2,4-diamine (0.25 mmol), [4-(trifluoroacetyl)phenyl] boronic ester (1.3 eq.), sodium carbonate (3.2 eq.), dioxane (2 mL) and water (0.5 mL) in a tube. The tube was sealed and the reaction was heated at 90° C. for 5 hours. The mixture was then filtrated and purified by preparative HPLC. LCMS [M+H]$^+$ 297.

Example 328

6-[3-(Aminomethyl)phenyl]-4-N-methylpyrimidine-2,4-diamine

Tetrakis(triphenylphosphine)palladium (0) (5 mol %) was added to a stirred mixture of 6-chloro-4-N-methylpyrimidine-2,4-diamine (2.00 mmol), [3-(aminomethyl)phenyl]boronic acid (1.3 eq.), sodium carbonate (3.2 eq.), dioxane (4 mL) and water (1 mL) in a tube. The tube was sealed and the reaction was heated at 90° C. overnight. The solvent were removed in vacuum and to the remaining solid was added ethyl acetate and washed with water. The organic phase was dried over magnesium sulfate. The crude material was then purified by flash chromatography (0→15% MeOH/DCM) to give the title compound. LCMS [M+H]$^+$ 230; $^1$H NMR (400 MHz, DMSO-d$_6$) $\delta_H$ ppm 7.90 (1 H, s), 7.75 (1 H, d, J=6.32 Hz), 7.35-7.42 (3 H, m), 6.82 (1 H, br. S), 6.21 (1 H, s), 5.98 (2 H, s), 3.79 (2 H, s), 2.79 (3 H, d, J=4.80 Hz).

Example 329

6-[4-(Aminomethyl)phenyl]-4-N-methylpyrimidine-2,4-diamine

Tetrakis(triphenylphosphine)palladium (0) (5 mol %) was added to a stirred mixture of 6-chloro-4-N-methylpyrimidine-2,4-diamine (1.00 mmol), [4-(aminomethyl)phenyl]boronic acid (1.3 eq.), sodium carbonate (4.2 eq.), dioxane (4 ml) and water (1 ml) in a tube. The tube was sealed and the reaction was heated at 90° C. overnight. The solvent were removed in vacuum and to the remaining solid was added ethyl acetate and washed with water. The organic phase was dried over magnesium sulfate. The crude material was then purified by flash chromatography (0→15% MeOH/DCM) to give the title compound. LCMS [M+H]$^+$ 230; $^1$H NMR (400

MHz, DMSO-d$_6$) δ$_H$ ppm 7.86 (2 H, d, J=7.58 Hz), 7.38 (2 H, d, J=8.59 Hz), 6.19 (1 H, s), 5.96 (2 H, s), 3.76 (2 H, s), 2.79 (3 H, d, J=4.80 Hz).

Example 330

4-(2-{[2-Amino-6-(2,3-dimethylphenyl)pyrimidin-4-yl]amino}ethyl)benzene-1-sulfonamide A mixture of 4-chloro-6-(2,3-dimethylphenyl)pyrimidin-2-amine (0.12 mmol), 4-(2-aminoethyl)benzene-1-sulfonamide (0.9 eq.) and triethylamine (1.5 eq.) in acetonitrile/ethanol/methanol 5:3:2 (1 mL) was heated in a sealed tube at 95° C. overnight. Methanol was added, and the mixture was filtered and purified by preparative HPLC. LCMS [M+H]$^+$ 398; $^1$H NMR (400 MHz, DMSO-d$_6$) δ$_H$ ppm 12.28 (1 H, br. s.), 8.87 (1 H, br. s.), 7.77 (2 H, d, J=8.34 Hz), 7.48 (2 H, d, J=8.34 Hz), 7.37 (1 H, d, J=7.33 Hz), 7.32 (2 H, s), 7.23-7.28 (1 H, m), 7.18-7.23 (1 H, m), 5.99 (1 H, s), 3.67 (2 H, q, J=6.82 Hz), 2.98 (2 H, t, J=7.20 Hz), 2.31 (3 H, s), 2.17 (3 H, s).

Example 331

6-(2,3-Dimethylphenyl)-4-N-[2-(4-methanesulfonylphenyl)ethyl]pyrimidine-2,4-diamine A mixture of 4-chloro-6-(2,3-dimethylphenyl)pyrimidin-2-amine (0.15 mmol), 2-(4-methanesulfonylphenyl)ethan-1-amine (1.2 eq.) and N,N-diisopropylethylamine (2.25 eq.) in n-butanol (0.3 mL) was heated in a sealed tube at 110° C. overnight.

Methanol was added and the mixture was filtered and purified by preparative HPLC. LCMS [M+H]$^+$ 397.

Example 332

6-(2,3-Dimethylphenyl)-4-N-[2-(5-methyl-1H-1,2,4-triazol-3-yl)ethyl]pyrimidine-2,4-diamine A mixture of 4-chloro-6-(2,3-dimethylphenyl)pyrimidin-2-amine (0.15 mmol), 2-(5-methyl-1H-1,2,4-triazol-3-yl)ethan-1-amine (0.9 eq.) and triethylamine (1.5 eq.) in acetonitrile/ethanol/methanol 5:3:2 (1 mL) was heated in a sealed tube at 95° C. overnight. Methanol was added, and the mixture was filtered and purified by preparative HPLC. LCMS [M+H]$^+$ 324.

Example 333

4-(2-{[2-Amino-6-(2,3-dimethylphenyl)pyrimidin-4-yl]amino}ethyl)benzonitrile

A mixture of 4-chloro-6-(2,3-dimethylphenyl)pyrimidin-2-amine (0.15 mmol), 4-(2-aminoethyl)benzonitrile (1.2 eq.) and N,N-diisopropylethylamine (2.25 eq.) in n-butanol (0.3 mL) was heated in a sealed tube at 110° C. overnight. Methanol was added, and the mixture was filtered and purified by preparative HPLC. LCMS [M+H]$^+$ 344; $^1$H NMR (400 MHz, DMSO-d$_6$) δ$_H$ ppm 12.36 (1 H, br. s.), 8.87 (1 H, t, J=5.31 Hz), 7.80 (2 H, d, J=8.08 Hz), 7.51 (2 H, d, J=8.34 Hz), 7.37 (1 H, d, J=7.33 Hz), 7.23-7.28 (1 H, m), 7.16-7.22 (1 H, m), 5.98 (1 H, s), 3.67 (2 H, q, J=6.65 Hz), 2.99 (2 H, t, J=7.20 Hz), 2.31 (3 H, s), 2.17 (3 H, s).

Example 334

6-(2,3-Dimethylphenyl)-4-N-[2-(pyridin-4-yl)ethyl]pyrimidine-2,4-diamine

A mixture of 4-chloro-6-(2,3-dimethylphenyl)pyrimidin-2-amine (0.15 mmol), 2-(pyridin-4-yl)ethan-1-amine (1.2 eq.) and N,N-diisopropylethylamine (1.25 eq.) in n-butanol (0.3 ml) was heated in a sealed tube at 110° C. overnight. Methanol was added, and the mixture was filtered and purified by preparative HPLC. LCMS [M+H]$^+$ 320; $^1$H NMR (400 MHz, DMSO-d$_6$) δ$_H$ ppm 12.45 (1 H, br. s.), 8.93 (1 H, t, J=5.56 Hz), 8.76 (2 H, d, J=6.32 Hz), 7.80 (2 H, d, J=6.32 Hz), 7.37 (1 H, d, J=7.33 Hz), 7.25 (1 H, t, J=7.58 Hz), 7.17-7.21 (1 H, m), 5.99 (1 H, s), 3.68-3.83 (2 H, m), 3.13 (2 H, t, J=7.07 Hz), 2.31 (3 H, s), 2.17 (3 H, s).

Example 335

4-(2-{[2-Amino-6-(2,3-dimethylphenyl)pyrimidin-4-yl]amino}ethoxy)benzonitrile

A mixture of 4-chloro-6-(2,3-dimethylphenyl)pyrimidin-2-amine (0.15 mmol), 4-(2-aminoethoxy)benzonitrile (1.2 eq.) and N,N-diisopropylethylamine (1.25 eq.) in n-butanol (0.3 mL) was heated in a sealed tube at 110° C. overnight. Methanol was added, and the mixture was filtered and purified by preparative HPLC. LCMS [M+H]$^+$ 360; $^1$H NMR (400 MHz, DMSO-d$_6$) δ$_H$ ppm 12.37 (1 H, br. s.), 9.02 (1 H, t, J=5.31 Hz), 7.77-7.83 (2 H, m), 7.37 (1 H, d, J=7.33 Hz), 7.23-7.29 (1 H, m), 7.18-7.22 (1 H, m), 7.12-7.18 (2 H, m), 6.06 (1 H, s), 4.29 (2 H, t, J=5.43 Hz), 3.82 (2 H, q, J=5.22 Hz), 2.31 (3 H, s), 2.17 (3 H, s).

Example 336

4-({[2-Amino-6-(2,3-dimethylphenyl)pyrimidin-4-yl]amino}methyl)benzene-1-sulfonamide A mixture of 4-chloro-6-(2,3-dimethylphenyl)pyrimidin-2-amine (0.08 mmol), 4-(aminomethyl)benzene-1-sulfonamide (0.9 eq.) and triethylamine (1.5 eq.) in acetonitrile/ethanol/methanol 5:3:2 (1 mL) was heated in a sealed tube at 95° C. overnight. Methanol was added, and the mixture was filtered and purified by preparative HPLC. LCMS [M+H]$^+$ 384; $^1$H NMR (400 MHz, DMSO-d$_6$) δ$_H$ ppm 7.74-7.81 (2 H, m), 7.49-7.54 (2 H, m), 7.46 (1 H, t, J=5.68 Hz), 7.30 (2 H, s), 7.12-7.21 (1 H, m), 7.01-7.12 (2 H, m), 6.00 (2 H, s), 5.76 (1 H, br. s.), 4.57 (2 H, br. s.), 2.26 (3 H, s), 2.15 (3 H, s).

Example 337

1-(2-{[2-Amino-6-(2,3-dimethylphenyl)pyrimidin-4-yl]amino}ethyl)-1,2-dihydropyridin-2-one A mixture of 4-chloro-6-(2,3-dimethylphenyl)pyrimidin-2-amine (0.11 mmol), 1-(2-aminoethyl)-1,2-dihydropyridin-2-one (0.9 eq.) and triethylamine (1.5 eq.) in acetonitrile/ethanol/methanol 5:3:2 (1 mL) was heated in a sealed tube at 95° C. overnight. Methanol was added, and the mixture was filtered and purified by preparative HPLC. LCMS [M+H]$^+$ 336.

Example 338

3-({[2-Amino-6-(2,3-dimethylphenyl)pyrimidin-4-yl]amino}methyl)-1,2-dihydropyridin-2-one A mixture of 4-chloro-6-(2,3-dimethylphenyl)pyrimidin-2-amine (0.11 mmol), 3-(aminomethyl)-1,2-dihydropyridin-2-one (0.9 eq.) and triethylamine (1.5 eq.) in acetonitrile/ethanol/methanol 5:3:2 (1 ml) was heated in a sealed tube at 95° C. overnight. Methanol was added, and the mixture was filtered and purified by preparative HPLC. LCMS [M+H]+ 322.

Example 339

6-(3-{[2-Amino-6-(2,3-dimethylphenyl)pyrimidin-4-yl]amino}propyl)-5H,6H,7H-pyrrolo[3,4-b]pyridin-5-one A mixture of 4-chloro-6-(2,3-dimethylphenyl)pyrimidin-2-amine (0.12 mmol), 6-(3-aminopropyl)-5H,6H,7H-pyrrolo[3,4-b]pyridin-5-one (0.9 eq.) and triethylamine (1.5 eq.) in acetonitrile/ethanol/methanol 5:3:2 (1 mL) was heated in a sealed tube at 95° C. overnight. Methanol was added, and the mixture was filtered and purified by preparative HPLC. LCMS [M+H]+ 389.

Example 340

6-({[2-Amino-6-(2,3-dimethylphenyl)pyrimidin-4-yl]amino}methyl)pyridin-3-ol

A mixture of 4-chloro-6-(2,3-dimethylphenyl)pyrimidin-2-amine (0.08 mmol), 6-(aminomethyl)pyridin-3-ol hydrochloride (0.9 eq.) and triethylamine (2.5 eq.) in acetonitrile/ethanol/methanol 5:3:2 (1 mL) was heated in a sealed tube at 95° C. overnight. Methanol was added, and the mixture was filtered and purified by preparative HPLC. LCMS [M+H]+ 322.

Example 341

4-N-[2-(3-Chlorophenyl)ethyl]-6-(2,3-dimethylphenyl)pyrimidine-2,4-diamine

Prepared according to general procedure 9 from 2-(3-chlorophenyl)ethan-1-amine and 4-chloro-6-(2,3-dimethylphenyl)pyrimidin-2-amine. LCMS [M+H]+ 353; $^1$H NMR (400 MHz, CDCl$_3$) $\delta_H$ ppm 2.24 (s, 3 H) 2.31 (s, 3 H) 2.88 (t, J=7.07 Hz, 2 H) 3.56 (d, J=5.81 Hz, 2 H) 4.86-5.12 (m, 3 H) 5.79 (s, 1 H) 7.07-7.15 (m, 3 H) 7.17 (q, J=4.04 Hz, 1 H) 7.20-7.26 (m, 3 H).

Example 342

6-(2,3-Dimethylphenyl)-4-N-[3-(1H-imidazol-1-yl)propyl]pyrimidine-2,4-diamine

Prepared according to general procedure 9 from 3-(1H-imidazol-1-yl)propan-1-amine and 4-chloro-6-(2,3-dimethylphenyl)pyrimidin-2-amine. LCMS [M+H]+ 323; $^1$H NMR (400 MHz, CD$_3$OD) $\delta_H$ ppm 2.11 (t, J=6.82 Hz, 2 H) 2.20 (s, 3 H) 2.32 (s, 3 H) 3.38 (br. s., 2 H) 4.13 (t, J=6.95 Hz, 2 H) 5.82 (s, 1 H) 6.98 (br. s., 1 H) 7.05-7.23 (m, 4 H) 7.69 (br. s., 1 H).

Example 343

4-N-[2-(4-Chlorophenyl)propyl]-6-(2,3-dimethylphenyl)pyrimidine-2,4-diamine

Prepared according to general procedure 9 from 2-(4-chlorophenyl)propan-1-amine and 4-chloro-6-(2,3-dimethylphenyl)pyrimidin-2-amine. LCMS [M+H]+ 367; $^1$H NMR (400 MHz, CDCl$_3$) $\delta_H$ ppm 1.31 (d, J=7.07 Hz, 3 H) 2.23 (s, 3 H) 2.31 (s, 3 H) 2.97-3.09 (m, 1 H) 3.28-3.40 (m, 1 H) 3.46-3.66 (m, 1 H) 4.74 (br. s., 1 H) 4.95 (br. s., 2 H) 5.74 (s, 1 H) 7.09-7.14 (m, 2 H) 7.14-7.19 (m, 3 H) 7.28-7.33 (m, 2 H).

Example 344

6-(2,3-Dimethylphenyl)-4-N-[2-(4-fluorophenyl)ethyl]pyrimidine-2,4-diamine

Prepared according to general procedure 9 from 2-(4-fluorophenyl)ethan-1-amine and 4-chloro-6-(2,3-dimethylphenyl)pyrimidin-2-amine. LCMS [M+H]+ 337; $^1$H NMR (400 MHz, CDCl$_3$) $\delta_H$ ppm 2.23 (s, 3 H) 2.29-2.34 (m, 3 H) 2.89-2.96 (m, 3 H) 3.49-3.60 (m, 1 H) 3.76 (d, J=6.06 Hz, 3 H) 5.77 (s, 4 H) 7.00-7.07 (m, 3 H) 7.08-7.12 (m, 2 H) 7.13-7.22 (m, 5 H) 7.28-7.32 (m, 1 H).

Example 345

6-(2,3-Dimethylphenyl)-4-N-[2-(4-methoxyphenyl)-2-(pyrrolidin-1-yl)ethyl]pyrimidine-2,4-diamine Prepared according to general procedure 9 from 2-(4-methoxyphenyl)-2-(pyrrolidin-1-yl)ethan-1-amine and 4-chloro-6-(2,3-dimethylphenyl)pyrimidin-2-amine. LCMS [M+H]+ 418; $^1$H NMR (400 MHz, CDCl$_3$) $\delta_H$ ppm 1.74-1.81 (m, 4 H) 2.22 (s, 3 H) 2.30 (s, 3 H) 2.46-2.69 (m, 5 H) 3.49 (br. s., 2 H) 3.81 (s, 3 H) 4.88 (br. s., 2 H) 5.04-5.18 (m, 1 H) 5.74 (s, 1 H) 6.85-6.90 (m, 2 H) 7.09-7.12 (m, 2 H) 7.13-7.17 (m, 1 H) 7.24-7.29 (m, 2 H).

Example 346

4-N-{[4-(Dimethylamino)phenyl]methyl}-6-(2,3-dimethylphenyl)pyrimidine-2,4-diamine Prepared according to general procedure 9 from 4-(aminomethyl)-N,N-dimethylaniline and 4-chloro-6-(2,3-dimethylphenyl)pyrimidin-2-amine. LCMS [M+H]+ 348.

Example 347

4-N-[2-(Benzenesulfonyl)ethyl]-6-(2,3-dimethylphenyl)pyrimidine-2,4-diamine

Prepared according to general procedure 9 from 2-(benzenesulfonyl)ethan-1-amine and 4-chloro-6-(2,3-dimethylphenyl)pyrimidin-2-amine. LCMS [M+H]+ 383; $^1$H NMR (400 MHz, CDCl$_3$) $\delta_H$ ppm 2.22 (s, 3 H) 2.31 (s, 3 H) 3.41-3.46 (m, 2 H) 3.86 (q, J=6.06 Hz, 2 H) 5.10 (br. s., 2 H) 5.41-5.53 (m, 1 H) 5.76 (s, 1 H) 7.07-7.16 (m, 2 H) 7.16-7.20 (m, 1 H) 7.57-7.63 (m, 2 H) 7.66-7.71 (m, 1 H) 7.92-7.97 (m, 2 H),

Example 348

6-(2,3-Dimethylphenyl)-4-N-{[1-(4-fluorophenyl)-1H-pyrazol-4-yl]methyl}pyrimidine-2,4-diamine Prepared according to general procedure 9 from [1-(4-fluorophenyl)-1H-pyrazol-4-yl]methanamine and 4-chloro-6-(2,3-dimethylphenyl)pyrimidin-2-amine. LCMS [M+H]$^+$ 389; $^1$H NMR (400 MHz, CDCl$_3$) $\delta_H$ ppm 2.22 (s, 3 H) 2.29 (s, 3 H) 4.47 (d, J=5.31 Hz, 2 H) 5.11-5.41 (m, 3 H) 5.85 (s, 1 H) 7.10-7.19 (m, 5 H) 7.59-7.65 (m, 2 H) 7.68 (s, 1 H) 7.85 (s, 1 H)

Example 349

6-(2,3-dimethylphenyl)-4-N-{2-[5-(pyridin-4-yl)-1H-1,2,4-triazol-3-yl]ethyl}pyrimidine-2,4-diamine Prepared according to general procedure 9 from 2-[5-(pyridin-4-yl)-1H-1,2,4-triazol-3-yl]ethan-1-amine and 4-chloro-6-(2,3-dimethylphenyl)pyrimidin-2-amine. LCMS [M+H]$^+$ 387.

Example 350

6-(2,3-Dimethylphenyl)-4-N-{[1-(pyrimidin-2-yl)piperidin-3-yl]methyl}pyrimidine-2,4-diamine Prepared according to general procedure 9 from [1-(pyrimidin-2-yl)piperidin-3-yl]methanamine and 4-chloro-6-(2,3-dimethylphenyl)pyrimidin-2-amine. LCMS [M+H]$^+$ 390; $^1$H NMR (400 MHz, CDCl$_3$) $\delta_H$ ppm 1.41 (m, 1 H) 1.48-1.60 (m, 1 H) 1.75 (m, 1 H) 1.85-1.98 (m, 2 H) 2.24 (s, 3 H) 2.31 (s, 3 H) 3.13-3.48 (m, 4 H) 4.15-4.24 (m, 1 H) 4.30 (m, 1 H) 5.11 (br. s., 2 H) 5.39 (br. s., 1 H) 5.82 (s, 1 H) 6.45 (t, J=4.80 Hz, 1 H) 7.10-7.19 (m, 3 H) 8.28-8.31 (d, J=4.80 Hz, 2 H).

Example 351

6-(2,3-Dimethylphenyl)-4-N-[2-(6-methoxy-1H-1,3-benzodiazol-2-yl)ethyl]pyrimidine-2,4-diamine Prepared according to general procedure 9 from 2-(6-methoxy-1H-1,3-benzodiazol-2-yl)ethan-1-amine and 4-chloro-6-(2,3-dimethylphenyl)pyrimidin-2-amine. LCMS [M+H]$^+$ 389; $^1$H NMR (400 MHz, CDCl$_3$) $\delta_H$ ppm 2.16 (s, 3 H) 2.24 (s, 3 H) 3.12 (t, J=6.19 Hz, 2 H) 3.81 (s, 3 H) 3.82-3.90 (m, 2 H) 5.11-5.43 (m, 2 H) 5.79 (s, 1 H) 5.88 (br. s., 1 H) 6.85 (dd, J=8.72, 2.40 Hz, 1 H) 7.01 (d, J=8.08 Hz, 2 H) 7.05 (t, J=7.58 Hz, 1 H) 7.12 (d, J=6.82 Hz, 1 H) 7.40 (d, J=8.59 Hz, 1 H).

Example 352

6-(2,3-Dimethylphenyl)-4-N-[2-(4-methyl-1,3-thiazol-5-yl)ethyl]pyrimidine-2,4-diamine Prepared according to general procedure 9 from 2-(4-methyl-1,3-thiazol-5-yl)ethan-1-amine and 4-chloro-6-(2,3-dimethylphenyl)pyrimidin-2-amine. LCMS [M+H]$^+$ 340; $^1$H NMR (400 MHz, CDCl$_3$) $\delta_H$ ppm 2.23 (s, 3 H) 2.30 (s, 3 H) 2.40 (s, 3 H) 3.07 (t, J=6.82 Hz, 2 H) 3.56 (q, J=6.48 Hz, 2 H) 5.01 (br. s., 2 H) 5.79 (s, 1 H) 7.11-7.14 (m, 2 H) 7.17 (q, J=4.55 Hz, 1 H) 8.59 (s, 1 H).

Example 353

4-N-[(3-Cyclopropyl-1H-pyrazol-5-yl)methyl]-6-(2,3-dimethylphenyl)pyrimidine-2,4-diamine Prepared according to general procedure 9 from (3-cyclopropyl-1H-pyrazol-5-yl)methanamine and 4-chloro-6-(2,3-dimethylphenyl)pyrimidin-2-amine. LCMS [M+H]$^+$ 335; $^1$H NMR (400 MHz, CD$_3$OD) $\delta_H$ ppm 0.63-0.71 (m, 2 H) 0.93 (br. d, J=7.33 Hz, 2 H) 1.83-1.93 (m, 1 H) 2.18 (s, 3 H) 2.31 (s, 3 H) 4.50 (br. s., 2 H) 5.86 (s, 1 H) 5.92 (s, 1 H) 7.03-7.22 (m, 3 H).

Example 354

4-N-[3-(3,5-Dimethyl-1H-pyrazol-1-yl)propyl]-6-(2,3-dimethylphenyl)pyrimidine-2,4-diamine Prepared according to general procedure 9 from 3-(3,5-dimethyl-1H-pyrazol-1-yl)propan-1-amine and 4-chloro-6-(2,3-dimethylphenyl)pyrimidin-2-amine. LCMS [M+H]$^+$ 351; $^1$H NMR (400 MHz, CDCl$_3$) $\delta_H$ ppm 2.05 (quin, J=6.44 Hz, 2 H) 2.20 (s, 3 H) 2.21 (d, J=0.51 Hz, 3 H) 2.23 (s, 3 H) 2.31 (s, 3 H) 3.28-3.38 (m, 2 H) 4.07 (t, J=6.57 Hz, 2 H) 5.00 (br. s., 2 H) 5.36 (br. s., 1 H) 5.74 (s, 1 H) 5.78 (s, 1 H) 7.10-7.14 (m, 2 H) 7.16 (q, J=4.29 Hz, 1 H).

Example 355

6-(2,3-Dimethylphenyl)-4-N-{[1-(pyridin-2-yl)piperidin-3-yl]methyl}pyrimidine-2,4-diamine Prepared according to general procedure 9 from [1-(pyridin-2-yl)piperidin-3-yl]methanamine and 4-chloro-6-(2,3-dimethylphenyl)pyrimidin-2-amine. LCMS [M+H]$^+$ 389; $^1$H NMR (400 MHz, CDCl$_3$) $\delta_H$ ppm 1.28-1.40 (m, 1 H) 1.53-1.67 (m, 1 H) 1.73-1.83 (m, 1 H) 1.88-2.00 (m, 2 H) 2.24 (s, 3 H) 2.31 (s, 3 H) 3.00 (br. t, J=11.40 Hz, 1 H) 3.09 (ddd, J=12.95, 10.04, 3.28 Hz, 1 H) 3.17-3.40 (m, 2 H) 3.91 (dt, J=12.88, 4.29 Hz, 1 H) 4.10 (dd, J=12.88, 3.03 Hz, 1 H) 4.99 (br. s., 2 H) 5.31 (d, J=2.02 Hz, 1 H) 5.83 (s, 1 H) 6.57 (ddd, J=7.07, 4.93, 0.88 Hz, 1 H) 6.62-6.67 (m, 1 H) 7.12-7.19 (m, 3 H) 7.45 (ddd, J=8.91, 7.01, 2.02 Hz, 1 H) 8.16 (ddd, J=4.93, 2.02, 0.88 Hz, 1 H).

Example 356

6-(2,3-Dimethylphenyl)-4-N-[(2-phenyl-2H-1,2,3-triazol-4-yl)methyl]pyrimidine-2,4-diamine Prepared according to general procedure 9 from (2-phenyl-2H-1,2,3-triazol-4-yl)methanamine and 4-chloro-6-(2,3-dimethylphenyl)pyrimidin-2-amine. LCMS [M+H]$^+$ 372; $^1$H NMR (400 MHz, CDCl$_3$) $\delta_H$ ppm 2.21 (s, 3 H) 2.28 (s, 3 H) 4.67 (br d, J=5.31 Hz, 2 H) 5.17 (br. s., 2 H) 5.58-5.70 (m, 1 H) 5.87 (s, 1 H) 7.08-7.18 (m, 3 H) 7.32-7.38 (m, 1 H) 7.45-7.51 (m, 2 H) 7.74 (s, 1 H) 8.01-8.06 (m, 2 H).

Example 357

N-(3-{[2-Amino-6-(2,3-dimethylphenyl)pyrimidin-4-yl]amino}propyl)-4-chlorobenzene-1-sulfonamide Prepared according to general procedure 10 from 4-chlorobenzene-1-sulfonyl chloride and 4-N-(3-aminopropyl)-6-(2,3-dimethylphenyl)pyrimidine-2,4-diamine. LCMS [M+H]$^+$ 446; $^1$H NMR (400 MHz, CDCl$_3$) $\delta_H$ ppm 1.72

(quin, J=6.06 Hz, 2 H) 2.21 (s, 3 H) 2.30 (s, 3 H) 2.90 (d, J=5.05 Hz, 2 H) 3.49 (q, J=6.32 Hz, 2 H) 3.44-3.52 (m, 2 H) 5.33-5.43 (m, 1 H) 5.57 (br. s., 2 H) 5.78 (s, 1 H) 7.05-7.09 (m, 1 H) 7.09-7.13 (m, 1 H) 7.16-7.20 (m, 1 H) 7.41-7.46 (m, 2 H) 7.79-7.84 (m, 2 H).

Example 358

3-(3-{[2-Amino-6-(2,3-dimethylphenyl)pyrimidin-4-yl]amino}propyl)-1-(4-chlorophenyl)urea Prepared according to general procedure 11 from 1-chloro-4-isocyanatobenzene and 4-N-(3-aminopropyl)-6-(2,3-dimethylphenyl)pyrimidine-2,4-diamine. LCMS [M+H]$^+$ 425; $^1$H NMR (400 MHz, CD$_3$OD) $\delta_H$ ppm 1.85 (t, J=6.69 Hz, 2 H) 2.23 (s, 3 H) 2.34 (s, 3 H) 3.28 (overlap with methanol) 3.50-3.61 (m, 2 H) 5.97 (s, 1 H) 7.15 (s, 1 H) 7.17-7.25 (m, 3 H) 7.28-7.37 (m, 3 H).

Example 359

N-(3-{[2-Amino-6-(2,3-dimethylphenyl)pyrimidin-4-yl]amino}propyl)-3,5-dimethyl-1,2-oxazole-4-sulfonamide Prepared according to general procedure 10 from dimethyl-1,2-oxazole-4-sulfonyl chloride and 4-N-(3-aminopropyl)-6-(2,3-dimethylphenyl)pyrimidine-2,4-diamine. LCMS [M+H]$^+$ 431; $^1$H NMR (400 MHz, CDCl$_3$) $\delta_H$ ppm 1.79 (br. quin, J=6.0 Hz, 2 H) 2.23 (s, 3 H) 2.30 (s, 3 H) 2.42 (s, 3 H) 2.64 (s, 3 H) 3.01 (br. q, J=5.90 Hz, 2 H) 3.53 (br. q, J=6.00 Hz, 2 H) 5.89 (s, 1 H) 7.05-7.13 (m, 2 H) 7.18-7.21 (m, 1 H).

Example 360

N-(3-{[2-Amino-6-(2,3-dimethylphenyl)pyrimidin-4-yl]amino}propyl)-2-(dimethylamino)acetamide In a vial 4-N-(3-aminopropyl)-6-(2,3-dimethylphenyl)pyrimidine-2,4-diamine (10 mg, 0.037 mmol) and 2-(dimethylamino)acetyl chloride hydrochloride (50 mg, 0.32 mmol) were suspended in DCM (1.0 ml), then Et$_3$N (0.013 ml, 0.092 mmol) was added. The resulting reaction mixture was stirred at r.t. for 1 h. Then MeOH was added and the mixture was stirred 30 min after which the mixture was concentrated and purified by preparative HPLC. LCMS [M+H]$^+$ 357; $^1$H NMR (400 MHz, CDCl$_3$) $\delta_H$ ppm 1.70-1.78 (m, 2 H) 2.28 (s, 3 H) 2.31 (s, 3 H) 2.35 (s, 6 H) 3.06 (s, 2 H) 3.34-3.41 (m, 2 H) 3.48-3.55 (m, 2 H) 5.85 (s, 1 H) 7.12-7.16 (m, 2 H) 7.17-7.22 (m, 1 H).

Example 361

3-(3-{[2-Amino-6-(2,3-dimethylphenyl)pyrimidin-4-yl]amino}propyl)-1-(2,6-dichloropyridin-4-yl)urea Prepared according to general procedure 11 from 2,6-dichloro-4-isocyanatopyridine and 4-N-(3-aminopropyl)-6-(2,3-dimethylphenyl)pyrimidine-2,4-diamine. LCMS [M+H]$^+$ 460; $^1$H NMR (400 MHz, CDCl$_3$) $\delta_H$ ppm 1.86 (br. quint, J=6.7 Hz, 2 H) 2.24 (s, 3 H) 2.34 (s, 3 H) 3.30-3.34 (m [overlap w MeOH], 2 H) 3.55 (br. s., 3 H) 5.98 (s, 1 H) 7.11-7.24 (m, 2 H) 7.27-7.33 (m, 1 H) 7.46 (s, 2 H).

Example 362

3-(3-{[2-Amino-6-(2,3-dimethylphenyl)pyrimidin-4-yl]amino}propyl)-1-(3,4-difluorophenyl)urea Prepared according to general procedure 11 from 1,2-difluoro-4-isocyanatobenzene and 4-N-(3-aminopropyl)-6-(2,3-dimethylphenyl)pyrimidine-2,4-diamine. LCMS [M+H]$^+$ 427; $^1$H NMR (400 MHz, CDCl$_3$) $\delta_H$ ppm 1.81-1.89 (m, 2 H) 2.24 (s, 3 H) 2.34 (s, 3 H) 3.25-3.30 (m [overlap w MeOH], 2 H) 3.55 (br. s., 2 H) 5.98 (s, 1 H) 6.94-7.01 (m, 1 H) 7.06-7.17 (m, 2 H) 7.17-7.23 (m, 1 H) 7.27-7.33 (m, 1H) 7.45-7.54 (m, 1 H).

Example 363

N-[3-(3-{[2-Amino-6-(2,3-dimethylphenyl)pyrimidin-4-yl]amino}propoxy)phenyl]acetamide Prepared according to general procedure 9 from N-[3-(3-aminopropoxy)phenyl]acetamide and 4-chloro-6-(2,3-dimethylphenyl)pyrimidin-2-amine. LCMS [M+H]$^+$ 406; $^1$H NMR (400 MHz, DMSO-d$_6$) $\delta_H$ ppm 1.96 (t, J=6.32 Hz, 2 H) 2.02 (s, 3 H) 2.15 (s, 3 H) 2.25 (s, 3 H) 4.00 (t, J=6.32 Hz, 2 H) 5.70 (s, 1 H) 5.92 (br. s., 2 H) 6.61 (dd, J=8.46, 1.64 Hz, 1 H) 6.85-6.99 (m, 1 H) 6.99-7.10 (m, 3 H) 7.11-7.19 (m, 2 H) 7.31 (s, 1 H) 9.88 (s, 1 H). A signal from one of the CH$_2$-groups is overlapping with solvent peaks and is not observed by NMR.

Example 364

6-(2,3-Dimethylphenyl)-4-N-[(2-methyl-1H-indol-5-yl)methyl]pyrimidine-2,4-diamine Prepared according to general procedure 9 from (2-methyl-1H-indol-5-yl)methanamine and 4-chloro-6-(2,3-dimethylphenyl)pyrimidin-2-amine. LCMS [M+H]$^+$ 358; $^1$H NMR (400 MHz, CDCl$_3$) $\delta_H$ ppm 2.22 (s, 3 H) 2.29 (s, 3 H) 2.45 (d, J=0.76 Hz, 3 H) 4.57 (br. s., 2 H) 5.16-5.32 (m, 2 H) 5.85 (s, 1 H) 6.18-6.21 (m, 1 H) 7.05-7.15 (m, 3 H) 7.15-7.19 (m, 1 H) 7.24-7.28 (m, 1 H) 7.47 (s, 1 H) 7.97 (br. s., 1 H).

Example 365

4-N-[2-(3,5-Dimethyl-1H-pyrazol-1-yl)ethyl]-6-(2,3-dimethylphenyl)pyrimidine-2,4-diamine Prepared according to general procedure 9 from 2-(3,5-dimethyl-1H-pyrazol-1-yl)ethan-1-amine and 4-chloro-6-(2,3-dimethylphenyl)pyrimidin-2-amine. LCMS [M+H]$^+$ 337; $^1$H NMR (400 MHz, CDCl$_3$) $\delta_H$ ppm 2.17 (d, J=0.51 Hz, 3 H) 2.18 (s, 3 H) 2.21 (s, 3 H) 2.29 (s, 3 H) 2.51-2.63 (m, 1 H) 3.68-3.76 (m, 2 H) 4.13 (t, J=5.56 Hz, 2 H) 5.03 (s, 2 H) 5.37-5.47 (m, 1 H) 5.71 (s, 1 H) 5.77 (s, 1 H) 7.07-7.12 (m, 2 H) 7.12-7.17 (m, 1 H).

Example 366

6-(2,3-Dimethylphenyl)-4-N-[4-(pyrrolidin-1-yl)butyl]pyrimidine-2,4-diamine

Prepared according to general procedure 9 from 4-(pyrrolidin-1-yl)butan-1-amine and 4-chloro-6-(2,3-dimethylphenyl)pyrimidin-2-amine. LCMS [M+H]⁺ 340; ¹H NMR (400 MHz, CDCl₃) δ_H ppm 1.60-1.73 (m, 4 H) 1.78-1.86 (m, 4 H) 2.24 (s, 3 H) 2.31 (s, 3 H) 2.49-2.60 (m, 6 H) 3.31 (br. s., 2 H) 4.79 (s, 2 H) 5.46-5.58 (m, 1 H) 5.78 (s, 1 H) 7.09-7.18 (m, 3 H).

Example 367

N-(3-{[2-Amino-6-(2,3-dimethylphenyl)pyrimidin-4-yl]amino}propyl)-3-bromobenzamide 4-N-(3-aminopropyl)-6-(2,3-dimethylphenyl)pyrimidine-2,4-diamine (1.0 eq) was dissolved in THF (0.50 mL) and NMP (0.050 mL), then Et₃N (1.5 eq) and 3-bromobenzoyl chloride (1.2 eq) were added. The resulting reaction mixture was stirred at rt overnight. The mixture was then concentrated and purified by column chromatography. LCMS [M+H]⁺ 454; ¹H NMR (400 MHz, CDCl₃) δ_H ppm 1.80-1.89 (m, 2 H) 2.23 (s, 3 H) 2.30 (s, 3 H) 2.37-2.59 (m, 1 H) 3.47-3.58 (m, 4 H) 5.14 (br. s., 2 H) 5.55-5.69 (m, 1 H) 5.85 (s, 1 H) 7.07-7.13 (m, 2 H) 7.17 (dd, J=6.19, 2.91 Hz, 1 H) 7.31 (t, J=7.83 Hz, 1 H) 7.63 (ddd, J=7.89, 1.96, 1.01 Hz, 1 H) 7.75 (dd, J=7.83, 1.01 Hz, 1 H) 7.98 (t, J=1.77 Hz, 1 H).

Example 368

N-(3-{[2-Amino-6-(2,3-dimethylphenyl)pyrimidin-4-yl]amino}propyl)benzamide

In a vial 4-N-(3-aminopropyl)-6-(2,3-dimethylphenyl)pyrimidine-2,4-diamine (1.0 eq) was dissolved in NMP (0.050 mL) and THF (0.50 mL), then Et₃N (1.5 eq) and benzoyl chloride (1.0 eq) were added. The resulting reaction mixture was stirred at rt for 1 h. The mixture was then concentrated and purified by column chromatography. LCMS [M+H]⁺ 376; ¹H NMR (400 MHz, CDCl₃) δ ppm 1.86 (t, J=6.06 Hz, 2 H) 2.22 (s, 3 H) 2.29 (s, 3 H) 3.54 (dt, J=12.32, 6.09 Hz, 4 H) 5.36-5.54 (m, 1 H) 5.89 (s, 1 H) 6.14-6.31 (m, 1 H) 7.06-7.13 (m, 2 H) 7.16-7.20 (m, 1 H) 7.40-7.46 (m, 2 H) 7.47-7.53 (m, 1 H) 7.80-7.85 (m, 2 H).

Example 369

1-(3-{[2-Amino-6-(2,3-dimethylphenyl)pyrimidin-4-yl]amino}propyl)-3-(propan-2-yl)urea Prepared according to general procedure 11 from 2-isocyanatopropane and 4-N-(3-aminopropyl)-6-(2,3-dimethylphenyl)pyrimidine-2,4-diamine. LCMS [M+H]⁺ 357; ¹H NMR (400 MHz, CDCl₃) δ_H ppm 1.12 (d, J=6.57 Hz, 6 H) 1.78 (t, J=6.69 Hz, 2 H) 2.24 (s, 3 H) 2.35 (s, 3 H) 3.20 (t, J=6.82 Hz, 2 H) 3.45-3.57 (m, 2 H) 3.74-3.85 (m, 1 H) 5.97 (s, 1 H) 7.19 (d, J=14.65 Hz, 2 H) 7.30 (s, 1 H).

Example 370 tert-Butyl N-(4-{[2-amino-6-(2,3-dimethylphenyl)pyrimidin-4-yl]amino}butyl)-carbamate Prepared according to general procedure 9 from tert-butyl N-(4-aminobutyl)carbamate. LCMS [M+H]⁺ 386; ¹H NMR (400 MHz, CDCl₃) δ_H ppm 1.45 (s, 9 H) 1.54-1.72 (m, 6 H) 2.24-2.28 (m, 3 H) 2.31 (s, 3 H) 3.20 (d, J=6.32 Hz, 3 H) 3.33-3.43 (m, 2 H) 4.79-4.91 (m, 1 H) 5.79-5.83 (m, 1 H) 7.14 (s, 2 H) 7.16-7.21 (m, 1 H).

Example 371 tert-Butyl N-(5-{[2-amino-6-(2,3-dimethylphenyl)pyrimidin-4-yl]amino}pentyl)-carbamate Step 1: 4-N-(5-Aminopentyl)-6-(2,3-dimethylphenyl)pyrimidine-2,4-diamine was prepared according to general procedure 9 from pentane-1,5-diamine and 4-chloro-6-(2,3-dimethylphenyl)pyrimidin-2-amine.

Step 2: 4-N-(5-Aminopentyl)-6-(2,3-dimethylphenyl)pyrimidine-2,4-diamine (15 mg, 0.028 mmol) and tert-butoxycarbonyl tert-butyl carbonate (7.2 mg, 0.033 mmol) were dissolved in THF (0.50 mL). Then Et₃N (0.011 mL, 0.085 mmol) was added and the resulting mixture was stirred at room temperature for 16 h. The reaction mixture was concentrated and purified by column chromatography (0→5% in DCM) to afford tert-butyl N-[5-[[2-amino-6-(2,3-dimethylphenyl)pyrimidin-4-yl]amino]pentyl]carbamate. LCMS [M+H]⁺ 400; ¹H NMR (400 MHz, CDCl₃) δ_H ppm 1.35-1.47 (m, 11 H) 1.52 (d, J=7.07 Hz, 2 H) 1.58-1.68 (m, 2 H) 2.24 (s, 3 H) 2.29 (s, 3 H) 3.13 (d, J=6.06 Hz, 2 H) 3.26-3.37 (m, 2 H) 4.58-4.68 (m, 1 H) 5.89 (s, 1 H) 7.11 (d, J=4.80 Hz, 2 H) 7.18 (d, J=4.80 Hz, 1 H).

Example 372 tert-Butyl N-(2-{[2-amino-6-(2,3-dimethylphenyl)pyrimidin-4-yl]amino}cyclohexyl)-carbamate Step 1: 4-N-(2-Aminocyclohexyl)-6-(2,3-dimethylphenyl)pyrimidine-2,4-diamine was prepared according to general procedure 9 from cyclohexane-1,2-diamine and 4-chloro-6-(2,3-dimethylphenyl)pyrimidin-2-amine.

Step 2: 4-N-(2-Aminocyclohexyl)-6-(2,3-dimethylphenyl)pyrimidine-2,4-diamine (15 mg, 0.028 mmol) and tert-butoxycarbonyl tert-butyl carbonate (7.0 mg, 0.032 mmol) were dissolved in THF (0.50 mL). Then Et₃N (0.0050 mL, 0.036 mmol) was added and the resulting mixture was stirred at rt for 16 h. The reaction mixture was concentrated and purified by column chromatography (0-→5% in DCM) to afford tert-butyl N-[2-[[2-amino-6-(2,3-dimethylphenyl)pyrimidin-4-yl]amino]cyclohexyl]carbamate. LCMS [M+H]⁺ 412; NMR: mixture of cis- and trans-diastereomers: ¹H NMR (400 MHz, CDCl₃) δ_H ppm 1.16-1.37 (m, 6 H) 1.38-1.42 (m, 18 H) 1.53 (br. s., 6 H) 1.79 (br. s., 4 H) 2.00-2.08 (m, 1 H) 2.18-2.23 (m, 1 H) 2.25 (d, J=3.79 Hz, 6 H) 2.31 (s, 6 H) 3.40-3.51 (m, 1 H) 3.62-3.75 (m, 1 H) 3.83-3.92 (m, 1 H) 3.97-4.10 (m, 1 H) 4.80-4.93 (m, 1 H) 4.97-5.10 (m, 1 H) 5.15-5.37 (m, 2 H) 5.43-5.67 (m, 2 H) 5.75 (s, 1 H) 5.83 (s, 1 H) 7.09-7.15 (m, 4 H) 7.16-7.21 (m, 2 H).

Example 373 tert-Butyl N-(1-{[2-amino-6-(2,3-dimethylphenyl)pyrimidin-4-yl]amino}-2-methylpropan-2-yl)carbamate Step 1: 4-N-(2-Amino-2-methyl-propyl)-6-(2,3-dimethylphenyl)pyrimidine-2,4-diamine was prepared according to general procedure 9 from 2-methylpropane-1,2-diamine and 4-chloro-6-(2,3-dimethylphenyl)pyrimidin-2-amine.

Step 2: 4-N-(2-Amino-2-methylpropyl)-6-(2,3-dimethylphenyl)pyrimidine-2,4-diamine (15 mg, 0.029 mmol) and tert-butoxycarbonyl tert-butyl carbonate (7.8 mg, 0.036 mmol) were dissolved in THF (0.50 mL). Then Et₃N (0.0061 mL, 0.044 mmol) was added and the resulting mixture was stirred at rt for 16 h. The reaction mixture was concentrated and purified by column chromatography (0→5% in DCM) to afford tert-butyl N-[2-[[2-amino-6-(2,3-dimethylphenyl)pyrimidin-4-yl]amino]-1,1-dimethylethyl]carbamate. LCMS [M+H]+ 386; 1H NMR (400 MHz, CDCl3) δ_H ppm 1.34 (s, 6 H) 1.43 (s, 9 H) 2.26 (s, 3 H) 2.31 (s, 3 H) 3.53 (d, J=5.81 Hz, 2 H) 5.14-5.47 (m, 2 H) 5.87 (s, 1 H) 7.10-7.16 (m, 2 H) 7.18 (d, J=3.28 Hz, 1 H).

Example 374

N-(3-{[2-Amino-6-(2,3-dimethylphenyl)pyrimidin-4-yl]amino}propyl)-3-cyanobenzene-1-sulfonamide Prepared according to general procedure 10 from 3-cyanobenzene-1-sulfonyl chloride and 4-N-(3-aminopropyl)-6-(2,3-dimethylphenyl)pyrimidine-2,4-diamine. LCMS [M+H]+ 437; 1H NMR (400 MHz, CDCl3) δ_H ppm 1.70-1.82 (m, 4 H) 2.23 (s, 3 H) 2.31 (s, 3 H) 2.98 (d, J=5.31 Hz, 2 H) 3.54 (d, J=5.81 Hz, 2 H) 4.71-4.80 (m, 1 H) 5.29 (br. s., 2 H) 5.76 (s, 1 H) 7.07-7.21 (m, 3 H) 7.59-7.65 (m, 1 H) 7.82 (dt, J=7.64, 1.36 Hz, 1 H) 8.14 (dq, J=7.96, 0.97 Hz, 1 H) 8.18-8.21 (m, 1 H).

Example 375

N-(3-{[2-Amino-6-(2,3-dimethylphenyl)pyrimidin-4-yl]amino}propyl)-4-methanesulfonylbenzene-1-sulfonamide Prepared according to general procedure 10 from 4-methanesulfonylbenzene-1-sulfonyl chloride and 4-N-(3-aminopropyl)-6-(2,3-dimethylphenyl)pyrimidine-2,4-diamine. LCMS [M+H]+ 490; 1H NMR (400 MHz, CDCl3) δ_H ppm 1.73-1.80 (m, 2 H) 2.23 (s, 3 H) 2.32 (s, 3 H) 2.95-3.01 (m, 2 H) 3.08 (s, 3 H) 3.51-3.58 (m, 2 H) 4.69-4.77 (m, 1 H) 5.31 (s, 2 H) 5.77 (s, 1 H) 7.08-7.21 (m, 3 H) 8.09 (q, J=8.76 Hz, 4 H).

Example 376

N-(3-{[2-Amino-6-(2,3-dimethylphenyl)pyrimidin-4-yl]amino}propyl)benzenesulfonamide Prepared according to general procedure 10 from benzenesulfonyl chloride and 4-N-(3-aminopropyl)-6-(2,3-dimethylphenyl)pyrimidine-2,4-diamine. LCMS [M+H]+ 412; 1H NMR (400 MHz, CDCl3) δ ppm 1.72 (dt, J=12.06, 5.97 Hz, 2 H) 1.76-1.89 (m, 1 H) 2.22 (s, 3 H) 2.31 (s, 3 H) 2.93 (q, J=6.15 Hz, 2 H) 3.49 (q, J=6.40 Hz, 2 H) 4.70-4.82 (m, 1 H) 5.28 (br. s., 2 H) 5.72-5.74 (m, 1 H) 7.08-7.15 (m, 2 H) 7.16-7.20 (m, 1 H) 7.45-7.51 (m, 2 H) 7.52-7.57 (m, 1 H) 7.87-7.92 (m, 2 H).

Example 377

N-(3-{[2-Amino-6-(2,3-dimethylphenyl)pyrimidin-4-yl]amino}-2,2-dimethylpropyl)-3-fluorobenzene-1-sulfonamide Step 1: tert-butyl N-(3-{[2-amino-6-(2,3-dimethylphenyl)pyrimidin-4-yl]amino}-2,2-dimethylpropyl)carbamate (prepared in example 239) (180 mg, 0.45 mmol) was dissolved in trifluoroacetic acid (2 ml) and stirred at reflux for 1 h. The TFA was evaporated and the crude residue was purified by silica gel chromatography using a gradient of 2-30% MeOH [containing 1 v/v % NH4OH] in DCM which afforded 4-N-(3-amino-2,2-dimethyl-propyl)-6-(2,3-dimethylphenyl)pyrimidine-2,4-diamine (110 mg, 0.37 mmol). LCMS [M+H]+ 300.

Step 2: N-(3-{[2-Amino-6-(2,3-dimethylphenyl)pyrimidin-4-yl]amino}-2,2-dimethylpropyl)-3-fluorobenzene-1-sulfonamide was prepared according to general procedure 10 from 3-fluorobenzene-1-sulfonyl chloride and 4-N-(3-amino-2,2-dimethyl-propyl)-6-(2,3-dimethylphenyl)pyrimidine-2,4-diamine (prepared in step 1). LCMS [M+H]+ 458; 1H NMR (400 MHz, CDCl3) δ_H ppm 0.92 (s, 6 H) 2.16-2.20 (m, 3 H) 2.29 (s, 3 H) 2.69 (d, J=7.07 Hz, 2 H) 3.38 (d, J=6.82 Hz, 2 H) 5.91 (s, 1 H) 6.53 (s, 1 H) 7.04-7.08 (m, 1 H) 7.09-7.15 (m, 1 H) 7.23-7.30 (m, 1 H) 7.38-7.45 (m, 1 H) 7.46-7.56 (m, 2 H) 7.64 (d, J=7.83 Hz, 1 H).

Example 378

N-(3-{[2-Amino-6-(2,3-dimethylphenyl)pyrimidin-4-yl]amino}-2,2-dimethylpropyl)-4-(morpholine-4-sulfonyl)benzene-1-sulfonamide Step 1: tert-butyl N-(3-{[2-amino-6-(2,3-dimethylphenyl)pyrimidin-4-yl]amino}-2,2-dimethylpropyl)carbamate (prepared in example 239) (180 mg, 0.45 mmol) was dissolved in trifluoroacetic acid (2 ml) and stirred at reflux for 1 h. The TFA was evaporated and the crude residue was purified by silica gel chromatography using a gradient of 2-30% MeOH [containing 1 v/v % NH4OH] in DCM which afforded 4-N-(3-amino-2,2-dimethyl-propyl)-6-(2,3-dimethylphenyl)pyrimidine-2,4-diamine (110 mg, 0.37 mmol). LCMS [M+H]+ 300.

Step 2: N-(3-{[2-Amino-6-(2,3-dimethylphenyl)pyrimidin-4-yl]amino}-2,2-dimethylpropyl)-4-(morpholine-4-sulfonyl)benzene-1-sulfonamide was prepared according to general procedure 10 from 4-(morpholine-4-sulfonyl)benzene-1-sulfonyl chloride and 4-N-(3-amino-2,2-dimethylpropyl)-6-(2,3-dimethyl-phenyl)pyrimidine-2,4-diamine (prepared in step 1 above). LCMS [M+H]+ 589; 1H NMR (400 MHz, CDCl3) δ_H ppm 0.92 (s, 6 H) 2.18 (d, J=0.51 Hz, 3 H) 2.28 (s, 3 H) 2.71 (d, J=6.82 Hz, 2 H) 2.99-3.06 (m, 4 H) 3.38 (d, J=6.82 Hz, 2 H) 3.70-3.78 (m, 4 H) 5.93 (s, 1 H) 6.94 (s, 1 H) 7.03-7.08 (m, 1 H) 7.09-7.15 (m, 1 H) 7.25 (d, J=7.58 Hz, 1 H) 7.42 (s, 1 H) 7.87 (d, J=8.59 Hz, 2 H) 8.02 (d, J=8.59 Hz, 2 H).

Example 379

6-(2,3-Dimethylphenyl)-4-N-(prop-2-en-1-yl)pyrimidine-2,4-diamine

Prepared according to general procedure 9 from prop-2-en-1-amine and 4-chloro-6-(2,3-dimethylphenyl)pyrimidin-2-amine. LCMS [M+H]+ 255; 1H NMR (400 MHz, CDCl3) δ_H ppm 2.23 (s, 3 H) 2.31 (s, 3 H) 3.92 (br. s., 2 H) 4.95 (br. s., 3 H) 5.18 (dq, J=10.23, 1.47 Hz, 1 H) 5.26 (dq, J=17.18, 1.60 Hz, 1 H) 5.81 (s, 1 H) 5.85-5.96 (m, 1 H) 7.10-7.15 (m, 2 H) 7.15-7.19 (m, 1 H).

Example 380

1-(3-{[2-Amino-6-(2,3-dimethylphenyl)pyrimidin-4-yl]amino}propyl)imidazolidin-2-one Prepared according to general procedure 9 from 1-(3-aminopropyl)imidazolidin-2-one and 4-chloro-6-(2,3-dimethylphenyl)pyrimidin-2-amine. LCMS [M+H]+ 341.

Example 381

N-(3-{[2-Amino-6-(2,3-dimethylphenyl)pyrimidin-4-yl]amino}propyl)-3-fluorobenzene-1-sulfonamide Prepared according to general procedure 9 from 3-fluorobenzene-1-sulfonyl chloride and 4-N-(3-aminopropyl)-6-(2,3-dimethylphenyl)pyrimidine-2,4-diamine. LCMS [M+H]$^+$ 430.

Example 382

N-{4-[(3-{[2-Amino-6-(2,3-dimethylphenyl)pyrimidin-4-yl]amino}propyl)sulfamoyl]-phenyl}acetamide Prepared according to general procedure 10 from 4-acetamidobenzene-1-sulfonyl chloride and 4-N-(3-aminopropyl)-6-(2,3-dimethylphenyl)pyrimidine-2,4-diamine. LCMS [M+H]$^+$ 469.

Example 383

N-(3-{[2-Amino-6-(2,3-dimethylphenyl)pyrimidin-4-yl]amino}propyl)methanesulfonamide Prepared according to general procedure 10 from methanesulfonyl chloride and 4-N-(3-aminopropyl)-6-(2,3-dimethylphenyl)pyrimidine-2,4-diamine. LCMS [M+H]$^+$ 350.

Example 384

N-(2-{[2-Amino-6-(2,3-dimethylphenyl)pyrimidin-4-yl]amino}ethyl)-3-fluorobenzene-1-sulfonamide Prepared according to general procedure 10 from 3-fluorobenzene-1-sulfonyl chloride and 4-N-(2-aminoethyl)-6-(2,3-dimethylphenyl)pyrimidine-2,4-diamine. LCMS [M+H]$^+$ 416.

Example 385

N-(2-{[2-Amino-6-(2,3-dimethylphenyl)pyrimidin-4-yl]amino}ethyl)-4-methoxybenzene-1-sulfonamide Prepared according to general procedure 10 from 4-methoxybenzene-1-sulfonyl chloride and 4-N-(2-aminoethyl)-6-(2,3-dimethylphenyl)pyrimidine-2,4-diamine. LCMS [M+H]$^+$ 428.

Example 386

6-(2,3-Dimethylphenyl)-4-N-(prop-2-yn-1-yl)pyrimidine-2,4-diamine

Prepared according to general procedure 9 from prop-2-yn-1-amine and 4-chloro-6-(2,3-dimethylphenyl)pyrimidin-2-amine. LCMS [M+H]$^+$ 253.

Example 387

2-{[2-Amino-6-(2,3-dimethylphenyl)pyrimidin-4-yl]amino}acetamide

Prepared according to general procedure 9 from 2-aminoacetamide and 4-chloro-6-(2,3-dimethylphenyl)pyrimidin-2-amine. LCMS [M+H]$^+$ 272.

Example 388

N-(3-{[2-Amino-6-(2,3-dimethylphenyl)pyrimidin-4-yl]amino}propyl)-4,5-dichlorothiophene-2-sulfonamide Prepared according to general procedure 10 from 4,5-dichlorothiophene-2-sulfonyl chloride and 4-N-(3-aminopropyl)-6-(2,3-dimethylphenyl)pyrimidine-2,4-diamine. LCMS [M+H]$^+$ 486.

Example 389

N-(3-{[2-Amino-6-(2,3-dimethylphenyl)pyrimidin-4-yl]amino}propyl)-5-chloro-1,3-dimethyl-1H-pyrazole-4-sulfonamide Prepared according to general procedure 10 from 5-chloro-1,3-dimethyl-1H-pyrazole-4-sulfonyl chloride and 4-N-(3-aminopropyl)-6-(2,3-dimethylphenyl)-pyrimidine-2,4-diamine. LCMS [M+H]$^+$ 464.

Example 390

2-{[2-Amino-6-(2,3-dimethylphenyl)pyrimidin-4-yl]amino}acetonitrile

Prepared according to general procedure 9 from 2-aminoacetonitrile and 4-chloro-6-(2,3-dimethylphenyl)pyrimidin-2-amine. LCMS [M+H]$^+$ 254.

Example 391

N-(3-{[2-Amino-6-(2,3-dimethylphenyl)pyrimidin-4-yl]amino}propyl)-1,2-dimethyl-1H-imidazole-4-sulfonamide Prepared according to general procedure 10 from 1,2-dimethyl-1H-imidazole-4-sulfonyl chloride and 4-N-(3-aminopropyl)-6-(2,3-dimethylphenyl)pyrimidine-2,4-diamine. LCMS [M+H]$^+$ 430; $^1$H NMR (400 MHz, CD$_3$OD) $\delta_H$ ppm 7.69 (s, 2 H), 7.33-7.38 (m, 1 H), 7.21-7.27 (m, 1 H), 7.16-7.20 (m, 1 H), 6.00 (s, 1 H), 3.71 (s, 3 H), 3.58 (s, 2 H), 3.06 (s, 2 H), 2.45 (s, 3 H), 2.36 (s, 3 H), 2.25 (s, 3 H), 1.80-1.90 (m, 2 H).

Example 392

N-(2-{[2-Amino-6-(2,3-dimethylphenyl)pyrimidin-4-yl]amino}ethyl)-5-chloro-1,3-dimethyl-1H-pyrazole-4-sulfonamide Prepared according to general procedure 10 from 5-chloro-1,3-dimethyl-1H-pyrazole-4-sulfonyl chloride and 4-N-(2-aminoethyl)-6-(2,3-dimethylphenyl)-pyrimidine-2,4-diamine. LCMS [M+H]$^+$ 450.

Example 393

4-N-{2-[(1,3-Benzoxazol-2-yl)amino]ethyl}-6-(2,3-dimethylphenyl)pyrimidine-2,4-diamine Prepared according to general procedure 12 from 2-chloro-1,3-benzoxazole and 4-N-(2-aminoethyl)-6-(2,3-dimethylphenyl)pyrimidine-2,4-diamine. LCMS [M+H]$^+$ 375.

Example 394

6-(2,3-Dimethylphenyl)-4-N-(4-phenylbutan-2-yl)pyrimidine-2,4-diamine

Prepared according to general procedure 9 from 4-phenylbutan-2-amine and 4-chloro-6-(2,3-dimethylphenyl)pyrimidin-2-amine. LCMS [M+H]$^+$ 347.

Example 395

4-N-(2,2-Dimethyloxan-4-yl)-6-(2,3-dimethylphenyl)pyrimidine-2,4-diamine

Prepared according to general procedure 9 from 2,2-dimethyloxan-4-amine and 4-chloro-6-(2,3-dimethylphenyl)pyrimidin-2-amine. LCMS [M+H]$^+$ 327.

Example 396

Ethyl 2-{[2-amino-6-(2,3-dimethylphenyl)pyrimidin-4-yl]amino}acetate

Prepared according to general procedure 9 from ethyl 2-aminoacetate and 4-chloro-6-(2,3-dimethylphenyl)pyrimidin-2-amine. LCMS [M+H]$^+$ 301.

Example 397

6-[(2-{[2-Amino-6-(2,3-dimethylphenyl)pyrimidin-4-yl]amino}ethyl)amino]pyridine-3-carbonitrile Prepared according to general procedure 12 from 6-chloropyridine-3-carbonitrile and 4-N-(2-aminoethyl)-6-(2,3-dimethylphenyl)pyrimidine-2,4-diamine. LCMS [M+H]$^+$ 360; $^1$H NMR (400 MHz, CD$_3$OD) $\delta_H$ ppm 8.32-8.34 (m, 1 H), 7.59-7.64 (m, 1 H), 7.34-7.38 (m, 1 H), 7.22-7.27 (m, 2 H), 7.15-7.18 (m, 1 H), 6.55-6.59 (m, 1 H), 5.97 (s, 1 H), 3.72-3.77 (m, 3 H), 3.66-3.71 (m, 3 H), 2.36 (s, 4 H), 2.24 (s, 3 H).

Example 398

4-N-{2-[(3-Bromo-1,2,4-thiadiazol-5-yl)amino]ethyl}-6-(2,3-dimethylphenyl)pyrimidine-2,4-diamine Prepared according to general procedure 12 from 3-bromo-5-chloro-1,2,4-thiadiazole and 4-N-(2-aminoethyl)-6-(2,3-dimethylphenyl)pyrimidine-2,4-diamine. LCMS [M+H]$^+$ 420.

Example 399

6-(2,3-Dimethylphenyl)-4-N-[(5-methyl-4H-1,2,4-triazol-3-yl)methyl]pyrimidine-2,4-diamine Prepared according to general procedure 9 from (5-methyl-4H-1,2,4-triazol-3-yl)methanamine and 4-chloro-6-(2,3-dimethylphenyl)pyrimidin-2-amine. LCMS [M+H]$^+$ 310; $^1$H NMR (400 MHz, CD$_3$OD) $\delta_H$ ppm 7.37-7.41 (m, 1 H), 7.25-7.30 (m, 1 H), 7.20-7.24 (m, 1 H), 6.12 (s, 1 H), 4.79 (s, 2 H), 2.47 (s, 3 H), 2.38 (s, 3 H), 2.29 (s, 3 H).

Example 400

6-(2,3-Dimethylphenyl)-4-N-{2-[5-(4-fluorophenyl)-1,3,4-oxadiazol-2-yl]ethyl}pyrimidine-2,4-diamine Prepared according to general procedure 9 from 2-[5-(4-fluorophenyl)-1,3,4-oxadiazol-2-yl]ethan-1-amine and 4-chloro-6-(2,3-dimethylphenyl)pyrimidin-2-amine. LCMS [M+H]$^+$ 405.

Example 401

N-(2-{[2-Amino-6-(2,3-dimethylphenyl)pyrimidin-4-yl]amino}ethyl)-4-methanesulfonylbenzene-1-sulfonamide Prepared according to general procedure 10 from 4-methanesulfonylbenzene-1-sulfonyl chloride and 4-N-(2-aminoethyl)-6-(2,3-dimethylphenyl)pyrimidine-2,4-diamine. LCMS [M+H]$^+$ 476; $^1$H NMR (400 MHz, CD$_3$OD) $\delta_H$ ppm 8.10-8.14 (m, 3 H), 8.05-8.09 (m, 3 H), 7.16-7.20 (m, 1 H), 7.09-7.14 (m, 1 H), 7.05-7.08 (m, 1 H), 5.73-5.76 (m, 1 H), 3.42-3.49 (m, 2 H), 3.14 (s, 6 H), 2.31 (s, 4 H), 2.18 (s, 3 H).

Example 402

N-(3-{[2-Amino-6-(2,3-dimethylphenyl)pyrimidin-4-yl]amino}propyl)-3-methanesulfonylbenzene-1-sulfonamide Prepared according to general procedure 10 from 3-methanesulfonylbenzene-1-sulfonyl chloride and 4-N-(3-aminopropyl)-6-(2,3-dimethylphenyl)pyrimidine-2,4-diamine. LCMS [M+H]$^+$ 490; $^1$H NMR (400 MHz, CDCl$_3$) $\delta_H$ ppm 8.43-8.45 (m, 1 H), 8.18 (ddd, J=7.8, 1.8, 1.0 Hz, 3 H), 8.11 (ddd, J=7.8, 1.8, 1.0 Hz, 3 H), 7.67-7.73 (m, 1 H), 7.15-7.19 (m, 1 H), 7.09-7.13 (m, 1 H), 7.08 (d, J=2.0 Hz, 1 H), 5.74 (s, 1 H), 5.31 (br. s., 2 H), 4.82-5.00 (m, 1 H), 3.50 (d, J=5.8 Hz, 2 H), 3.09 (s, 3 H), 2.94 (d, J=4.0 Hz, 2 H), 2.29 (s, 3 H), 2.20 (s, 3 H), 1.71 (t, J=5.8 Hz, 2 H).

Example 403

N-(3-{[2-Amino-6-(2,3-dimethylphenyl)pyrimidin-4-yl]amino}propyl)-2-methanesulfonylbenzene-1-sulfonamide Prepared according to general procedure 10 from 2-methanesulfonylbenzene-1-sulfonyl chloride and 4-N-(3-aminopropyl)-6-(2,3-dimethylphenyl)pyrimidine-2,4-diamine. LCMS [M+H]$^+$ 490; $^1$H NMR (400 MHz, CD$_3$OD) $\delta_H$ ppm 8.20-8.33 (m, 3 H), 8.10-8.17 (m, 1 H), 7.84-7.90 (m, 5 H), 7.68-7.80 (m, 3 H), 7.16-7.21 (m, 3 H), 7.12 (s, 3 H), 7.08 (d, J=1.5 Hz, 3 H), 5.74 (s, 3 H), 3.46 (s, 3 H), 3.43 (s, 8 H), 3.32-3.36 (m, 3 H), 3.07 (t, J=6.7 Hz, 5 H), 2.31 (s, 8 H), 2.19 (s, 3 H), 1.66 (t, J=6.7 Hz, 5 H).

Example 404

6-(2,3-Dimethylphenyl)-4-N-[2-(4-methanesulfonylphenyl)ethyl]pyrimidine-2,4-diamine A mixture of 4-chloro-6-(2,3-dimethylphenyl)pyrimidin-2-amine (0.15 mmol), 2-(4-methylsulfonylphenyl)ethanamine (1.2 eq.) and N,N-diisopropylethylamine (2.25 eq.) in n-butanol (0.3 mL) was heated in a sealed tube at 110° C. overnight. Methanol was added and the mixture was filtered and purified by preparative HPLC. LCMS [M+H]+ 397.

Example 405

6-(2,3-dichlorophenyl)-4-N-[2-(4-methyl-1,3-thiazol-5-yl)ethyl]pyrimidine-2,4-diamine A mixture of 4-chloro-6-(2,3-dichlorophenyl)pyrimidin-2-amine (0.08 mmol), 2-(4-methylthiazol-5-yl)ethanamine; dihydrobromide (1.2 eq.) and N,N-diisopropylethylamine (4.25 eq.) in n-butanol (0.3 ml) was heated in a sealed tube at 110° C. overnight. Methanol was added and the mixture was filtered and purified by preparative HPLC. LCMS [M+H]+ 380.

Example 406

6-(3-chloro-2-methylphenyl)-4-N-[2-(4-methyl-1,3-thiazol-5-yl)ethyl]pyrimidine-2,4-diamine A mixture of 4-chloro-6-(3-chloro-2-methyl-phenyl)pyrimidin-2-amine (0.14 mmol), 2-(4-methylthiazol-5-yl)ethanamine; dihydrobromide (1.2 eq.) and N,N-diisopropylethylamine (4.25 eq.) in n-butanol (0.3 mL) was heated in a sealed tube at 110° C. overnight. Methanol was added and the mixture was filtered and purified by preparative HPLC. LCMS [M+H]+ 360.

Example 407

4-N-{[2-(difluoromethyl)pyridin-4-yl]methyl}-6-(2,3-dimethylphenyl)pyrimidine-2,4-diamine A mixture of 4-chloro-6-(2,3-dimethylphenyl)pyrimidin-2-amine (0.13 mmol), [2-(difluoromethyl)-4-pyridyl]methanamine; hydrochloride (1.2 eq.) and N,N-diisopropylethylamine (3.25 eq.) in n-butanol (0.3 ml) was heated in a sealed tube at 110° C. overnight. Methanol was added and the mixture was filtered and purified by preparative HPLC. LCMS [M+H]+ 356.

Example 408

6-(2,3-dimethylphenyl)-4-N-[2-(1H-imidazol-4-yl)ethyl]pyrimidine-2,4-diamine

A mixture of 4-chloro-6-(2,3-dimethylphenyl)pyrimidin-2-amine (0.13 mmol), 2-(1H-imidazol-4-yl)ethanamine; dihydrochloride (1.2 eq.) and N,N-diisopropylethylamine (3.25 eq.) in n-butanol (0.3 mL) was heated in a sealed tube at 110° C. overnight. Methanol was added and the mixture was filtered and purified by preparative HPLC. LCMS [M+H]+ 309.

Example 409

4-N-[3-(1H-1,3-benzodiazol-2-yl)propyl]-6-(2,3-dimethylphenyl)pyrimidine-2,4-diamine A mixture of 4-chloro-6-(2,3-dimethylphenyl)pyrimidin-2-amine (0.13 mmol), 3-(1H-benzimidazol-2-yl)propan-1-amine (1.2 eq.) and N,N-diisopropylethylamine (3.25 eq.) in n-butanol (0.3 mL) was heated in a sealed tube at 110° C. overnight. Methanol was added and the mixture was filtered and purified by preparative HPLC. LCMS [M+H]+ 373.

Example 410

6-(2,3-dimethylphenyl)-4-N-[(1-methyl-1H-1,3-benzodiazol-2-yl)methyl]pyrimidine-2,4-diamine A mixture of 4-chloro-6-(2,3-dimethylphenyl)pyrimidin-2-amine (0.14 mmol), (1-methylbenzimidazol-2-yl)methanamine (1.2 eq.) and N,N-diisopropylethylamine (1.25 eq.) in n-butanol (0.3 mL) was heated in a sealed tube at 110° C. overnight. Methanol was added and the mixture was filtered and purified by preparative HPLC. LCMS [M+H]+ 359.

Example 411

6-(2,3-dimethylphenyl)-4-N-[(2-phenyl-1,3-thiazol-5-yl)methyl]pyrimidine-2,4-diamine A mixture of 4-chloro-6-(2,3-dimethylphenyl)pyrimidin-2-amine (0.13 mmol), (2-phenylthiazol-5-yl)methanamine hydrochloride (1.2 eq.) and N,N-diisopropylethylamine (2.25 eq.) in n-butanol (0.3 mL) was heated in a sealed tube at 110° C. overnight. Methanol was added and the mixture was filtered and purified by preparative HPLC. LCMS [M+H]+ 388.

Example 412

6-(3-chloro-2-methylphenyl)-4-N-[2-(5-methyl-1H-1,2,4-triazol-3-yl)ethyl]pyrimidine-2,4-diamine A mixture 4-chloro-6-(3-chloro-2-methyl-phenyl)pyrimidin-2-amine (0.14 mmol), 2-(5-methyl-1H-1,2,4-triazol-3-yl)ethanamine hydrochloride (1.2 eq.) and N, N-diisopropylethylamine (3.25 eq.) in n-butanol (0.3 mL) was heated in a sealed tube at 110° C. overnight. Methanol was added and the mixture was filtered and purified by preparative HPLC. LCMS [M+H]+ 344.

Example 413

6-(2,3-dichlorophenyl)-4-N-[2-(5-methyl-1H-1,2,4-triazol-3-yl)ethyl]pyrimidine-2,4-diamine A mixture of 4-chloro-6-(2,3-dichlorophenyl)pyrimidin-2-amine (0.13 mmol), 2-(5-methyl-1H-1,2,4-triazol-3-yl)ethanamine hydrochloride (1.0 eq.) and N, N-diisopropylethylamine (3.25 eq.) in n-butanol (0.3 mL) was heated in a sealed tube at 110° C. overnight. Methanol was added and the mixture was filtered and purified by preparative HPLC. LCMS [M+H]+ 364.

Example 414

4-(2-{[2-amino-6-(3-chloro-2-methylphenyl)pyrimidin-4-yl]amino}ethyl)-N,N-dimethylbenzene-1-sulfonamide A mixture of 4-chloro-6-(3-chloro-2-methyl-phenyl)pyrimidin-2-amine (0.14 mmol), 4-(2-aminoethyl)-N,N-dimethyl-benzenesulfonamide (1.0 eq.) and N,N-diisopropylethylamine (2.25 eq.) in n-butanol (0.3 mL) was heated in a sealed tube at 110° C. overnight. Methanol was added and the mixture was filtered and purified by preparative HPLC. LCMS [M+H]+ 446.

Example 415

4-(2-{[2-amino-6-(2,3-dichlorophenyl)pyrimidin-4-yl]amino}ethyl)-N,N-dimethylbenzene-1-sulfonamide A mixture of 4-chloro-6-(2,3-dichlorophenyl)pyrimidin-2-amine (0.13 mmol), 4-(2-aminoethyl)-N, N-dimethyl-benzenesulfonamide (1.0 eq.) and N,N-diisopropylethylamine (2.25 eq.) in n-butanol (0.3 mL) was heated in a sealed tube at 110° C. overnight. Methanol was added and the mixture was filtered and purified by preparative HPLC. LCMS [M+H]$^+$ 466.

Example 416

4-(2-{[2-amino-6-(2,3-dimethylphenyl)pyrimidin-4-yl]amino}ethyl)-N,N-dimethylbenzene-1-sulfonamide A mixture of 4-chloro-6-(2,3-dimethylphenyl)pyrimidin-2-amine (0.15 mmol), 4-(2-aminoethyl)-N, N-dimethyl-benzenesulfonamide (1.0 eq.) and N,N-diisopropylethylamine (2.25 eq.) in n-butanol (0.3 mL) was heated in a sealed tube at 110° C. overnight. Methanol was added and the mixture was filtered and purified by preparative HPLC. LCMS [M+H]$^+$ 426.

Example 417

4-N-{1-[(4-Chlorophenyl)methyl]cyclopropyl}-6-(2,3-dimethylphenyl)pyrimidine-2,4-diamine A mixture of 4-chloro-6-(2,3-dimethylphenyl)pyrimidin-2-amine (47 mg, 0.20 mmol), 1-[(4-chlorophenyl)methyl]cyclopropan-1-amine hydrochloride (52 mg, 0.24 mmol) and triethylamine (50 µL, 0.36 mmol) in n-butanol (3 mL) was heated in a sealed tube at 130° C. overnight. The reaction mixture was concentrated and purified by preparative HPLC. LCMS [M+H]$^+$ 379.

Example 418

4-N-Cyclopropyl-6-(2,3,4-trichlorophenyl)pyrimidine-2,4-diamine

A mixture of 4-chloro-6-(2,3,4-trichlorophenyl)pyrimidin-2-amine (21 mg, 0.050 mmol), cyclopropanamine (25 µL, 0.36 mmol) and triethylamine (25 µL, 0.18 mmol) in n-butanol (1.5 mL) was heated in a sealed tube at 90° C. overnight. The reaction mixture was concentrated and purified by preparative HPLC. LCMS [M+H]$^+$ 329.

Example 419

4-N-[2-(4-Chlorophenyl)ethyl]-6-(2,3,4-trichlorophenyl)pyrimidine-2,4-diamine

A mixture of 4-chloro-6-(2,3,4-trichlorophenyl)pyrimidin-2-amine (21 mg, 0.050 mmol), 2-(4-chlorophenyl)ethan-1-amine (30 µL, 0.24 mmol) and triethylamine (25 µL, 0.18 mmol) in n-butanol (1.5 mL) was heated in a sealed tube at 90° C. overnight. The reaction mixture was concentrated and purified by preparative HPLC. LCMS [M+H]$^+$ 427.

Example 420

6-(2,3-dimethylphenyl)-4-N—($^2$H$_3$)methylpyrimidine-2,4-diamine

A solution of 4-chloro-6-(2,3-dimethylphenyl)pyrimidin-2-amine (0.15 mmol) and d$_3$-methanamine hydrochloride (70 mg; 1 mmol) and triethylamine (101 mg; 1 mmol) in n-BuOH (2.0 mL) was heated at 95° C. overnight. The reaction mixture was concentrated and purified by preparative HPLC. LCMS [M+H]$^+$ 232.

Example 421

6-(2,3-dichlorophenyl)-4-N—($^2$H$_3$)methylpyrimidine-2,4-diamine

A solution of 4-chloro-6-(2,3-dichlorophenyl)pyrimidin-2-amine (0.15 mmol) and d$_3$-methanamine hydrochloride (70 mg; 1 mmol) and triethylamine (101 mg; 1 mmol) in n-BuOH (2.0 mL) was heated at 95° C. overnight. The reaction mixture was concentrated and purified by preparative HPLC to afford the product. LCMS [M+H]$^+$ 272.

Example 422

6-(2-chloro-3-methylphenyl)-4-N—($^2$H$_3$)methylpyrimidine-2,4-diamine

A solution of 4-chloro-6-(2-chloro-3-methylphenyl)pyrimidin-2-amine (0.15 mmol) and d$_3$-methanamine hydrochloride (70 mg; 1 mmol) and triethylamine (101 mg; 1 mmol) in n-BuOH (2.0 mL) was heated at 95° C. overnight. The reaction mixture was concentrated and purified by preparative HPLC to afford the product. LCMS [M+H]$^+$ 252.

Example 423

4-N-[2-(4-Chlorophenyl)ethyl]-6-(1H-pyrrol-2-yl)pyrimidine-2,4-diamine

Prepared according to general procedure 10 from 6-chloro-4-N-[2-(4-chlorophenyl)ethyl]pyrimidine-2,4-diamine and (1-tert-butoxycarbonylpyrrol-2-yl)boronic acid. The t-butoxycarbonyl group was removed during work-up. LCMS [M+H]$^+$ 314; $^1$H NMR (400 MHz, CD$_3$OD) $\delta_H$ ppm 7.29-7.33 (m, 5H), 7.27 (s, 2 H), 7.10-7.13 (m, 1 H), 6.88-6.92 (m, 1 H), 6.33-6.37 (m, 1 H), 6.12 (s, 1 H), 3.70-3.76 (m, 2 H), 2.91-2.96 (m, 2 H).

Example 424

N-(4-{[2-amino-6-(2,3-dimethylphenyl)pyrimidin-4-yl]amino}butyl)-4-methanesulfonylbenzene-1-sulfonamide Prepared according to general procedure 10 from 4-(methylsulfonyl)-benzenesulfonyl chloride and 4-N-(4-aminobutyl)-6-(2,3-dimethylphenyl)-pyrimidine-2,4-diamine. LCMS [M+H]$^+$ 504; $^1$H NMR (400 MHz, CD$_3$OD) $\delta_H$ ppm 8.12-8.17 (m, 2 H), 8.06-8.10 (m, 2 H), 7.16-7.20 (m, 1 H), 7.09-7.14 (m, 1 H), 7.05-7.09 (m, 1 H), 5.76-5.79 (m, 1 H), 3.18 (s, 3 H), 2.94-2.99 (m, 2 H), 2.31 (s, 3 H), 2.19 (s, 3 H), 1.50-1.66 (m, 4 H).

Example 425

4-(2-{[2-amino-6-(4-fluoro-2,3-dimethylphenyl)pyrimidin-4-yl]amino}ethyl)benzene-1-sulfonamide Prepared according to general procedure 2 from 4-[2-[(2-amino-6-chloro-pyrimidin-4-yl)amino]ethyl]benzenesulfonamide and 4-fluoro-2,3-dimethyl-benzeneboronic acid. LCMS [M+H]$^+$ 416; $^1$H NMR (400 MHz, CD$_3$OD) $\delta_H$ ppm 7.81-7.85 (m, 2 H), 7.44 (d, J=8.6 Hz, 2 H), 7.07 (dd, J=8.5, 5.9 Hz, 1 H), 6.92 (t, J=8.8 Hz, 1 H), 5.75 (s, 1 H), 3.63 (br. s., 2 H), 2.99 (t, J=7.2 Hz, 2 H), 2.20-2.23 (m, 6 H).

Example 426

4-(2-{[2-amino-6-(3-cyano-2-methylphenyl)pyrimidin-4-yl]amino}ethyl)benzene-1-sulfonamide Prepared according to general procedure 2 from 4-[2-[(2-amino-6-chloro-pyrimidin-4-yl)amino]ethyl]benzenesulfonamide and 3-cyano-2-methyl-benzeneboronic acid. LCMS [M+H]$^+$ 409; $^1$H NMR (400 MHz, CD$_3$OD) $\delta_H$ ppm 7.80-7.86 (m, 2 H), 7.70 (dd, J=7.8, 1.3 Hz, 1 H), 7.53 (d, J=6.8 Hz, 1 H), 7.37-7.47 (m, 3 H), 5.80 (s, 1 H), 3.65 (br. s., 2 H), 3.00 (t, J=7.2 Hz, 2 H), 2.49 (s, 3 H).

Example 427

4-(2-{[2-amino-6-(5-chloro-2-methylphenyl)pyrimidin-4-yl]amino}ethyl)benzene-1-sulfonamide Prepared according to general procedure 2 from 4-[2-[(2-amino-6-chloro-pyrimidin-4-yl)amino]ethyl]benzenesulfonamide and 5-chloro-2-methyl-benzeneboronic acid. LCMS [M+H]$^+$ 418; $^1$H NMR (400 MHz, CD$_3$OD) $\delta_H$ ppm 7.81-7.85 (m, 2 H), 7.44 (d, J=8.3 Hz, 2 H), 7.21-7.29 (m, 3 H), 5.80 (s, 1 H), 3.64 (br. s., 2 H), 2.99 (t, J=7.2 Hz, 2 H), 2.28 (s, 3 H).

Example 428

4-(2-{[2-amino-6-(3,4-dichloro-2-methylphenyl)pyrimidin-4-yl]amino}ethyl)benzene-1-sulfonamide Prepared according to general procedure 2 from 4-[2-[(2-amino-6-chloro-pyrimidin-4-yl)amino]ethyl]benzenesulfonamide and 3,4-dichloro-2-methyl-benzeneboronic acid. LCMS [M+H]$^+$ 452; $^1$H NMR (400 MHz, CDCl$_3$) $\delta_H$ ppm 7.88 (d, J=8.3 Hz, 2 H), 7.38 (d, J=8.3 Hz, 2 H), 7.33-7.36 (m, 1 H), 7.15 (s, 1 H), 5.73 (s, 1 H), 4.87 (s, 2 H), 4.81-4.84 (m, 2 H), 4.70-4.77 (m, 1 H), 3.61-3.69 (m, 2 H), 3.01 (s, 2 H), 2.41 (s, 3 H).

Example 429

6-(3-chloro-2-methylphenyl)-4-N-(prop-2-yn-1-yl)pyrimidine-2,4-diamine

Prepared according to general procedure 7 from propargylamine and 4-chloro-6-(3-chloro-2-methyl-phenyl)pyrimidin-2-amine. LCMS [M+H]$^+$ 273; $^1$H NMR (400 MHz, CD$_3$OD) $\delta_H$ ppm 7.40-7.43 (m, 1 H), 7.21 (s, 2 H), 5.85-5.88 (m, 1 H), 4.13-4.18 (m, 2 H), 2.59 (s, 1 H), 2.33 (s, 3 H).

Example 430

6-(4-fluoro-2,3-dimethylphenyl)-4-N-[2-(4-methanesulfonylphenyl)ethyl]pyrimidine-2,4-diamine Prepared according to general procedure 2 from 6-chloro-4-N-[2-(4-methylsulfonylphenyl)ethyl]pyrimidine-2,4-diamine and 4-fluoro-2,3-dimethyl-benzeneboronic acid. LCMS [M+H]$^+$ 415; $^1$H NMR (400 MHz, CD$_3$OD) $\delta_H$ ppm 7.88 (s, 2 H), 7.53-7.58 (m, 2 H), 7.06-7.11 (m, 1 H), 6.91-6.97 (m, 1 H), 5.76 (s, 1 H), 3.64-3.72 (m, 2 H), 3.11 (s, 3 H), 3.02-3.08 (m, 2 H), 2.22-2.25 (m, 6 H).

Example 431

6-(3,4-dichloro-2-methylphenyl)-4-N-[2-(4-methanesulfonylphenyl)ethyl]pyrimidine-2,4-diamine Prepared according to general procedure 2 from 6-chloro-4-N-[2-(4-methylsulfonylphenyl)ethyl]pyrimidine-2,4-diamine and 3,4-dichloro-2-methyl-benzeneboronic acid. LCMS [M+H]$^+$ 451; $^1$H NMR (400 MHz, CD$_3$OD) $\delta_H$ ppm 7.89 (d, J=8.6 Hz, 2 H), 7.57 (s, 2 H), 7.43-7.46 (m, 1 H), 7.17-7.21 (m, 1 H), 5.78 (s, 1 H), 3.63-3.75 (m, 2 H), 3.11 (s, 3 H), 3.03-3.08 (m, 2 H), 2.39 (s, 3 H).

Example 432

4-(2-{[2-amino-6-(4-chloro-2-methylphenyl)pyrimidin-4-yl]amino}ethyl)benzene-1-sulfonamide Prepared according to general procedure 2 from 4-[2-[(2-amino-6-chloro-pyrimidin-4-yl)amino]ethyl]benzenesulfonamide and 4-chloro-2-methyl-benzeneboronic acid. LCMS [M+H]$^+$ 418; $^1$H NMR (400 MHz, CD$_3$OD) $\delta_H$ ppm 7.81-7.85 (m, 2 H), 7.42-7.46 (m, 2 H), 7.27-7.28 (m, 1 H), 7.23 (d, J=1.3 Hz, 2 H), 5.78 (s, 1 H), 3.63 (br. s., 2 H), 2.99 (t, J=7.1 Hz, 2 H), 2.30 (d, J=0.8 Hz, 3 H).

Example 433

4-(2-{[2-amino-6-(2-chloro-4-fluorophenyl)pyrimidin-4-yl]amino}ethyl)benzene-1-sulfonamide Prepared according to general procedure 2 from 4-[2-[(2-amino-6-chloro-pyrimidin-4-yl)amino]ethyl]benzenesulfonamide and 2-chloro-4-fluoro-benzeneboronic acid. LCMS [M+H]$^+$ 422.

Example 434

4-(2-{[2-amino-6-(2,3,4-trifluorophenyl)pyrimidin-4-yl]amino}ethyl)benzene-1-sulfonamide Prepared according to general procedure 2 from 4-[2-[(2-amino-6-chloro-pyrimidin-4-yl)amino]ethyl]benzenesulfonamide and 2,3,4-trifluorobenzeneboronic acid. LCMS [M+H]$^+$ 424.

Example 435

4-(2-{[2-amino-6-(4-fluoro-3-methylphenyl)pyrimidin-4-yl]amino}ethyl)benzene-1-sulfonamide Prepared according to general procedure 2 from 4-[2-[(2-amino-6-chloro-pyrimidin-4-yl)amino]ethyl]benzenesulfonamide and 4-fluoro-3-methyl-benzeneboronic acid. LCMS [M+H]⁺ 402; ¹H NMR (400 MHz, CD₃OD) δ$_H$ ppm 7.80-7.85 (m, 2 H), 7.67-7.72 (m, 1 H), 7.59-7.65 (m, 1 H), 7.41-7.46 (m, 2 H), 7.07 (dd, J=9.6, 8.6 Hz, 1 H), 6.12 (s, 1H), 3.64 (t, J=7.2 Hz, 2 H), 2.99 (t, J=7.1 Hz, 2 H), 2.31 (d, J=2.0 Hz, 3 H).

Example 436

4-N-cyclopropyl-6-(4-fluoro-2,3-dimethylphenyl) pyrimidine-2,4-diamine

Prepared according to general procedure 2 from 6-chloro-4-N-cyclopropylpyrimidine-2,4-diamine and 4-fluoro-2,3-dimethyl-benzeneboronic acid. LCMS [M+H]⁺ 273; ¹H NMR (400 MHz, CD₃OD) δ$_H$ ppm 7.08-7.15 (m, 1 H), 6.90-6.98 (m, 1 H), 5.90-6.07 (m, 1 H), 2.53-2.66 (m, 1 H), 2.21-2.26 (m, 6 H), 0.78 (dd, J=7.1, 2.0 Hz, 2 H), 0.54 (dd, J=3.7, 1.9 Hz, 2 H).

Example 437

3-[2-amino-6-(cyclopropylamino)pyrimidin-4-yl]-2-methylbenzonitrile

Prepared according to general procedure 2 from 6-chloro-4-N-cyclopropylpyrimidine-2,4-diamine and 3-cyano-2-methyl-benzeneboronic acid. LCMS [M+H]⁺ 266; ¹H NMR (400 MHz, CD₃OD) δ$_H$ ppm 7.73-7.77 (m, 1 H), 7.58-7.63 (m, 1 H), 7.42-7.48 (m, 1 H), 5.91-6.17 (m, 1 H), 2.59-2.70 (m, 1 H), 2.54 (s, 3 H), 0.81 (d, J=4.8 Hz, 2 H), 0.54-0.59 (m, 2 H).

Example 438

6-(2,3-dichlorophenyl)-4-N-(prop-2-yn-1-yl)pyrimidine-2,4-diamine

Prepared according to general procedure 9 from 4-chloro-6-(2,3-dichlorophenyl)pyrimidin-2-amine and propargyl amine. LCMS [M+H]⁺ 293.

Example 439

4-(2-{[2-amino-6-(4-fluoro-2,5-dimethylphenyl) pyrimidin-4-yl]amino}ethyl)benzene-1-sulfonamide Prepared according to general procedure 9 from 4-chloro-6-(4-fluoro-2,5-dimethyl-phenyl)pyrimidin-2-amine and 2-(4-sulfamoylphenyl)ethylammonium chloride. LCMS [M+H]⁺ 416.

Example 440

4-N-[2-(3,5-dimethyl-1H-pyrazol-4-yl)ethyl]-6-(2,3-dimethylphenyl)pyrimidine-2,4-diamine Prepared according to general procedure 9 from 4-chloro-6-(2,3-dimethylphenyl)pyrimidin-2-amine and 2-(3,5-dimethyl-1H-pyrazol-1-ium-4-yl)ethylammonium dichloride. [M+H]+ 337; ¹H NMR (400 MHz, CD₃OD) δ$_H$ ppm 7.34 (s, 1 H), 7.21-7.26 (m, 1 H), 7.18 (dd, J=1.0, 0.5 Hz, 1 H), 6.00 (s, 1 H), 3.70 (t, J=6.8 Hz, 2 H), 2.83 (t, J=6.9 Hz, 2 H), 2.39 (s, 6 H), 2.35 (s, 3 H), 2.24 (s, 3 H).

Example 441

4-N-{2-[(6-chloropyridazin-3-yl)amino]ethyl}-6-(2,3-dimethylphenyl)pyrimidine-2,4-diamine Prepared according to general procedure 12 from 4-N-(2-aminoethyl)-6-(2,3-dimethylphenyl)pyrimidine-2,4-diamine and 3,6-dichloropyridazine. [M+H]+ 370.

Example 442

2-[(2-{[2-amino-6-(2,3-dimethyl phenyl)pyrimidin-4-yl]amino}ethyl)amino]pyridine-4-carbonitrile Prepared according to general procedure 12 from 4-N-(2-aminoethyl)-6-(2,3-dimethylphenyl)pyrimidine-2,4-diamine and 2-chloropyridine-4-carbonitrile. LCMS [M+H]⁺ 360.

Example 443

6-[(2-{[2-amino-6-(2,3-dimethylphenyl)pyrimidin-4-yl]amino}ethyl)amino]pyridine-3-sulfonamide Prepared according to general procedure 12 from 4-N-(2-aminoethyl)-6-(2,3-dimethylphenyl)pyrimidine-2,4-diamine and 6-chloropyridine-3-sulfonamide. LCMS [M+H]⁺ 414.

Example 444

1-N-(3-{[2-amino-6-(2,3-dimethylphenyl)pyrimidin-4-yl]amino}propyl)benzene-1,4-disulfonamide Prepared according to general procedure 10 from 4-N-(4-aminopropyl)-6-(2,3-dimethylphenyl)pyrimidine-2,4-diamine and 4-(aminosulfonyl)benzenesulfonyl chloride. LCMS [M+H]⁺ 491; ¹H NMR (400 MHz, CD₃OD) δ$_H$ ppm 8.04-8.08 (m, 2 H), 7.98-8.02 (m, 2 H), 7.28 (d, J=7.1 Hz, 1 H), 7.16-7.22 (m, 1 H), 7.15 (d, J=1.5 Hz, 1 H), 5.91 (s, 1 H), 3.48 (d, J=1.5 Hz, 2 H), 2.98 (t, J=6.8 Hz, 2 H), 2.34 (s, 3 H), 2.22 (s, 3 H), 1.78 (t, J=6.8 Hz, 2 H).

Example 445

6-(2,3-dichlorophenyl)-4-N-[2-(4-methanesulfonylphenyl)ethyl]pyrimidine-2,4-diamine Prepared according to general procedure 2 from 6-chloro-4-N-[2-(4-methylsulfonylphenyl)ethyl]pyrimidine-2,4-diamine and 2,3-dichlorobenzene-boronic acid. LCMS [M+H]⁺ 437; ¹H NMR (400 MHz, CD₃OD) δ$_H$ ppm 7.90 (d, J=8.6 Hz, 2 H), 7.78 (t, J=4.9 Hz, 1 H), 7.56 (d, J=8.6 Hz, 2 H), 7.49 (dd, J=4.9, 0.6 Hz, 2 H), 6.08 (s, 1 H), 3.84 (s, 2 H), 3.06-3.11 (m, 5 H).

Example 446

6-(2,3-dimethylphenyl)-4-N-[1-(1H-pyrazol-1-yl) propan-2-yl]pyrimidine-2,4-diamine Prepared according to general procedure 9 from 4-chloro-6-(2,3-dimethylphenyl)-pyrimidin-2-amine and 1-pyrazol-1-ylpropan-2-amine. LCMS [M+H]⁺ 323; ¹H NMR (400

MHz, CDCl₃) δ_H ppm 7.71 (d, J=7.8 Hz, 1 H), 7.57 (d, J=1.8 Hz, 1 H), 7.51 (d, J=2.3 Hz, 1 H), 7.24 (d, J=7.3 Hz, 1 H), 7.12 (t, J=7.6 Hz, 1 H), 7.04-7.08 (m, 1 H), 6.30 (t, J=2.3 Hz, 1 H), 5.85 (s, 1 H), 4.65-4.75 (m, 1 H), 4.34-4.41 (m, 1 H), 4.23 (dd, J=14.1, 6.3 Hz, 1 H), 2.29 (s, 3 H), 2.18 (s, 3 H), 1.16 (d, J=6.8 Hz, 3 H).

Example 447

6-(2,3-dimethylphenyl)-4-N-{2-[(3-methoxyphenyl)amino]ethyl}pyrimidine-2,4-diamine Prepared according to general procedure 9 from 4-chloro-6-(2,3-dimethylphenyl)pyrimidin-2-amine and N'-(3-methoxyphenyl)ethane-1,2-diamine.
LCMS [M+H]⁺ 364; ¹H NMR (400 MHz, CDCl₃) δ_H ppm 7.18-7.26 (m, 1 H), 7.01-7.07 (m, 1 H), 6.96-7.00 (m, 1 H), 6.95 (t, J=2.0 Hz, 1 H), 6.84 (d, J=7.8 Hz, 1 H), 6.76 (dd, J=8.3, 2.0 Hz, 1 H), 5.91 (s, 1 H), 3.82 (d, J=4.8 Hz, 2 H), 3.75 (s, 3 H), 3.48 (br. s., 2 H), 2.24 (s, 3 H), 2.10 (s, 3 H).

Example 448

6-(2,3-dimethylphenyl)-4-N-{2-[(3-fluoro-4-methylphenyl)amino]ethyl}pyrimidine-2,4-diamine Step 1: A vial was charged with 2-fluoro-4-iodo-1-methyl-benzene (240 mg, 1.0 mmol), ethane-1,2-diamine (0.20 mL, 3.0 mmol), CuCl (9.9 mg, 0.10 mmol), and KOH (110 mg, 2.0 mmol). The vial was then flushed with nitrogen and sealed. The mixture was stirred at r.t. for 16 h, thereafter the mixture was extracted with EtOAc. The combined organic phases were dried, concentrated and purified by column chromatography to afford N'-(3-fluoro-4-methyl-phenyl)ethane-1,2-diamine.
Step 2: A mixture of 6-(2,3-dimethylphenyl)-4-chloropyrimidin-2-amine (30 mg, 0.13 mmol), N'-(3-fluoro-4-methyl-phenyl)ethane-1,2-diamine (20 mg, 0.12 mmol), and diisopropylethylamine (0.040 mL, 0.23 mmol) in 2-propanol (0.50 mL) was heated in a sealed tube at 150° C. for 30 min in a microwave reactor. The reaction mixture was then concentrated and purified by preparative HPLC. LCMS [M+H]⁺ 366; ¹H NMR (400 MHz, CD₃OD) δ_H ppm 7.33-7.37 (m, 1 H), 7.21-7.27 (m, 1 H), 7.15-7.18 (m, 1 H), 6.93-6.99 (m, 1 H), 6.38-6.45 (m, 2 H), 5.99 (s, 1 H), 3.72 (s, 2 H), 3.39 (s, 2 H), 2.36 (s, 3 H), 2.24 (s, 3 H), 2.11 (d, J=1.5 Hz, 3 H).

Example 449

4-N-{2-[(3,4-dichlorophenyl)amino]ethyl}-6-(2,3-dimethylphenyl)pyrimidine-2,4-diamine Prepared according to general procedure 9 from 4-chloro-6-(2,3-dimethylphenyl)pyrimidin-2-amine and N'-(3,4-dichlorophenyl)ethane-1,2-diamine. LCMS [M+H]⁺ 402; ¹H NMR (400 MHz, CD₃OD) δ_H ppm 7.33-7.37 (m, 1 H), 7.24 (s, 1 H), 7.18 (m, 2 H), 6.76 (d, J=2.8 Hz, 1 H), 6.57 (dd, J=8.8, 2.8 Hz, 1 H), 5.97 (s, 3 H), 3.69-3.73 (m, 2 H), 3.37-3.42 (m, 2 H), 2.35 (s, 3 H), 2.23 (s, 3 H).

Example 450

4-N-{2-[(5-chloropyridin-2-yl)amino]ethyl}-6-(2,3-dimethylphenyl)pyrimidine-2,4-diamine Prepared according to general procedure 9 from 4-chloro-6-(2,3-dimethylphenyl)pyrimidin-2-amine and N'-(5-chloro-2-pyridyl)ethane-1,2-diamine. LCMS [M+H]⁺ 369; ¹H NMR (400 MHz, CDCl₃) δ_H ppm 7.61-7.69 (m, 2 H), 7.30 (d, J=7.6 Hz, 1 H), 7.10-7.22 (m, 3 H), 6.17 (br. s., 1 H), 3.71 (br. s., 4 H), 2.33 (s, 3 H), 2.24 (s, 3 H).

Example 451

4-N-{2-[(5-bromopyridin-2-yl)amino]ethyl}-6-(2,3-dimethylphenyl)pyrimidine-2,4-diamine Prepared according to general procedure 9 from 4-chloro-6-(2,3-dimethylphenyl)pyrimidin-2-amine and N'-(5-bromo-2-pyridyl)ethane-1,2-diamine. LCMS [M+H]⁺ 413; ¹H NMR (400 MHz, CD₃OD) δ_H ppm 8.07 (dd, J=2.3, 0.8 Hz, 1 H), 7.86 (dd, J=9.3, 2.3 Hz, 2 H), 7.33-7.37 (m, 2 H), 7.24 (t, J=7.6 Hz, 1 H), 7.15-7.19 (m, 1 H), 6.90 (dd, J=9.5, 0.6 Hz, 1 H), 6.03 (s, 1 H), 3.77-3.82 (m, 2 H), 3.64-3.69 (m, 2 H), 2.35 (s, 3 H), 2.24 (s, 3 H).

Example 452

4-[(2-{[2-amino-6-(2,3-dimethylphenyl)pyrimidin-4-yl]amino}ethyl)amino]benzene-1-sulfonamide Prepared according to general procedure 9 from 4-chloro-6-(2,3-dimethylphenyl)pyrimidin-2-amine and 4-(2-aminoethylamino)benzenesulfonamide. LCMS [M+H]⁺ 413; ¹H NMR (400 MHz, CD₃OD) δ_H ppm 7.64 (d, J=9.1 Hz, 2 H), 7.33-7.37 (m, 1 H), 7.24 (s, 1 H), 7.15-7.19 (m, 1 H), 6.70 (d, J=9.1 Hz, 2 H), 6.00 (s, 1 H), 3.72-3.77 (m, 2 H), 3.45-3.50 (m, 2 H), 2.35 (s, 3 H), 2.24 (s, 3 H).

Example 453

4-N-[2-(4-chlorophenyl)ethyl]-6-(dimethyl-1,2-oxazol-4-yl)pyrimidine-2,4-diamine Prepared according to general procedure 2 from 6-chloro-4-N-[2-(4-chlorophenyl)ethyl]pyrimidine-2,4-diamine and (3,5-dimethylisoxazol-4-yl)boronic acid. LCMS [M+H]⁺ 344.

Example 454

6-(2,3-dimethylphenyl)-4-N-{2-[(pyridin-3-yl)amino]ethyl}pyrimidine-2,4-diamine

Prepared according to general procedure 9 from 4-chloro-6-(2,3-dimethylphenyl)pyrimidin-2-amine and N'-(3-pyridyl)ethane-1,2-diamine. LCMS [M+H]⁺ 335; ¹H NMR (400 MHz, CD₃OD) δ_H ppm 8.10-8.12 (m, 1 H), 7.97-8.00 (m, 1 H), 7.72-7.80 (m, 2 H), 7.34-7.38 (m, 1 H), 7.22-7.27 (m, 1 H), 7.19 (dd, J=1.0, 0.5 Hz, 1 H), 6.04 (s, 1 H), 3.75-3.80 (m, 2 H), 3.54 (t, J=6.2 Hz, 2 H), 2.36 (s, 3 H), 2.25 (s, 3 H).

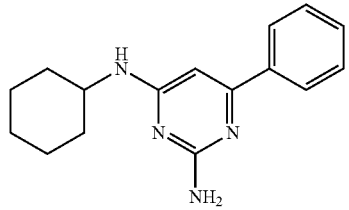

Example 1

Example 2
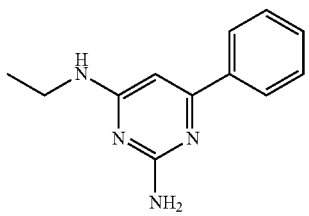
Example 3
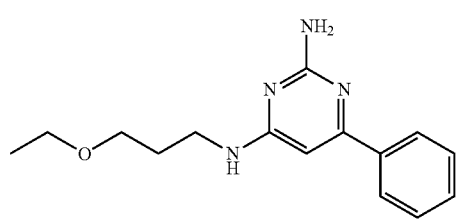
Example 4
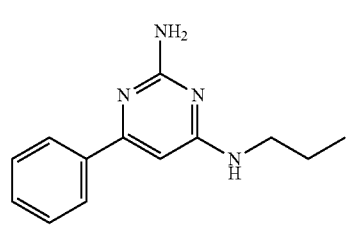
Example 5
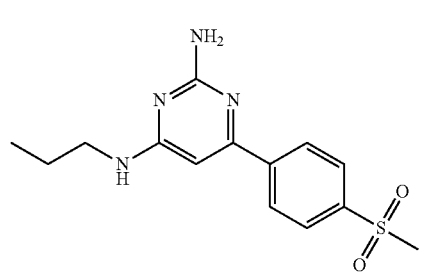
Example 6
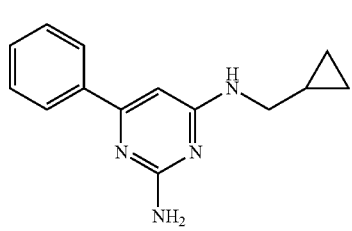
Example 7
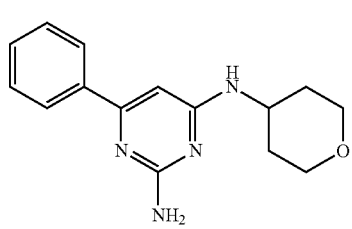
Example 8
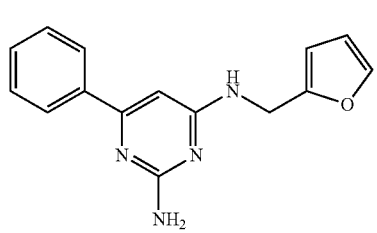
Example 9
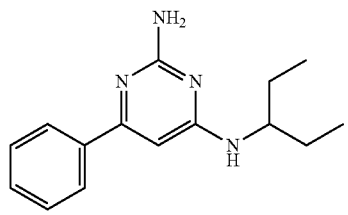
Example 10
Example 11
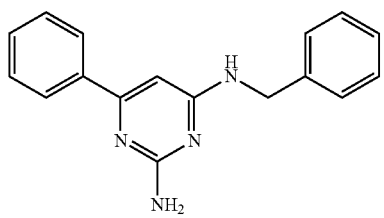
Example 12
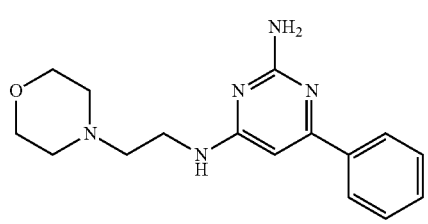
Example 13
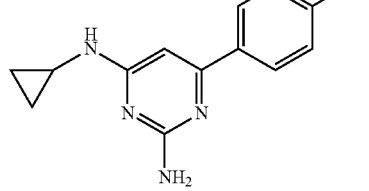
Example 14
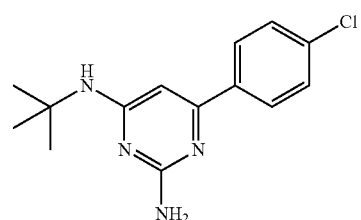
Example 15
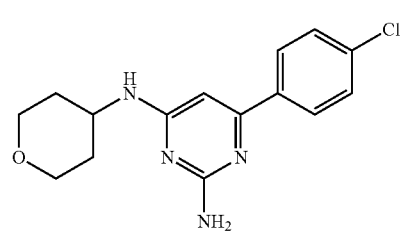

Example 16
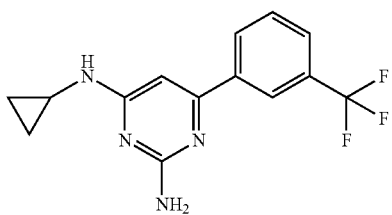
Example 17
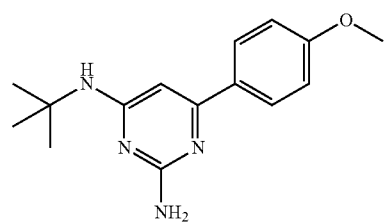
Example 18
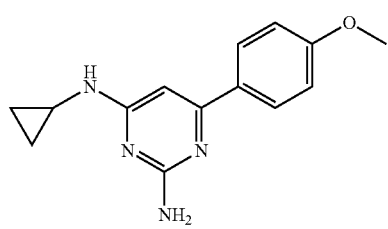
Example 19
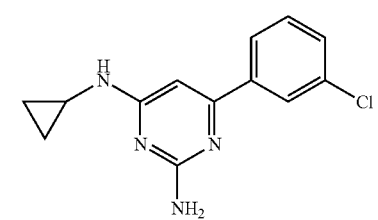
Example 20
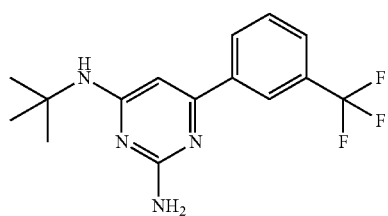
Example 21
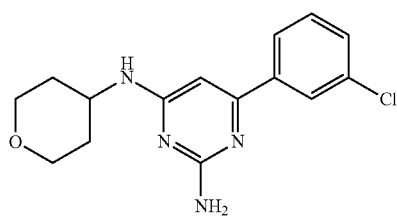
Example 22
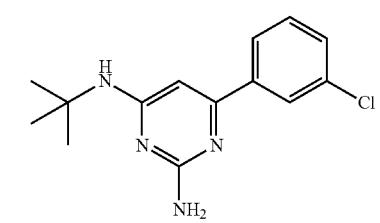
Example 23
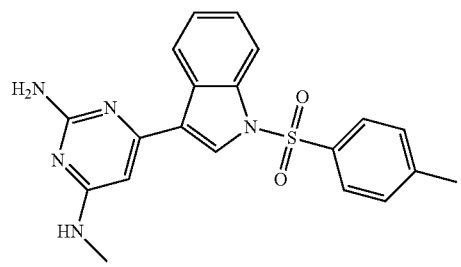
Example 24
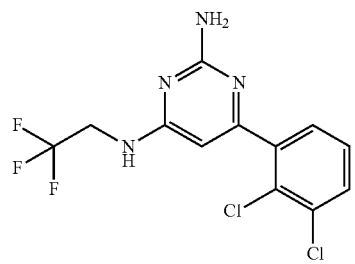
Example 25
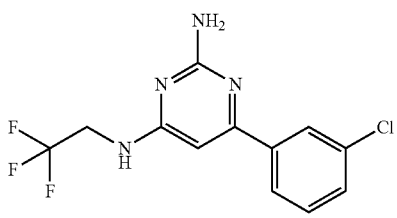
Example 26
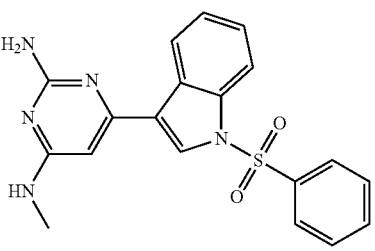
Example 27
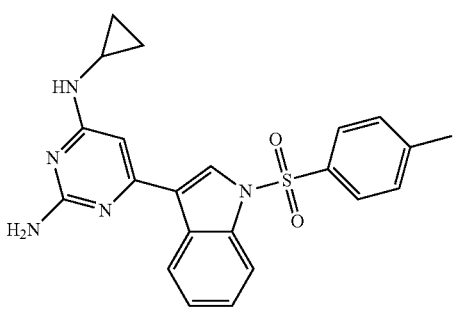
Example 28
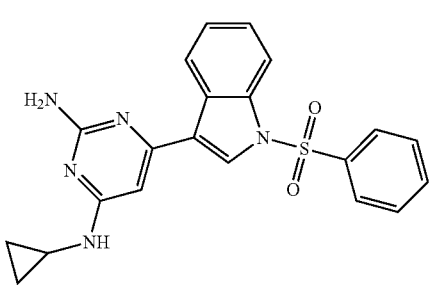

-continued
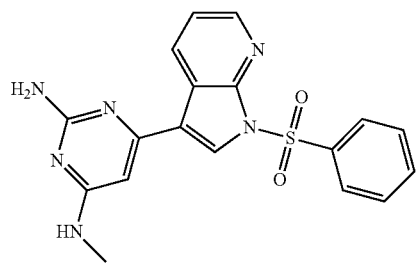
Example 29
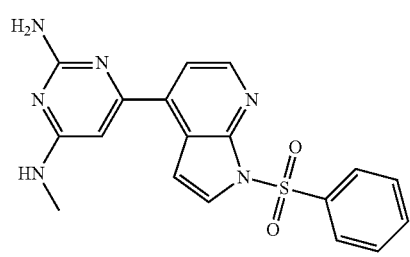
Example 30
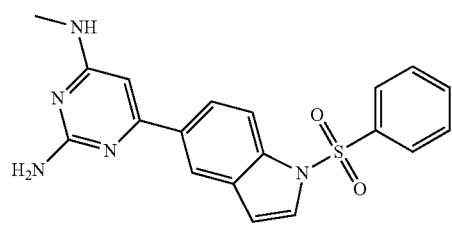
Example 31
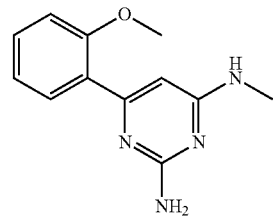
Example 32
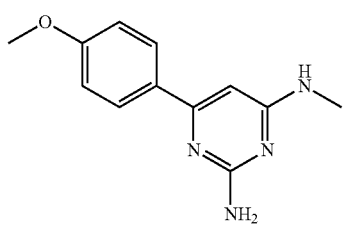
Example 33
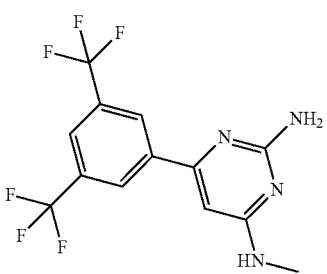
Example 34
-continued
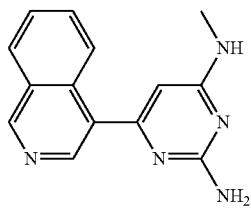
Example 35
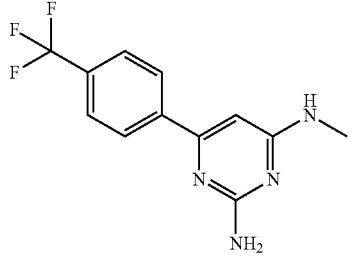
Example 36
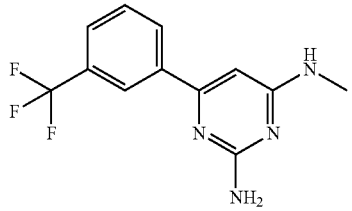
Example 37
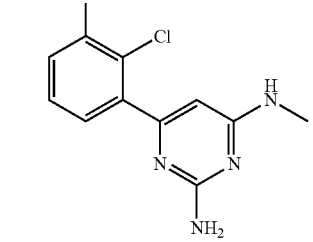
Example 38
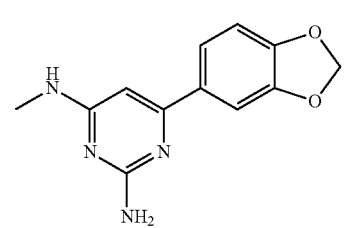
Example 39
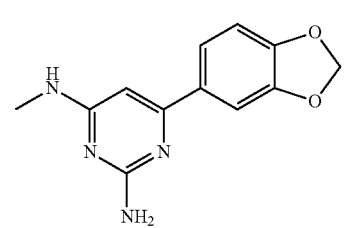
Example 40
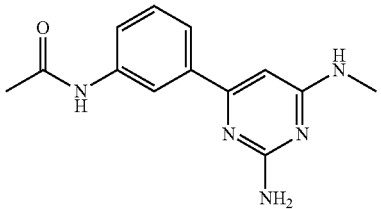
Example 41

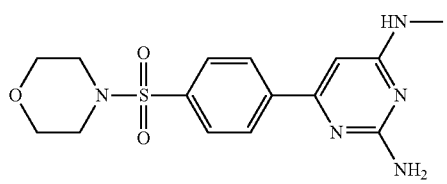
Example 42
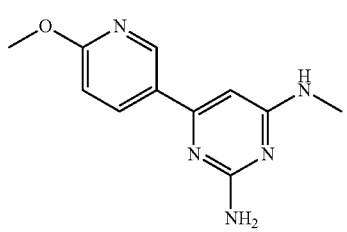
Example 49
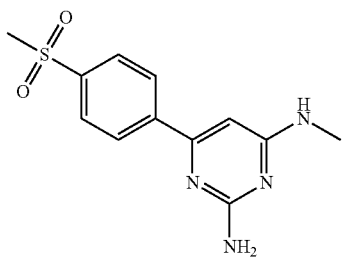
Example 43
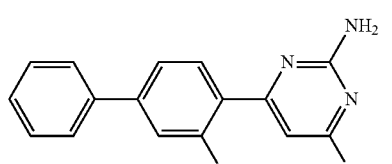
Example 50
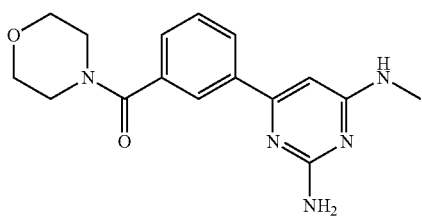
Example 44
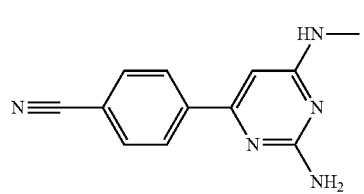
Example 51
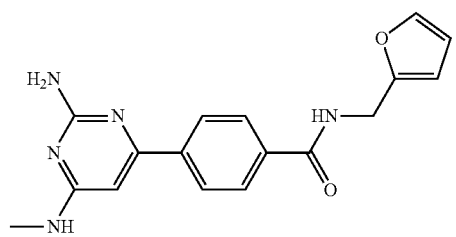
Example 45
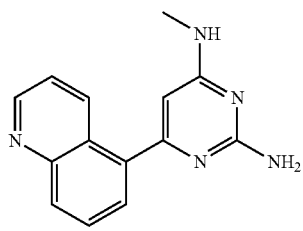
Example 52
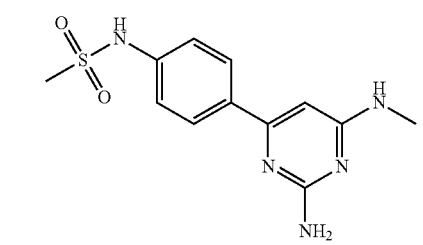
Example 46
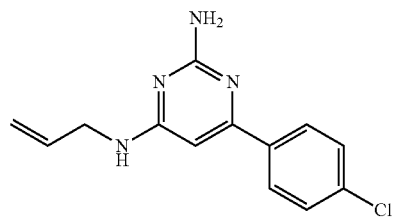
Example 53
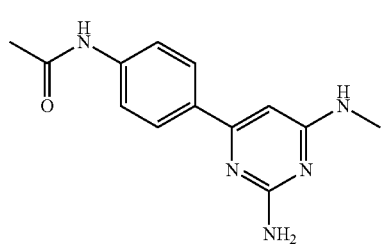
Example 47
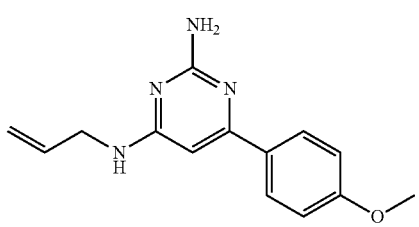
Example 54
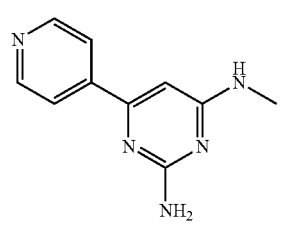
Example 48
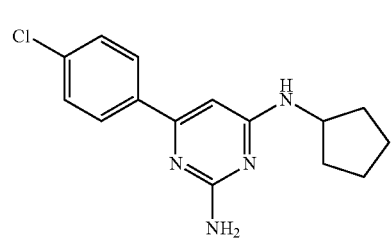
Example 55

Example 56

Example 57

Example 58

Example 59

Example 60

Example 61

Example 62

Example 63

Example 64

Example 65

Example 66

Example 67

Example 68

Example 69
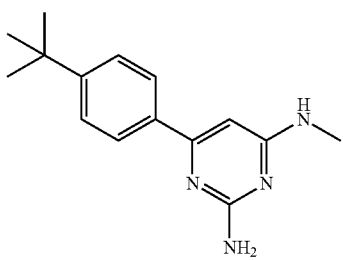
Example 70
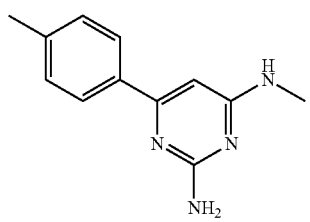
Example 71
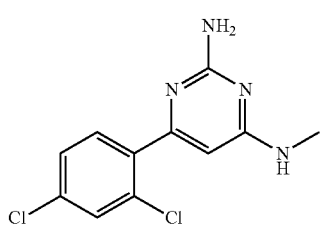
Example 72
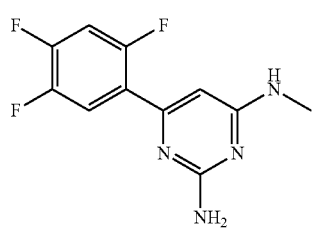
Example 73
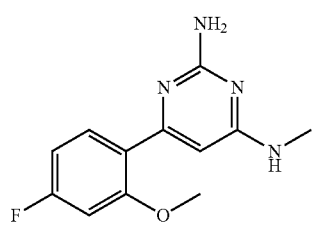
Example 74
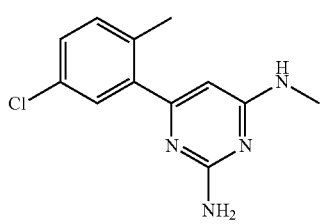
Example 75
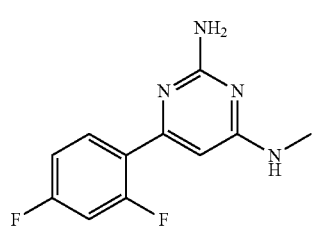
Example 76
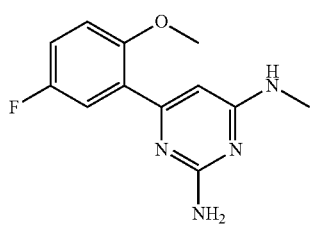
Example 77
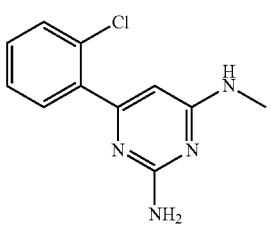
Example 78
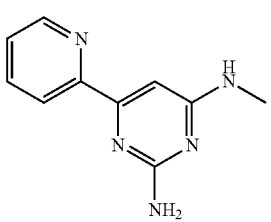
Example 79
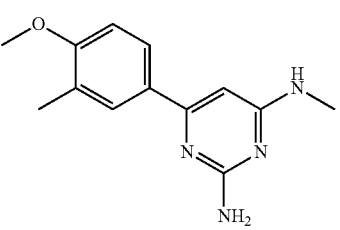
Example 80
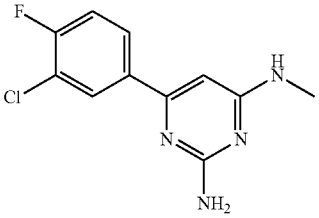
Example 81
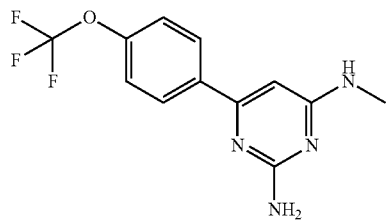
Example 82
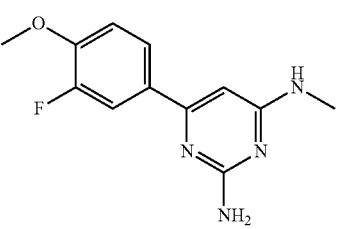

-continued
Example 83
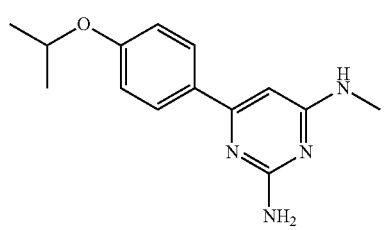
Example 84
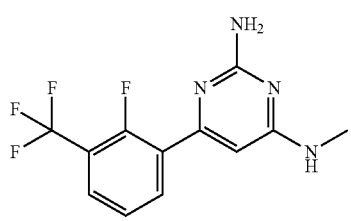
Example 85
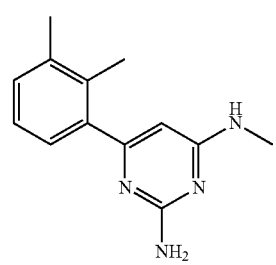
Example 86
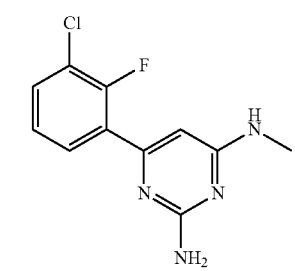
Example 87
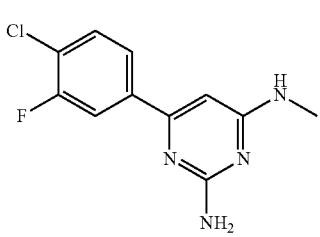
Example 88
-continued
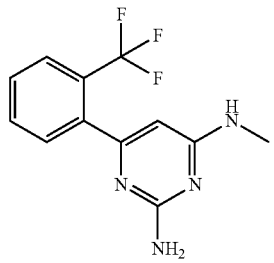
Example 89
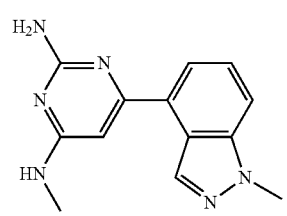
Example 90
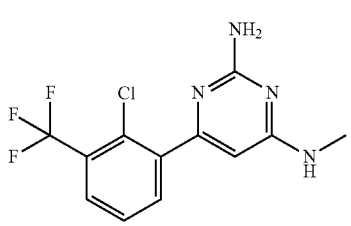
Example 91
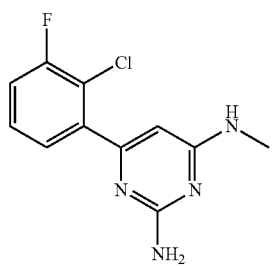
Example 92
Example 93
Example 94
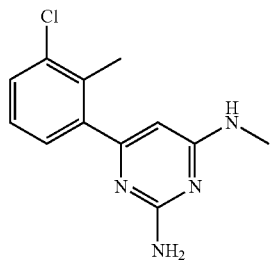

-continued
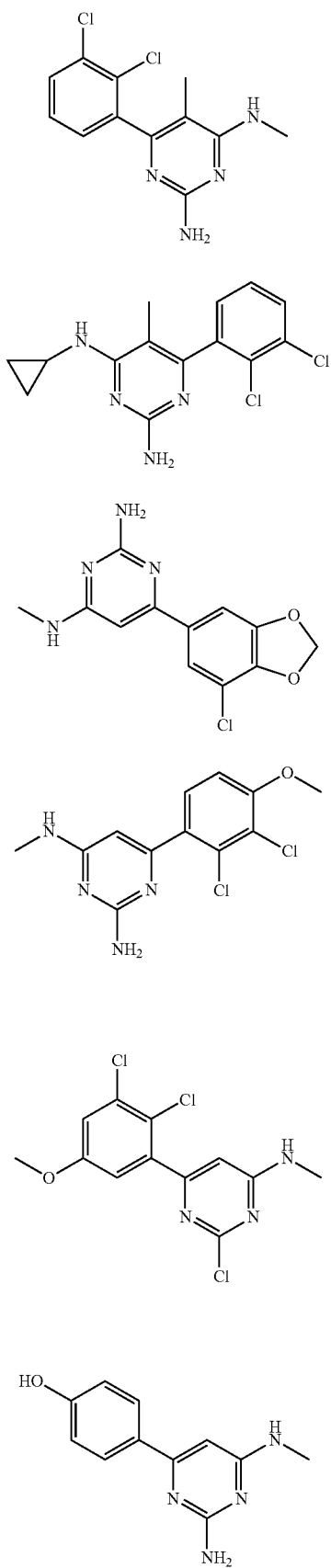
Example 95
Example 96
Example 97
Example 98
Example 99
Example 100
-continued
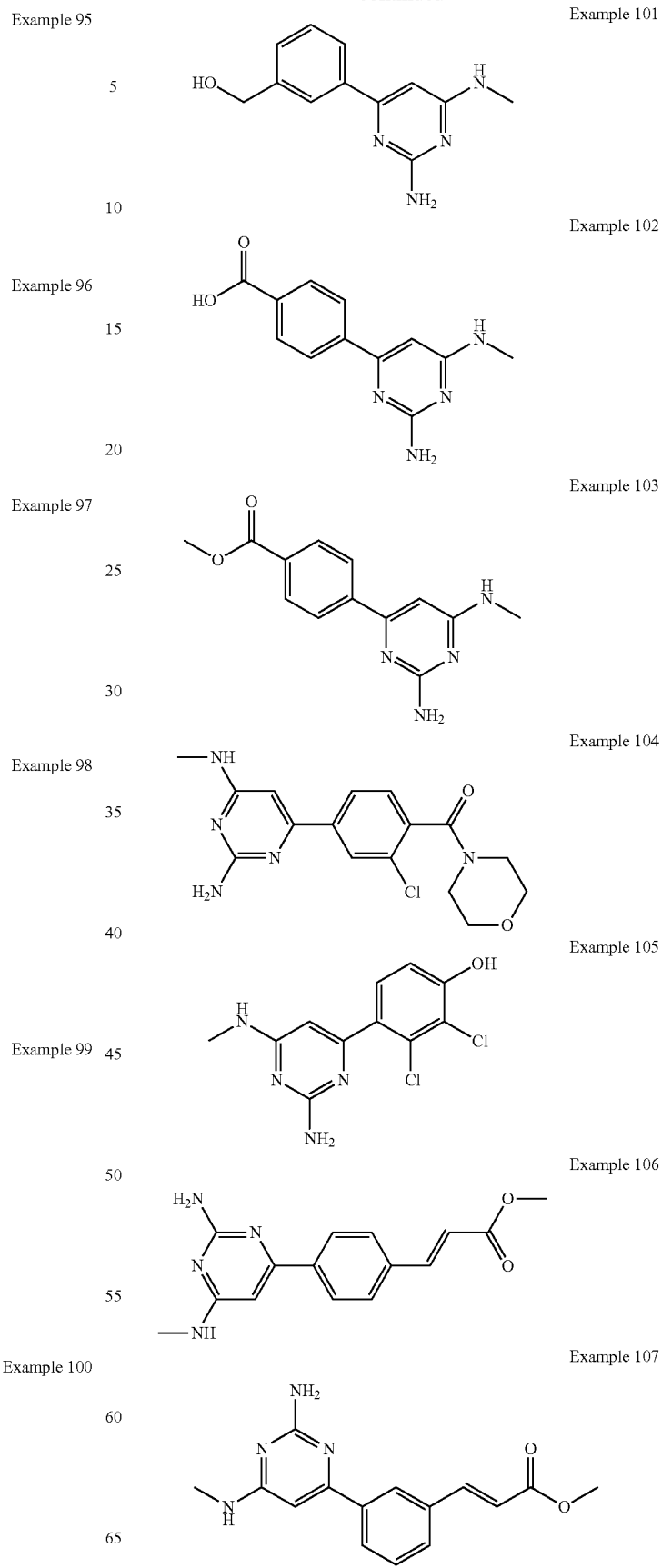
Example 101
Example 102
Example 103
Example 104
Example 105
Example 106
Example 107

Example 108
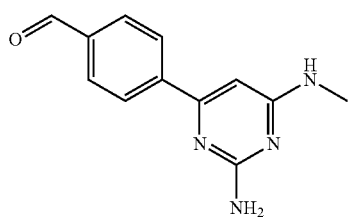
Example 109
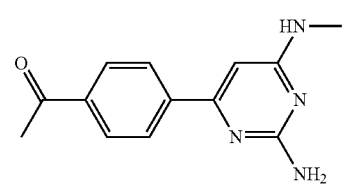
Example 110
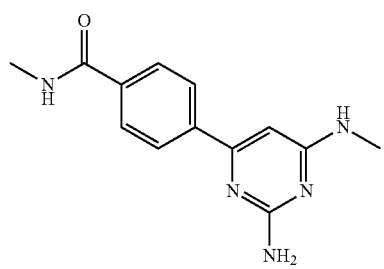
Example 111
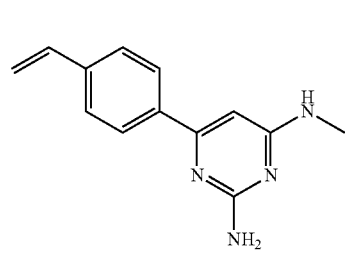
Example 112
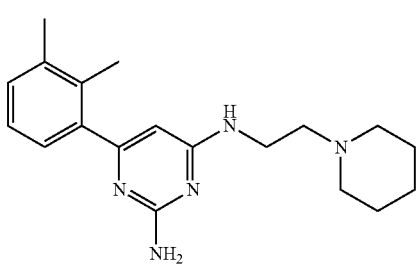
Example 113
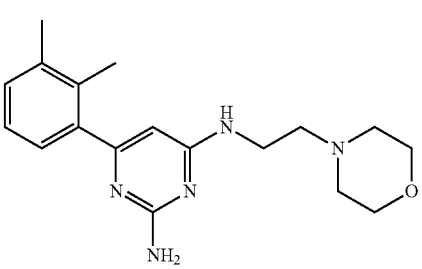
Example 114
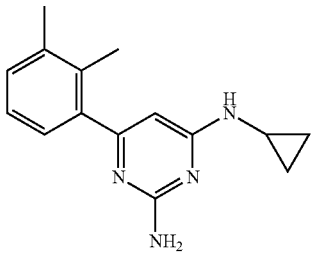
Example 115
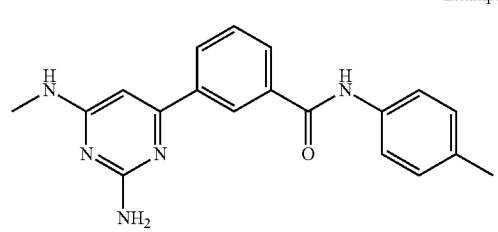
Example 116
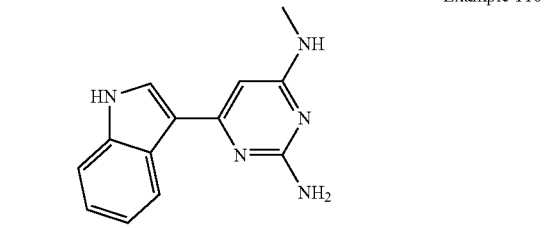
Example 117
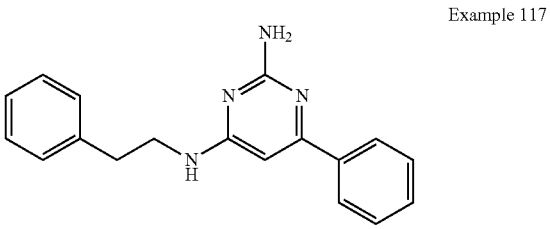
Example 118
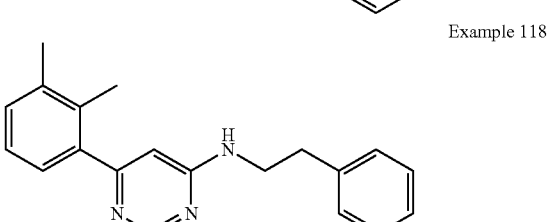
Example 119
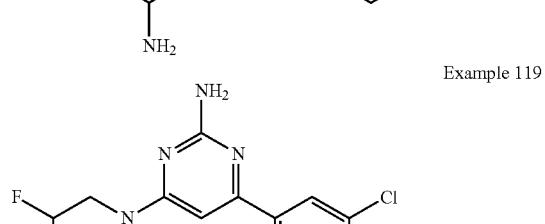
Example 120
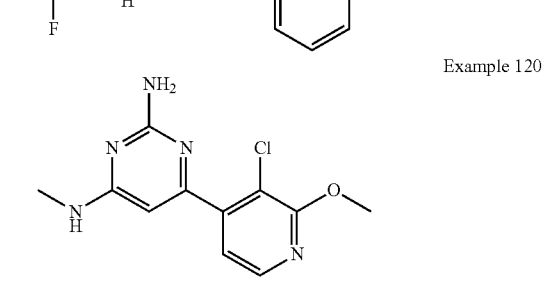

Example 121
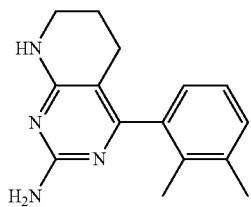
Example 122
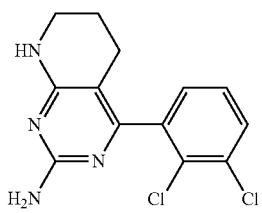
Example 123
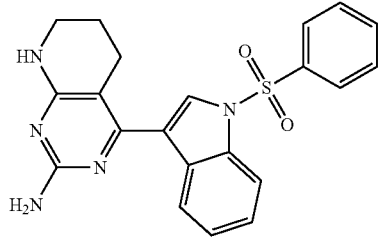
Example 124
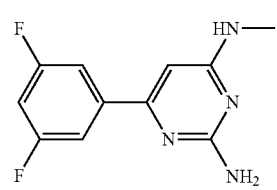
Example 125
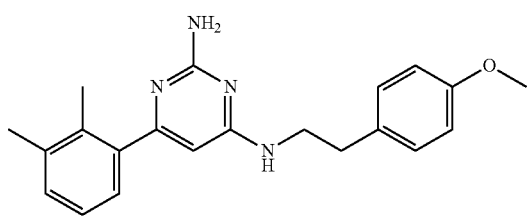
Example 126
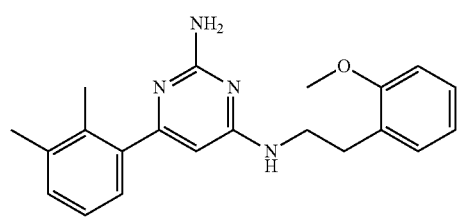
Example 127
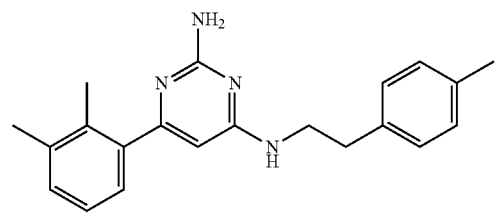
Example 128
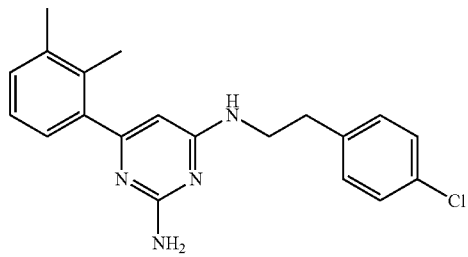
Example 129
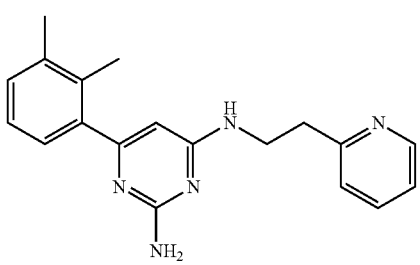
Example 130
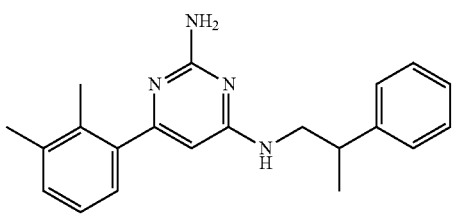
Example 131
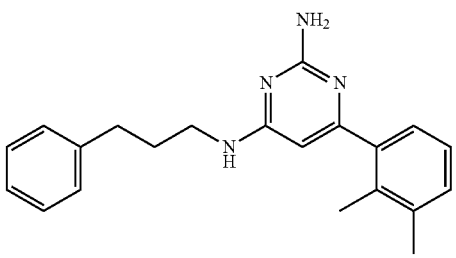
Example 132
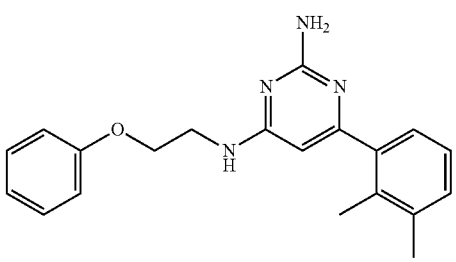

Example 133
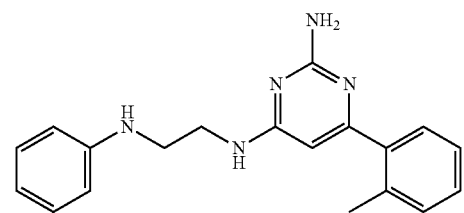
Example 134
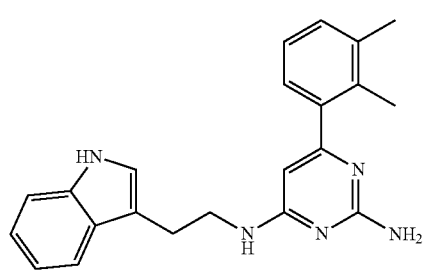
Example 135
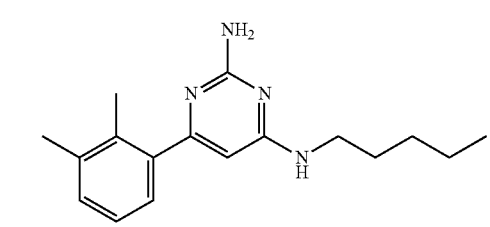
Example 136
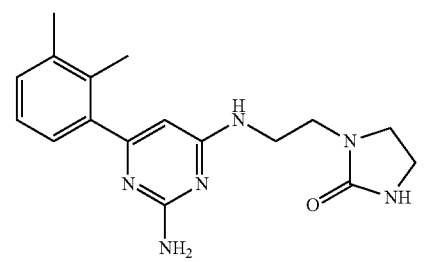
Example 137
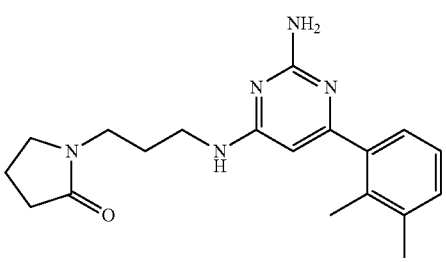
Example 138
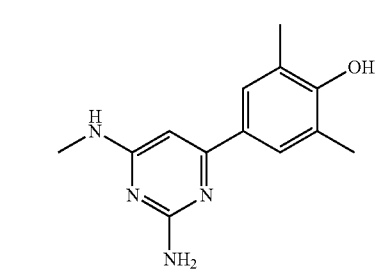
Example 139
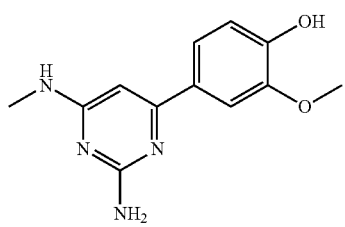
Example 140
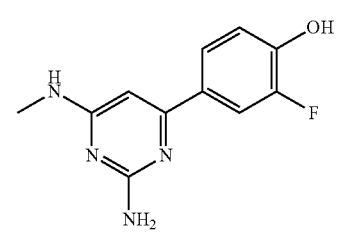
Example 141
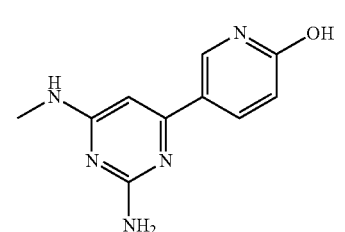
Example 142
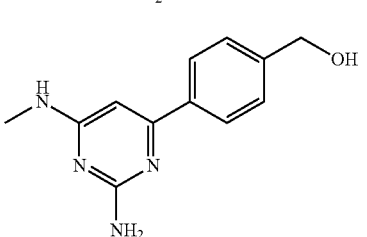
Example 143
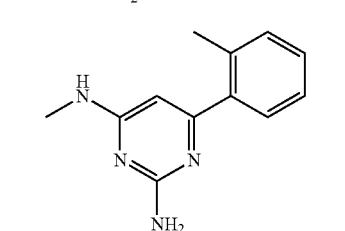
Example 144
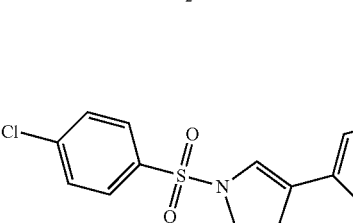
Example 145
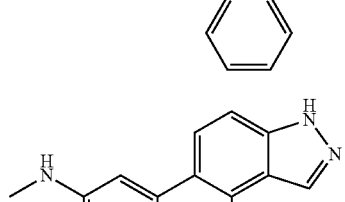

Example 146
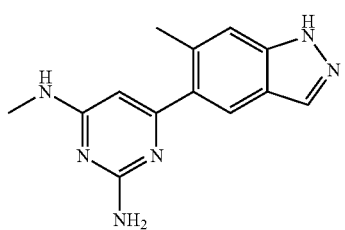
Example 147
Example 148
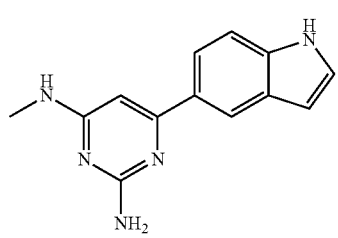
Example 149
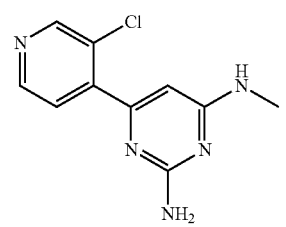
Example 150
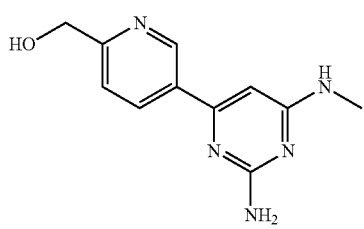
Example 151
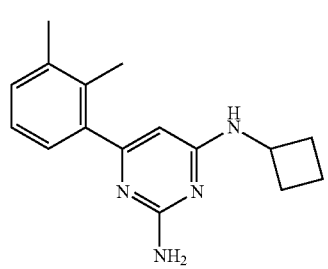
Example 152
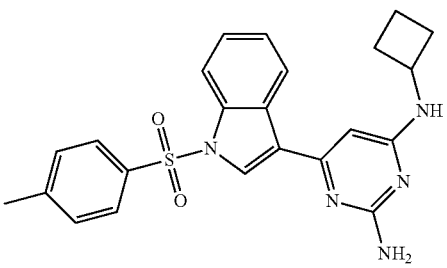
Example 153
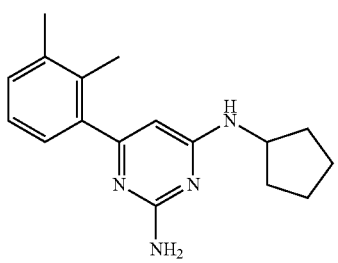
Example 154
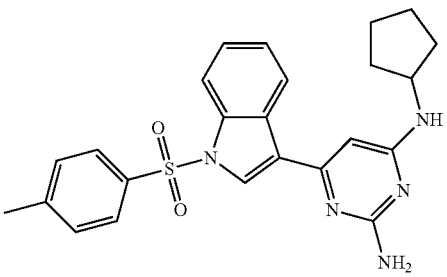
Example 155
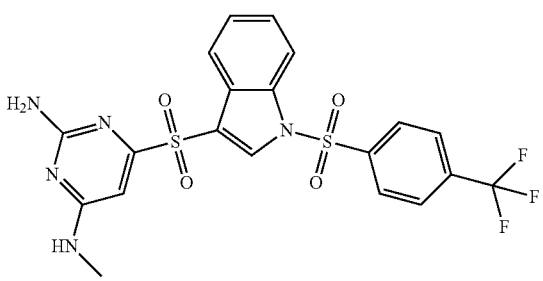
Example 156
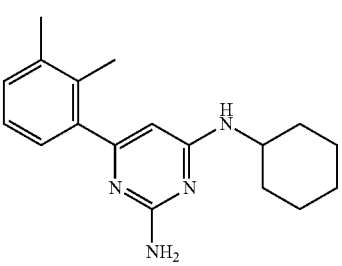

Example 157
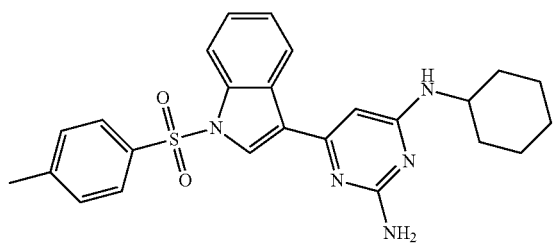
Example 158
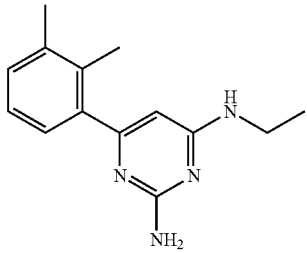
Example 159
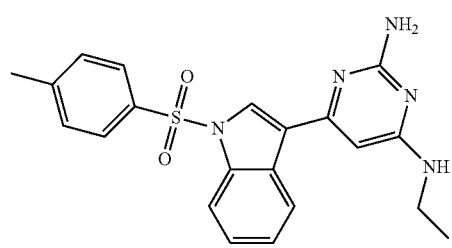
Example 160
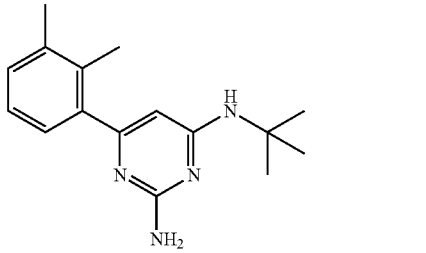
Example 161
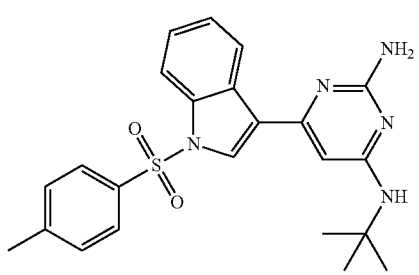
Example 162
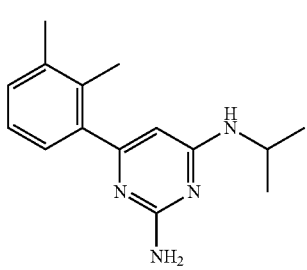
Example 163
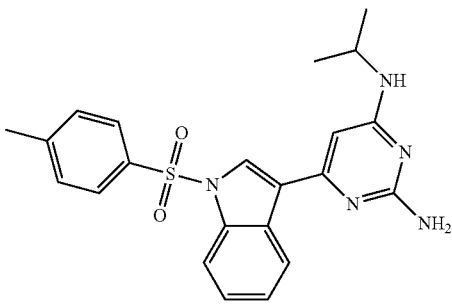
Example 164
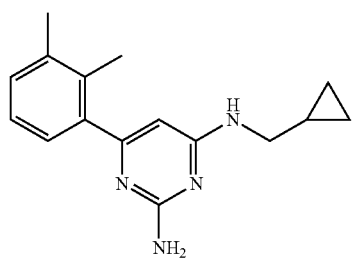
Example 165
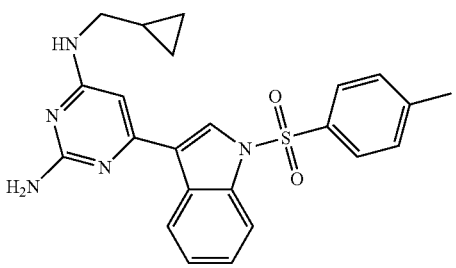
Example 166
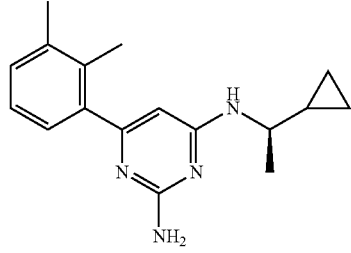
Example 167
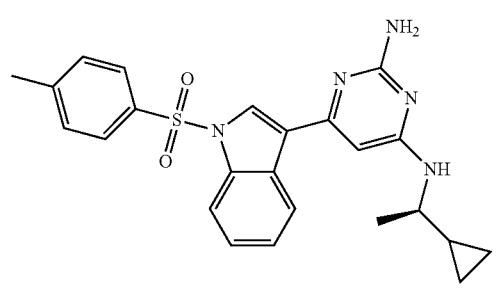

Example 168
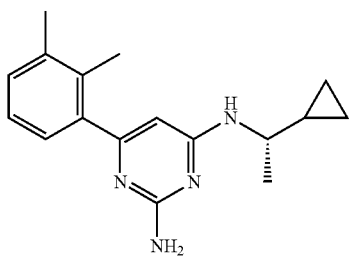
Example 169
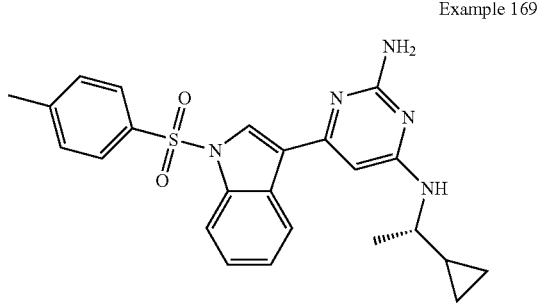
Example 170
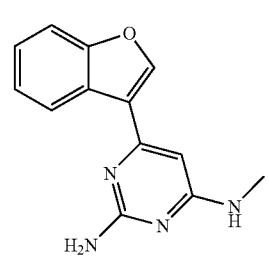
Example 171
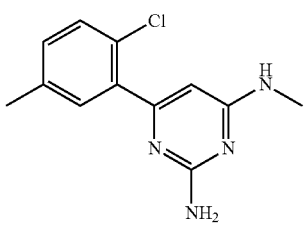
Example 172
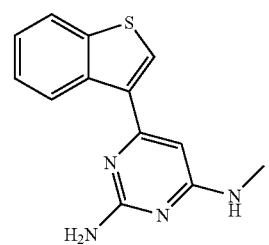
Example 173
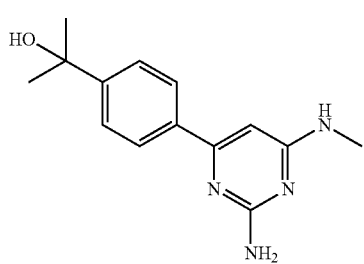
Example 174
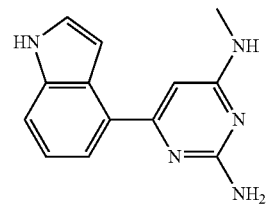
Example 175
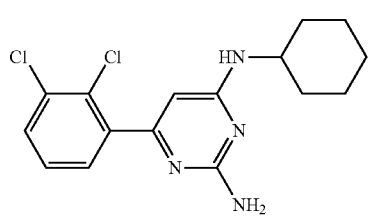
Example 176
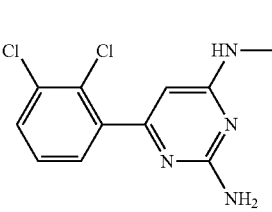
Example 177
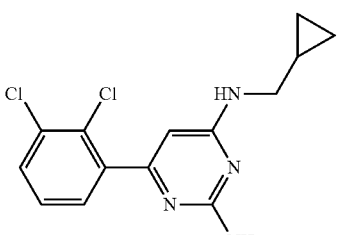
Example 178
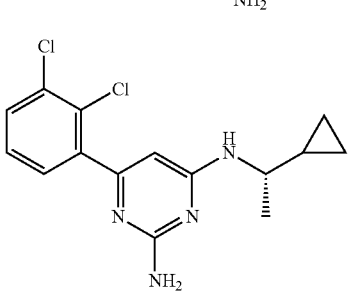
Example 179
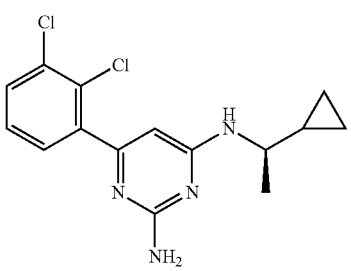
Example 180
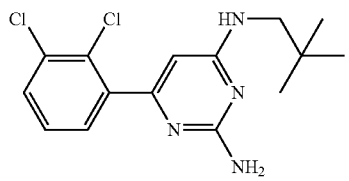

Example 181
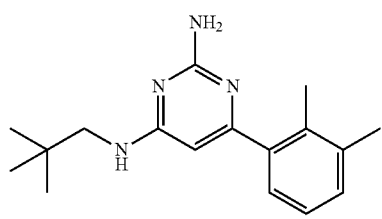
Example 182
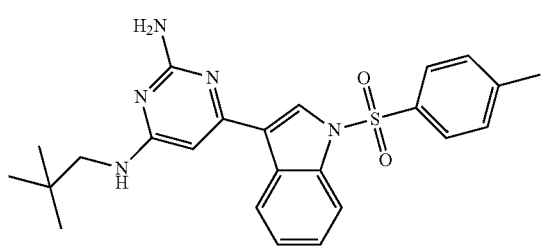
Example 183
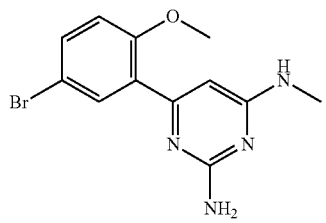
Example 184
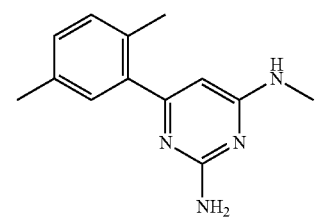
Example 185
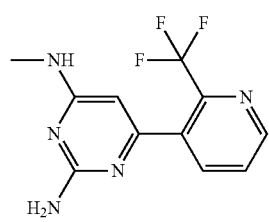
Example 186
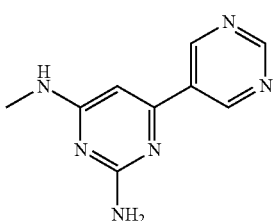
Example 187
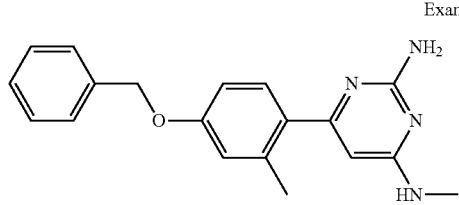
Example 188
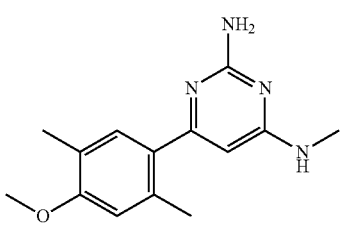
Example 189
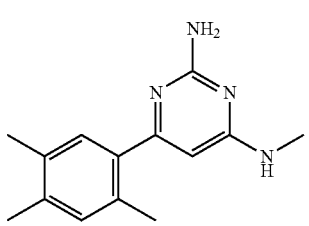
Example 190
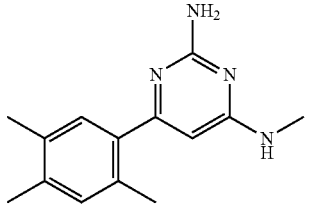
Example 191
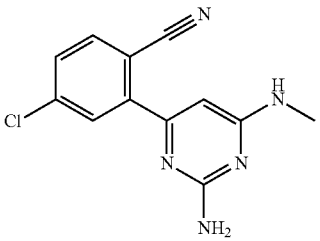
Example 192
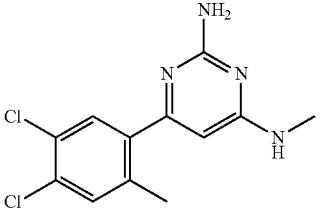
Example 193
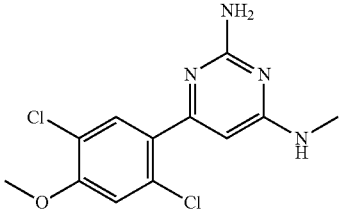
Example 194
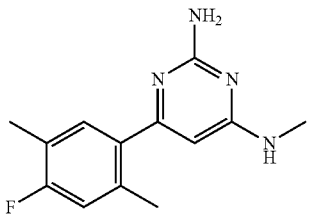

Example 195
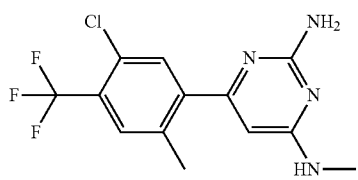
Example 196
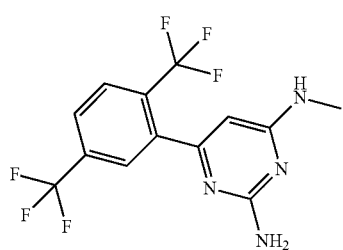
Example 197
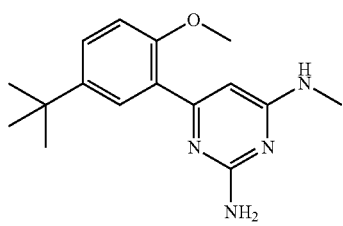
Example 198
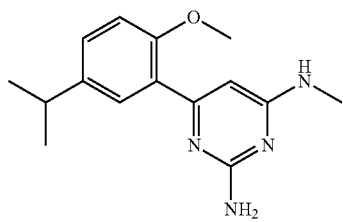
Example 199
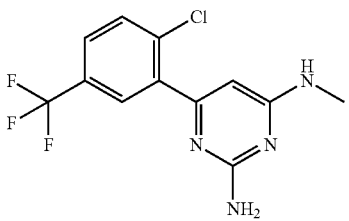
Example 200
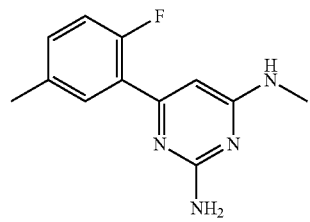
Example 201
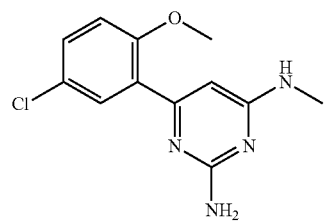
Example 202
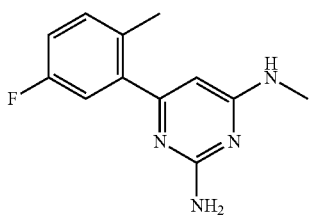
Example 203
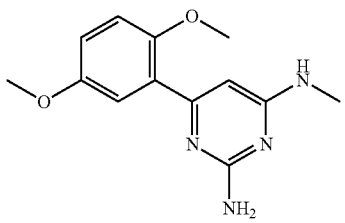
Example 204
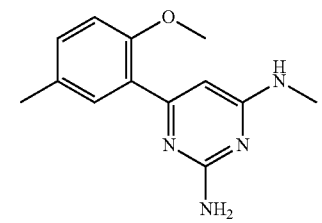
Example 205
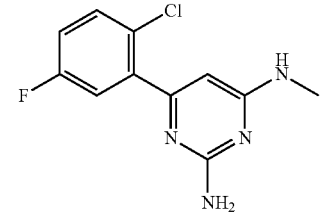
Example 206
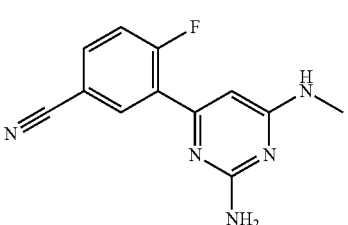
Example 207
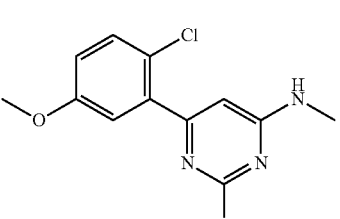
Example 208
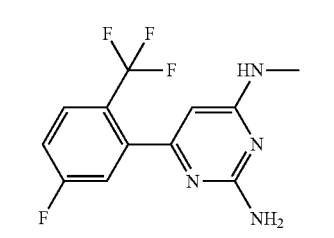

-continued

Example 209

Example 210

Example 211

Example 212

Example 213

Example 214

Example 215

-continued

Example 216

Example 217

Example 218

Example 219

Example 220

Example 221

Example 222

Example 223
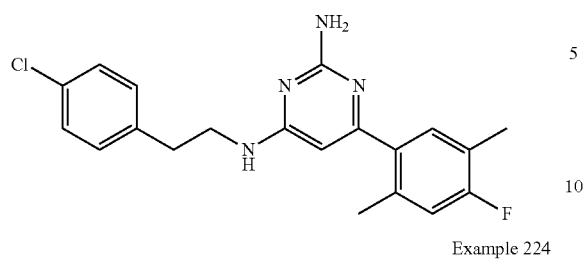
Example 224
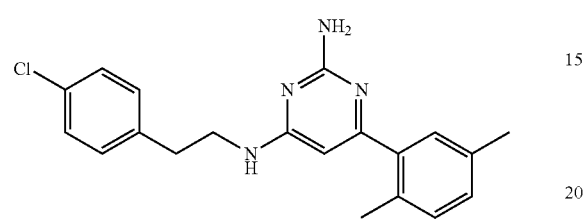
Example 225
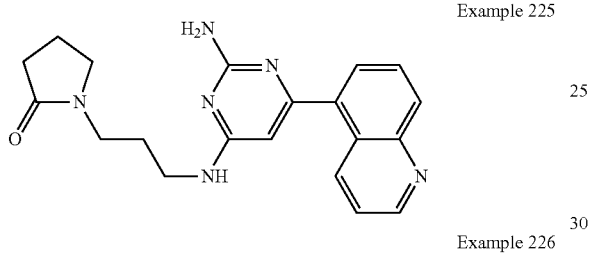
Example 226
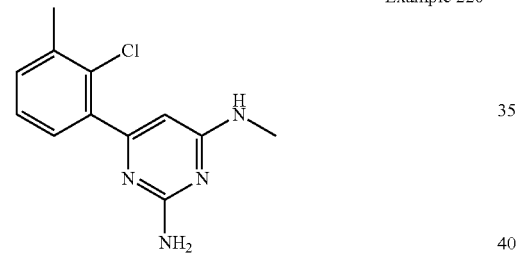
Example 227
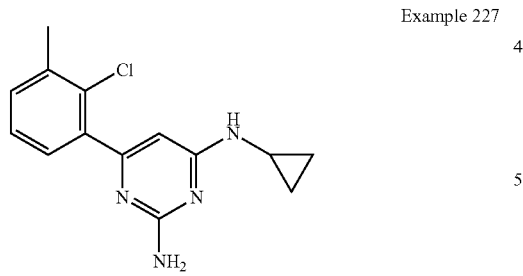
Example 228
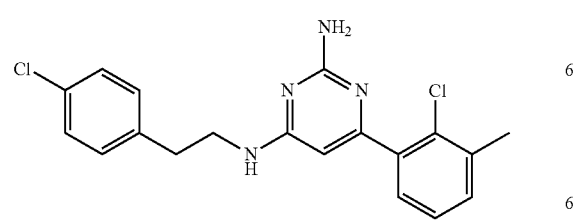
Example 229
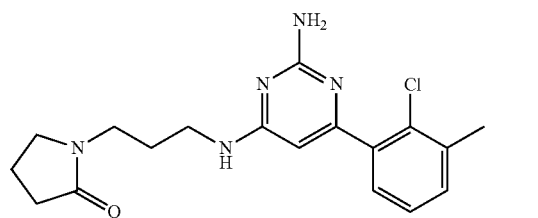
Example 230
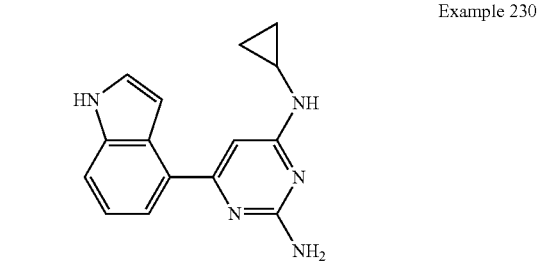
Example 231
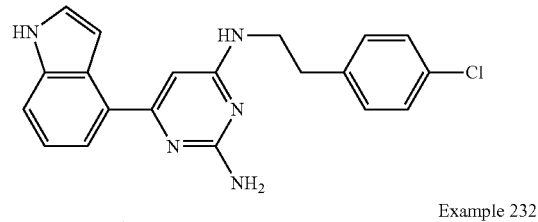
Example 232
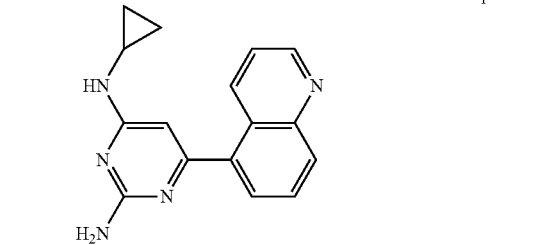
Example 233
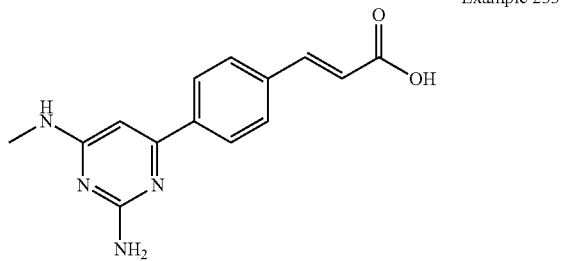
Example 234
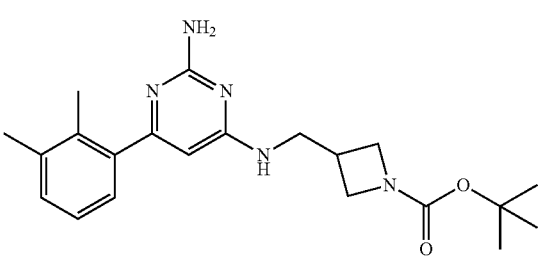

Example 235
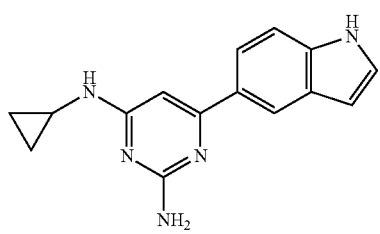
Example 236
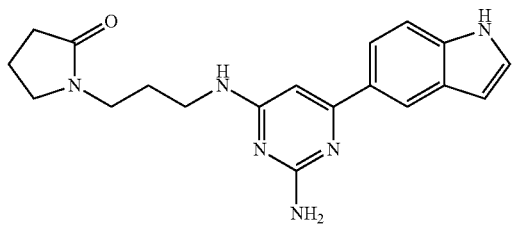
Example 237
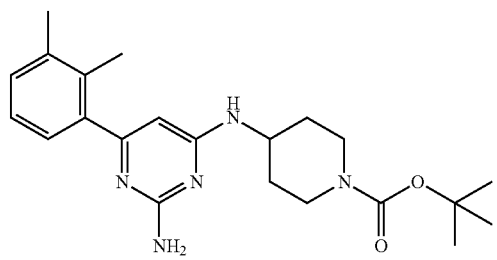
Example 238
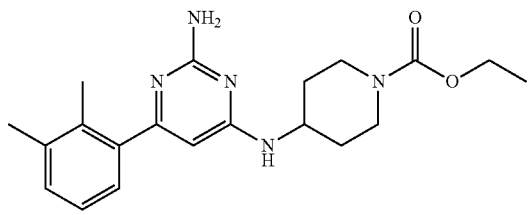
Example 239
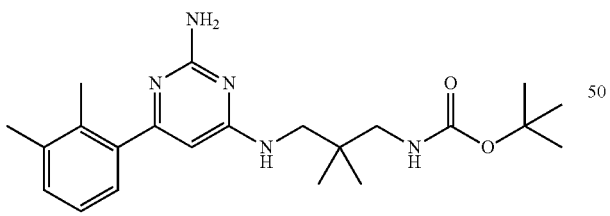
Example 240
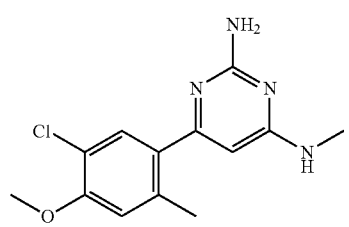
Example 241
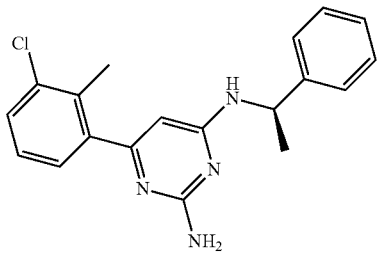
Example 242
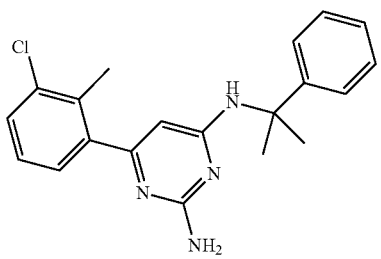
Example 243
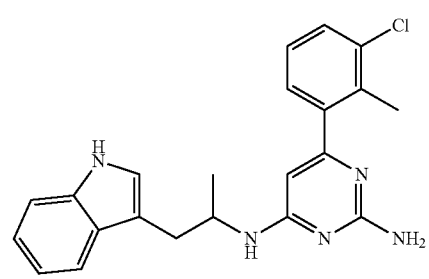
Example 244
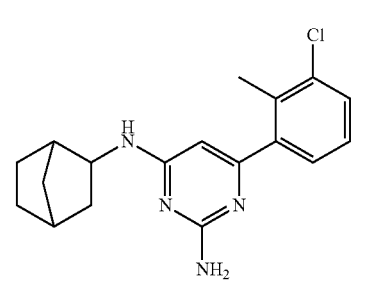
Example 245
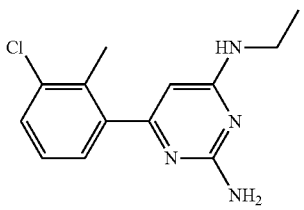
Example 246
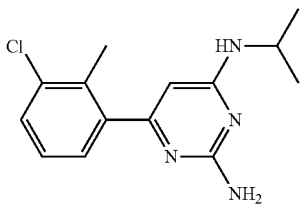

Example 247
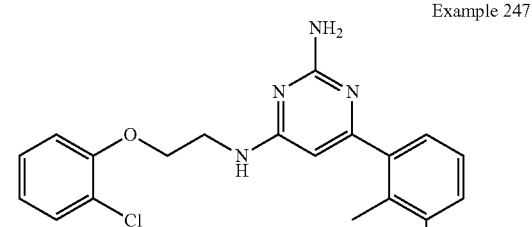
Example 248
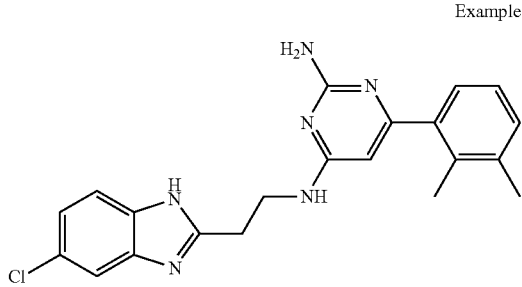
Example 249
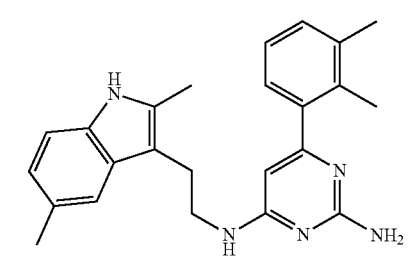
Example 250
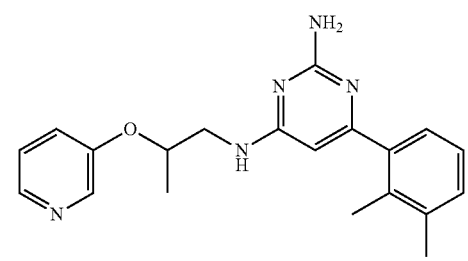
Example 251
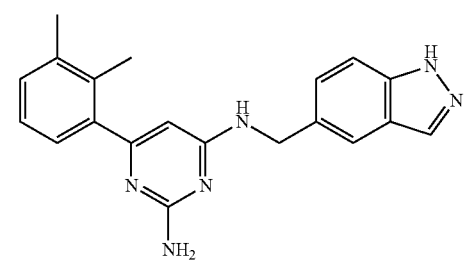
Example 252
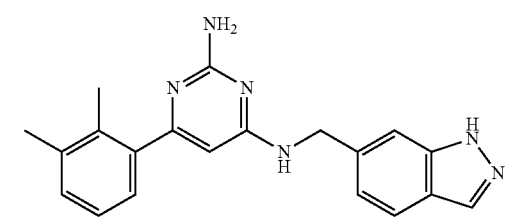
Example 253
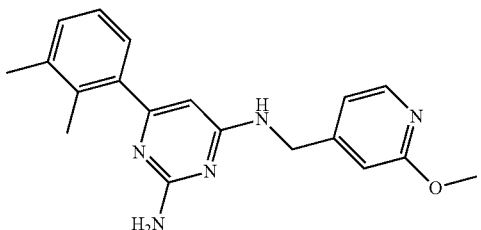
Example 254
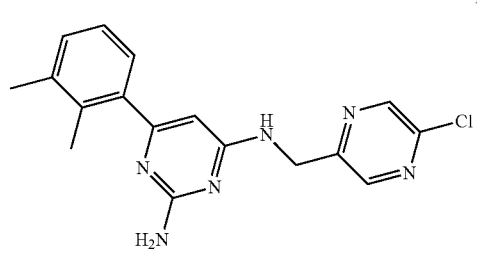
Example 255
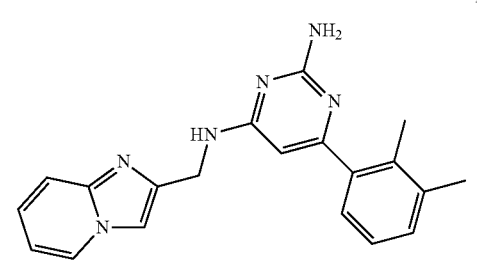
Example 256
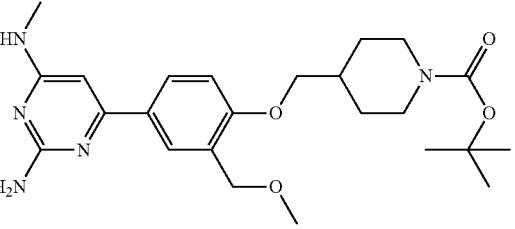
Example 257
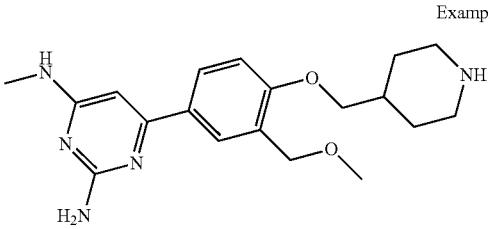
Example 258
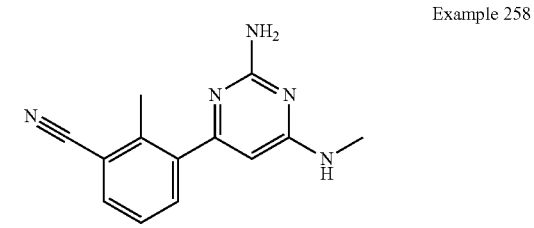

Example 259
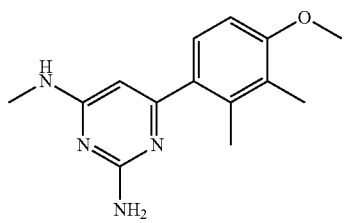
Example 260
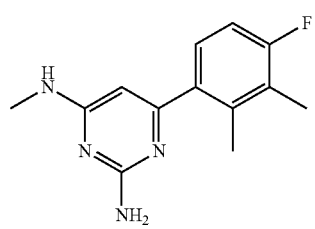
Example 261
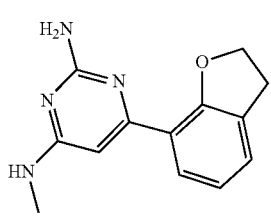
Example 262
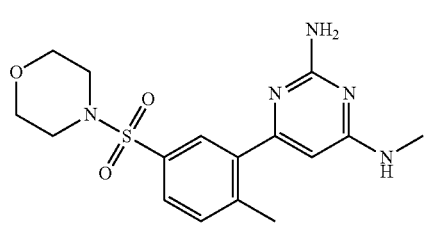
Example 263
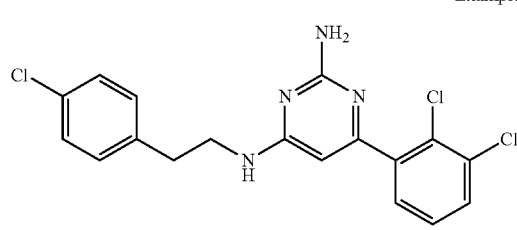
Example 264
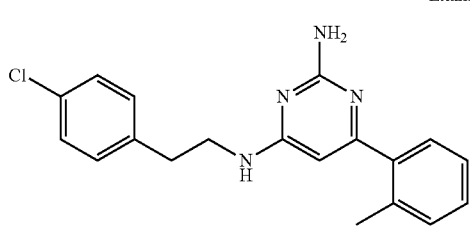
Example 265
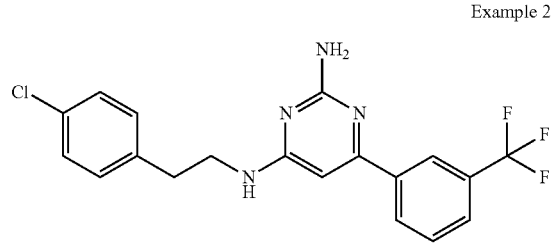
Example 266
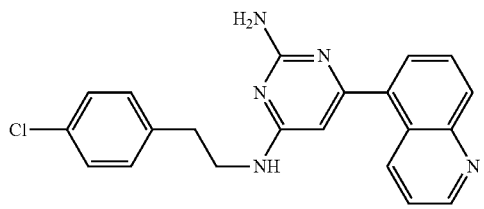
Example 267
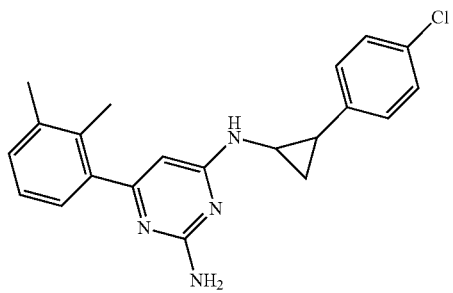
Example 268
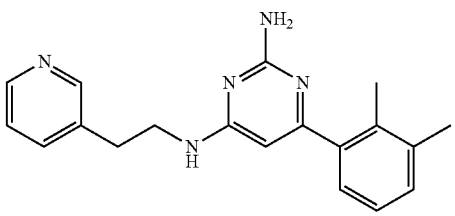
Example 269
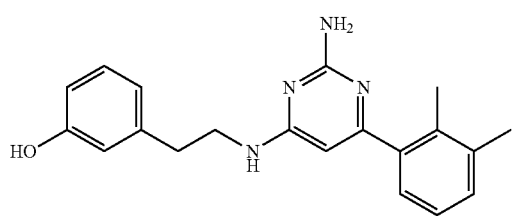
Example 270
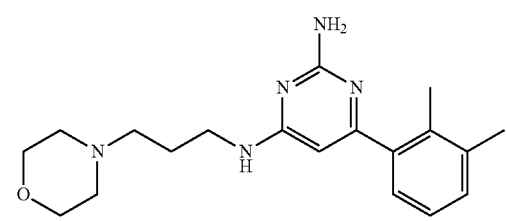
Example 271
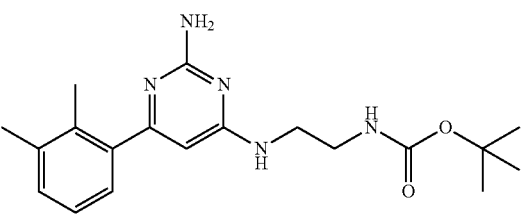

Example 272
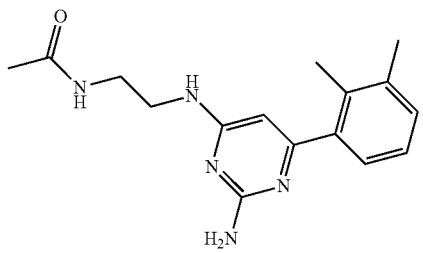
Example 273
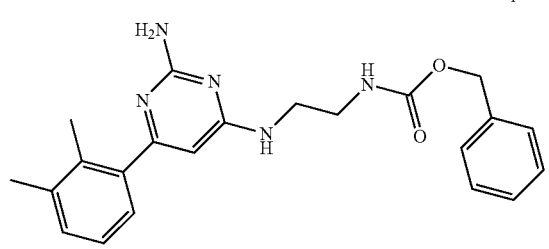
Example 274
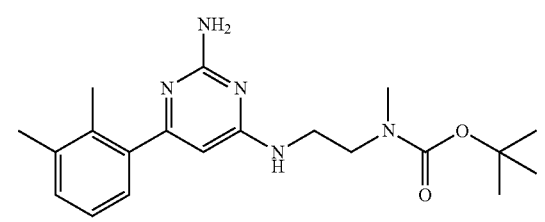
Example 275
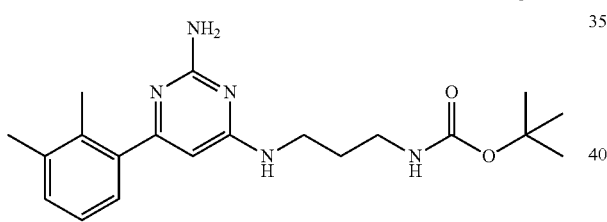
Example 276
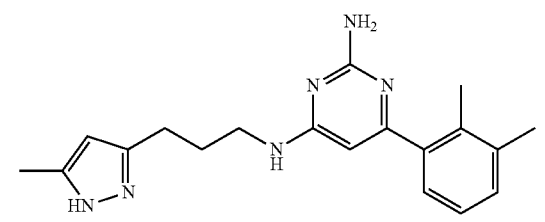
Example 277
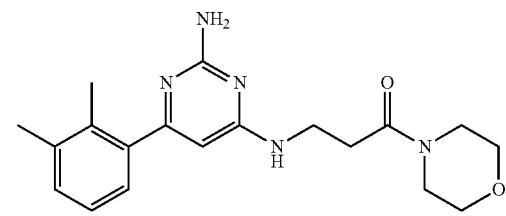
Example 278
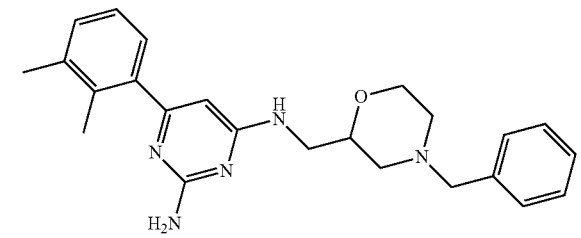
Example 279
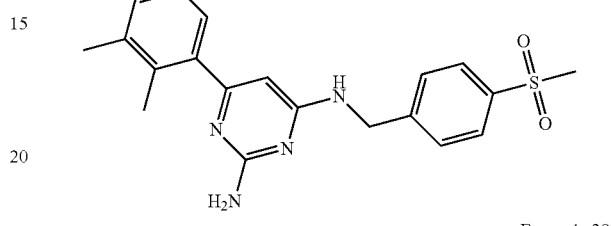
Example 280
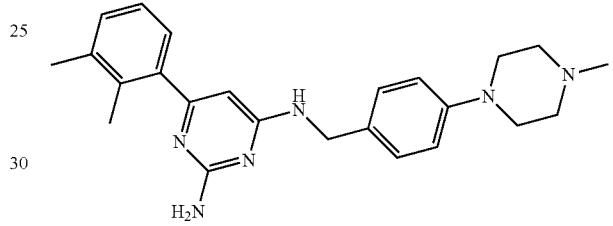
Example 281
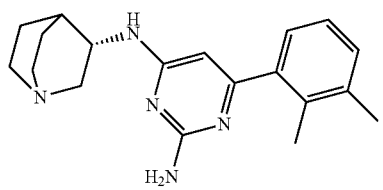
Example 282
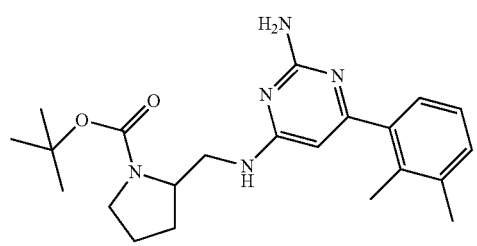
Example 283
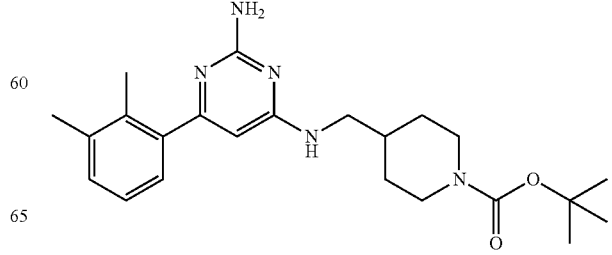

Example 284
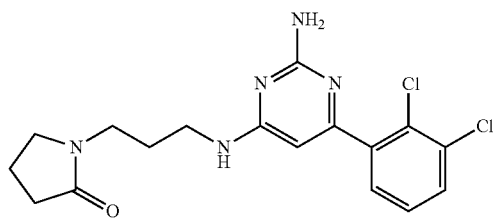
Example 285
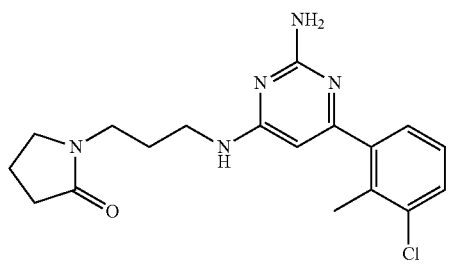
Example 286
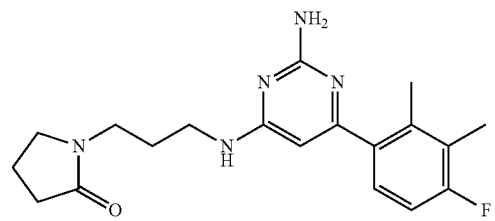
Example 287
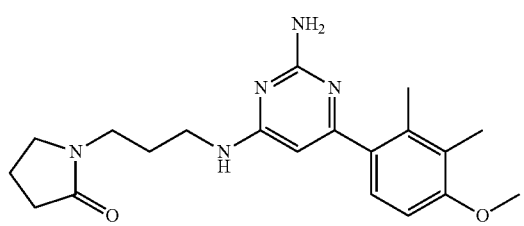
Example 288
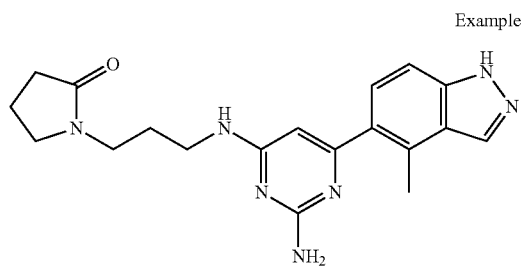
Example 289
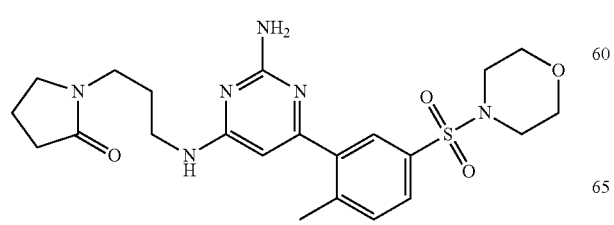
Example 290
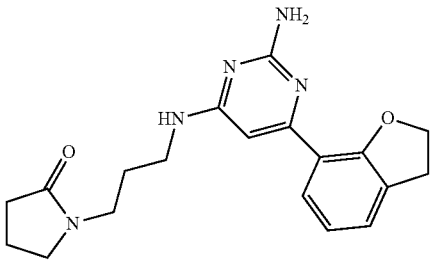
Example 291
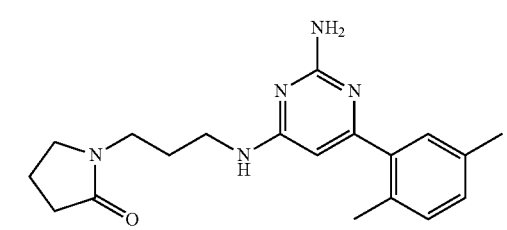
Example 292
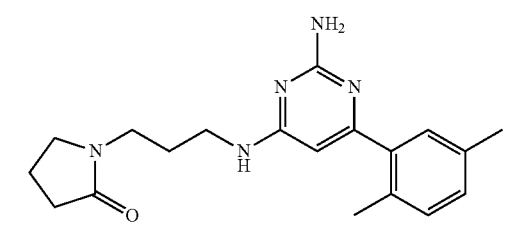
Example 293
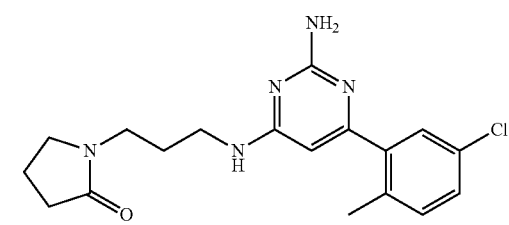
Example 294
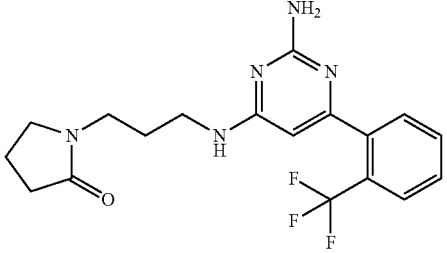
Example 295
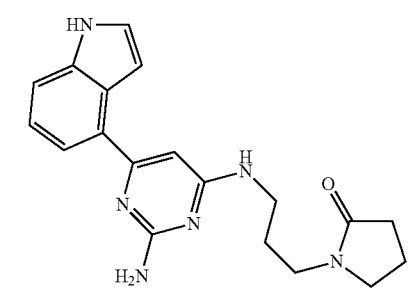

Example 296
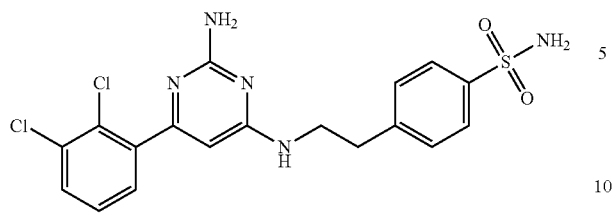
Example 297
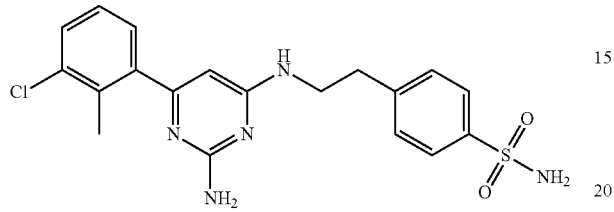
Example 298
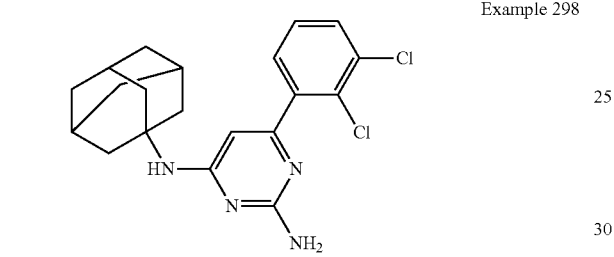
Example 299
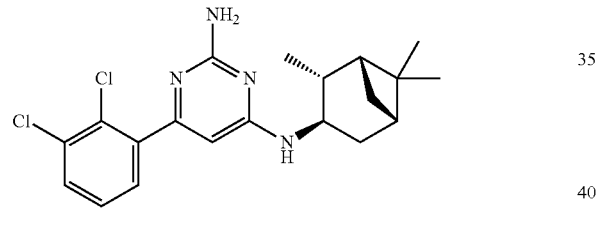
Example 300
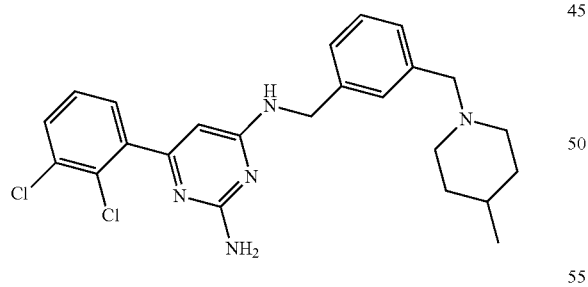
Example 301
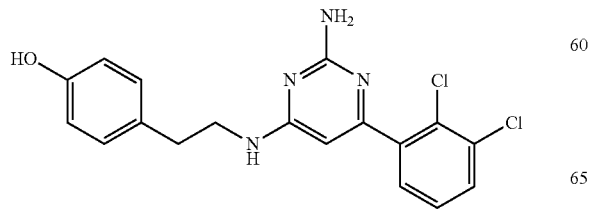
Example 302
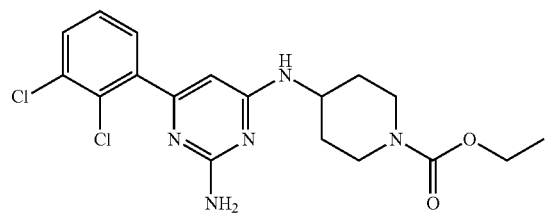
Example 303
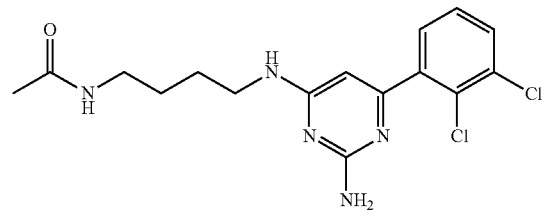
Example 304
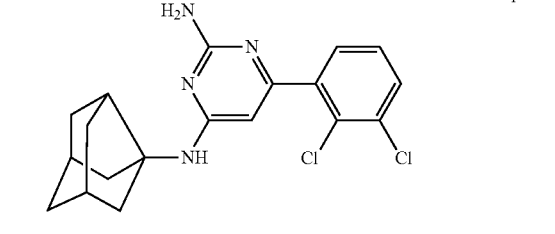
Example 305
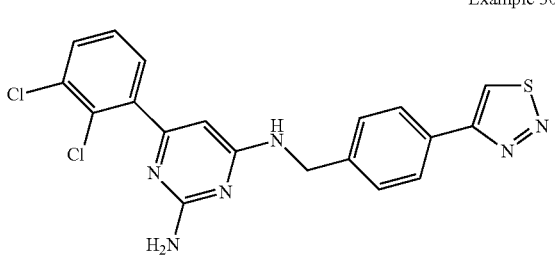
Example 306
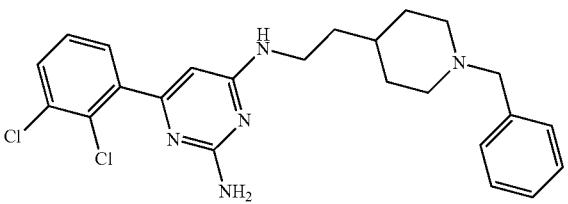
Example 307
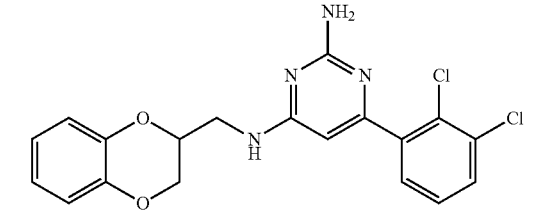

Example 308
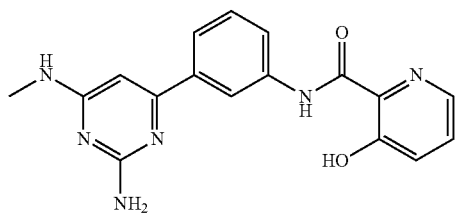
Example 309
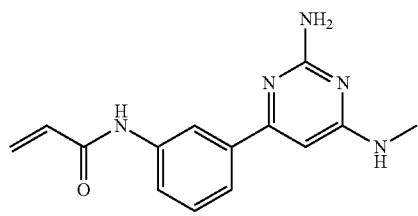
Example 310
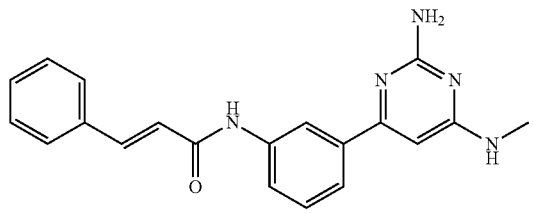
Example 311
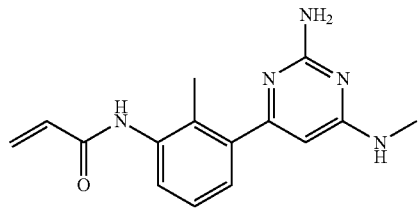
Example 312
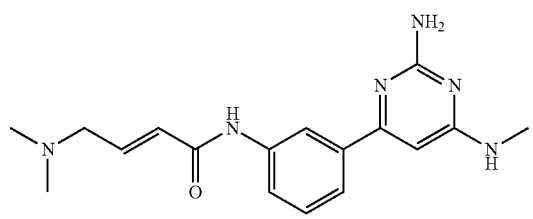
Example 313
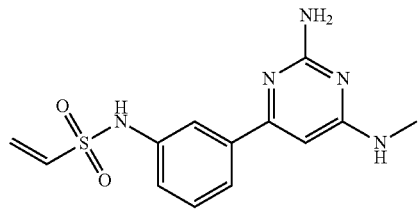
Example 314
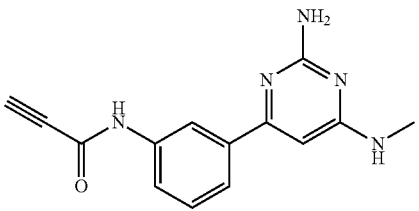
Example 315
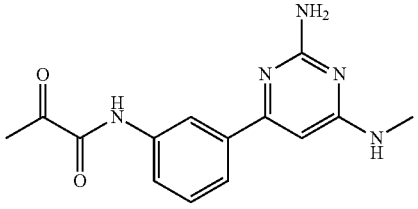
Example 316
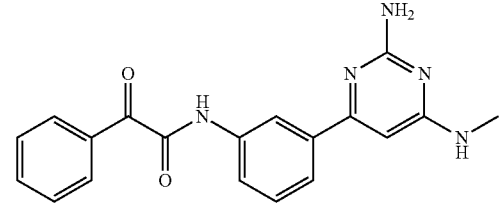
Example 317
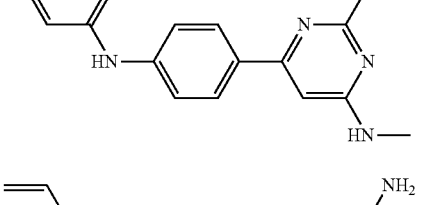
Example 318
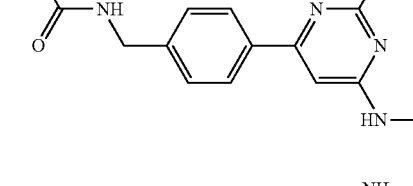
Example 319
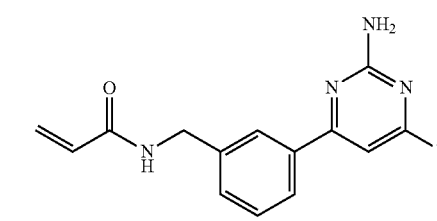
Example 320
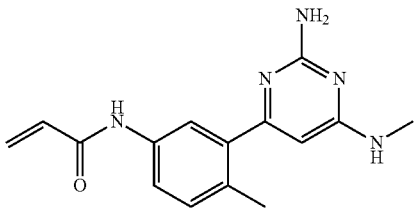

Example 321
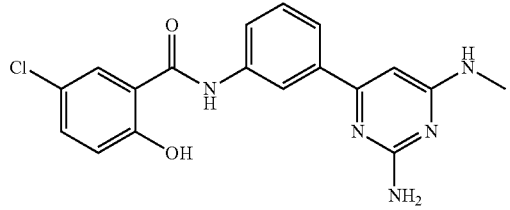
Example 322
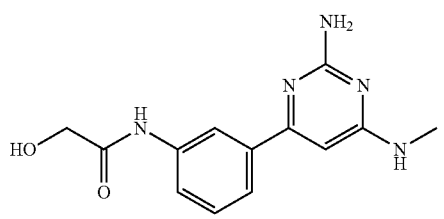
Example 323
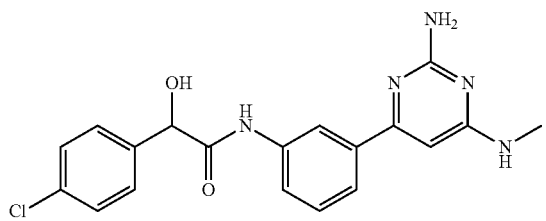
Example 324
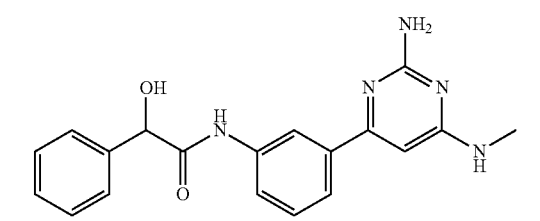
Example 325
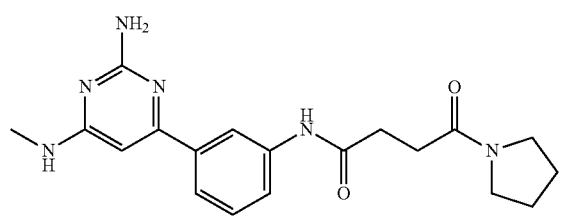
Example 326
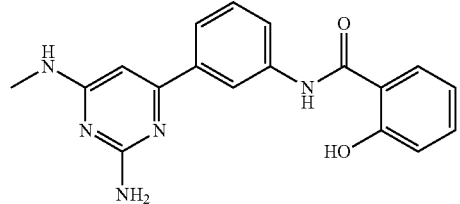
Example 327
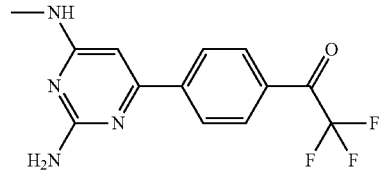
Example 328
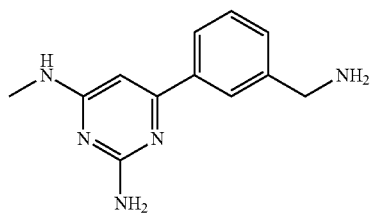
Example 329
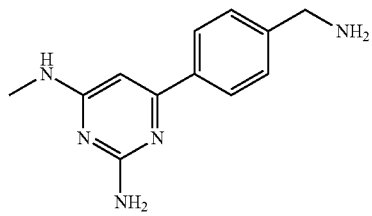
Example 330
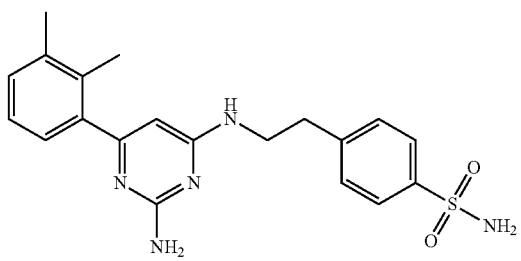
Example 331
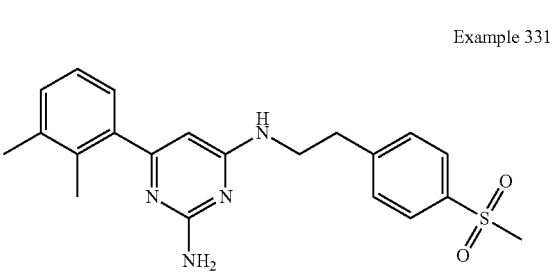
Example 332
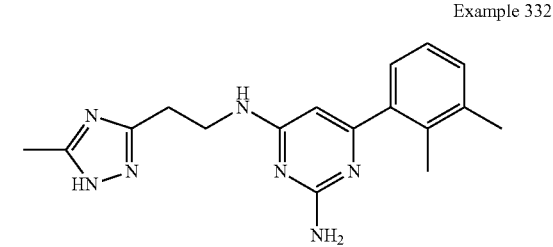
Example 333
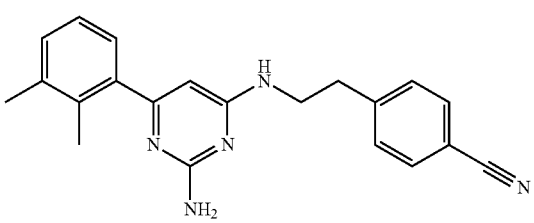

-continued

Example 334

Example 335

Example 336

Example 337

Example 338

Example 339

-continued

Example 340

Example 341

Example 342

Example 343

Example 344

Example 345

Example 346
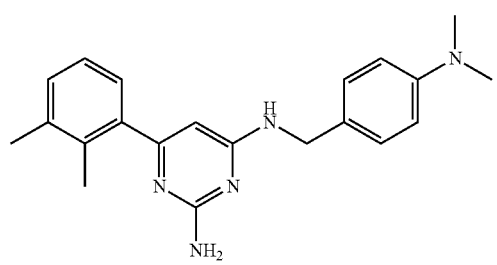
Example 347
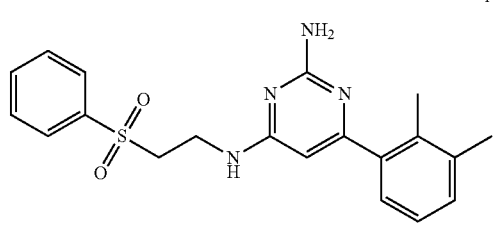
Example 348
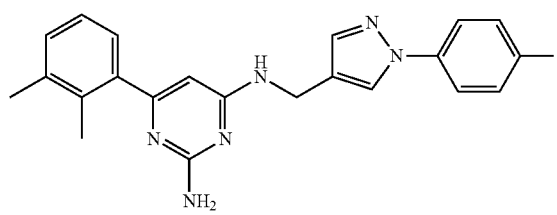
Example 349
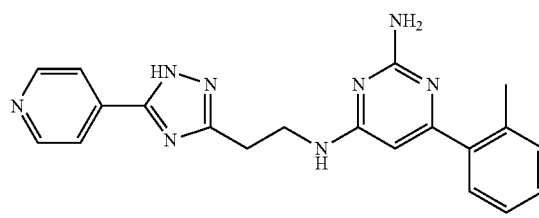
Example 350
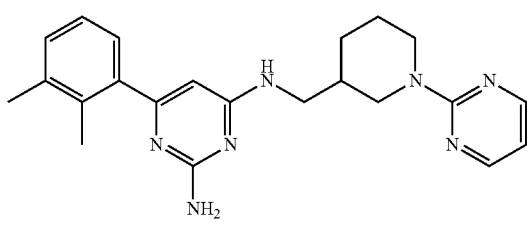
Example 351
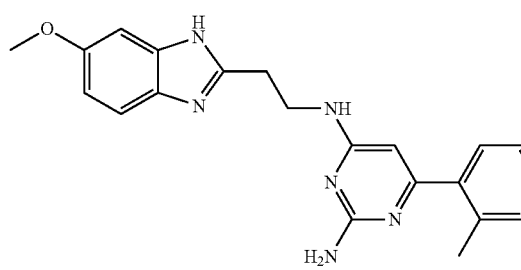
Example 352
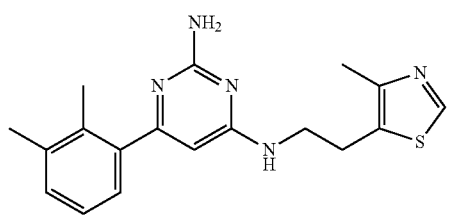
Example 353
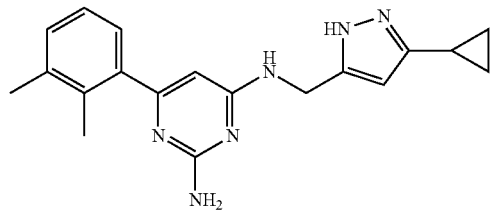
Example 354
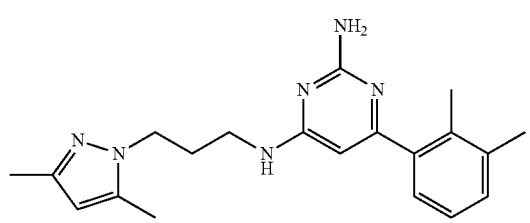
Example 355
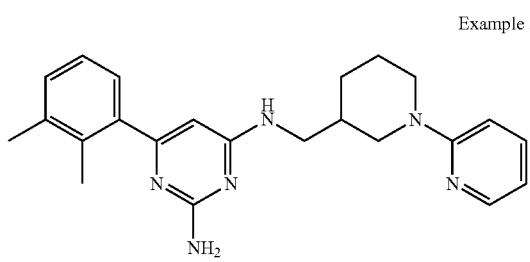
Example 356
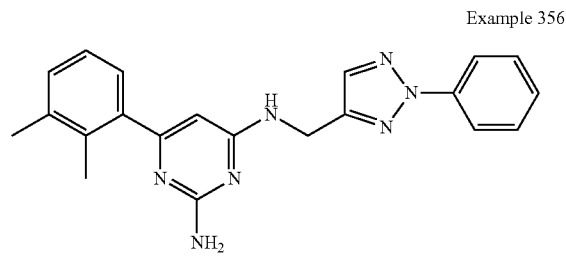
Example 357
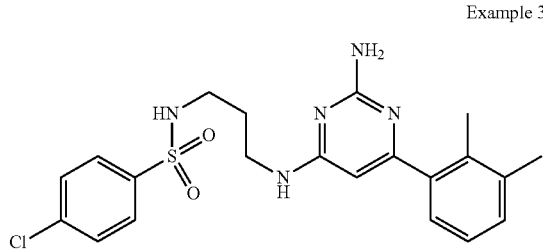

-continued
Example 358
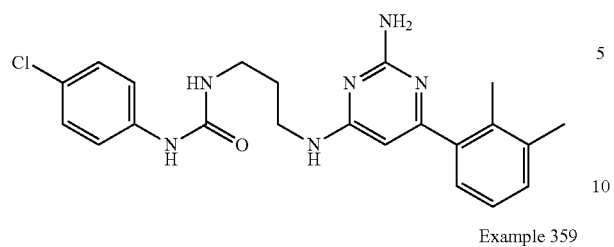
Example 359
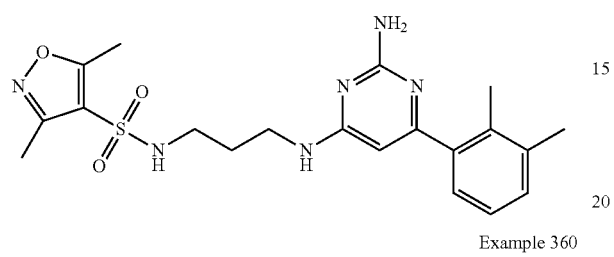
Example 360
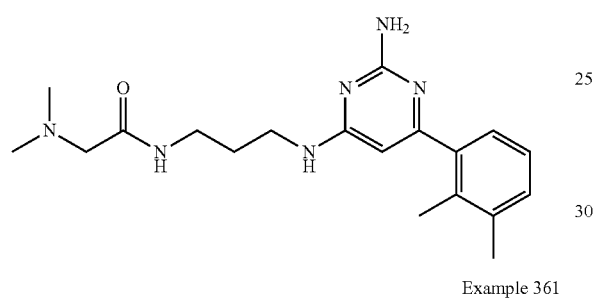
Example 361
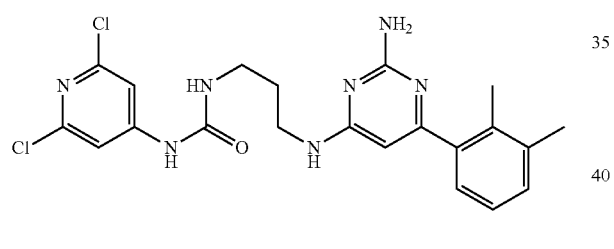
Example 362
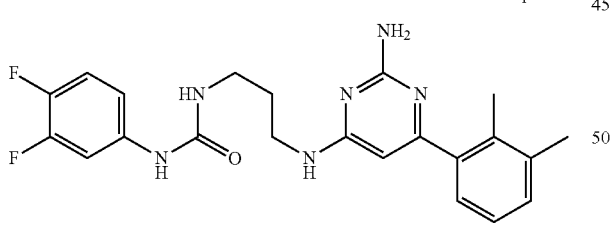
Example 363
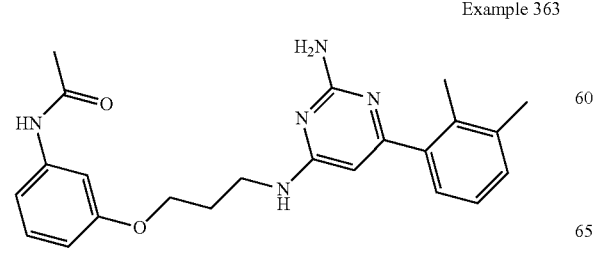
-continued
Example 364
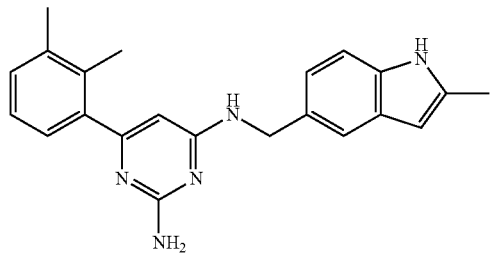
Example 365
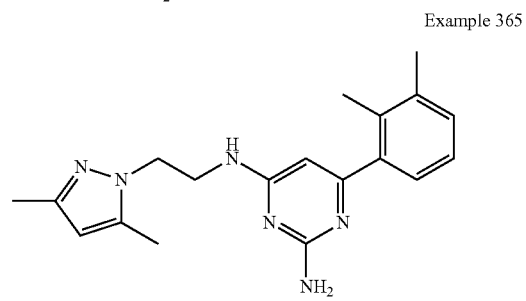
Example 366
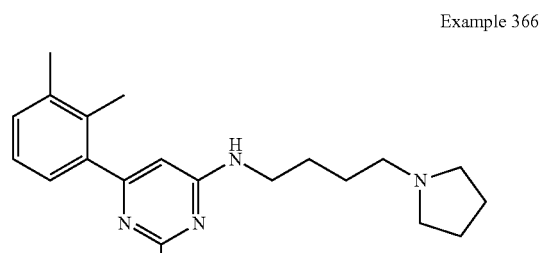
Example 367
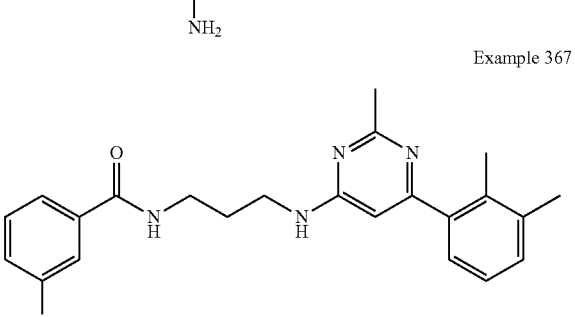
Example 368
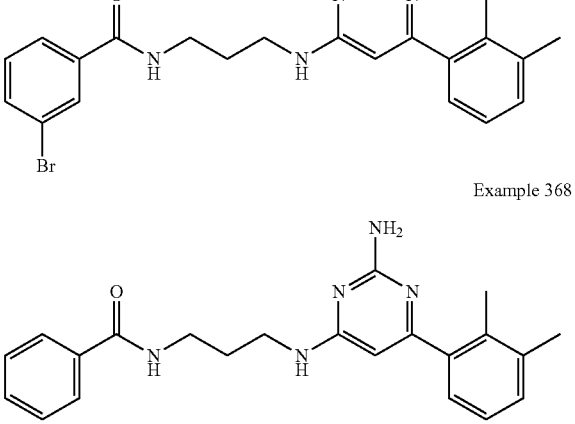
Example 369
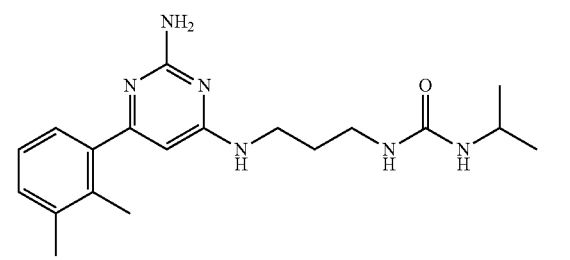

Example 370
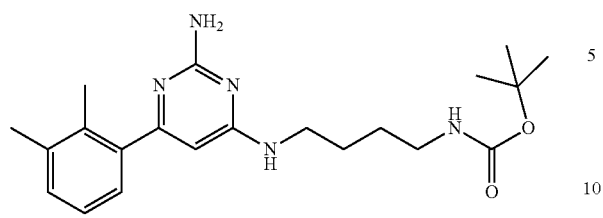
Example 371
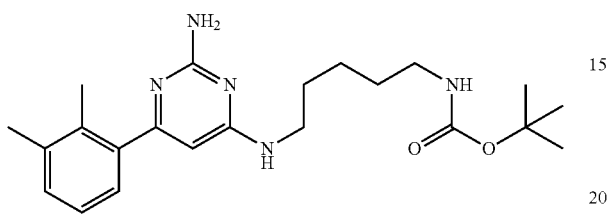
Example 372
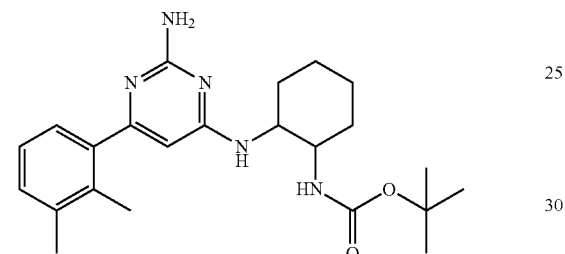
Example 373
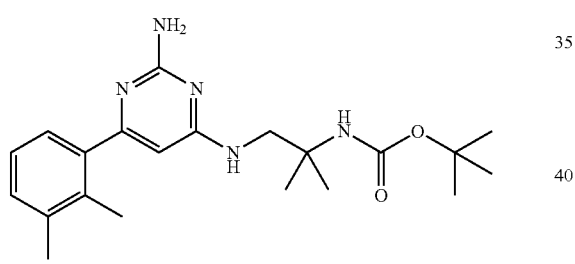
Example 374
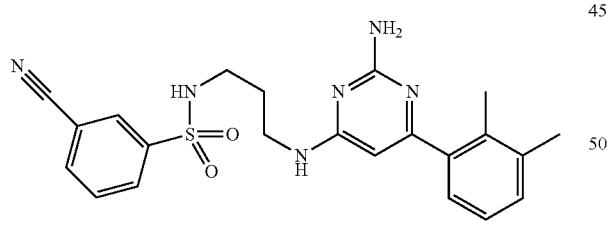
Example 375
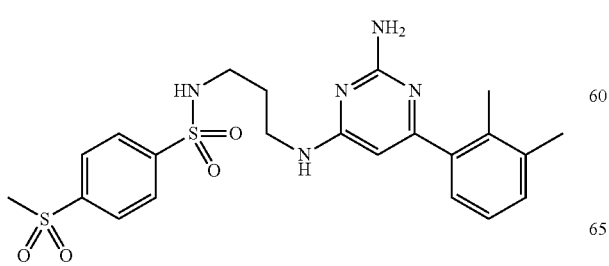
Example 376
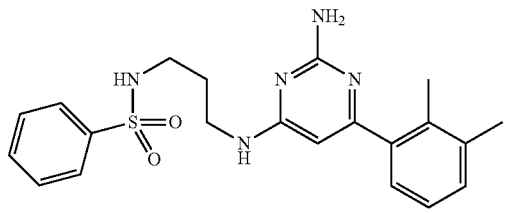
Example 377
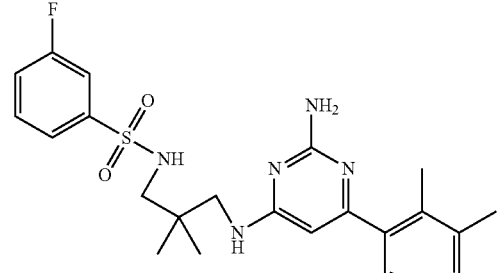
Example 378
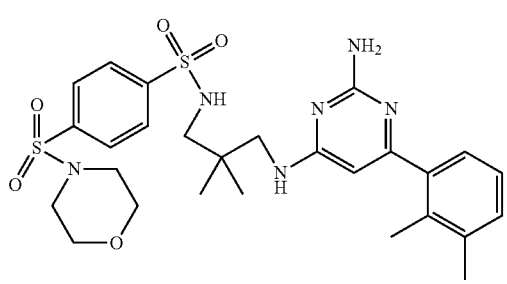
Example 379
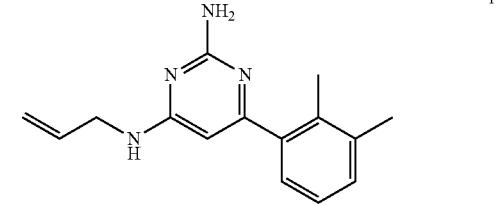
Example 380
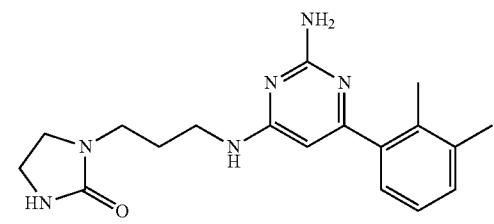
Example 381
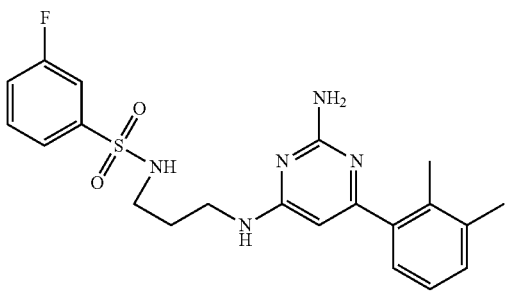

Example 382
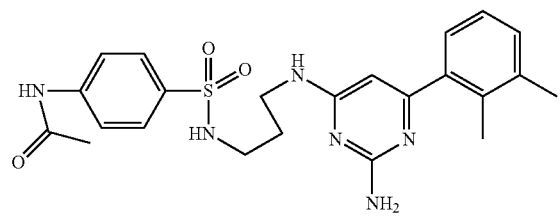
Example 383
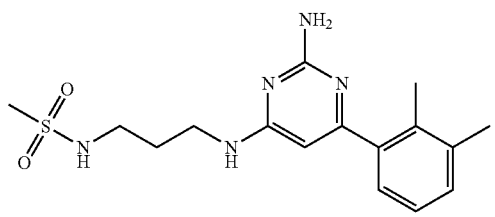
Example 384
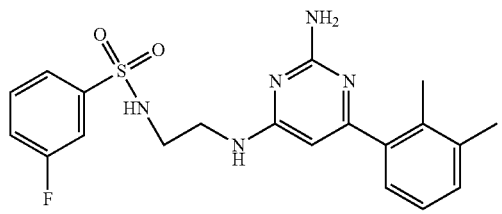
Example 385
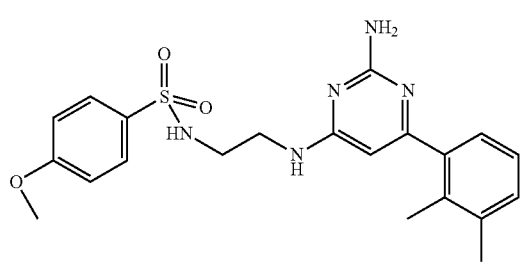
Example 386
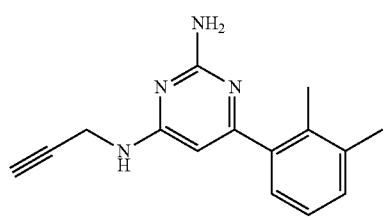
Example 387
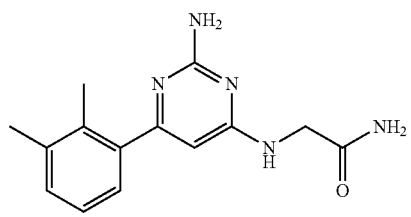
Example 388
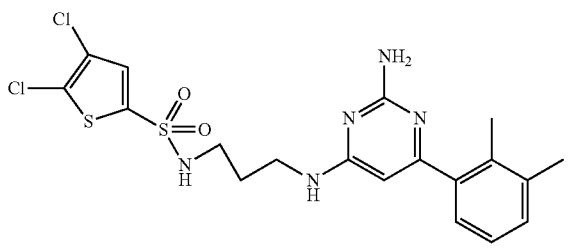
Example 389
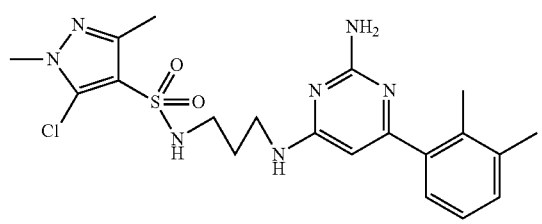
Example 390
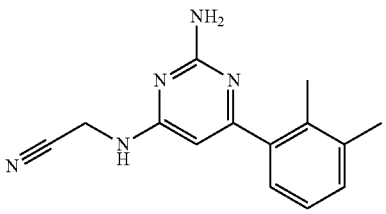
Example 391
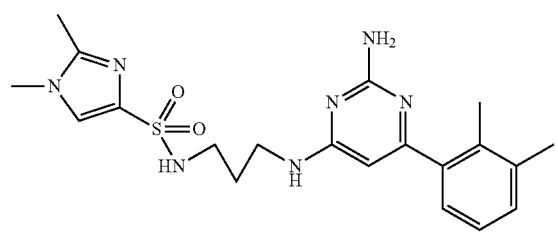
Example 392
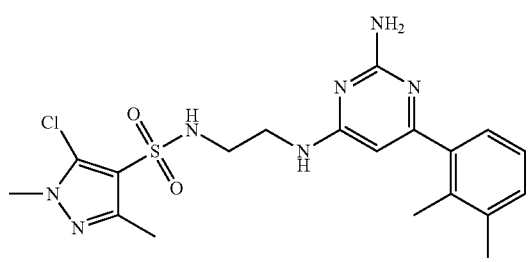
Example 393
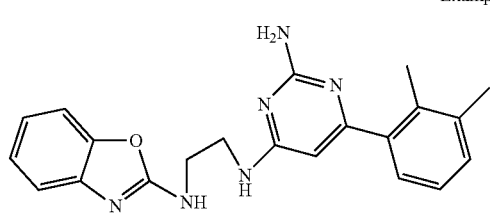

Example 394
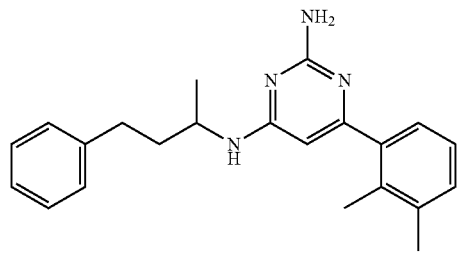
Example 395
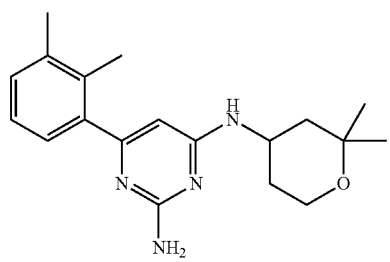
Example 396
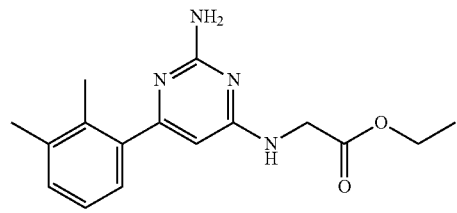
Example 397
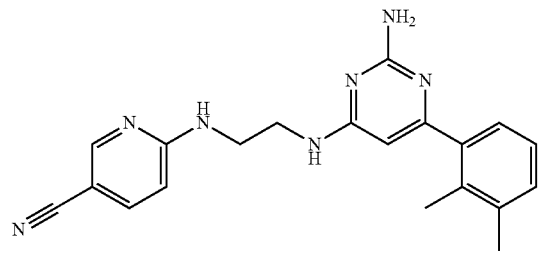
Example 398
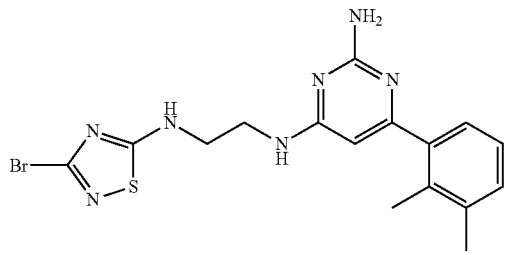
Example 399
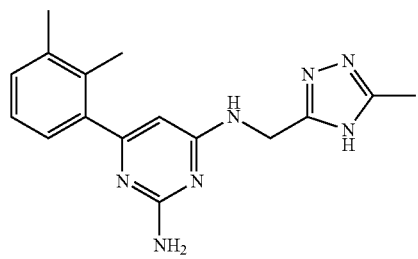
Example 400
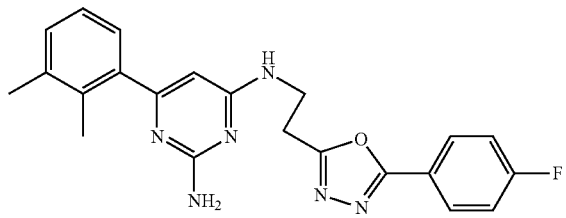
Example 401
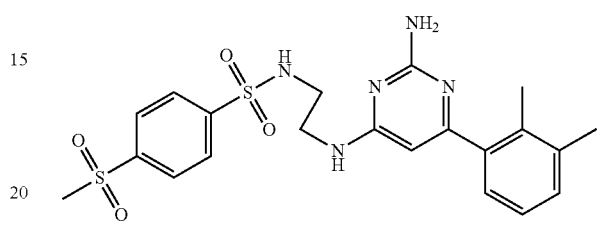
Example 402
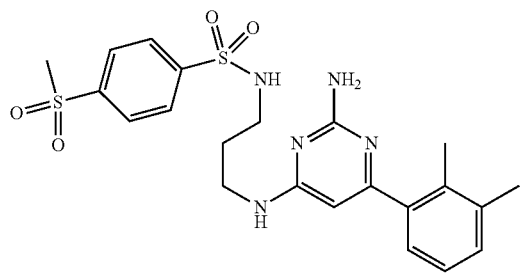
Example 403
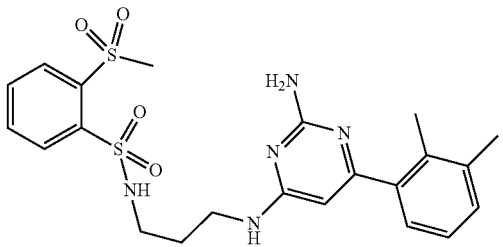
Example 404
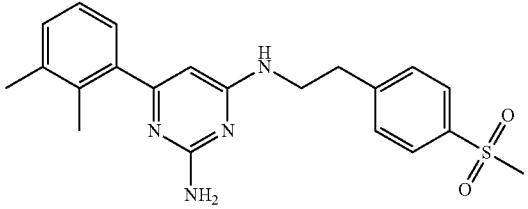
Example 405
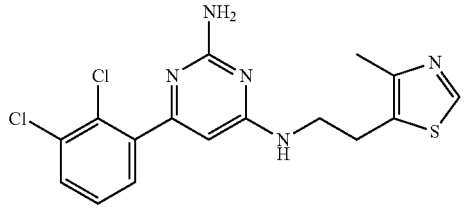

-continued

Example 406

Example 407

Example 408

Example 409

Example 410

Example 411

-continued

Example 412

Example 413

Example 414

Example 415

Example 416

Example 417

Example 418
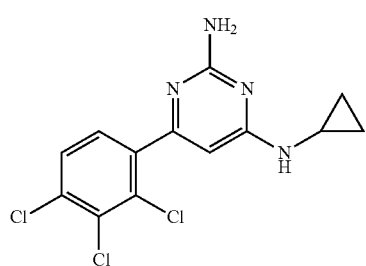
Example 419
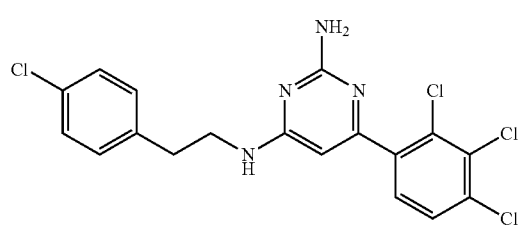
Example 420
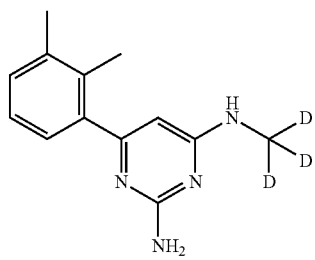
Example 421
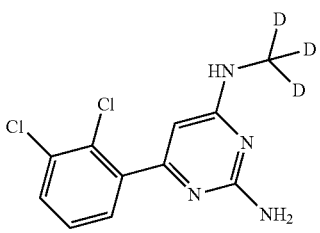
Example 422
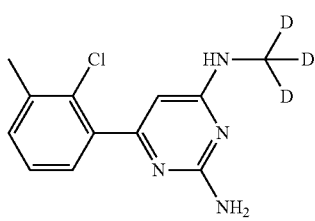
Example 423
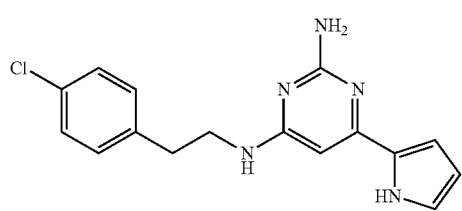
Example 424
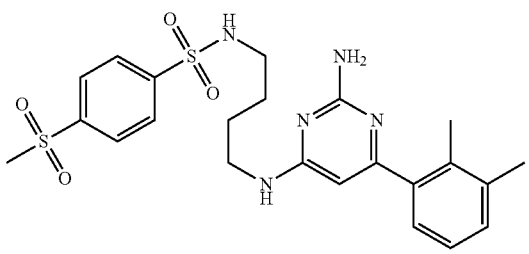
Example 425
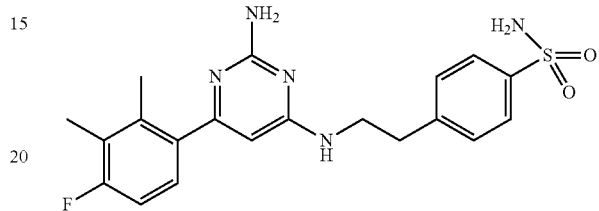
Example 426
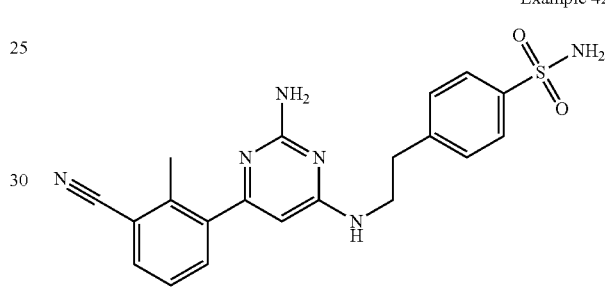
Example 427
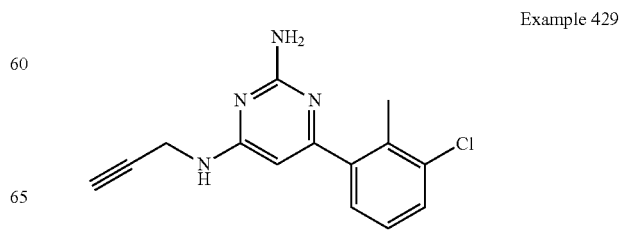
Example 428
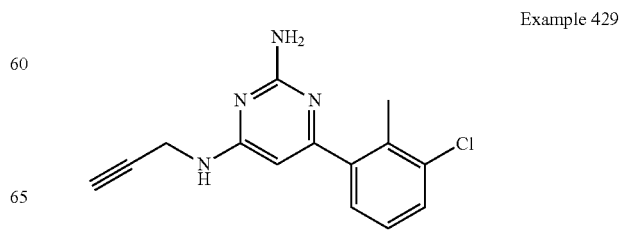
Example 429
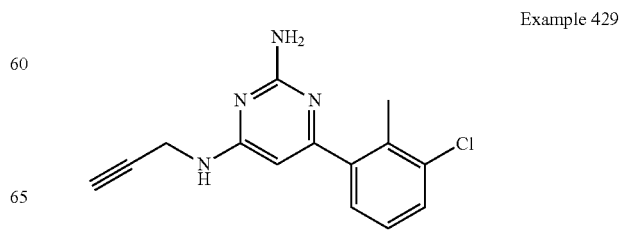

Example 430
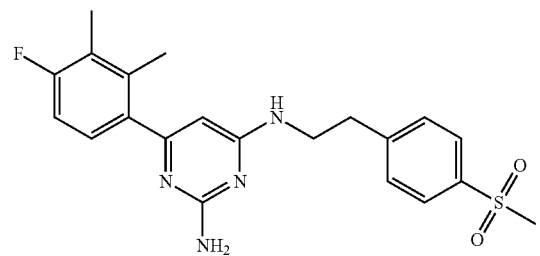
Example 431
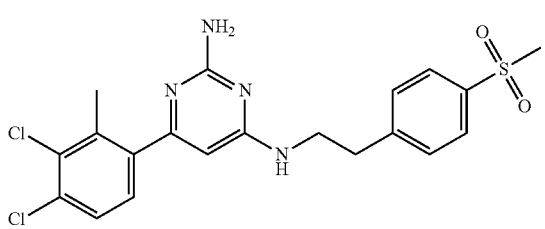
Example 432
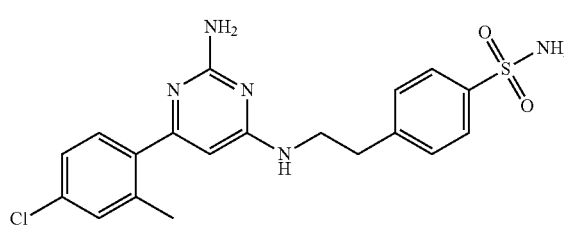
Example 433
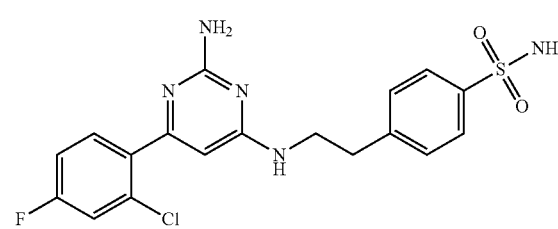
Example 434
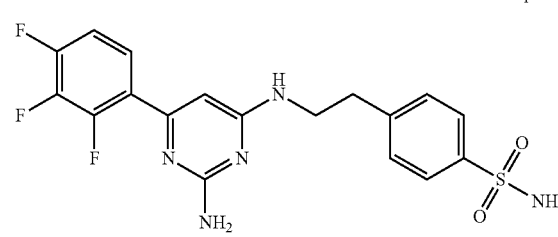
Example 435
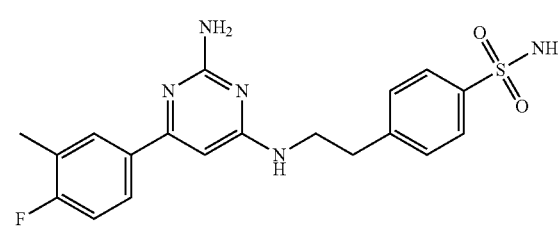
Example 436
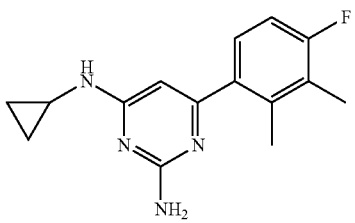
Example 437
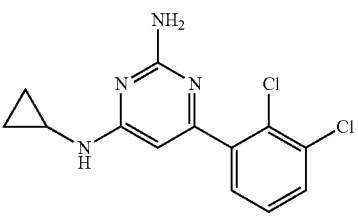
Example 438
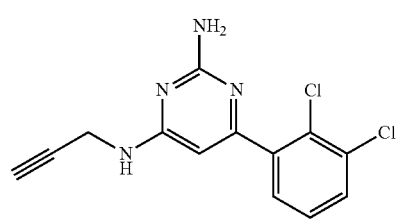
Example 439
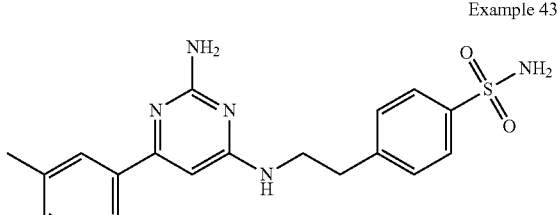
Example 440
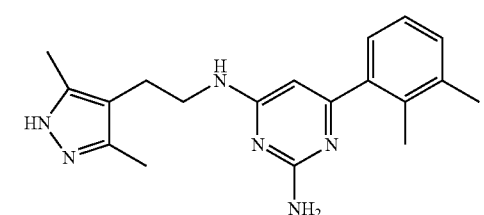
Example 441
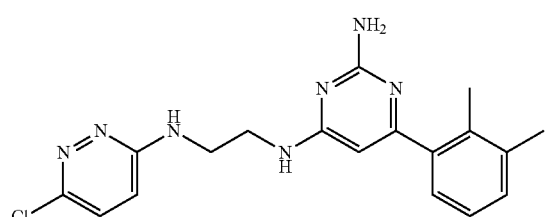
Example 442
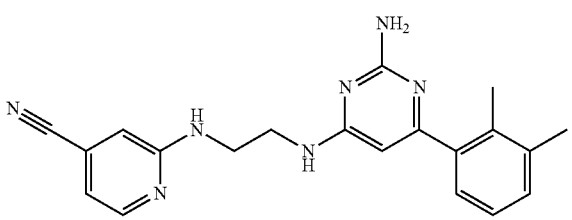

Example 443
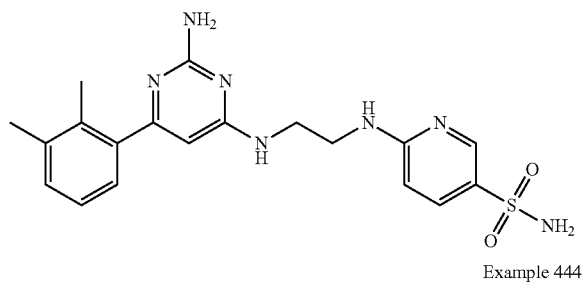
Example 444
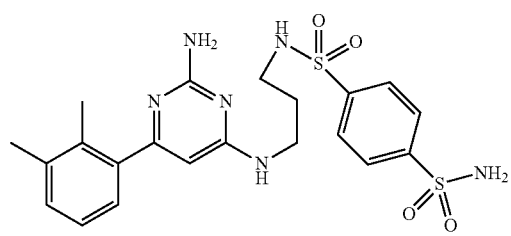
Example 445
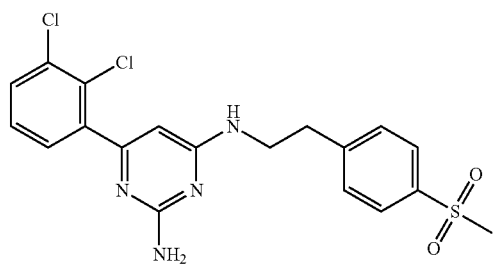
Example 446
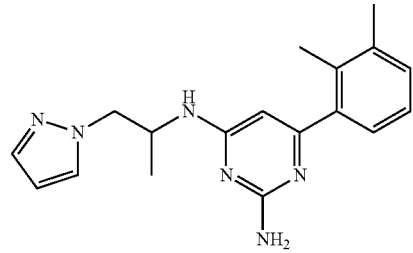
Example 447
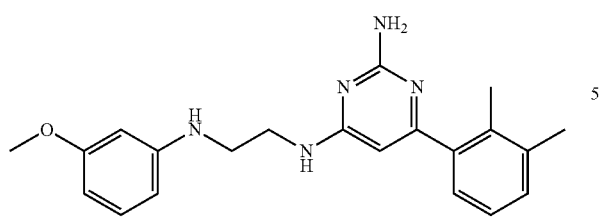
Example 448
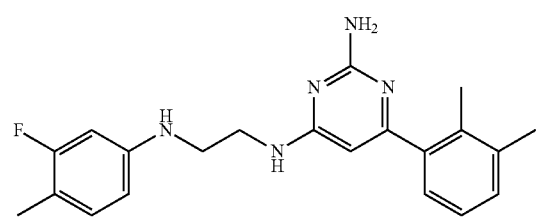
Example 449
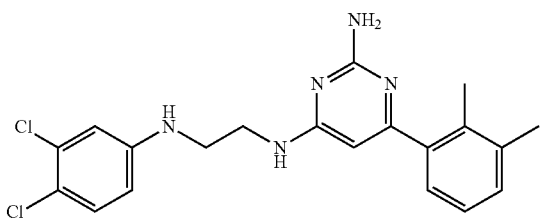
Example 450
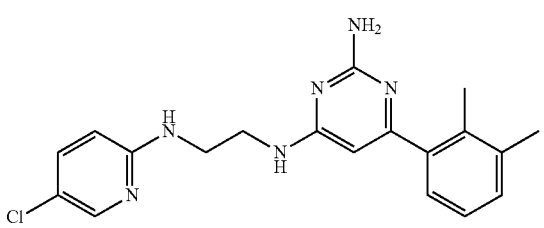
Example 451
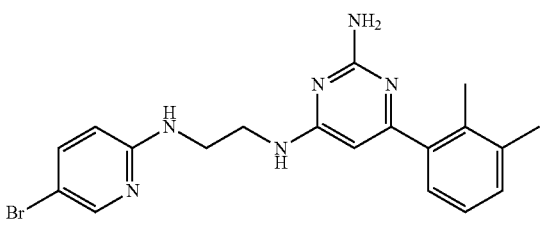
Example 452
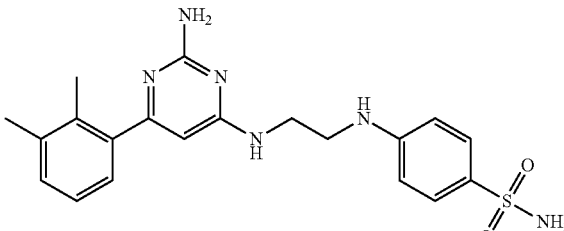
Example 453
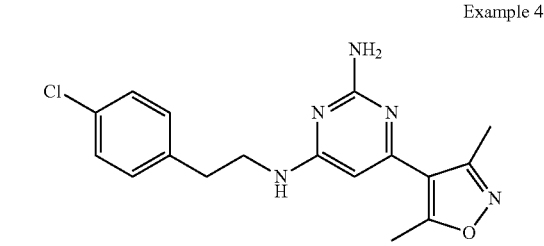
Example 454
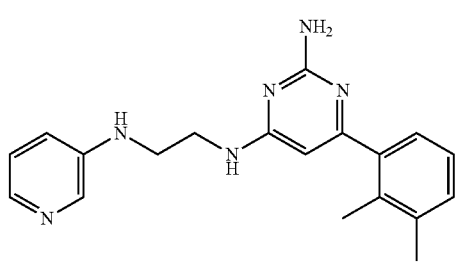

BIOLOGICAL EXAMPLES

Biological Example 1

MTH1 Enzymatic Assay and IC50 Value Determination

MTH1 catalyzes the hydrolysis of dGTP to dGMP and PPi. By coupling the reaction to pyrophosphatase added in excess PPi is converted to Pi that can be detected by using the malachite green assay reagent. Briefly, for $IC_{50}$ value determination the compound to be analyzed is diluted in assay buffer in a 1:3 dilution series generating 12 different compound concentrations giving a final DMSO concentration of 1% in the assay well. MTH1 diluted in assay buffer (100 mM Tris-acetate, 40 mM NaCl, 10 mM magnesium acetate, 1 mM DTT and 0.005% Tween 20) fortified with *E. coli* pyrophosphatase (0.8 U/ml) is added to a final concentration of 4.8 nM. dGTP diluted in assay buffer is added to a final concentration of 100 µM. The reaction mixture is incubated with shaking for 15 minutes at 22° C. To 100 µl reaction mixture is 25 µl Malachite green assay regent (0.095% Malachite green in 17% $H_2SO_4$, 1.5% Ammonium molybdate, 0.17% Tween 20) added followed by incubation with shaking for 15 minutes at 22° C. The absorbance of the assay plate is read at 630 nm using an EnVision Multilabel plate reader. The $IC_{50}$ value is determined by fitting a dose response curve to the data points using nonlinear regression analysis and the equation Y=Bottom+(Top−Bottom)/(1+10^((Log $IC_{50}$−X)*HillSlope)), where Y is the read absorbance at 630 nm and X is log [compound].

Using this approach the following representative $IC_{50}$ values were derived. Examples—4, 6, 11, 18, 31, 32, 35, 36, 40, 43, 44, 46, 51, 52, 55, 56, 57, 59, 64, 65, 66, 67, 72, 73, 74, 77, 79, 80, 81, 85, 87, 89, 90, 93, 97, 98, 101, 103, 105, 108, 110, 111, 115, 120, 126, 127, 129, 131, 132, 135, 141, 142, 144, 146, 148, 149, 151, 159, 164, 165, 168, 171, 173, 174, 175, 192, 197, 198, 201, 202, 203, 208, 209, 210, 211, 213, 215, 219, 220, 222, 226, 227, 228, 230, 231, 232, 244, 245, 246, 249, 252, 254, 256, 257, 259, 260, 264, 266, 267, 269, 273, 275, 276, 282, 295, 296, 300, 301, 304, 308, 312, 313, 315, 316, 317, 322, 323, 324, 326, 327, 329, 330, 331, 333, 334, 335, 336, 343, 346, 348, 349, 350, 351, 359, 361, 363, 367, 374, 376, 379, 381, 386, 389, 391, 397, 402, 403, 404, 405, 406, 408, 409, 411, 415, 416, 418, 419, 420, 422, 424, 426, 428, 429, 430, 432, 434, 436, 439, 443, 444, 445, 447, 451, 453, 454 had $IC_{50}$'s of less than 200 nM Examples—3, 8, 9, 10, 17, 22, 24, 25, 42, 45, 54, 60, 95, 96, 102, 113, 117, 119, 150, 154, 157, 160, 162, 169, 178, 186, 199, 212, 225, 229, 236, 238, 241, 242, 255, 265, 270, 272, 278, 284, 285, 286, 287, 288, 290, 291, 292, 293, 294, 298, 302, 306, 318, 319, 320, 339, 340, 347, 353, 354, 358, 360, 365, 366, 368, 369, 373, 377, 378, 380, 383, 384, 387, 390, 392, 395, 410, 413, 423, 446 had $IC_{50}$'s of between 200 nM and 2 µM Examples—5, 12, 14, 15, 20, 21, 78, 112, 161, 166, 167, 179, 180, 181, 182, 237, 277, 281, 289, 299, 345, 372, 396, 399 had $IC_{50}$'s of between 2 µM and 10 µM

Biological Example 2

MTH1 siRNA Knock Down and Cell Survival

Cells were cultivated in suitable medium supplemented with 10% FBS and 10 U/ml PeSt. On day 1, cells were seeded at approximately 30% confluency in 6-well plates in complete medium. The day after, the medium was aspired and fresh medium without antibiotics was added. The cells were transfected with All-stars Non-targeting RNA (NT RNA, Qiagen) and MTH1 siRNA (5'-CGACGACAGC-UACUGGUUU-3') and Interferin (Polyplus) according to the manufacturer's protocol. On day 5, cells were either trypsinized, counted and re-seeded for clonogenic outgrowth on 10-cm plates at 500 cells/plate or washed with PBS and scraped in lysis buffer (10 mM Hepes pH 7.1, 50 mM NaCl, 0.3 M sucrose, 0.1 mM EDTA, 0.5% Triton X100, 1 mM DTT and 1× protease inhib. cocktail (Pierce)) and processed for Western blot. Blots were stained with anti-MTH1 antibody (rabbit polyclonal, HPA, KTH, Sweden) and anti-tubulin (mouse monoclonal, Sigma Aldrich). After additional 7-10 days, survival plates were fixed/stained with 4% methylene blue in MeOH and colonies were counted manually. FIG. 1 shows the effect on cell survival following MTH1 siRNA depletion in various human cancer and normal cell lines.

Biological Example 3

Cell Survival Assay

Figure 2:
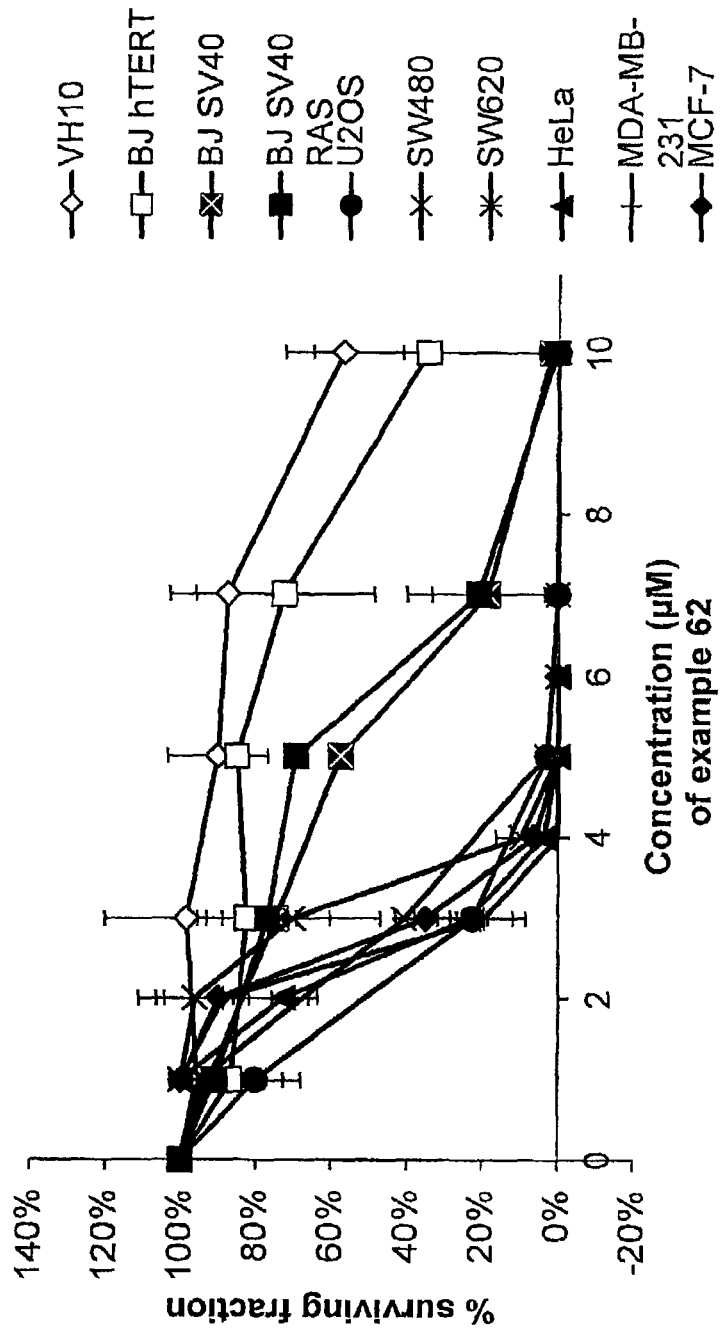
FIG. 2. MTH1 inhibitor reduce cell survival in various cancer cell lines, with less effect on normal immortalised cells (VH10 and BJ hTERT)

Cells are cultured in DMEM GlutaMAX™ or other suitable cell medium and plated in cell culture dishes (100 mm×20 mm) (500 cells/dish) and incubated in 5% $CO_2$ at 37° C. After 5 hours of incubation cells are treated with compound at various concentrations and left in the incubator for 7-14 days dependent on cell line. Clonogenic survival is measured by fixating and staining the cells with methylene blue (4 g/L in methanol) and number of colonies are counted and compared to vehicle treated dishes. FIG. 2 shows how an MTH1 inhibitor reduces cell survival in various cancer cell lines, with less effect on normal immortalised cells (VH10 and BJ hTERT).

Biological Example 4

Cell Viability Assay

Cells are seeded into 96 well plates (1500 cells/well) in DMEM GlutaMAX™ or other suitable media dependent on cell line and incubated overnight in 5% $CO_2$, 37° C. Thereafter cells are treated with compound or vehicle and left in incubator for 3 days until staining with resazurin. Cells are incubated in resazurin (diluted in suitable media) at 37° C. for 2 hours before measuring the fluorescence.

The invention claimed is:
1. A compound of formula I,

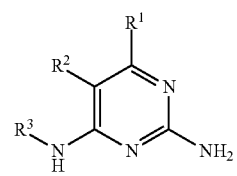

(I)

or a pharmaceutically acceptable salt thereof,
wherein:
$R^1$ represents
heteroaryl selected from benzofuran-3-yl, benzothiophen-3-yl, dihydrobenzofuran-7-yl, indol-3-yl, indol-4-yl, indol-5-yl, isoquinolin-4-yl, isoxazol-4-yl, pyridin-3-yl, pyridin-4-yl, pyrrol-2-yl and quinolin-5-yl, which heteroaryl ring is substituted by one or more substituents selected from $Y^1$, —$C_{1-6}$alkyl optionally substituted by one or more $Y^2$ and heterocycloalkyl optionally substituted by one or more $Y^3$; or aryl represented by

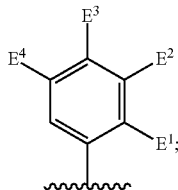

$E^1$ represents H, $Y^{1a}$, or —$C_{1-6}$alkyl optionally substituted by one or more $Y^2$;

$E^2$, $E^3$ and $E^4$ are selected from H, $Y^{1b}$ and —$C_{1-6}$alkyl optionally substituted by one or more $Y^2$; and at least one of $E^2$, $E^3$ and $E^4$ represents $Y^{1b}$ or —$C_{1-6}$alkyl optionally substituted by one or more $Y^2$;

$R^2$ represents hydrogen or methyl;

$R^3$ represents —$C_{1-12}$alkyl optionally substituted by one or more $Z^1$ or heterocycloalkyl optionally substituted by one or more $Z^2$; or $R^2$ and $R^3$ are linked together to form, along with the atoms to which they are attached, a 5-or 6-membered non-aromatic ring, wherein the link formed by $R^2$ and $R^3$ is optionally substituted by one or more substituents selected from $Z^3$ and —$C_{1-9}$alkyl optionally substituted by one or more $Z^4$;

each $Y^1$ independently represents halogen, —CN, —C(O)$R^a$, —C(O)N($R^b$)$R^c$, —C(O)O$R^d$, —N($R^e$)$R^f$, —N($R^g$)C(O)$R^h$, —N($R^i$)C(O)O$R^j$, —N($R^k$)C(O)N($R^l$)$R^m$, —NO$_2$, —N($R^n$)S(O)$_2$$R^o$, —O$R^p$, —OC(O)$R^q$, —OS(O)$_2$$R^r$, —S(O)$_m$$R^s$, —S(O)$_2$N($R^t$)$R^u$, heterocycloalkyl optionally substituted by one or more substituents selected from $W^2$, aryl optionally substituted by one or more substituents selected from $W^3$ or heteroaryl optionally substituted by one or more substituents selected from $W^3$;

$Y^{1a}$ represents halogen, —CN, —C(O)$R^a$, —C(O)N($R^b$)$R^c$, —C(O)O$R^d$, —N($R^e$)$R^f$, —N($R^g$)C(O)$R^h$, —N($R^i$)C(O)O$R^j$, —N($R^k$)C(O)N($R^l$)$R^m$, —NO$_2$, —N($R^n$)S(O)$_2$$R^o$, —O$R^{px}$, —OC(O)$R^q$, —OS(O)$_2$$R^r$, —S(O)$_m$$R^s$, —S(O)$_2$N($R^t$)$R^u$, heterocycloalkyl optionally substituted by one or more substituents selected from $W^2$, aryl optionally substituted by one or more substituents selected from $W^3$ or heteroaryl optionally substituted by one or more substituents selected from $W^3$;

$Y^{1b}$ represents halogen, —CN, —C(O)$R^a$, —C(O)N($R^b$)$R^c$, —C(O)O$R^d$, —N($R^e$)$R^f$, —N($R^g$)C(O)$R^h$, —N($R^i$)C(O)O$R^j$, —N($R^k$)C(O)N($R^l$)$R^m$, —NO$_2$, —N($R^n$)S(O)$_2$$R^o$, —O$R^p$, —OC(O)$R^q$, —OS(O)$_2$$R^r$, —S(O)$_m$$R^s$, —S(O)$_2$N($R^t$)$R^u$, heterocycloalkyl optionally substituted by one or more substituents selected from $W^2$, aryl optionally substituted by one or more substituents selected from $W^3$ or heteroaryl optionally substituted by one or more substituents selected from $W^3$;

each $R^a$, $R^b$, $R^c$, $R^d$, $R^e$, $R^g$, $R^h$, $R^i$, $R^k$, $R^l$, $R^m$, $R^n$, $R^p$, $R^q$, $R^s$, $R^t$ and $R^u$ independently represents hydrogen, —$C_{1-6}$ alkyl optionally substituted by one or more substituents selected from $W^1$, heterocycloalkyl optionally substituted by one or more substituents selected from $W^2$, aryl optionally substituted by one or more substituents selected from $W^3$, or heteroaryl optionally substituted by one or more substituents selected from $W^3$; or any two $R^b$ and $R^c$, $R^e$ and $R^f$, $R^l$ and $R^m$ and/or $R^t$ and $R^u$ are linked together to form, along with the nitrogen atom to which they are attached, a 3- to 8-membered monocyclic or bicyclic ring, which ring optionally contains one or two further heteroatoms and which ring optionally is substituted by one or more substituents selected from $W^2$, $C_{1-3}$alkyl optionally substituted by one or more substituents selected from $W^1$, and =O;

each $R^f$, $R^j$, $R^o$, $R^r$ and $R^{px}$ independently represents $C_{1-6}$ alkyl optionally substituted by one or more substituents selected from $W^1$, heterocycloalkyl optionally substituted by one or more substituents selected from $W^2$, aryl optionally substituted by one or more substituents selected from $W^3$ or heteroaryl optionally substituted by one or more substituents selected from $W^3$;

each $Y^2$ independently represents halogen, —CN, —C(O)$R^{b1}$, —C(O)N($R^{c1}$)$R^{d1}$, —C(O)(O$R^{e1}$, —N($R^{f1}$)$R^{g1}$, —N($R^{h1}$)C(O)$R^{i1}$, —N($R^{j1}$)C(O)O$R^{k1}$, —N($R^{l1}$)C(O)N($R^{m1}$)$R^{n1}$, —N($R^{o1}$)S(O)$_2$$R^{p1}$, —O$R^{q1}$, —OC(O)$R^{r1}$, —OS(O)$_2$$R^{s1}$, —S(O)$_m$$R^{t1}$, —S(O)$_2$N($R^{u1}$)$R^{v1}$, heterocycloalkyl optionally substituted by one or more substituents selected from $W^1$, aryl optionally substituted by one or more substituents selected from $W^2$, heteroaryl optionally substituted by one or more substituents selected from $W^2$, or =O;

each $Y^3$ independently represents halogen, —$R^{a1}$, —CN, —C(O)$R^{b1}$, —C(O)N($R^{c1}$)$R^{d1}$, —C(O)O$R^{e1}$, —N($R^{f1}$)$R^{g1}$, —N($R^{h1}$)C(O)$R^{i1}$, —N($R^{j1}$)C(O)O$R^{k1}$, —N($R^{l1}$)C(O)N($R^{m1}$)$R^{n1}$, —N($R^{o1}$)S(O)$_2$$R^{p1}$, —O$R^{q1}$, —OC(O)$R^{r1}$, —OS(O)$_2$$R^{s1}$, —S(O)$_m$$R^{t1}$, —S(O)$_2$N($R^{u1}$)$R^{v1}$, heterocycloalkyl optionally substituted by one or more substituents selected from $W^1$, aryl optionally substituted by one or more substituents selected from $W^2$, heteroaryl optionally substituted by one or more substituents selected from $W^2$, or =O;

each $R^{a1}$, $R^{b1}$, $R^{c1}$, $R^{d1}$, $R^{e1}$, $R^{f1}$, $R^{h1}$, $R^{i1}$, $R^{j1}$, $R^{l1}$, $R^{m1}$, $R^{n1}$, $R^{o1}$, $R^{q1}$, $R^{r1}$, $R^{t1}$, $R^{u1}$ and $R^{v1}$ independently represents hydrogen, $C_{1-6}$ alkyl optionally substituted by one or more substituents selected from $W^1$, heterocycloalkyl optionally substituted by one or more substituents selected from $W^2$, aryl optionally substituted by one or more substituents selected from $W^3$, or heteroaryl optionally substituted by one or more substituents selected from $W^3$; or any two $R^{c1}$ and $R^{d1}$, $R^{f1}$ and $R^{g1}$, $R^{m1}$ and $R^{n1}$ and/or $R^{u1}$ and $R^{v1}$ are linked together to form, along with the nitrogen atom to which they are attached, a 3- to 8-membered monocyclic or bicyclic ring, which ring optionally contains one or two heteroatoms and which ring optionally is substituted by one or more substituents selected from $W^2$, $C_{1-3}$alkyl optionally substituted by one or more substituents selected from $W^1$, and =O;

each $R^{g1}$, $R^{k1}$, $R^{p1}$ and $R^{s1}$ independently represents —$C_{1-6}$ alkyl optionally substituted by one or more substituents selected from $W^1$, heterocycloalkyl optionally substituted by one or more substituents selected from $W^2$, aryl optionally substituted by one or more substituents selected from $W^3$, or heteroaryl optionally substituted by one or more substituents selected from $W^3$;

each $Z^1$ independently represents halogen, —CN, —C(O)$R^{b2}$, —C(O)N($R^{c2}$)$R^{d2}$, —C(O)O$R^{e2}$, —N($R^{f2}$)$R^{g2}$, —N($R^{h2}$)C(O)$R^{i2}$, —N($R^{j2}$)C(O)O$R^{k2}$, —N($R^{l2}$)C(O)N($R^{m2}$)$R^{n2}$, —N($R^{o2}$)S(O)$_2R^{p2}$, —O$R^{q2}$, —OC(O)$R^{r2}$, —OS(O)$_2R^{s2}$, —S(O)$_mR^{t2}$, —S(O)$_2$N($R^{u2}$)$R^{v2}$, heterocycloalkyl optionally substituted by one or more substituents selected from $W^5$, aryl represented by

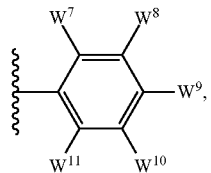

or heteroaryl having 1 to 3 nitrogen atoms, one oxygen atom and/or one sulfur atom and optionally substituted by one or more substituents selected from $W^6$, or =O;

each $Z^2$ and $Z^3$ independently represents halogen, —$R^{a2}$, —CN, —C(O)$R^{b2}$, —C(O)N($R^{c2}$)$R^{d2}$, —C(O)O$R^{e2}$, —N($R^{f2}$)$R^{g2}$, —N($R^{h2}$)C(O)$R^{i2}$, —N($R^{j2}$)C(O)O$R^{k2}$, —N($R^{l2}$)C(O)N($R^{m2}$)$R^{n2}$, —N($R^{o2}$)S(O)$_2R^{p2}$, —O$R^{q2}$, —OC(O)$R^{r2}$, —OS(O)$_2R^{s2}$, —S(O)$_mR^{t2}$, —S(O)$_2$N($R^{u2}$)$R^{v2}$, heterocycloalkyl optionally substituted by one or more substituents selected from $W^5$, aryl optionally substituted by one or more substituents selected from $W^6$, or heteroaryl optionally substituted by one or more substituents selected from $W^6$;

each $Z^4$ independently represents halogen, —CN, —C(O)$R^{b2}$, —C(O)N($R^{c2}$)$R^{d2}$, —C(O)O$R^{e2}$, —N($R^{f2}$)$R^{g2}$, —N($R^{h2}$)C(O)$R^{i2}$, —N($R^{j2}$)C(O)O$R^{k2}$, —N($R^{l2}$)C(O)N($R^{m2}$)$R^{n2}$, —N($R^{o2}$)S(O)$_2R^{p2}$, —O$R^{q2}$, —OC(O)$R^{r2}$, —OS(O)$_2R^{s2}$, —S(O)$_mR^{t2}$, —S(O)$_2$N($R^{u2}$)$R^{v2}$, heterocycloalkyl optionally substituted by one or more substituents selected from $W^5$, aryl optionally substituted by one or more substituents selected from $W^6$, heteroaryl optionally substituted by one or more substituents selected from $W^6$, or =O;

each $R^{a2}$, $R^{b2}$, $R^{c2}$, $R^{d2}$, $R^{e2}$, $R^{f2}$, $R^{h2}$, $R^{i2}$, $R^{j2}$, $R^{l2}$, $R^{m2}$, $R^{n2}$, $R^{o2}$, $R^{q2}$, $R^{r2}$, $R^{t2}$, $R^{u2}$ and $R^{v2}$ independently represents hydrogen, $C_{1-6}$ alkyl optionally substituted by one or more substituents selected from $W^4$, heterocycloalkyl optionally substituted by one or more substituents selected from $W^5$, aryl optionally substituted by one or more substituents selected from $W^6$, or heteroaryl optionally substituted by one or more substituents selected from $W^6$; or any two $R^{c2}$ and $R^{d2}$, $R^{f2}$ and $R^{g2}$, $R^{m2}$ and $R^{n2}$ and/or $R^{u2}$ and $R^{v2}$ are linked together to form, along with the nitrogen atom to which they are attached, a 3- to 8-membered monocyclic or bicyclic ring, which ring optionally contains one or two heteroatoms and which ring optionally is substituted by one or more substituents selected from $W^5$, $C_{1-3}$alkyl optionally substituted by one or more substituents selected from $W^4$), and =O;

each $R^{g2}$, $R^{k2}$, $R^{p2}$ and $R^{s2}$ independently represents $C_{1-6}$ alkyl optionally substituted by one or more substituents selected from $W^4$, heterocycloalkyl optionally substituted by one or more substituents selected from $W^5$, aryl optionally substituted by one or more substituents selected from $W^6$, or heteroaryl optionally substituted by one or more substituents selected from $W^6$;

each $W^1$ and $W^4$ independently represents halogen, —CN, —N($R^{f3}$)$R^{g3}$, —N($R^{h3}$)C(O)$R^{i3}$, —N($R^{j3}$)C(O)O$R^{k3}$, —N($R^{l3}$)C(O)N($R^{m3}$)$R^{n3}$, —N($R^{o3}$)S(O)$_2R^{p3}$, —O$R^{q3}$, —OC(O)$R^{r3}$, —OS(O)$_2R^{s3}$, —S(O)$_mR^{t3}$, —S(O)$_2$N($R^{u3}$)$R^{v3}$, heterocycloalkyl optionally substituted by one or more substituents selected from $G^1$, aryl optionally substituted by one or more substituents selected from $G^2$, heteroaryl optionally substituted by one or more substituents selected from $G^2$, or =O;

each $W^2$, $W^3$, $W^5$ and $W^6$ independently represents halogen, —$R^{a3}$, —CN, —C(O)$R^{b3}$, —C(O)N($R^{c3}$)$R^{d3}$, —C(O)O$R^{e3}$, —N($R^{f3}$)$R^{g3}$, —N($R^{h3}$)C(O)$R^{i3}$, —N($R^{j3}$)C(O)O$R^{k3}$, —N($R^{l3}$)C(O)N($R^{m3}$)$R^{n3}$, —N($R^{o3}$)S(O)$_2R^{p3}$, —O$R^{q3}$, —OC(O)$R^{r3}$, —OS(O)$_2R^{s3}$, —S(O)$_mR^{t3}$, —S(O)$_2$N($R^{u3}$)$R^{v3}$, heterocycloalkyl optionally substituted by one or more substituents selected from $G^1$, aryl optionally substituted by one or more substituents selected from $G^2$, heteroaryl (optionally substituted by one or more substituents selected from $G^2$, or =O;

each $W^7$, $W^8$, $W^9$, $W^{10}$ and $W^{11}$ independently represents hydrogen, halogen, —$R^{a3}$, —CN, —C(O)$R^{b3}$, —C(O)N($R^{c3}$)$R^{d3}$, —C(O)O$R^{e3}$, —N($R^{f3}$)$R^{g3}$, —N($R^{h3}$)C(O)$R^{i3}$, —N($R^{j3}$)C(O)O$R^{k3}$, —N($R^{l3}$)C(O)N($R^{m3}$)$R^{n3}$, —N($R^{o3}$)S(O)$_2R^{p3}$, —O$R^{q3}$, —OC(O)$R^{r3}$, —OS(O)$_2R^{s3}$, —S(O)$_mR^{t3}$, —S(O)$_2$N($R^{u3}$)$R^{v3}$, heterocycloalkyl optionally substituted by one or more substituents selected from $G^1$, aryl optionally substituted by one or more substituents selected from $G^2$, or heteroaryl optionally substituted by one or more substituents selected from $G^2$;

each $R^{a3}$, $R^{b3}$, $R^{c3}$, $R^{d3}$, $R^{e3}$, $R^{f3}$, $R^{h3}$, $R^{i3}$, $R^{j3}$, $R^{l3}$, $R^{m3}$, $R^{n3}$, $R^{o3}$, $R^{r3}$, $R^{t3}$, $R^{u3}$ and $R^{v3}$ independently represents hydrogen or $C_{1-6}$ alkyl optionally substituted by one or more $G^3$; or any two $R^{c3}$ and $R^{d3}$, $R^{f3}$ and $R^{g3}$, $R^{m3}$ and $R^{n3}$ and/or $R^{u3}$ and $R^{v3}$ are linked together to form, along with the nitrogen atom to which they are attached, a 4- to 6-membered ring, which ring optionally contains one heteroatom and which ring optionally is substituted by one or more $G^2$;

each $R^{g3}$, $R^{k3}$, $R^{p3}$, and $R^{s3}$ independently represents $C_{1-6}$ alkyl optionally substituted by one or more $G^3$;

each $G^1$ and $G^2$ independently represents halogen, —$R^{a4}$, —CN, —C(O)$R^{b4}$, —C(O)N($R^{c4}$)$R^{d4}$, —C(O)O$R^{e4}$, —N($R^{f4}$)$R^{g4}$, —N($R^{h4}$)C(O)$R^{i4}$, —N($R^{j4}$)C(O)O$R^{k4}$, —N($R^{l4}$)C(O)N($R^{m4}$)$R^{n4}$, —N($R^{o4}$)S(O)$_2R^{p4}$, —O$R^{q4}$, —OC(O)$R^{r4}$, —OS(O)$_2R^{s4}$, —S(O)$_mR^{t4}$, —S(O)$_2$N($R^{u4}$)$R^{v4}$, or =O;

$G^3$ represents halogen, —CN, —C(O)$R^{b4}$, —C(O)N($R^{c4}$)$R^{d4}$, —C(O)O$R^{e4}$, —N($R^{f4}$)$R^{g4}$, —N($R^{h4}$)C(O)$R^{i4}$, —N($R^{j4}$)C(O)O$R^{k4}$, —N($R^{l4}$)C(O)N($R^{m4}$)$R^{n4}$, —N($R^{o4}$)S(O)$_2R^{p4}$, —O$R^{q4}$, —OC(O)$R^{r4}$, —OS(O)$_2R^{s4}$, —S(O)$_mR^{t4}$, —S(O)$_2$N($R^{u4}$)$R^{v4}$, or =O;

each $R^{a4}$, $R^{b4}$, $R^{c4}$, $R^{d4}$, $R^{e4}$, $R^{f4}$, $R^{h4}$, $R^{i4}$, $R^{j4}$, $R^{l4}$, $R^{m4}$, $R^{n4}$, $R^{o4}$, $R^{r4}$, $R^{t4}$, $R^{u4}$ and $R^{v4}$ independently represents hydrogen or $C_{1-6}$ alkyl optionally substituted by one or more —F; or any two $R^{c4}$ and $R^{d4}$, $R^{f4}$ and $R^{g4}$, $R^{m4}$ and $R^{n4}$ and/or $R^{u4}$ and $R^{v4}$ are linked together to form, along with the nitrogen atom to which they are attached, a 3- to 6-membered ring, which ring optionally substituted by one or more —F, —$CH_3$, —$CH_2CH_3$, —$CHF_2$, —$CF_3$, —$CH_2CF_3$, or =O;

each $R^{g4}$, $R^{k4}$, $R^{p4}$ and $R^{s4}$ independently represent $C_{1-6}$ alkyl optionally substituted by one or more —F;

each m independently represents 0, 1 or 2;

provided that the compound is not $N^4$-cyclopropyl-6-(4-methoxy-2-methylphenyl)-2,4-pyrimidinediamine.

2. The compound as claimed in claim 1, wherein:
$R^1$ is represented by

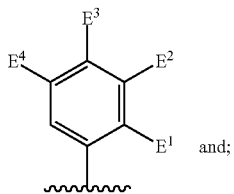 and;

$E^3$ and $E^4$ represent hydrogen; and
$E^1$ represents —F and $E^2$ represent —F, —Cl, —CH$_3$ or —CF$_3$; or
$E^1$ represents —Cl and $E^2$ represents —F, —Cl, —CH$_3$ or —CF$_3$; or
$E^1$ represents —CH$_3$ and $E^2$ represents —F, —Cl, —CH$_3$, —CF$_3$, —CN or —N(H)C(O)CH=CH$_2$; or
$E^2$ and $E^4$ represent hydrogen; and
$E^1$ represents —F and $E^3$ represents —F or phenyl; or
$E^1$ represents —Cl and $E^3$ represents —F or —Cl; or
$E^1$ represents —CH$_3$ and $E^3$ represents —Cl or —OCH$_2$phenyl; or
$E^1$ represents —OCH$_3$ and $E^3$ represents —F; or
$E^2$ and $E^3$ represent hydrogen; and
$E^1$ represents —F and $E^4$ represents —Cl, —CH$_3$ or —CN; or
$E^1$ represents —Cl and $E^4$ represent —F, —Cl, —CH$_3$, —CF$_3$ or —OCH$_3$; or
$E^1$ represents —CH$_3$ and $E^4$ represent —F, —Cl, —CH$_3$, —CF$_3$, —CN, —N(H)C(O)CH=CH$_2$ or —S(O)$_2$(4-morpholinyl); or
$E^1$ represents —CF$_3$ and $E^4$ represents —F or —CF$_3$; or
$E^1$ represents —CN and $E^4$ represents —Cl; or
$E^1$ represents —OCH$_3$ and $E^4$ represents —F, —Cl, Br, —CH$_3$, —CH(CH$_3$)$_2$, —C(CH$_3$)$_3$, —CN or —OCH$_3$; or
$E^1$ and $E^4$ represent hydrogen; and
$E^2$ represents —F and $E^3$ represents —F, —Cl, —OH or —OCH$_3$; or
$E^2$ represents —Cl and $E^3$ represents —F or —C(O)(4-morpholinyl); or
$E^2$ represents —CH$_3$ and $E^3$ represents —F or —OCH$_3$; or
$E^1$ represents —OCH$_3$ and $E^3$ represents —OH; or
$E^1$ represents-CH$_2$OCH$_3$ and $E^3$ represents (piperidin-4-yl)methoxy or ((1-tertbutoxycarbonyl)piperidin-4-yl)methoxy; or
$E^1$ and $E^3$ represent hydrogen; and
$E^2$ and $E^4$ represent —F; or
$E^2$ and $E^4$ represent —CF$_3$; or
$E^4$ represents hydrogen; and
$E^1$, $E^2$ and $E^3$ represent —F; or
$E^1$ and $E^2$ represent —Cl and $E^3$ represents —Cl, —OH or —OCH$_3$; or
$E^1$ and $E^2$ represent —CH$_3$ and $E^3$ represents —F or —OCH$_3$; or
$E^2$ and $E^3$ represent —Cl and $E^1$ represents —CH$_3$; or
$E^2$ represents hydrogen; and
$E^1$, $E^3$ and $E^4$ represent —F; or
$E^1$, $E^3$ and $E^4$ represent —Cl and $E^1$ represents —CH$_3$; or
$E^1$ and $E^4$ represent —Cl and $E^1$ represents —OCH$_3$; or
$E^1$ and $E^4$ represent —CH$_3$ and $E^3$ represents —F, —CH$_3$ or —OCH$_3$; or
$E^1$ represents —F, $E^3$ represents —CH$_3$ and $E^4$ represents —Cl; or
$E^1$ represents —Cl, $E^3$ represents —F and $E^4$ represents —CH$_3$; or
$E^1$ represents —Cl, $E^3$ represents —CH$_3$ and $E^4$ represents —F; or
$E^1$ and $E^4$ represent —CH$_3$ and $E^3$ represents —F; or
$E^1$ represents —CH$_3$, $E^4$ represents —Cl and $E^3$ represents —CF$_3$ or —OCH$_3$; or
$E^1$ represents hydrogen; and
$E^2$ and $E^4$ represent —CH$_3$ and $E^3$ represents —OH; or
$E^3$ represents hydrogen; and
$E^1$ and $E^2$ represent —Cl and $E^4$ represents —CH$_3$.

3. The compound as claimed in claim 2, wherein:
$E^3$ and $E^4$ represent hydrogen; and
$E^1$ represents —F and $E^2$ represents —F, —Cl, or —CF$_3$; or
$E^1$ represents —Cl and $E^2$ represents —Cl, —CH$_3$ or —CF$_3$; or
$E^1$ represents —CH$_3$ and $E^2$ represents —Cl, —CH$_3$, —CN or —N(H)C(O)CH=CH$_2$; or
$E^2$ and $E^4$ represent hydrogen; and
$E^1$ and $E^3$ represent —F; or
$E^1$ represents —Cl and $E^3$ represents —F or —Cl; or
$E^1$ represents —CH$_3$ and $E^3$ represents —Cl; or
$E^2$ and $E^3$ represent hydrogen; and
$E^1$ represents —F and $E^4$ represents —Cl, —CH$_3$ or —CN; or
$E^1$ represents —Cl and $E^4$ represents —F, —Cl, —CH$_3$ or —CF$_3$; or
$E^1$ represents —CH$_3$ and $E^4$ represent, —Cl, —CH$_3$, —CF$_3$, —CN or —N(H)C(O)CH=CH; or
$E^1$ represents —CF$_3$ and $E^4$ represents —F or —CF$_3$; or
$E^1$ represents —CN and $E^4$ represents —Cl; or
$E^4$ represents hydrogen; and
$E^1$, $E^2$ and $E^3$ represent —F; or
$E^1$ and $E^2$ represent —CH$_3$ and $E^3$ represents —F$_3$; or
$E^2$ and $E^3$ represent —Cl and $E^1$ represents —CH$_3$; or
$E^2$ represents hydrogen; and
$E^1$, $E^3$ and $E^4$ represent —F; or
$E^3$ and $E^4$ represent —Cl and $E^1$ represents —CH$_3$; or
$E^1$ and $E^4$ represent —CH$_3$ and $E^3$ represents —F or —CH$_3$; or
$E^1$ represents —F, $E^3$ represents —CH$_3$ and $E^4$ represents —Cl; or
$E^1$ represents —Cl, $E^3$ represents —F and $E^4$ represents —CH$_3$; or
$E^1$ represents —Cl, $E^3$ represents —CH$_3$ and $E^4$ represents —F; or
$E^1$ and $E^4$ represent —CH$_3$ and $E^3$ represents —F; or
$E^1$ represents —CH$_3$, $E^3$ represents —CF$_3$ and $E^4$ represents —Cl; or
$E^1$ represents hydrogen; and
$E^2$ and $E^4$ represent —CH$_3$ and $E^3$ represents —OH; or
$E^3$ represents hydrogen; and
$E^1$ and $E^2$ represent —Cl and $E^4$ represents —CH$_3$.

4. The compound as claimed in claim 1, wherein:
$R^2$ represents hydrogen or methyl.

5. The compound as claimed in claim 1, wherein:
$R^3$ represents —C$_{1-6}$alkyl optionally substituted by $Z^1$.

6. The compound as claimed in claim 1, wherein:
$R^3$ represents —C$_{2-6}$alkyl optionally substituted by $Z^1$ or heterocycloalkyl optionally substituted by $Z^2$.

7. The compound as claimed in claim 1, wherein:
$R^3$ represents —C$_{1-2}$alkyl optionally substituted with one or more —F.

8. The compound as claimed in any claim 1, wherein:
R³ represents

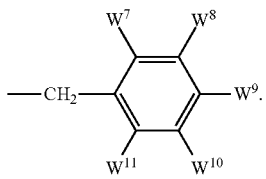

9. The compound as claimed in claim 1, wherein:
R³ represents —C$_{1-6}$alkyl substituted by heteroaryl having 1 to 3 nitrogen atoms, one oxygen atom and/or one sulfur atom and which heteroaryl is optionally substituted by one or more substituents selected from W³.

10. The compound as claimed in claim 1, wherein:
R³ represents —C$_{3-6}$alkyl or a heterocycloalkyl selected from cyclopropyl, cyclobutyl, cyclopentyl, cyclohexyl, cyclopropylmethyl, cyclobutylmethyl, cyclopentylmethyl, cyclopropylethyl, cyclobutylethyl, cyclopropylpropyl, oxetanyl, tetrahydrofuryl, tetrahydropyranyl, azetidinyl, pyrrolidinyl, piperidinyl, piperazinyl or morpholinyl wherein the C$_{3-6}$alkyl is optionally substituted by Z¹ and the heterocycloalkyl is optionally substituted by Z².

11. The compound as claimed in claim 5, wherein:
Z¹ represents —F, —CN, —C(O)R$^{b2}$, —C(O)N(R$^{c2}$)R$^{d2}$, —C(O)OR$^{e2}$, —N(R$^{f2}$)R$^{g2}$, —N(R$^{h2}$)C(O)R$^{i2}$, —N(R$^{j2}$)C(O)OR$^{k2}$, —N(R$^{j2}$)C(O)N(R$^{m2}$)R$^{n2}$, —N(R$^{o2}$)S(O)$_2$R$^{p2}$, —OR$^{q2}$, —S(O)$_m$R$^{r2}$, —S(O)$_2$N(R$^{u2}$)R$^{v2}$, heterocycloalkyl optionally substituted by one or more substituents selected from W⁵, aryl represented by

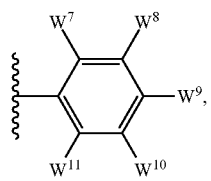

or heteroaryl having 1 to 3 nitrogen atoms, one oxygen atom and/or one sulfur atom and optionally substituted by one or more substituents selected from W⁶.

12. The compound as claimed in claim 11 wherein:
Z¹ represents —F, —CN, —C(O)NH$_2$, —C(O)N(R$^{c2}$)R$^{d2}$, —C(O)-(4-morpholinyl), —C(O)OEt, —N(H)C(O)Me, —N(H)C(O)R$^{i2}$, —N(H)C(O)CH$_2$NMe$_2$, —N(H)C(O)OCMe$_3$, —N(H)C(O)OCH$_2$Ph, —N(Me)C(O)OCMe$_3$, —N(H)C(O)N(H)Me, —N(H)C(O)N(H)CHMe$_2$, —N(H)S(O)$_2$Me, —OMe, —OCF$_3$, —OEt, or heterocycloalkyl selected from dihydropyridinyl, imidazolinyl, morpholinyl, oxanyl, piperazinyl, piperidinyl, pyrrolidinyl and quinuclidinyl, wherein the heterocycloalkyl is optionally substituted by one or more substituents selected from W⁵.

13. The compound as claimed in claim 11 wherein:
each W⁷, W¹⁰ and W¹¹ independently represents hydrogen, halogen, —R$^{a3}$ or —CN; and one of W⁸ and W⁹ represents hydrogen, halogen, —R$^{a3}$ or —CN and the other represents halogen, —R$^{a3}$, —CN, —C(O)R$^{b3}$, —C(O)N(R$^{c3}$)R$^{d3}$, —C(O)OR$^{e3}$, —N(R$^{f3}$)R$^{g3}$, —N(R$^{h3}$)C(O)R$^{i3}$, —N(R$^{j3}$)C(O)OR$^{k3}$, —N(R$^{j3}$)C(O)N(R$^{m3}$)R$^{n3}$, —N(R$^{o3}$)S(O)$_2$R$^{p3}$, —OR$^{q3x}$, —OC(O)R$^{r3}$, —OS(O)$_2$R$^{s3}$, —S(O)$_m$R$^{t3}$, —S(O)$_2$N(R$^{u3}$)R$^{v3}$, heterocycloalkyl optionally substituted by one or more substituents selected from G¹, aryl optionally substituted by one or more substituents selected from G², or heteroaryl optionally substituted by one or more substituents selected from G².

14. The compound as claimed in claim 1, wherein:
R² and R³ are linked together to form, along with the atoms to which they are attached, a 5- to 6-membered non-aromatic ring, wherein the link formed by R² and R³ is optionally substituted by one or more substituents selected from Z³ or —C$_{1-9}$alkyl optionally substituted by one or more Z⁴.

15. The compound as claimed in claim 14, wherein:
Z³ is not present or is selected from —F, —R$^{a2}$, —C(O)N(R$^{c2}$)R$^{d2}$, —N(R$^{f2}$)R$^{g2}$, —N(R$^{h2}$)C(O)R$^{i2}$, —N(R$^{j2}$)C(O)OR$^{k2}$, —N(R$^{j2}$)C(O)N(R$^{m2}$)R$^{n2}$, —N(R$^{o2}$)S(O)$_2$R$^{p2}$, —OR$^{q2}$, —S(O)$_m$R$^{r2}$, —S(O)$_2$N(R$^{u2}$)R$^{v2}$, heterocycloalkyl optionally substituted by one or more substituents selected from W⁵, aryl optionally substituted by one or more substituents selected from W⁶, or heteroaryl optionally substituted by one or more substituents selected from W⁶; and/or Z⁴ is not present or is selected from —F, —C(O)N(R$^{c2}$)R$^{d2}$, —N(R$^{f2}$)R$^{g2}$, —N(R$^{h2}$)C(O)R$^{i2}$, —N(R$^{j2}$)C(O)OR$^{k2}$, —N(R$^{j2}$)C(O)N(R$^{m2}$)R$^{n2}$, —N(R$^{o2}$)S(O)$_2$R$^{p2}$, —OR$^{q2}$, —S(O)$_m$R$^{r2}$, —S(O)$_2$N(R$^{u2}$)R$^{v2}$, heterocycloalkyl optionally substituted by one or more substituents selected from W⁵, aryl optionally substituted by one or more substituents selected from W⁶, or heteroaryl optionally substituted by one or more substituents selected from W⁶.

16. A pharmaceutical formulation comprising a compound as claimed in claim 1, or a pharmaceutically acceptable salt thereof, in admixture with a pharmaceutically acceptable adjuvant, diluent or carrier.

17. A method of treatment of a disease selected from
Soft Tissue Cancers selected from sarcoma, myxoma, rhabdomyoma, fibroma, lipoma and teratoma;
Lung cancers/diseases selected from bronchogenic carcinoma, alveolar carcinoma, bronchial adenoma, sarcoma, lymphoma, chondromatous hamartoma, mesothelioma;
Gastrointestinal cancers/diseases selected from cancers of the esophagus, stomach, pancreas, small bowel, and large bowel;
Genitourinary tract cancers/diseases selected from cancers of the kidney, bladder and urethra, prostate, and testis;
Liver cancers/diseases selected from hepatoma, cholangiocarcinoma, hepatoblastoma, angiosarcoma, hepatocellular adenoma, hemangioma;
Bone cancers/diseases selected from osteogenic sarcoma, fibrosarcoma, malignant fibrous histiocytoma, chondrosarcoma, Ewing's sarcoma, malignant lymphoma, multiple myeloma, malignant giant cell tumor chordoma, osteochronfroma, benign chondroma, chondroblastoma, chondromyxofibroma, osteoid osteoma and giant cell tumors;
Nervous system cancers/diseases selected from cancer of the skull, meninges brain, and the spinal cord;
Gynecological cancers/diseases selected from cancers of the uterus, cervix, ovaries, vulva, vagina, fallopian tubes;
Hematologic cancers;

Skin cancers/diseases selected from malignant melanoma, basal cell carcinoma, squamous cell carcinoma, Kaposi's sarcoma, moles dysplastic nevi, lipoma, angioma, dermatofibroma, keloids;

Adrenal glands cancers/diseases, neuroblastoma, neurofibromatosis and head and neck cancers, and breast cancer;

which method comprises administration of a therapeutically effective amount a compound as claimed in claim 1, or a pharmaceutically acceptable salt thereof, to a patient in need of such treatment; and wherein the treatment does not comprise prevention or prophylaxis.

18. The method as claimed in claim 17, wherein the disease is selected from the group consisting of breast cancers, prostate cancers, lung cancers, oesophageal cancers, colon cancers, brain cancers, skin cancers, ovarian cancers, testicular cancers, neurofibromatosis and leukemias.

19. A combination product comprising:
(A) a compound as claimed in claim 1, or a pharmaceutically acceptable salt thereof; and
(B) one or more other therapeutic agent(s) that is/are useful in the treatment of a disease,
wherein each one of components (A) and (B) is formulated in admixture with a pharmaceutically-acceptable adjuvant, diluent or carrier, and
wherein the disease is selected from:
Soft Tissue Cancers selected from sarcoma, myxoma, rhabdomyoma, fibroma, lipoma and teratoma;
Lung cancers/diseases selected from bronchogenic carcinoma, alveolar carcinoma, bronchial adenoma, sarcoma, lymphoma, chondromatous hamartoma, mesothelioma;
Gastrointestinal cancers/diseases selected from cancers of the esophagus, stomach, pancreas, small bowel, and large bowel;
Genitourinary tract cancers/diseases selected from cancers of the kidney, bladder and urethra, prostate, and testis;
Liver cancers/diseases selected from hepatoma, cholangiocarcinoma, hepatoblastoma, angiosarcoma, hepatocellular adenoma, hemangioma;
Bone cancers/diseases selected from osteogenic sarcoma, fibrosarcoma, malignant fibrous histiocytoma, chondrosarcoma, Ewing's sarcoma, malignant lymphoma, multiple myeloma, malignant giant cell tumor chordoma,
osteochronfroma, benign chondroma, chondroblastoma, chondromyxofibroma, osteoid osteoma and giant cell tumors;
Nervous system cancers/diseases selected from cancer of the skull, meninges brain, and the spinal cord;
Gynecological cancers/diseases selected from cancers of the uterus, cervix, ovaries, vulva, vagina, fallopian tubes;
Hematologic cancers;
Skin cancers/diseases selected from malignant melanoma, basal cell carcinoma, squamous cell carcinoma, Kaposi's sarcoma, moles dysplastic nevi, lipoma, angioma, dermatofibroma, keloids;
Adrenal glands cancers/diseases, neuroblastoma, neurofibromatosis and head and neck cancers, and breast cancer.

20. The combination product as claimed in claim 19, wherein component (B) is selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors; kinase inhibitors; angiogenesis inhibitors; immunotherapeutic agents; pro-apoptotic agents; and cell cycle signaling inhibitors.

21. The compound as claimed in claim 2, wherein:
$R^3$ represents —$C_{1-6}$alkyl optionally substituted by $Z^1$.

22. The compound as claimed in claim 2, wherein:
$R^3$ represents —$C_{1-2}$alkyl optionally substituted with one or more —F.

23. The compound as claimed in claim 21, wherein:
$E^3$ and $E^4$ represent hydrogen; and
$E^1$ represents —F and $E^2$ represent —F, —Cl, —$CH_3$ or —$CF_3$; or
$E^1$ represents —Cl and $E^2$ represents —F, —Cl, —$CH_3$ or —$CF_3$; or
$E^1$ represents —$CH_3$ and $E^2$ represents —F, —Cl, —$CH_3$, —$CF_3$, —CN or —N(H)C(O)CH=$CH_2$.

24. The compound as claimed in claim 22, wherein:
$R^3$ represents —$C_{1-2}$alkyl optionally substituted with one or more —F.

25. The compound as claimed in claim 1, selected from
4-N-cyclopropyl-6-(2,3-dichlorophenyl)pyrimidine-2,4-diamine,
4-[2-amino-6-(methylamino)pyrimidin-4-yl]-2,3-dichlorophenol,
methyl (2E)-3-{3-[2-amino-6-(methylamino)pyrimidin-4-yl]phenyl}prop-2-enoate,
6-(2,3-dimethylphenyl)-4-N-(2-phenylethyl)pyrimidine-2,4-diamine,
6-(3-chloro-2-methoxypyridin-4-yl)-4-N-methylpyrimidine-2,4-diamine,
4-(2,3-dimethylphenyl)-5H,6H,7H,8H-pyrido[2,3-d]pyrimidin-2-amine,
4-(2,3-dichlorophenyl)-5H,6H,7H,8H-pyrido[2,3-d]pyrimidin-2-amine,
4-[1-(benzenesulfonyl)-1H-indol-3-yl]-5H,6H,7H,8H-pyrido[2,3-d]pyrimidin-2-amine,
6-(2,3-dimethylphenyl)-4-N-[2-(4-methoxyphenyl)ethyl]pyrimidine-2,4-diamine,
6-(2,3-dimethylphenyl)-4-N-[2-(2-methoxyphenyl)ethyl]pyrimidine-2,4-diamine,
6-(2,3-dimethylphenyl)-4-N-[2-(4-methylphenyl)ethyl]pyrimidine-2,4-diamine,
4-N-[2-(4-chlorophenyl)ethyl]-6-(2,3-dimethylphenyl)pyrimidine-2,4-diamine,
6-(2,3-dimethylphenyl)-4-N-(3-phenylpropyl)pyrimidine-2,4-diamine,
6-(2,3-dimethylphenyl)-4-N-[2-(phenylamino)ethyl]pyrimidine-2,4-diamine,
6-(2,3-dimethylphenyl)-4-N-[2-(1H-indol-3-yl)ethyl]pyrimidine-2,4-diamine,
6-(2,3-dimethylphenyl)-4-N-pentylpyrimidine-2,4-diamine,
4-[2-amino-6-(methylamino)pyrimidin-4-yl]-2,6-dimethylphenol,
4-[2-amino-6-(methylamino)pyrimidin-4-yl]-2-methoxyphenol,
4-[2-amino-6-(methylamino)pyrimidin-4-yl]-2-fluorophenol,
4-N-methyl-6-(2-methylphenyl)pyrimidine-2,4-diamine,
6-[1-(4-chlorobenzenesulfonyl)-1H-indol-3-yl]-4-N-methylpyrimidine-2,4-diamine,
4-N-methyl-6-(4-methyl-1H-indazol-5-yl)pyrimidine-2,4-diamine,
4-N-methyl-6-(3-methylphenyl)pyrimidine-2,4-diamine, 6-(1H-indol-5-yl)-4-N-methylpyrimidine-2,4-diamine,
6-(3-chloropyridin-4-yl)-4-N-methylpyrimidine-2,4-diamine,
4-N-cyclobutyl-6-(2,3-dimethylphenyl)pyrimidine-2,4-diamine,
4-N-cyclopentyl-6-(2,3-dimethylphenyl)pyrimidine-2,4-diamine,
6-(1-benzofuran-3-yl)-4-N-methylpyrimidine-2,4-diamine,
6-(1-benzothiophen-3-yl)-4-N-methylpyrimidine-2,4-diamine,
6-(5-bromo-2-methoxyphenyl)-4-N-methylpyrimidine-2,4-diamine,
6-[4-(benzyloxy)-2-methylphenyl]-4-N-methylpyrimidine-2,4-diamine,
6-(4-methoxy-2,5-dimethylphenyl)-4-N-methylpyrimidine-2,4-diamine,
6-(4,5-dichloro-2-methylphenyl)-4-N-methylpyrimidine-2,4-diamine,
6-(2,5-dichloro-4-methoxyphenyl)-4-N-methylpyrimidine-2,4-diamine,
6-(4-fluoro-2,5-dimethylphenyl)-4-N-methylpyrimidine-2,4-diamine,
6-[5-chloro-2-methyl-4-(trifluoromethyl)phenyl]-4-N-methylpyrimidine-2,4-diamine,
6-(5-tert-butyl-2-methoxyphenyl)-4-N-methylpyrimidine-2,4-diamine,
6-(2-fluoro-5-methylphenyl)-4-N-methylpyrimidine-2,4-diamine,
6-(5-chloro-2-methoxyphenyl)-4-N-methylpyrimidine-2,4-diamine,
6-(5-fluoro-2-methylphenyl)-4-N-methylpyrimidine-2,4-diamine,
6-(2-chloro-5-fluorophenyl)-4-N-methylpyrimidine-2,4-diamine,
6-[5-fluoro-2-(trifluoromethyl)phenyl]-4-N-methylpyrimidine-2,4-diamine,
6-(2,5-dichlorophenyl)-4-N-methylpyrimidine-2,4-diamine,
6-(5-chloro-2-fluoro-4-methylphenyl)-4-N-methylpyrimidine-2,4-diamine,
6-(5-chloro-2-methylphenyl)-4-N-[2-(4-chlorophenyl)ethyl]pyrimidine-2,4-diamine,
4-N-[2-(4-chlorophenyl)ethyl]-6-(4-fluoro-2,5-dimethylphenyl)pyrimidine-2,4-diamine,
4-N-[2-(4-chlorophenyl)ethyl]-6-(2,5-dimethylphenyl)pyrimidine-2,4-diamine,
6-(2-chloro-3-methylphenyl)-4-N-methylpyrimidine-2,4-diamine,
6-(2-chloro-3-methylphenyl)-4-N-[2-(4-chlorophenyl)ethyl]pyrimidine-2,4-diamine,
4-N-[2-(4-chlorophenyl)ethyl]-6-(1H-indol-4-yl)pyrimidine-2,4-diamine,
6-[5-fluoro-2-(trifluoromethyl)phenyl]-4-N-methylpyrimidine-2,4-diamine,
6-(2,5-dichlorophenyl)-4-N-methylpyrimidine-2,4-diamine,
4-N-cyclopropyl-6-(1H-indol-5-yl)pyrimidine-2,4-diamine,
tert-Butyl (3-((2-amino-6-(2,3-dimethylphenyl)pyrimidin-4-yl)amino)-2,2-dimethyl-propyl)carbamate,
6-(5-chloro-4-methoxy-2-methylphenyl)-4-N-methylpyrimidine-2,4-diamine,
4-N-{bicyclo[2,2,1]heptan-2-yl}-6-(3-chloro-2-methylphenyl)pyrimidine-2,4-diamine,
6-(3-chloro-2-methylphenyl)-4-N-ethylpyrimidine-2,4-diamine,
4-N-[2-(2-chlorophenoxy)ethyl]-6-(2,3-dimethylphenyl)pyrimidine-2,4-diamine,
6-(2,3-dimethylphenyl)-4-N-[2-(pyridin-3-yloxy)propyl]pyrimidine-2,4-diamine,
6-(2,3-dimethylphenyl)-4-N-(1H-indazol-5-ylmethyl)pyrimidine-2,4-diamine,
3-[2-amino-6-(methylamino)pyrimidin-4-yl]-2-methyl-benzonitrile,
6-(4-fluoro-2,3-dimethylphenyl)-4-N-methylpyrimidine-2,4-diamine,
6-(2,3-dihydro-1-benzofuran-7-yl)-4-N-methylpyrimidine-2,4-diamine,
4-N-methyl-6-[2-methyl-5-(morpholine-4-sulfonyl)phenyl]pyrimidine-2,4-diamine,
6-(2,3-dimethylphenyl)-4-N-[2-(pyridin-3-yl)ethyl]pyrimidine-2,4-diamine,
benzyl N-(2-{[2-amino-6-(2,3-dimethylphenyl)pyrimidin-4-yl]amino}ethyl)-carbamate,
tert-butyl 4-({[2-amino-6-(2,3-dimethylphenyl)pyrimidin-4-yl]amino}methyl)piperidine-1-carboxylate,
N-{3-[2-amino-6-(methylamino)pyrimidin-4-yl]phenyl}-3-hydroxypyridine-2-carboxamide,
N-{3-[2-Amino-6-(methylamino)pyrimidin-4-yl]phenyl}prop-2-enamide,
(2E)-N-{3-[2-Amino-6-(methylamino)pyrimidin-4-yl]phenyl}-4-(dimethylamino)but-2-enamide,
N-{3-[2-amino-6-(methylamino)pyrimidin-4-yl]phenyl}ethene-1-sulfonamide,
N-{3-[2-Amino-6-(methylamino)pyrimidin-4-yl]phenyl}prop-2-ynamide,
N-{3-[2-Amino-6-(methylamino)pyrimidin-4-yl]phenyl}-2-oxopropanamide,
6-(2,3-Dimethylphenyl)-4-N-[2-(5-methyl-1H-1,2,4-triazol-3-yl)ethyl]pyrimidine-2,4-diamine,
4-N-{[4-(Dimethylamino)phenyl]methyl}-6-(2,3-dimethylphenyl)pyrimidine-2,4-diamine,
6-(2,3-Dimethylphenyl)-4-N-{[1-(pyrimidin-2-yl)piperidin-3-yl]methyl}pyrimidine-2,4-diamine,
6-(2,3-Dimethylphenyl)-4-N-[2-(4-methyl-1,3-thiazol-5-yl)ethyl]pyrimidine-2,4-diamine,
6-(2,3-Dimethylphenyl)-4-N-{[1-(pyridin-2-yl)piperidin-3-yl]methyl}pyrimidine-2,4-diamine,
6-(2,3-Dimethylphenyl)-4-N-[(2-phenyl-2H-1,2,3-triazol-4-yl)methyl]pyrimidine-2,4-diamine,
tert-Butyl N-(4-{[2-amino-6-(2,3-dimethylphenyl)pyrimidin-4-yl]amino}butyl)-carbamate,
tert-Butyl N-(5-{[2-amino-6-(2,3-dimethylphenyl)pyrimidin-4-yl]amino}pentyl)-carbamate,
6-(2,3-Dimethylphenyl)-4-N-(prop-2-en-1-yl)pyrimidine-2,4-diamine,
6-(2,3-dichlorophenyl)-4-N-[2-(4-methyl-1,3-thiazol-5-yl)ethyl]pyrimidine-2,4-diamine
6-(3-chloro-2-methylphenyl)-4-N-[2-(4-methyl-1,3-thiazol-5-yl)ethyl]pyrimidine-2,4-diamine
4-N-Cyclopropyl-6-(2,3,4-trichlorophenyl)pyrimidine-2,4-diamine,
6-(2,3-dimethylphenyl)-4-N—($^2$H$_3$)methylpyrimidine-2,4-diamine,
6-(2-chloro-3-methylphenyl)-4-N—($^2$H$_3$)methylpyrimidine-2,4-diamine, and
3-[2-amino-6-(cyclopropylamino)pyrimidin-4-yl]-2-methylbenzonitrile, or a pharmaceutically acceptable salt thereof.

* * * * *